US012054537B2

(12) United States Patent
Weiner et al.

(10) Patent No.: US 12,054,537 B2
(45) Date of Patent: Aug. 6, 2024

(54) OPTIMIZED NUCLEIC ACID ANTIBODY CONSTRUCTS ENCODING ANTI-RESPIRATORY SYNCYTIAL VIRUS (RSV) ANTIBODIES

(71) Applicants: The Wistar Institute of Anatomy and Biology, Philadelphia, PA (US); INOVIO PHARMACEUTICALS, INC., Plymouth Meeting, PA (US)

(72) Inventors: David Weiner, Merion, PA (US); Ghiabe Guibinga, La Mesa, CA (US); Neil Cooch, Oreland, PA (US); Charles Reed, Souderton, PA (US)

(73) Assignees: The Wistar Institute of Anatomy and Biology, Philadelphia, PA (US); Inovio Pharmaceuticals, Inc., Plymouth Meeting, PA (US)

( * ) Notice: Subject to any disclaimer, the term of this patent is extended or adjusted under 35 U.S.C. 154(b) by 418 days.

(21) Appl. No.: 16/611,943

(22) PCT Filed: May 10, 2018

(86) PCT No.: PCT/US2018/032023
§ 371 (c)(1),
(2) Date: Nov. 8, 2019

(87) PCT Pub. No.: WO2018/209055
PCT Pub. Date: Nov. 15, 2018

(65) Prior Publication Data
US 2021/0188947 A1    Jun. 24, 2021

Related U.S. Application Data

(60) Provisional application No. 62/624,367, filed on Jan. 31, 2018, provisional application No. 62/624,320, filed on Jan. 31, 2018, provisional application No. 62/504,460, filed on May 10, 2017, provisional application No. 62/504,448, filed on May 10, 2017.

(51) Int. Cl.
| C07K 16/10 | (2006.01) |
| C07K 16/00 | (2006.01) |
| A61K 39/00 | (2006.01) |
| A61K 48/00 | (2006.01) |
| C12N 15/10 | (2006.01) |
| G16B 15/20 | (2019.01) |
| G16B 30/10 | (2019.01) |

(52) U.S. Cl.
CPC .......... *C07K 16/1027* (2013.01); *C07K 16/00* (2013.01); *A61K 2039/505* (2013.01); *A61K 48/00* (2013.01); *C07K 16/10* (2013.01); *C07K 2317/522* (2013.01); *C07K 2317/524* (2013.01); *C07K 2317/53* (2013.01); *C07K 2317/565* (2013.01); *C07K 2317/567* (2013.01); *C07K 2317/622* (2013.01); *C07K 2317/66* (2013.01); *C12N 15/1031* (2013.01); *C12N 15/1079* (2013.01); *G16B 15/20* (2019.02); *G16B 30/10* (2019.02)

(58) Field of Classification Search
CPC .................................................. C07K 16/1027
See application file for complete search history.

(56) References Cited

U.S. PATENT DOCUMENTS

| 5,858,725 A | 1/1999 | Crowe | |
| 8,324,350 B2 * | 12/2012 | Hsieh | C07K 16/245 424/130.1 |
| 2012/0065379 A1 | 3/2012 | Igawa | |
| 2014/0072551 A1 | 3/2014 | McEver | |

FOREIGN PATENT DOCUMENTS

| WO | 2000053623 | 9/2000 |
| WO | 2010095031 | 8/2010 |
| WO | 2012135345 | 10/2012 |
| WO | 2012145572 | 10/2012 |
| WO | 2015089492 | 6/2015 |
| WO | 2016145385 | 9/2016 |
| WO | 2017040529 | 3/2017 |

OTHER PUBLICATIONS

Muthumani, K., et al., Aug. 2016, Rapid and long-term immunity elicited by DNA-encoded antibody prophylaxis and DNA vaccination against Chikungunya virus, J. Infect. Dis. 214:369-378.*
Sela-Culang, I., et al., Oct. 2013, The structural basis of antibody-antigen recognition, Front. Immunol. 4:Article 302, pp. 1-13.*
Anna Z. Wec et al: "Anti bodi es from a Human Survivor Define Sites of Vulnerability for Broad Protection against Ebolaviruses," Cell, vol. 169, No. 5, May 1, 2017 (May 1, 2017), pp. 878-890.e15.
Bishnu P DE et al: "Rapid/sustained anti-anthrax passive immunity mediated by co-administration of Ad/AAV", Molecular Therapy, vol. 16, No. 1, Jan. 1, 2008, pp. 203-209.
International Search Report and Written Opinion issued in App. No. PCT/US18/32023, mailing date Sep. 14, 2018, 13 pages.
Jonathan Audet et al: Molecular Characterization of the Monoclonal Antibodies Composing ZMAb: A Protective Cocktail Against Ebola Virus|, Scientific Reports, vol. 4, No. 1, Nov. 6, 2014 (Nov. 6, 2014).
Maria P. Limberis et al: "Adena-Associated Virus Serotype 9-Expressed ZMapp in Mice Confers Protection Against Systemic and Airway-Acquired Ebola Virus Infection", Journal of Infectious Diseases, vol. 214, No. 12, Sep. 28, 2016, pp. 1975-1979.
Z. A. Bornholdt et al: "Isolation of potent neutralizing antibodies from a survivor of the 2014 Ebola virus outbreak (Author Manuscript)", Science, vol. 351, No. 6277, Feb. 18, 2016 (Feb. 18, 2016), pp. 1078-1083.

* cited by examiner

*Primary Examiner* — Jeffrey S Parkin
(74) *Attorney, Agent, or Firm* — Riverside Law LLP

(57) ABSTRACT

Disclosed herein are compositions comprising structurally modified DNA encoded antibodies (DMAbs), methods of structurally modifying DMAbs, and methods of using structurally modified DMAbs.

5 Claims, 36 Drawing Sheets
Specification includes a Sequence Listing.

Figure 8A – 8D

| Antibodies | Group 1 | | | | Control |
|---|---|---|---|---|---|
| | EBOMAb-10 IgG (Control) | EBOMAb-10-2 ScFv-Fc | EBOMAb-10-3 IgG Partial Graft | EBOMAb-10-4 ScFv-Fc Partial Graft | KZ52-IgG |
| IC50 µg/ml | 0.062 | 0.026 | 0.019 | 0.029 | 0.45 |
| IC90 (µg/ml) | 0.2 | 0.41 | 0.053 | 0.073 | 1.83 |
| % Max Neutralization | 99 | 99 | 99 | 99 | 92 |
| IC90 (% of IgG Control) | n.a | 184% | 24% | 33% | |

| Antibodies | Group 2 | | | |
|---|---|---|---|---|
| | EBOMAb-14 IgG | EBOMAb-14-2 ScFv-Fc | EBOMAb-14-3 IgG Partial Graft | EBOMAb-14-4 IgG Partial Graft |
| IC50 µg/ml | 0.26 | 0.37 | 0.11 | 0.37 |
| IC90 (µg/ml) | 0.84 | 1.07 | 0.28 | 0.84 |
| % Max Neutralization | 99 | 91 | 99 | 92 |
| IC90 (% of IgG Control) | n.a | 127% | 33% | 65% |

SEQUENCE LISTING

<160> NUMBER OF SEQ ID NOS: 128

<210> SEQ ID NO 1
<211> LENGTH: 2193
<212> TYPE: DNA
<213> ORGANISM: Artificial Sequence
<220> FEATURE:
<223> OTHER INFORMATION: Chemically Synthesized, pGX9291, Ebola Z5D2
      modified

<400> SEQUENCE: 1

```
atggactgga cctggagaat cctgttcctg gtggcagcag caaccggaac acacgcagag      60
gtgcagctgc aggagagcgg accaggcctg gtgcggccca gccagtccct gtctctgacc     120
tgcacagtga ccggctacag catcacatcc gattatgcct ggaactggat caggcagttc     180
cctggctaca agatcgagtg gctgggctat atcacaaaca ccggcagcac cggctttaat     240
ccatctctga gagccggat ctccatcaca agagacacct ccaagaatca gttctttctg     300
cagctgatct ctgtgaccac agaggataca gcaacctacc actgcgccag aggcctggca     360
tattggggac agggcacact ggtgaccgtg agctccgcct ctaccaaggg accaagcgtg     420
tttccactgg caccttctag caagagcaca tccggcggca ccgccgccct gggatgtctg     480
gtgaaggact acttccctga gccagtgacc gtgtcttgga acagcggcgc cctgacatcc     540
ggagtgcaca cctttccagc cgtgctgcag tcctctggcc tgtacagcct gagctccgtg     600
gtgaccgtgc cctctagctc cctgggcaca cagacctata tctgcaacgt gaatcacaag     660
ccctctaata caaaggtgga caagaaggtg gagcctaaga gctgtgataa gacacacacc     720
tgccctccct gtccagcacc tgagctgctg ggcggcccaa gcgtgttcct gtttccaccc     780
aagcccaagg acaccctgat gatctccagg acacctgagg tgacctgcgt ggtggtggac     840
gtgtctcacg aggaccccga ggtgaagttc aactggtacg tggatggcgt ggaggtgcac     900
```

```
aatgccaaga ccaagccacg ggaggagcag tacaactcca cctatagagt ggtgtctgtg     960
ctgacagtgc tgcaccagga ctggctgaac ggcaaggagt ataagtgcaa ggtgtccaat    1020
aaggccctgc cagcccccat cgagaagacc atcagcaagg caaagggaca gccaagggag    1080
ccacaggtgt acacactgcc tccaagccgc gacgagctga ccaagaacca ggtgtccctg    1140
acatgtctgg tgaagggctt ctatccatct gatatcgccg tggagtggga gagcaatggc    1200 cagccccgaga caattacaa gaccacaccc cctgtgctgg actccgatgg ctcttcttt    1260 ctgtattcca agctgaccgt ggataagtct cgctggcagc agggcaacgt gttttcttgc    1320
agcgtgatgc acgaggccct gcacaatcac tacacccaga agtccctgtc tctgagccct    1380
ggcaagaggg gaaggaagcg gagatccggc tctggagcca caaacttctc cctgctgaag    1440
caggcaggcg acgtggagga gaatcctgga ccaatggtgc tgcagaccca ggtgtttatc    1500
agcctgctgc tgtggatctc cggcgcctac ggcgatgtgg tgctgacaca gaccccctcg    1560
acactgagcg tgaccatcgg ccagccagcc agcatctcct gtaactctag ccagtctctg    1620
ctggacagcg atggcaagac ctacctgaat tggctgctgc agaggcctgg ccagtcccca    1680
aagcgcctga tctatctggt gtccaagctg actctggcg tgacagatga gttcaccggc    1740
tctggcagcg gcacagactt taccctgaag atcagccgcg tggaggccga ggatctgggc    1800
atctactatt gctggcaggg cacacactct cccttcacct ttggcagcgg cacaaagctg    1860
gagatcaaga ccgtggccgc ccctagcgtg ttcatctttc caccctccga cgagcagctg    1920
aagagcggca cagcctccgt ggtgtgcctg ctgaacaatt tctaccccg ggaggccaag    1980 gtgcagtgga aggtggataa cgccctgcag agcggcaatt cccaggagtc tgtgaccgag    2040
caggacagca aggattccac atattccctg tctaacacac tgaccctgtc caaggccgac    2100
tacgagaagc acaaggtgta tgcatgcgag gtgacccacc agggcctgtc ctctcctgtg    2160
acaaagagct ttaatcgggg cgagtgttga taa    2193
```

<210> SEQ ID NO 2
<211> LENGTH: 729
<212> TYPE: PRT
<213> ORGANISM: Artificial Sequence
<220> FEATURE:
<223> OTHER INFORMATION: Chemically Synthesized, pGX9291, Ebola Z5D2
      modified

<400> SEQUENCE: 2

Met Asp Trp Thr Trp Arg Ile Leu Phe Leu Val Ala Ala Ala Thr Gly
1               5                   10                  15

Thr His Ala Glu Val Gln Leu Gln Glu Ser Gly Pro Gly Leu Val Arg
                20                  25                  30

Pro Ser Gln Ser Leu Ser Leu Thr Cys Thr Val Thr Gly Tyr Ser Ile
            35                  40                  45

Thr Ser Asp Tyr Ala Trp Asn Trp Ile Arg Gln Phe Pro Gly Tyr Lys
        50                  55                  60

Ile Glu Trp Leu Gly Tyr Ile Thr Asn Thr Gly Ser Thr Gly Phe Asn
65                  70                  75                  80

Pro Ser Leu Lys Ser Arg Ile Ser Ile Thr Arg Asp Thr Ser Lys Asn
                85                  90                  95

Gln Phe Phe Leu Gln Leu Ile Ser Val Thr Thr Glu Asp Thr Ala Thr
            100                 105                 110

Tyr His Cys Ala Arg Gly Leu Ala Tyr Trp Gly Gln Gly Thr Leu Val
        115                 120                 125

```
Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Arg Gly
    450                 455                 460

Arg Lys Arg Arg Ser Gly Ser Gly Ala Thr Asn Phe Ser Leu Leu Lys
465                 470                 475                 480

Gln Ala Gly Asp Val Glu Glu Asn Pro Gly Pro Met Val Leu Gln Thr
                485                 490                 495

Gln Val Phe Ile Ser Leu Leu Leu Trp Ile Ser Gly Ala Tyr Gly Asp
            500                 505                 510

Val Val Leu Thr Gln Thr Pro Leu Thr Leu Ser Val Thr Ile Gly Gln
        515                 520                 525

Pro Ala Ser Ile Ser Cys Asn Ser Ser Gln Ser Leu Leu Asp Ser Asp
    530                 535                 540
```

```
Gly Lys Thr Tyr Leu Asn Trp Leu Leu Gln Arg Pro Gly Gln Ser Pro
545                 550                 555                 560

Lys Arg Leu Ile Tyr Leu Val Ser Lys Leu Asp Ser Gly Val Thr Asp
                565                 570                 575

Glu Phe Thr Gly Ser Gly Ser Gly Thr Asp Phe Thr Leu Lys Ile Ser
            580                 585                 590

Arg Val Glu Ala Glu Asp Leu Gly Ile Tyr Tyr Cys Trp Gln Gly Thr
        595                 600                 605

His Ser Pro Phe Thr Phe Gly Ser Gly Thr Lys Leu Glu Ile Lys Thr
    610                 615                 620

Val Ala Ala Pro Ser Val Phe Ile Phe Pro Pro Ser Asp Glu Gln Leu
625                 630                 635                 640

Lys Ser Gly Thr Ala Ser Val Val Cys Leu Leu Asn Asn Phe Tyr Pro
                645                 650                 655

Arg Glu Ala Lys Val Gln Trp Lys Val Asp Asn Ala Leu Gln Ser Gly
            660                 665                 670

Asn Ser Gln Glu Ser Val Thr Glu Gln Asp Ser Lys Asp Ser Thr Tyr
        675                 680                 685

Ser Leu Ser Asn Thr Leu Thr Leu Ser Lys Ala Asp Tyr Glu Lys His
    690                 695                 700

Lys Val Tyr Ala Cys Glu Val Thr His Gln Gly Leu Ser Ser Pro Val
705                 710                 715                 720

Thr Lys Ser Phe Asn Arg Gly Glu Cys
                725

<210> SEQ ID NO 3
<211> LENGTH: 2196
<212> TYPE: DNA
<213> ORGANISM: Artificial Sequence
<220> FEATURE:
<223> OTHER INFORMATION: Chemically Synthesized, pGX9292, Ebola Z5D2
      partial graft

<400> SEQUENCE: 3
atggactgga cctggagaat cctgttcctg gtggcagcag caaccggaac acacgcagag    60
gtgcagctgc aggagtccgg accaggcctg gtgcgcccta gccagtccct gtctctgacc   120
tgcacagtga ccggctacag catcacatcc gattatgcct ggaactggat cagacagttc   180
cctggcaata agctggagtg gctgggctac atcacaaaca ccggcagcac cggctttaat   240
ccatctctga gagccggat ctccatcaca agagacacct ccaagaacca gttctttctg   300
cagctgatct ctgtgaccac agaggataca gcaacctacc actgcgccag aggcctggca   360
tattggggac agggcacact ggtgaccgtg agctccgcct ctaccaaggg accaagcgtg   420
tttccactgg caccttctag caagagcaca tccggcggca ccgccgccct gggatgtctg   480
gtgaaggact acttccctga gccagtgacc gtgtcttgga cagcggcgc cctgacatcc   540 ggagtgcaca ccttttccagc cgtgctgcag tcctctggcc tgtacagcct gagctccgtg   600
gtgaccgtgc cttctagctc cctgggcaca cagacctata tctgcaacgt gaatcacaag   660
ccctctaata caaaggtgga caagaaggtg gagcctaaga ctgtgataa cacacaccc   720 tgccctccct gtccagcacc tgagctgctg gcggcccttc cgtgttcct gtttccaccc   780 aagccaaagg acaccctgat gatctccagg acacctgagg tgacctgcgt ggtggtggac   840
gtgtctcacg aggaccccga ggtgaagttc aactggtacg tggatggcgt ggaggtgcac   900
aatgccaaga ccaagccacg ggaggagcag tacaattcca cctatagagt ggtgtctgtg   960
```

```
ctgacagtgc tgcaccagga ttggctgaac ggcaaggagt ataagtgcaa ggtgagcaat   1020
aaggccctgc cagcccccat cgagaagacc atctccaagg caaagggaca gccaagggag   1080
ccacaggtgt acacactgcc tccaagccgc gacgagctga ctaagaacca ggtgtccctg   1140
acatgtctgg tgaagggctt ctatccatct gatatcgccg tggagtggga gagcaatggc   1200
cagcccgaga caattacaa gaccacaccc cctgtgctgg actccgatgg ctctttcttt   1260
ctgtattcca agctgaccgt ggacaagtct cgctggcagc agggcaacgt gttttcttgc   1320
agcgtgatgc acgaggccct gcacaatcac tacacccaga agtccctgtc tctgagccct   1380
ggcaagaggg gaaggaagcg gagatccggc tctggagcca caaacttcag cctgctgaag   1440
caggccggcg atgtggagga gaatcctggc ccaatggtgc tgcagaccca ggtgtttatc   1500
agcctgctgc tgtggatctc cggcgcctat ggcgagacaa ccctgacaca gtctccaggc   1560
accctgagcc tgtccccagg agagagggcc accctgagct gtaagtctag ccagtctctg   1620
ctggacagcg atggcaagac atacctgaac tggctgctgc agaggcctgg acagtcccca   1680
aagcgcctga tctatctggt gtccaagctg actctggcg tgacagatcg gttcaccggc   1740
tctggcagcg gcacagactt taccctgaag atcagcagag tggaggccga ggatctgggc   1800
gtgtactatt gctggcaggg cacacactct ccattcacct ttggcagcgg cacaaagctg   1860
gagatcaaga gaaccgtggc cgcccccagc gtgttcatct ttccaccctc cgacgagcag   1920
ctgaagagcg gcacagcctc cgtggtgtgc ctgctgaaca atttctaccc cagggaggcc   1980
aaggtgcagt ggaaggtgga taacgccctg cagagcggca attcccagga gtctgtgacc   2040
gagcaggaca gcaaggattc cacatattcc ctgtctaaca cactgaccct gtccaaggcc   2100
gactacgaga agcacaaggt gtatgcatgc gaggtgaccc accagggcct gtcctctcct   2160
gtgacaaaga gctttaatcg gggcgagtgt tgataa                              2196

<210> SEQ ID NO 4
<211> LENGTH: 730
<212> TYPE: PRT
<213> ORGANISM: Artificial Sequence
<220> FEATURE:
<223> OTHER INFORMATION: Chemically Synthesized, pGX9292, Ebola Z5D2
      partial graft

<400> SEQUENCE: 4

Met Asp Trp Thr Trp Arg Ile Leu Phe Leu Val Ala Ala Ala Thr Gly
1               5                   10                  15

Thr His Ala Glu Val Gln Leu Gln Glu Ser Gly Pro Gly Leu Val Arg
            20                  25                  30

Pro Ser Gln Ser Leu Ser Leu Thr Cys Thr Val Thr Gly Tyr Ser Ile
        35                  40                  45

Thr Ser Asp Tyr Ala Trp Asn Trp Ile Arg Gln Phe Pro Gly Asn Lys
    50                  55                  60

Leu Glu Trp Leu Gly Tyr Ile Thr Asn Thr Gly Ser Thr Gly Phe Asn
65                  70                  75                  80

Pro Ser Leu Lys Ser Arg Ile Ser Ile Thr Arg Asp Thr Ser Lys Asn
                85                  90                  95

Gln Phe Phe Leu Gln Leu Ile Ser Val Thr Thr Glu Asp Thr Ala Thr
            100                 105                 110

Tyr His Cys Ala Arg Gly Leu Ala Tyr Trp Gly Gln Gly Thr Leu Val
        115                 120                 125

Thr Val Ser Ser Ala Ser Thr Lys Gly Pro Ser Val Phe Pro Leu Ala
    130                 135                 140
```

```
Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
            210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys Arg Gly
            450                 455                 460

Arg Lys Arg Arg Ser Gly Ser Gly Ala Thr Asn Phe Ser Leu Leu Lys
465                 470                 475                 480

Gln Ala Gly Asp Val Glu Glu Asn Pro Gly Pro Met Val Leu Gln Thr
            485                 490                 495

Gln Val Phe Ile Ser Leu Leu Leu Trp Ile Ser Gly Ala Tyr Gly Glu
            500                 505                 510

Thr Thr Leu Thr Gln Ser Pro Gly Thr Leu Ser Leu Ser Pro Gly Glu
            515                 520                 525

Arg Ala Thr Leu Ser Cys Lys Ser Ser Gln Ser Leu Leu Asp Ser Asp
            530                 535                 540

Gly Lys Thr Tyr Leu Asn Trp Leu Leu Gln Arg Pro Gly Gln Ser Pro
545                 550                 555                 560
```

```
Lys Arg Leu Ile Tyr Leu Val Ser Lys Leu Asp Ser Gly Val Thr Asp
            565                 570                 575

Arg Phe Thr Gly Ser Gly Ser Gly Thr Asp Phe Thr Leu Lys Ile Ser
        580                 585                 590

Arg Val Glu Ala Glu Asp Leu Gly Val Tyr Tyr Cys Trp Gln Gly Thr
        595                 600                 605

His Ser Pro Phe Thr Phe Gly Ser Gly Thr Lys Leu Glu Ile Lys Arg
        610                 615                 620

Thr Val Ala Ala Pro Ser Val Phe Ile Phe Pro Ser Asp Glu Gln
625                 630                 635                 640

Leu Lys Ser Gly Thr Ala Ser Val Val Cys Leu Leu Asn Asn Phe Tyr
        645                 650                 655

Pro Arg Glu Ala Lys Val Gln Trp Lys Val Asp Asn Ala Leu Gln Ser
        660                 665                 670

Gly Asn Ser Gln Glu Ser Val Thr Glu Gln Asp Ser Lys Asp Ser Thr
        675                 680                 685

Tyr Ser Leu Ser Asn Thr Leu Thr Leu Ser Lys Ala Asp Tyr Glu Lys
        690                 695                 700

His Lys Val Tyr Ala Cys Glu Val Thr His Gln Gly Leu Ser Ser Pro
705                 710                 715                 720

Val Thr Lys Ser Phe Asn Arg Gly Glu Cys
        725                 730

<210> SEQ ID NO 5
<211> LENGTH: 2196
<212> TYPE: DNA
<213> ORGANISM: Artificial Sequence
<220> FEATURE:
<223> OTHER INFORMATION: Chemically Synthesized, pGX9293, Ebola Z5D2
      graft on MERSYTE_1

<400> SEQUENCE: 5
atggactgga cctggagaat cctgttcctg gtggcagcag caaccggaac acacgcacag     60
gtgcagctgg tgcagtctgg agccgaggtg aagaagccag gcagctccgt gaaggtgtcc    120
tgcaaggcct ccggctactc tatcacaagc gattatgcca tcagctgggt gcggcaggca    180
ccaggacagg gcctggagtg gatgggcggc atcaccaaca aggctccac caattacgcc    240 cagaagttcc agggcagagt gaccatcaca gccgacacct ccacatctac cgcctatatg    300
gagctgtcta gcctgcggag cgaggatacc gccgtgtact attgcgccag aggcctggca    360
tactggggac agggcaccac agtgaccgtg tcctctgcct ccacaaaggg accaagcgtg    420
ttcccactgg cacctagctc caagagcaca tccggcggca ccgccgccct gggatgtctg    480
gtgaaggact atttccctga gccagtgacc gtgtcctgga actctggcgc cctgacaagc    540
ggagtgcaca cctttccagc cgtgctgcag tctagcggcc tgtactccct gtcctctgtg    600
gtgaccgtgc ctagctcctc tctgggcaca cagacctata tctgcaacgt gaatcacaag    660
ccttccaata caaaggtgga caagaaggtg gagcccaaag tcttgtgataa gacacacacc    720 tgccctccct gtccagcacc tgagctgctg ggcggcccaa gcgtgttcct gtttccaccc    780
aagcccaagg acacactgta catcacccgg gagccagagg tgacctgcgt ggtggtggac    840
gtgtcccacg aggaccccga ggtgaagttc aactggtacg tggatggcgt ggaggtgcac    900
aatgccaaga ccaagcctcg ggaggagcag tacaactcta cctatagagt ggtgagcgtg    960
ctgacagtgc tgcaccagga ctggctgaac ggcaaggagt acaagtgcaa ggtgagcaat   1020
aaggccctgc cagcccccat cgagaagacc atctccaagg caaagggaca gccaagggag   1080
```

```
ccacaggtgt acacactgcc tccaagccgc gacgagctga ccaagaacca ggtgtccctg    1140
acatgtctgg tgaagggctt ctatccctcc gatatcgccg tggagtggga gtctaatggc    1200
cagcctgaga caattacaa gaccacaccc cctgtgctgg acagcgatgg ctccttcttt     1260
ctgtatagca agctgaccgt ggacaagtcc cggtggcagc agggcaacgt gttttcttgc    1320
agcgtgatgc acgaggccct gcacaatcac tacacccaga agtccctgtc tctgagccca    1380
ggcaagaggg gaaggaagcg gagatccggc tctggagcca caaacttcag cctgctgaag    1440
caggccggcg atgtggagga gaatcctggc ccaatggtgc tgcagaccca ggtgtttatc    1500
tccctgctgc tgtggatctc tggcgcctac ggcgagacaa ccctgacaca gtccccaggc    1560
accctgagcc tgtcccctgg agagagggcc accctgtctt gtagagcctc tcagagcctg    1620
ctggacagcg atggcaagac atacatcgcc tggtatcagc agaagcctgg ccaggcccca    1680
agactgctga tgttcctggt gagcacaagg gccaccggca tccctgaccg cttctccggc    1740
tctggcagcg gcacagactt caccctgaac atcagctccc tggagcctga ggactttgcc    1800
gtgtactatt gctggcaggg cacacacagc ccattcacct ttggccaggg cacaaagctg    1860
gagatcaaga ggaccgtggc cgcccctagc gtgttcatct tccacccag cgacgagcag    1920 ctgaagtctg gcacagccag cgtggtgtgc ctgctgaaca atttctaccc acgcgaggcc    1980
aaggtgcagt ggaaggtgga taacgccctg cagtctggca atagccagga gtccgtgacc    2040
gagcaggact ctaaggatag cacatattcc ctgtctagca cactgaccct gagcaaggcc    2100
gattacgaga agcacaaggt gtatgcatgc gaggtgaccc accagggcct gaggagcccc    2160
gtgacaaagt cctttaatcg cggcgagtgt tgataa                              2196
```

<210> SEQ ID NO 6
<211> LENGTH: 730
<212> TYPE: PRT
<213> ORGANISM: Artificial Sequence
<220> FEATURE:
<223> OTHER INFORMATION: Chemically Synthesized, pGX9293, Ebola Z5D2
      graft on MERSYTE_1

<400> SEQUENCE: 6

Met Asp Trp Thr Trp Arg Ile Leu Phe Leu Val Ala Ala Thr Gly
1               5                   10                  15

Thr His Ala Gln Val Gln Leu Val Gln Ser Gly Ala Glu Val Lys Lys
            20                  25                  30

Pro Gly Ser Ser Val Lys Val Ser Cys Lys Ala Ser Gly Tyr Ser Ile
        35                  40                  45

Thr Ser Asp Tyr Ala Ile Ser Trp Val Arg Gln Ala Pro Gly Gln Gly
    50                  55                  60

Leu Glu Trp Met Gly Gly Ile Thr Asn Thr Gly Ser Thr Asn Tyr Ala
65                  70                  75                  80

Gln Lys Phe Gln Gly Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Leu Ala Tyr Trp Gly Gln Gly Thr Thr Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

```
Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
            210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Tyr Ile Thr Arg Glu Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys Arg Gly
            450                 455                 460

Arg Lys Arg Arg Ser Gly Ser Gly Ala Thr Asn Phe Ser Leu Leu Lys
465                 470                 475                 480

Gln Ala Gly Asp Val Glu Glu Asn Pro Gly Pro Met Val Leu Gln Thr
            485                 490                 495

Gln Val Phe Ile Ser Leu Leu Leu Trp Ile Ser Gly Ala Tyr Gly Glu
            500                 505                 510

Thr Thr Leu Thr Gln Ser Pro Gly Thr Leu Ser Leu Ser Pro Gly Glu
            515                 520                 525

Arg Ala Thr Leu Ser Cys Arg Ala Ser Gln Ser Leu Leu Asp Ser Asp
            530                 535                 540

Gly Lys Thr Tyr Ile Ala Trp Tyr Gln Gln Lys Pro Gly Gln Ala Pro
545                 550                 555                 560

Arg Leu Leu Met Phe Leu Val Ser Thr Arg Ala Thr Gly Ile Pro Asp
            565                 570                 575
```

-continued

```
Arg Phe Ser Gly Ser Gly Ser Gly Thr Asp Phe Thr Leu Asn Ile Ser
            580                 585                 590
Ser Leu Glu Pro Glu Asp Phe Ala Val Tyr Tyr Cys Trp Gln Gly Thr
        595                 600                 605
His Ser Pro Phe Thr Phe Gly Gln Gly Thr Lys Leu Glu Ile Lys Arg
    610                 615                 620
Thr Val Ala Ala Pro Ser Val Phe Ile Phe Pro Pro Ser Asp Glu Gln
625                 630                 635                 640
Leu Lys Ser Gly Thr Ala Ser Val Val Cys Leu Leu Asn Asn Phe Tyr
                645                 650                 655
Pro Arg Glu Ala Lys Val Gln Trp Lys Val Asp Asn Ala Leu Gln Ser
            660                 665                 670
Gly Asn Ser Gln Glu Ser Val Thr Glu Gln Asp Ser Lys Asp Ser Thr
        675                 680                 685
Tyr Ser Leu Ser Ser Thr Leu Thr Leu Ser Lys Ala Asp Tyr Glu Lys
    690                 695                 700
His Lys Val Tyr Ala Cys Glu Val Thr His Gln Gly Leu Arg Ser Pro
705                 710                 715                 720
Val Thr Lys Ser Phe Asn Arg Gly Glu Cys
                725                 730
```

<210> SEQ ID NO 7
<211> LENGTH: 2196
<212> TYPE: DNA
<213> ORGANISM: Artificial Sequence
<220> FEATURE:
<223> OTHER INFORMATION: Chemically Synthesized, pGX9294, Ebola Z5D2
      graft on MERSYTE_2

<400> SEQUENCE: 7

| | |
|---|---|
| atggactgga cctggagaat cctgttcctg gtggcagcag caaccggaac acacgcacag | 60 |
| gtgcagctgg tgcagtctgg agccgaggtg aagaagccag gcagctccgt gaaggtgtcc | 120 |
| tgcaaggcct ccggctactc tatcacaagc gattatgcct ggagctgggt gcggcaggca | 180 |
| ccaggacagg gcctggagtg gatgggcggc atcaccaaca caggctccac caattacgcc | 240 |
| cagaagttcc agggcagagt gaccatcaca gccgacacct ccacatctac cgcctatatg | 300 |
| gagctgtcta gcctgcggag cgaggatacc gccgtgtact attgcgccag aggcctggca | 360 |
| tactggggac agggcaccac agtgaccgtg tcctctgcct ccacaaaggg accaagcgtg | 420 |
| ttcccactgg cacctagctc aagagcaca tccggcggca ccgccgccct gggatgtctg | 480 |
| gtgaaggact atttccctga ccagtgacc gtgtcctgga actctggcgc cctgacaagc | 540 |
| ggagtgcaca cctttccagc cgtgctgcag tctagcggcc tgtactccct gtcctctgtg | 600 |
| gtgaccgtgc ctagctcctc tctgggcaca cagacctata tctgcaacgt gaatcacaag | 660 |
| ccttccaata caaggtgga caagaaggtg agccaaagt cttgtgataa gacacacacc | 720 |
| tgccctccct gtccagcacc tgagctgctg gcggcccaa gcgtgttcct gtttccaccc | 780 |
| aagcccaagg acacactgta catcacccgg gagccagagg tgacctgcgt ggtggtggac | 840 |
| gtgtcccacg aggaccccga ggtgaagttc aactggtacg tggatggcgt ggaggtgcac | 900 |
| aatgccaaga ccaagcctcg ggaggagcag tacaactcta cctatagagt ggtgagcgtg | 960 |
| ctgacagtgc tgcaccagga ctggctgaac ggcaaggagt acaagtgcaa ggtgagcaat | 1020 |
| aaggccctgc cagcccccat cgagaagacc atctccaagg caaagggaca gccaagggag | 1080 |
| ccacaggtgt acacactgcc tccaagccgc gacgagctga ccaagaacca ggtgtccctg | 1140 |

```
acatgtctgg tgaagggctt ctatccctcc gatatcgccg tggagtggga gtctaatggc    1200
cagcctgaga acaattacaa gaccacaccc cctgtgctgg acagcgatgg ctccttcttt    1260
ctgtatagca agctgaccgt ggacaagtcc cggtggcagc agggcaacgt gttttcttgc    1320
agcgtgatgc acgaggccct gcacaatcac tacacccaga agtccctgtc tctgagccca    1380
ggcaagaggg gaaggaagcg gagatccggc tctggagcca caaacttcag cctgctgaag    1440
caggccggcg atgtggagga gaatcctggc ccaatggtgc tgcagaccca ggtgtttatc    1500
tccctgctgc tgtggatctc tggcgcctac ggcgagacaa ccctgacaca gtccccaggc    1560
accctgagcc tgtcccctgg agagagggcc accctgtctt gtagagcctc tcagagcctg    1620
ctggacagcg atggcaagac atacatcgcc tggtatcagc agaagcctgg ccaggcccca    1680
agactgctga tgttcctggt gagcacaagg gccaccggca tccctgaccg cttctccggc    1740
tctggcagcg gcacagactt caccctgaac atcagctccc tggagcctga ggactttgcc    1800
gtgtactatt gctggcaggg cacacacagc ccattcacct ttggccaggg cacaaagctg    1860
gagatcaaga ggaccgtggc cgcccctagc gtgttcatct tccacccag cgacgagcag    1920 ctgaagtctg gcacagccag cgtggtgtgc ctgctgaaca atttctaccc acgcgaggcc    1980
aaggtgcagt ggaaggtgga taacgccctg cagtctggca atagccagga gtccgtgacc    2040
gagcaggact ctaaggatag cacatattcc ctgtctagca cactgaccct gagcaaggcc    2100
gattacgaga agcacaaggt gtatgcatgc gaggtgaccc accagggcct gaggagcccc    2160
gtgacaaagt cctttaatcg cggcgagtgt tgataa                              2196
```

<210> SEQ ID NO 8
<211> LENGTH: 730
<212> TYPE: PRT
<213> ORGANISM: Artificial Sequence
<220> FEATURE:
<223> OTHER INFORMATION: Chemically Synthesized, pGX9294, Ebola Z5D2
      graft on MERSYTE_2

<400> SEQUENCE: 8

Met Asp Trp Thr Trp Arg Ile Leu Phe Leu Val Ala Ala Thr Gly
1               5                   10                  15

Thr His Ala Gln Val Gln Leu Val Gln Ser Gly Ala Glu Val Lys Lys
            20                  25                  30

Pro Gly Ser Ser Val Lys Val Ser Cys Lys Ala Ser Gly Tyr Ser Ile
        35                  40                  45

Thr Ser Asp Tyr Ala Trp Ser Trp Val Arg Gln Ala Pro Gly Gln Gly
    50                  55                  60

Leu Glu Trp Met Gly Gly Ile Thr Asn Thr Gly Ser Thr Asn Tyr Ala
65                  70                  75                  80

Gln Lys Phe Gln Gly Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Leu Ala Tyr Trp Gly Gln Gly Thr Thr Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

```
Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Tyr Ile Thr Arg Glu Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys Arg Gly
    450                 455                 460

Arg Lys Arg Arg Ser Gly Ser Gly Ala Thr Asn Phe Ser Leu Leu Lys
465                 470                 475                 480

Gln Ala Gly Asp Val Glu Glu Asn Pro Gly Pro Met Val Leu Gln Thr
                485                 490                 495

Gln Val Phe Ile Ser Leu Leu Leu Trp Ile Ser Gly Ala Tyr Gly Glu
            500                 505                 510

Thr Thr Leu Thr Gln Ser Pro Gly Thr Leu Ser Leu Ser Pro Gly Glu
            515                 520                 525

Arg Ala Thr Leu Ser Cys Arg Ala Ser Gln Ser Leu Leu Asp Ser Asp
    530                 535                 540

Gly Lys Thr Tyr Ile Ala Trp Tyr Gln Gln Lys Pro Gly Gln Ala Pro
545                 550                 555                 560

Arg Leu Leu Met Phe Leu Val Ser Thr Arg Ala Thr Gly Ile Pro Asp
                565                 570                 575

Arg Phe Ser Gly Ser Gly Ser Gly Thr Asp Phe Thr Leu Asn Ile Ser
            580                 585                 590
```

```
Ser Leu Glu Pro Glu Asp Phe Ala Val Tyr Tyr Cys Trp Gln Gly Thr
        595                 600                 605

His Ser Pro Phe Thr Phe Gly Gln Gly Thr Lys Leu Glu Ile Lys Arg
    610                 615                 620

Thr Val Ala Ala Pro Ser Val Phe Ile Phe Pro Pro Ser Asp Glu Gln
625                 630                 635                 640

Leu Lys Ser Gly Thr Ala Ser Val Val Cys Leu Leu Asn Asn Phe Tyr
                645                 650                 655

Pro Arg Glu Ala Lys Val Gln Trp Lys Val Asp Asn Ala Leu Gln Ser
            660                 665                 670

Gly Asn Ser Gln Glu Ser Val Thr Glu Gln Asp Ser Lys Asp Ser Thr
        675                 680                 685

Tyr Ser Leu Ser Ser Thr Leu Thr Leu Ser Lys Ala Asp Tyr Glu Lys
    690                 695                 700

His Lys Val Tyr Ala Cys Glu Val Thr His Gln Gly Leu Arg Ser Pro
705                 710                 715                 720

Val Thr Lys Ser Phe Asn Arg Gly Glu Cys
                725                 730

<210> SEQ ID NO 9
<211> LENGTH: 2196
<212> TYPE: DNA
<213> ORGANISM: Artificial Sequence
<220> FEATURE:
<223> OTHER INFORMATION: Chemically Synthesized, pGX9295, Ebola Z5D2
      graft on V2L2

<400> SEQUENCE: 9
atggactgga cctggagaat cctgttcctg gtggcagcag caaccggaac acacgcagag      60
gtgcagctgc tggagagcgg cggcggcctg gtgcagcccg gcggctctct gaggctgagc     120
tgcgccgcct ctggctacag catcacctcc gattatgcaa tgaactgggt gcgccaggca     180
cctggcaagg gcctggagtg ggtgtctgcc atcaccaata caggcagcac cggctacaca     240
gacgatgtga agggccggtt cacaatctcc agagacaact ctaagaatac cctgtatctg     300
cagatgaact ccctgagggc cgaggatacc gccgtgtact attgcgcccg cggcctggca     360
tactggggac agggcaccac agtgacagtg agctccgcct ctaccaaggg accaagcgtg     420
tttccactgg cacctcctag caagtctacc agcggcggca cagccgccct gggatgtctg     480
gtgaaggact atttccctga gccagtgacc gtgtcttgga acagcggcgc cctgaccagc     540
ggagtgcaca catttcctgc cgtgctgcag tcctctggcc tgtactccct gagctccgtg     600
gtgaccgtgc catctagctc cctgggcacc cagacatata tctgcaacgt gaatcacaag     660
ccaagcaata caaaggtgga caagaaggtg gagcccaagt cctgtgataa gacccacaca     720
tgccctccct gtccagcacc tgagctgctg ggcggcccaa gcgtgttcct gttcccaccc     780
aagcctaagg acacccctga tctctctcgg accccgagg tgacatgcgt ggtggtggac     840
gtgagccacg aggaccccga ggtgaagttt aactggtacg tggatggcgt ggaggtgcac     900
aatgccaaga ccaagcccg ggaggagcag tacaactcca catatagagt ggtgtctgtg     960
ctgaccgtgc tgcaccagga ctggctgaac ggcaaggagt ataagtgcaa ggtgtccaat    1020
aaggccctgc cagcccccat cgagaagaca atctctaagg caaagggaca gccacgggag    1080
ccacaggtgt acaccctgcc tccatccaga gacgagctga caaagaacca ggtgtctctg    1140
acctgtctgg tgaagggctt ctatccttct gatatcgccg tggagtggga gagcaatggc    1200
cagccagaga acaattacaa gaccacaccc cctgtgctgg actccgatgg ctctttcttt    1260
```

```
ctgtattcca agctgaccgt ggataagtct aggtggcagc agggcaacgt gttttcctgc   1320
tctgtgatgc acgaggccct gcacaatcac tacacccaga gagcctgtc cctgtctcct    1380 ggcaagaggg gaaggaagcg gagaagcggc tccggagcca caaacttcag cctgctgaag   1440
caggcaggcg acgtggagga gaatcctgga ccaatggtgc tgcagaccca ggtgtttatc   1500
agcctgctgc tgtggatctc cggagcatac ggagccatcc agatgacaca gagcccttct   1560
agcctgtctg ccagcgtggg cgataggtg accatcacat gtcgcgcctc ccagtctctg   1620
ctggactccg atggcaagac ctacctgggc tggtatcagc agaagcctgg caaggcccca   1680
aagctgctga tctacctggt gagcacactg cagtccggag tgccatctcg cttcagcggc   1740
tccggctctg gaaccgactt taccctgaca atctcctctc tgcagccaga ggatttcgcc   1800
acatactatt gctggcaggg cacccactcc cccttcacat ttggccaggg caccaaggtg   1860
gagatcaaga ggaccgtggc agcaccaagc gtgttcatct ttccaccctc cgacgagcag   1920
ctgaagagcg gcacagcctc cgtggtgtgc ctgctgaaca acttctaccc cagagaggcc   1980
aaggtgcagt ggaaggtgga taacgccctg cagagcggca attcccagga gtctgtgaca   2040
gagcaggaca gcaaggattc cacctatagc ctgtccaaca ccctgacact gagcaaggcc   2100
gactacgaga agcacaaggt gtatgcctgc gaggtgacac accagggcct gagctccccc   2160
gtgaccaagt ccttcaatag aggcgagtgt tgataa                             2196

<210> SEQ ID NO 10
<211> LENGTH: 730
<212> TYPE: PRT
<213> ORGANISM: Artificial Sequence
<220> FEATURE:
<223> OTHER INFORMATION: Chemically Synthesized, pGX9295, Ebola Z5D2
      graft on V2L2

<400> SEQUENCE: 10

Met Asp Trp Thr Trp Arg Ile Leu Phe Leu Val Ala Ala Ala Thr Gly
1               5                   10                  15

Thr His Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Tyr Ser Ile
        35                  40                  45

Thr Ser Asp Tyr Ala Met Asn Trp Val Arg Gln Ala Pro Gly Lys Gly
    50                  55                  60

Leu Glu Trp Val Ser Ala Ile Thr Asn Thr Gly Ser Thr Gly Tyr Thr
65                  70                  75                  80

Asp Asp Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Leu Ala Tyr Trp Gly Gln Gly Thr Thr Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190
```

```
Gly Leu Tyr Ser Leu Ser Ser Val Val Thr Val Pro Ser Ser Leu
            195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys Arg Gly
    450                 455                 460

Arg Lys Arg Arg Ser Gly Ser Gly Ala Thr Asn Phe Ser Leu Leu Lys
465                 470                 475                 480

Gln Ala Gly Asp Val Glu Glu Asn Pro Gly Pro Met Val Leu Gln Thr
                485                 490                 495

Gln Val Phe Ile Ser Leu Leu Leu Trp Ile Ser Gly Ala Tyr Gly Ala
            500                 505                 510

Ile Gln Met Thr Gln Ser Pro Ser Ser Leu Ser Ala Ser Val Gly Asp
            515                 520                 525

Arg Val Thr Ile Thr Cys Arg Ala Ser Gln Ser Leu Leu Asp Ser Asp
    530                 535                 540

Gly Lys Thr Tyr Leu Gly Trp Tyr Gln Gln Lys Pro Gly Lys Ala Pro
545                 550                 555                 560

Lys Leu Leu Ile Tyr Leu Val Ser Thr Leu Gln Ser Gly Val Pro Ser
                565                 570                 575

Arg Phe Ser Gly Ser Gly Ser Gly Thr Asp Phe Thr Leu Thr Ile Ser
            580                 585                 590

Ser Leu Gln Pro Glu Asp Phe Ala Thr Tyr Tyr Cys Trp Gln Gly Thr
            595                 600                 605
```

His Ser Pro Phe Thr Phe Gly Gln Gly Thr Lys Val Glu Ile Lys Arg
        610                 615                 620

Thr Val Ala Ala Pro Ser Val Phe Ile Phe Pro Pro Ser Asp Glu Gln
625                 630                 635                 640

Leu Lys Ser Gly Thr Ala Ser Val Val Cys Leu Leu Asn Asn Phe Tyr
                645                 650                 655

Pro Arg Glu Ala Lys Val Gln Trp Lys Val Asp Asn Ala Leu Gln Ser
                660                 665                 670

Gly Asn Ser Gln Glu Ser Val Thr Glu Gln Asp Ser Lys Asp Ser Thr
            675                 680                 685

Tyr Ser Leu Ser Asn Thr Leu Thr Leu Ser Lys Ala Asp Tyr Glu Lys
    690                 695                 700

His Lys Val Tyr Ala Cys Glu Val Thr His Gln Gly Leu Ser Ser Pro
705                 710                 715                 720

Val Thr Lys Ser Phe Asn Arg Gly Glu Cys
                725                 730

<210> SEQ ID NO 11
<211> LENGTH: 2208
<212> TYPE: DNA
<213> ORGANISM: Artificial Sequence
<220> FEATURE:
<223> OTHER INFORMATION: Chemically Synthesized, pGX9296, Ebola ZBDBV223
      modified

<400> SEQUENCE: 11
atggattgga cctggagaat cctgttcctg gtggcagcag caacaggaac ccacgcacag      60
gtgcagctgc agcagtgggg cgccggcctg ctgaagccaa gcgagacact gtccctgaca     120
tgcgccgtgt acggcggcag ctttaccaca acctattgga attggatcag gcagccccct     180
ggcaagggcc tggagtggat cggcgaggtg aactactctg caacgccaa ttataaccca     240 agcctgcagg aagggtggc aatctctgtg gacacaagca agaatcagtt ctctctgcag     300
ctgaacagcg tgaccgccgc cgatacagcc atctactatt gcaccagccg gatcagaagc     360
cacatcgcct actcctggaa gggctgggtg tggggcaagg gcacaaccgt gaccgtgagc     420
tccgcctcca caagggacc aagcgtgttc ccactggcac cctctagcaa gagcacctcc     480
ggcggcacag ccgccctggg ctgtctggtg aaggattatt tccccgagcc tgtgaccgtg     540
agctggaatt ccggcgccct gaccagcgga gtgcacacat tccagccgt gctgcagtcc     600 tctggcctgt actccctgag ctccgtggtg accgtgccct agctccct gggcacacag     660 acctatatct gcaatgtgaa ccacaagccc tctaacacaa aggtggacaa gaaggtggag     720
cctaagagct gtgataagac acacacctgc ccaccctgtc cagcaccaga gctgctgggc     780
ggccctagcg tgttcctgtt tcctccaaag ccaaaggata ccctgatgat ctcccgcacc     840
cctgaggtga catgcgtggt ggtggacgtg tctcacgagg accccgaggt gaagttcaat     900
tggtacgtgg acggcgtgga ggtgcacaac gccaagacca gcctaggga ggagcagtac     960 aatagcacct atcgcgtggt gtccgtgctg acagtgctgc accaggactg gctgaatggc    1020
aaggagtata agtgcaaggt gagcaacaag gccctgcctg ccccaatcga aaagaccatc    1080
tccaaggcaa agggacagcc tcgggagcca caggtgtaca cactgccccc tagcagagac    1140
gagctgacca gaatcaggt gtccctgaca tgtctggtga agggcttcta ccatccgat    1200 atcgccgtgg agtgggagtc taacggccag ccgagaaca attacaagac aacccccaccc    1260 gtgctggact ctgatggcag cttctttctg tattccaagc tgaccgtgga taagtctcgg    1320

```
tggcagcagg gcaacgtgtt cagctgcagc gtgatgcacg aggccctgca caaccactac    1380
acccagaagt ccctgtctct gagcccaggc aagcggggca gaaagcggag atccggctct    1440
ggcgccacaa atttcagcct gctgaagcag gcaggcgacg tggaggagaa cccaggacct    1500
atggtgctgc agacccaggt gtttatctct ctgctgctgt ggatcagcgg cgcctacggc    1560
gagatcgtga tgacccagag cccaggcaca ctgagcctgt ccccaggaga gcaggccacc    1620
ctgtcctgta gggcctctca gagcgtgccc cgcaactaca tcggctggtg cagcagaca    1680 ccaggacagg cccctcggct gctgatctat ggagcctcta gccggccgc aggattccct    1740 gacagatttt ccggctctgg cagcggcacc gatttcacac tgaccatcac agacctggag    1800
cccgaggatt ttgccatgta ctattgccac cagtacgaca gactgcctta ccttcggc    1860 cagggcacaa agctggagat caagaccgtg gccgcccta gcgtgttcat ctttcctcca    1920
tccgatgagc agctgaagag cggcacagcc tccgtggtgt gcctgctgaa caacttctac    1980
ccaagggagg ccaaggtgca gtggaaggtg gacaatgccc tgcagtccgg caactctcag    2040
gagagcgtga ccgagcagga ctccaaggat tctacatatt ccctgtctaa taccctgaca    2100
ctgagcaagg ccgactacga gaagcacaag gtgtatgcat gcgaggtgac ccaccagggc    2160
ctgtcctctc ctgtgacaaa gtccttcaac agaggcgagt gttgataa              2208
```

<210> SEQ ID NO 12
<211> LENGTH: 734
<212> TYPE: PRT
<213> ORGANISM: Artificial Sequence
<220> FEATURE:
<223> OTHER INFORMATION: Chemically Synthesized, pGX9296, Ebola ZBDBV223
      modified

<400> SEQUENCE: 12

```
Met Asp Trp Thr Trp Arg Ile Leu Phe Leu Val Ala Ala Ala Thr Gly
1               5                   10                  15

Thr His Ala Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Thr Thr Thr Tyr Trp Asn Trp Ile Arg Gln Pro Pro Gly Lys Gly Leu
    50                  55                  60

Glu Trp Ile Gly Glu Val Asn Tyr Ser Gly Asn Ala Asn Tyr Asn Pro
65                  70                  75                  80

Ser Leu Gln Gly Arg Val Ala Ile Ser Val Asp Thr Ser Lys Asn Gln
                85                  90                  95

Phe Ser Leu Gln Leu Asn Ser Val Thr Ala Ala Asp Thr Ala Ile Tyr
            100                 105                 110

Tyr Cys Thr Ser Arg Ile Arg Ser His Ile Ala Tyr Ser Trp Lys Gly
        115                 120                 125

Trp Val Trp Gly Lys Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205
```

```
Val Val Thr Val Pro Ser Ser Leu Gly Thr Gln Thr Tyr Ile Cys
    210             215             220

Asn Val Asn His Lys Pro Ser Asn Thr Lys Val Asp Lys Lys Val Glu
225             230             235             240

Pro Lys Ser Cys Asp Lys Thr His Thr Cys Pro Pro Cys Pro Ala Pro
                245             250             255

Glu Leu Leu Gly Gly Pro Ser Val Phe Leu Phe Pro Pro Lys Pro Lys
            260             265             270

Asp Thr Leu Met Ile Ser Arg Thr Pro Glu Val Thr Cys Val Val Val
        275             280             285

Asp Val Ser His Glu Asp Pro Glu Val Lys Phe Asn Trp Tyr Val Asp
    290             295             300

Gly Val Glu Val His Asn Ala Lys Thr Lys Pro Arg Glu Glu Gln Tyr
305             310             315             320

Asn Ser Thr Tyr Arg Val Val Ser Val Leu Thr Val Leu His Gln Asp
                325             330             335

Trp Leu Asn Gly Lys Glu Tyr Lys Cys Lys Val Ser Asn Lys Ala Leu
            340             345             350

Pro Ala Pro Ile Glu Lys Thr Ile Ser Lys Ala Lys Gly Gln Pro Arg
        355             360             365

Glu Pro Gln Val Tyr Thr Leu Pro Pro Ser Arg Asp Glu Leu Thr Lys
    370             375             380

Asn Gln Val Ser Leu Thr Cys Leu Val Lys Gly Phe Tyr Pro Ser Asp
385             390             395             400

Ile Ala Val Glu Trp Glu Ser Asn Gly Gln Pro Glu Asn Asn Tyr Lys
                405             410             415

Thr Thr Pro Pro Val Leu Asp Ser Asp Gly Ser Phe Phe Leu Tyr Ser
            420             425             430

Lys Leu Thr Val Asp Lys Ser Arg Trp Gln Gln Gly Asn Val Phe Ser
        435             440             445

Cys Ser Val Met His Glu Ala Leu His Asn His Tyr Thr Gln Lys Ser
    450             455             460

Leu Ser Leu Ser Pro Gly Lys Arg Gly Arg Lys Arg Arg Ser Gly Ser
465             470             475             480

Gly Ala Thr Asn Phe Ser Leu Leu Lys Gln Ala Gly Asp Val Glu Glu
                485             490             495

Asn Pro Gly Pro Met Val Leu Gln Thr Gln Val Phe Ile Ser Leu Leu
            500             505             510

Leu Trp Ile Ser Gly Ala Tyr Gly Glu Ile Val Met Thr Gln Ser Pro
        515             520             525

Gly Thr Leu Ser Leu Ser Pro Gly Glu Gln Ala Thr Leu Ser Cys Arg
    530             535             540

Ala Ser Gln Ser Val Pro Arg Asn Tyr Ile Gly Trp Trp Gln Gln Thr
545             550             555             560

Pro Gly Gln Ala Pro Arg Leu Leu Ile Tyr Gly Ala Ser Ser Arg Ala
                565             570             575

Ala Gly Phe Pro Asp Arg Phe Ser Gly Ser Gly Ser Gly Thr Asp Phe
            580             585             590

Thr Leu Thr Ile Thr Asp Leu Glu Pro Glu Asp Phe Ala Met Tyr Tyr
        595             600             605

Cys His Gln Tyr Asp Arg Leu Pro Tyr Thr Phe Gly Gln Gly Thr Lys
    610             615             620
```

```
Leu Glu Ile Lys Thr Val Ala Ala Pro Ser Val Phe Ile Phe Pro Pro
625                 630                 635                 640

Ser Asp Glu Gln Leu Lys Ser Gly Thr Ala Ser Val Val Cys Leu Leu
                645                 650                 655

Asn Asn Phe Tyr Pro Arg Glu Ala Lys Val Gln Trp Lys Val Asp Asn
            660                 665                 670

Ala Leu Gln Ser Gly Asn Ser Gln Glu Ser Val Thr Glu Gln Asp Ser
        675                 680                 685

Lys Asp Ser Thr Tyr Ser Leu Ser Asn Thr Leu Thr Leu Ser Lys Ala
690                 695                 700

Asp Tyr Glu Lys His Lys Val Tyr Ala Cys Glu Val Thr His Gln Gly
705                 710                 715                 720

Leu Ser Ser Pro Val Thr Lys Ser Phe Asn Arg Gly Glu Cys
                725                 730
```

<210> SEQ ID NO 13
<211> LENGTH: 2211
<212> TYPE: DNA
<213> ORGANISM: Artificial Sequence
<220> FEATURE:
<223> OTHER INFORMATION: Chemically Synthesized, pGX9297, Ebola ZBDBV223
      partial graft

<400> SEQUENCE: 13

```
atggactgga cctggagaat cctgttcctg gtggcagcag caacaggaac ccacgcacag      60
gtgcagctgc agcagtgggg cgccggcctg ctgaagccaa gcgagacact gtccctgaca     120
tgcgccgtgt acggcggcag ctttaccaca acctattgga attggatcag acagcccct     180 ggcaagggcc tggagtggat cggcgaggtg aactactctg caacgccaa ttataacccc     240 agcctgaagg gcagggtggc catctctgtg gacacaagca agaatcagtt ctctctgcgc     300
ctgaacagcg tgaccgcagc agatacagcc atctactatt gcaccagccg gatcagaagc     360
cacatcgcct actcctggaa gggcgacgtg tggggcaagg gcacaaccgt gaccgtgagc     420
tccgcctcca caaagggacc aagcgtgttc ccactggcac cctctagcaa gagcacctcc     480
ggcggcacag ccgccctggg ctgtctggtg aaggattatt tccccgagcc tgtgaccgtg     540
agctggaatt ccggcgccct gaccagcgga gtgcacacat ttccagccgt gctgcagtcc     600
tctggcctgt actccctgag ctccgtggtg accgtgccct ctagctccct gggcacacag     660
acctatatct gcaatgtgaa ccacaagccc tctaacacaa aggtggacaa gaaggtggag     720
cctaagagct gtgataagac acacacctgc ccacccgtc cagcaccaga gctgctgggc     780
ggccctagcg tgttcctgtt tcctccaaag ccaaaggaca cctgatgat ctcccggacc     840 cctgaggtga catgcgtggt ggtggacgtg tctcacgagg accccgaggt gaagttcaat     900
tggtacgtgg atggcgtgga ggtgcacaac gccaagacca gcctaggga ggagcagtac     960 aatagcacct atcgcgtggt gtccgtgctg acagtgctgc accaggattg gctgaatggc    1020
aaggagtata agtgcaaggt gagcaacaag gccctgcctg ccccaatcga aagaccatc    1080 tccaaggcaa agggacagcc tcgggagcca caggtgtaca cactgccccc tagcagagac    1140
gagctgacca gaatcaggt gtccctgaca tgtctggtga agggcttcta tccatccgat    1200
atcgccgtgg agtgggagtc taacggccag cccgagaaca attacaagac aaccccaccc    1260
gtgctggact ctgatggcag cttctttctg tattccaagc tgaccgtgga caagtctaga    1320
tggcagcagg gcaacgtgtt cagctgcagc gtgatgcacg aggccctgca caaccactac    1380
acccagaagt ccctgtctct gagcccaggc aagcggggca gaaagcggag atccggctct    1440
```

```
ggcgccacaa atttcagcct gctgaagcag gcaggcgatg tggaggagaa cccaggacct    1500
atggtgctgc agacccaggt gtttatctct ctgctgctgt ggatcagcgg agcatacgga    1560
gagacaaccc tgacccagag cccaggcaca ctgagcctgt ccccaggaga gagggccacc    1620
ctgtcctgta gggcatctca gagcgtgcca cggaactaca tcggatggtt ccagcagaag    1680
ccaggacagg cccctagact gctgatctat ggagcctcta gccgggccgc aggattccct    1740
gacagatttt ccggctctgg cagcggcacc gatttcacac tgaccatcac aaggctggag    1800
cccgaggact ttgccatgta ctattgccac cagtacgata ggctgcctta ccttcggc     1860 cagggcacaa agctggagat caagaggacc gtggcagcac tagcgtgtt catctttcct    1920 ccatccgacg agcagctgaa gagcggcaca gcctccgtgg tgtgcctgct gaacaacttc    1980
tacccacgcg aggccaaggt gcagtggaag gtggataatg ccctgcagtc cggcaactct    2040
caggagagcg tgaccgagca ggactccaag gattctacat attccctgtc taataccctg    2100
acactgagca aggccgacta cgagaagcac aaggtgtatg catgcgaggt gacccaccag    2160
ggcctgtcct ctcctgtgac aaagtccttt aacaggggcg agtgttgata a             2211

<210> SEQ ID NO 14
<211> LENGTH: 735
<212> TYPE: PRT
<213> ORGANISM: Artificial Sequence
<220> FEATURE:
<223> OTHER INFORMATION: Chemically Synthesized, pGX9297, Ebola ZBDBV223
      partial graft

<400> SEQUENCE: 14

Met Asp Trp Thr Trp Arg Ile Leu Phe Leu Val Ala Ala Thr Gly
1               5                   10                  15

Thr His Ala Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Thr Thr Thr Tyr Trp Asn Trp Ile Arg Gln Pro Pro Gly Lys Gly Leu
    50                  55                  60

Glu Trp Ile Gly Glu Val Asn Tyr Ser Gly Asn Ala Asn Tyr Asn Pro
65                  70                  75                  80

Ser Leu Lys Gly Arg Val Ala Ile Ser Val Asp Thr Ser Lys Asn Gln
                85                  90                  95

Phe Ser Leu Arg Leu Asn Ser Val Thr Ala Ala Asp Thr Ala Ile Tyr
            100                 105                 110

Tyr Cys Thr Ser Arg Ile Arg Ser His Ile Ala Tyr Ser Trp Lys Gly
        115                 120                 125

Asp Val Trp Gly Lys Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220
```

```
Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
            245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys Arg Gly Arg Lys Arg Arg Ser Gly Ser
465                 470                 475                 480

Gly Ala Thr Asn Phe Ser Leu Leu Lys Gln Ala Gly Asp Val Glu Glu
                485                 490                 495

Asn Pro Gly Pro Met Val Leu Gln Thr Gln Val Phe Ile Ser Leu Leu
            500                 505                 510

Leu Trp Ile Ser Gly Ala Tyr Gly Glu Thr Thr Leu Thr Gln Ser Pro
            515                 520                 525

Gly Thr Leu Ser Leu Ser Pro Gly Glu Arg Ala Thr Leu Ser Cys Arg
            530                 535                 540

Ala Ser Gln Ser Val Pro Arg Asn Tyr Ile Gly Trp Phe Gln Gln Lys
545                 550                 555                 560

Pro Gly Gln Ala Pro Arg Leu Leu Ile Tyr Gly Ala Ser Ser Arg Ala
                565                 570                 575

Ala Gly Phe Pro Asp Arg Phe Ser Gly Ser Gly Ser Gly Thr Asp Phe
            580                 585                 590

Thr Leu Thr Ile Thr Arg Leu Glu Pro Glu Asp Phe Ala Met Tyr Tyr
            595                 600                 605

Cys His Gln Tyr Asp Arg Leu Pro Tyr Thr Phe Gly Gln Gly Thr Lys
610                 615                 620

Leu Glu Ile Lys Arg Thr Val Ala Ala Pro Ser Val Phe Ile Phe Pro
625                 630                 635                 640
```

| | | | | | | | | | | | |
|---|---|---|---|---|---|---|---|---|---|---|---|
|Pro|Ser|Asp|Glu|Gln|Leu|Lys|Ser|Gly|Thr|Ala|Ser|Val|Val|Cys|Leu|
| | | | |645| | | |650| | | |655| | | |

Leu Asn Asn Phe Tyr Pro Arg Glu Ala Lys Val Gln Trp Lys Val Asp
                660                 665                 670

Asn Ala Leu Gln Ser Gly Asn Ser Gln Glu Ser Val Thr Glu Gln Asp
            675                 680                 685

Ser Lys Asp Ser Thr Tyr Ser Leu Ser Asn Thr Leu Thr Leu Ser Lys
        690                 695                 700

Ala Asp Tyr Glu Lys His Lys Val Tyr Ala Cys Glu Val Thr His Gln
705                 710                 715                 720

Gly Leu Ser Ser Pro Val Thr Lys Ser Phe Asn Arg Gly Glu Cys
                725                 730                 735

<210> SEQ ID NO 15
<211> LENGTH: 2211
<212> TYPE: DNA
<213> ORGANISM: Artificial Sequence
<220> FEATURE:
<223> OTHER INFORMATION: Chemically Synthesized, pGX9298, Ebola ZBDBV223
      graft on MERSYTE

<400> SEQUENCE: 15

```
atggactgga cctggagaat cctgttcctg gtggcagcag caacaggaac ccacgcacag    60
gtgcagctgg tgcagagcgg agccgaggtg aagaagccag cagctccgt gaaggtgtcc    120 tgcaaggcca gcggcggctc cttcaccaca acctacatct cttgggtgcg ccaggcacca    180
ggacagggcc tggagtggat gggcggcgtg aactacagcg gcaacgccaa ttatgcccag    240
aagtttcagg gccgggtgac aatcaccgcc gacacaagca cctccacagc ctacatggag    300
ctgtctagcc tgagaagcga ggataccgcc gtgtactatt gcaccagccg gatcagaagc    360
cacatcgcct attcctggaa gggcgacgtg tggggacagg gaacaaccgt gaccgtgtcc    420
tctgcctcca caaagggacc aagcgtgttc ccactggcac ctagctccaa gtctaccagc    480
ggcggcacag ccgccctggg atgtctggtg aaggattact ccctgagcc agtgaccgtg    540 tcttggaaca gcggcgccct gaccagcgga gtgcacacat tccccgccgt gctgcagtct    600
agcggcctgt actccctgtc ctctgtggtg accgtgccta gtcctctct gggcacccag    660 acatatatct gcaacgtgaa tcacaagcct tctaatacaa aggtggacaa gaaggtggag    720
ccaaagagct gtgataagac ccacacatgc cctccctgtc cagcacctga gctgctgggc    780
ggcccaagcg tgttcctgtt tccacccaag cccaaggaca ccctgtacat cacgggag    840 ccagaggtga cctgcgtggt ggtggacgtg tcccacgagg accccgaggt gaagttcaac    900
tggtacgtgg atggcgtgga ggtgcacaat gccaagacca gccaaggga ggagcagtac    960 aattctacct atcgcgtggt gagcgtgctg acagtgctgc accaggattg gctgaacggc    1020
aaggagtaca agtgcaaggt gtccaataag gccctgccag cccccatcga aagaccatc    1080 tctaaggcaa agggacagcc aagggagcca caggtgtaca cactgcctcc aagccgcgac    1140
gagctgacca gaaccaggt gtccctgaca tgtctggtga agggcttcta tcccctcgat    1200
atcgccgtgg agtgggagtc taatggccag cctgagaaca attacaagac aaccccctccc    1260 gtgctggact ccgatggctc tttcttcctg tatagcaagc tgaccgtgga caagtccaga    1320
tggcagcagg gcaacgtgtt ttcctgctct gtgatgcacg aggccctgca caatcactac    1380
acccagaaga gcctgtccct gtctcctggc aagagggaa gaaagcggag aagcggctcc    1440
ggcgccacaa acttcagcct gctgaagcag gccggcgatg tggaggagaa tcctggccca    1500
```

```
atggtgctgc agacccaggt gtttatctcc ctgctgctgt ggatctctgg cgcctatgga    1560
gagacaaccc tgacccagag cccaggcaca ctgtctctga gccctggaga gagggccacc    1620
ctgtcctgta gggcatccca gtctgtgcca cggaactaca tcgcctggta tcagcagaag    1680
cctggccagg ccccaagact gctgatgttc ggagccagct cccgggccgc aggcatccct    1740
gacagattca gcggctccgg ctctggaacc gacttcaccc tgaacatctc tagcctggag    1800
cctgaggact cgccgtgta ctattgccac cagtacgata ggctgccata tacctttggc    1860
cagggcacaa agctggagat caagaggacc gtggcagcac tagcgtgtt catctttcca    1920 cccagcgacg agcagctgaa gtctggcaca gccagcgtgg tgtgcctgct gaacaatttc    1980
tacccaaggg aggccaaggt gcagtggaag gtggataacg ccctgcagag cggcaattcc    2040
caggagtctg tgaccgagca ggacagcaag gattccacat attctctgtc ctctaccctg    2100
acactgtcca aggccgacta cgagaagcac aaggtgtatg catgcgaggt gacccaccag    2160
ggcctgcgga gccccgtgac aaagtccttt aacagaggcg agtgttgata a              2211
```

<210> SEQ ID NO 16
<211> LENGTH: 735
<212> TYPE: PRT
<213> ORGANISM: Artificial Sequence
<220> FEATURE:
<223> OTHER INFORMATION: Chemically Synthesized, pGX9298, Ebola ZBDBV223 graft on MERSYTE

<400> SEQUENCE: 16

```
Met Asp Trp Thr Trp Arg Ile Leu Phe Leu Val Ala Ala Ala Thr Gly
1               5                   10                  15

Thr His Ala Gln Val Gln Leu Val Gln Ser Gly Ala Glu Val Lys Lys
                20                  25                  30

Pro Gly Ser Ser Val Lys Val Ser Cys Lys Ala Ser Gly Gly Ser Phe
            35                  40                  45

Thr Thr Thr Tyr Ile Ser Trp Val Arg Gln Ala Pro Gly Gln Gly Leu
        50                  55                  60

Glu Trp Met Gly Gly Val Asn Tyr Ser Gly Asn Ala Asn Tyr Ala Gln
65                  70                  75                  80

Lys Phe Gln Gly Arg Val Thr Ile Thr Ala Asp Thr Ser Thr Ser Thr
                85                  90                  95

Ala Tyr Met Glu Leu Ser Ser Leu Arg Ser Glu Asp Thr Ala Val Tyr
            100                 105                 110

Tyr Cys Thr Ser Arg Ile Arg Ser His Ile Ala Tyr Ser Trp Lys Gly
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240
```

```
Pro Lys Ser Cys Asp Lys Thr His Thr Cys Pro Pro Cys Pro Ala Pro
            245                 250                 255

Glu Leu Leu Gly Gly Pro Ser Val Phe Leu Phe Pro Pro Lys Pro Lys
            260                 265                 270

Asp Thr Leu Tyr Ile Thr Arg Glu Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
            325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys Arg Gly Arg Lys Arg Arg Ser Gly Ser
465                 470                 475                 480

Gly Ala Thr Asn Phe Ser Leu Leu Lys Gln Ala Gly Asp Val Glu Glu
                485                 490                 495

Asn Pro Gly Pro Met Val Leu Gln Thr Gln Val Phe Ile Ser Leu Leu
            500                 505                 510

Leu Trp Ile Ser Gly Ala Tyr Gly Glu Thr Thr Leu Thr Gln Ser Pro
            515                 520                 525

Gly Thr Leu Ser Leu Ser Pro Gly Glu Arg Ala Thr Leu Ser Cys Arg
            530                 535                 540

Ala Ser Gln Ser Val Pro Arg Asn Tyr Ile Ala Trp Tyr Gln Gln Lys
545                 550                 555                 560

Pro Gly Gln Ala Pro Arg Leu Leu Met Phe Gly Ala Ser Ser Arg Ala
            565                 570                 575

Ala Gly Ile Pro Asp Arg Phe Ser Gly Ser Gly Ser Gly Thr Asp Phe
            580                 585                 590

Thr Leu Asn Ile Ser Ser Leu Glu Pro Glu Asp Phe Ala Val Tyr Tyr
            595                 600                 605

Cys His Gln Tyr Asp Arg Leu Pro Tyr Thr Phe Gly Gln Gly Thr Lys
            610                 615                 620

Leu Glu Ile Lys Arg Thr Val Ala Ala Pro Ser Val Phe Ile Phe Pro
625                 630                 635                 640

Pro Ser Asp Glu Gln Leu Lys Ser Gly Thr Ala Ser Val Val Cys Leu
            645                 650                 655
```

```
Leu Asn Asn Phe Tyr Pro Arg Glu Ala Lys Val Gln Trp Lys Val Asp
            660                 665                 670

Asn Ala Leu Gln Ser Gly Asn Ser Gln Glu Ser Val Thr Glu Gln Asp
        675                 680                 685

Ser Lys Asp Ser Thr Tyr Ser Leu Ser Ser Thr Leu Thr Leu Ser Lys
        690                 695                 700

Ala Asp Tyr Glu Lys His Lys Val Tyr Ala Cys Glu Val Thr His Gln
705                 710                 715                 720

Gly Leu Arg Ser Pro Val Thr Lys Ser Phe Asn Arg Gly Glu Cys
            725                 730                 735

<210> SEQ ID NO 17
<211> LENGTH: 2211
<212> TYPE: DNA
<213> ORGANISM: Artificial Sequence
<220> FEATURE:
<223> OTHER INFORMATION: Chemically Synthesized, pGX9299, Ebola ZBDBV223
      graft on V2L2

<400> SEQUENCE: 17
atggactgga cctggagaat cctgttcctg gtggcagcag caacaggaac ccacgcagag    60
gtgcagctgc tggagagcgg cggcggcctg gtgcagccag cgggctccct gaggctgtct   120
tgcgcagcat ctggcggcag cttcaccaca acctacatga actgggtgcg ccaggcacca   180
ggcaagggcc tggagtgggt gagcgccgtg aactattccg caatgcctac ctatacagac   240
gatgtgaagg gccggtttac catcagcgtg gacacatcca gaacaccct gtacctgcag    300 atgaattccc tgagagccga ggatacagcc gtgtactatt gcaccagccg gatcagaagc   360
cacatcgcct atagctggaa gggcgacgtg tggggacagg gaacaaccgt gacagtgagc   420
tccgcctcta ccaagggccc aagcgtgttt cccctggccc cttctagcaa gtctacaagc   480
ggcggcaccg ccgccctggg atgtctggtg aaggattact cccctgagcc agtgaccgtg   540
tcctggaact ctggcgccct gacatccggc gtgcacacct tcctgccgt gctgcagtcc    600 tctggcctgt acagcctgag ctccgtggtg accgtgccat ctagctccct gggcacacag   660
acctatatct gcaacgtgaa tcacaagcca tccaatacaa aggtggacaa gaaggtggag   720
cccaagtctt gtgataagac acacacctgc cctccctgtc cagcacctga gctgctgggc   780
ggcccaagcg tgttcctgtt tccacccaag cctaaggaca ccctgatgat cagcaggaca   840
cccgaggtga cctgcgtggt ggtggacgtg tcccacgagg accccgaggt gaagttcaac   900
tggtacgtgg atggcgtgga ggtgcacaat gccaagacca gcctcggga ggagcagtac    960 aactccacat atagagtggt gtctgtgctg accgtgctgc accaggactg gctgaacggc   1020
aaggagtata agtgcaaggt gtctaataag gccctgccag cccccatcga aagacaatc    1080 agcaaggcaa agggacagcc aagggagcca caggtgtaca ccctgcctcc atctcgcgac   1140
gagctgacaa agaaccaggt gagcctgacc tgtctggtga agggcttcta tcctagcgat   1200
atcgccgtgg agtgggagtc caatggccag ccagagaaca attacaagac aacccctccc   1260
gtgctggaca gcgatggctc cttctttctg tattctaagc tgaccgtgga taagagccgc   1320
tggcagcagg gcaacgtgtt ttcctgctct gtgatgcacg aggccctgca caatcactac   1380
acccagaaga gcctgtccct gtctccaggc aagaggggaa gaaagcggag aagcggctcc   1440
ggagcaacca acttctcccct gctgaagcag caggcgacg tggaggagaa tcctggacca   1500
atggtgctgc agacccaggt gtttatcagc ctgctgctgt ggatctccgg agcatacgga   1560
gccatccaga tgacacagag cccctctagc ctgtctgcca gcgtgggcga tagggtgaca   1620
```

-continued

```
atcacctgtc gcgcctccca gtctgtgcct aggaattacc tgggctggta tcagcagaag    1680
cctggcaagg ccccaaagct gctgatctac ggagcatcca cactgcagtc tggagtgcct    1740
agccgcttca gcggctccgg ctctggaacc gactttacac tgaccatctc ctctctgcag    1800
ccagaggact tcgccacata ctattgccac cagtacgatc ggctgcccta catatttggc    1860
cagggcacca aggtggagat caagagaacc gtggccgccc cttccgtgtt catctttcca    1920
ccctctgacg agcagctgaa gtccggcaca gcctctgtgg tgtgcctgct gaacaatttc    1980
tacccacggg aggccaaggt gcagtggaag gtggataacg ccctgcagtc tggcaatagc    2040
caggagtccg tgacagagca ggactctaag gatagcacct atagcctgtc caacacactg    2100
accctgtcca aggccgatta cgagaagcac aaggtgtatg cctgcgaggt gacacaccag    2160
ggcctgagct cccccgtgac caagagcttt aatagaggcg agtgttgata a             2211
```

<210> SEQ ID NO 18
<211> LENGTH: 735
<212> TYPE: PRT
<213> ORGANISM: Artificial Sequence
<220> FEATURE:
<223> OTHER INFORMATION: Chemically Synthesized, pGX9299, Ebola ZBDBV223 graft on V2L2

<400> SEQUENCE: 18

```
Met Asp Trp Thr Trp Arg Ile Leu Phe Leu Val Ala Ala Ala Thr Gly
1               5                   10                  15

Thr His Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Gly Ser Phe
        35                  40                  45

Thr Thr Thr Tyr Met Asn Trp Val Arg Gln Ala Pro Gly Lys Gly Leu
    50                  55                  60

Glu Trp Val Ser Ala Val Asn Tyr Ser Gly Asn Ala Tyr Tyr Thr Asp
65                  70                  75                  80

Asp Val Lys Gly Arg Phe Thr Ile Ser Val Asp Thr Ser Lys Asn Thr
                85                  90                  95

Leu Tyr Leu Gln Met Asn Ser Leu Arg Ala Glu Asp Thr Ala Val Tyr
            100                 105                 110

Tyr Cys Thr Ser Arg Ile Arg Ser His Ile Ala Tyr Ser Trp Lys Gly
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255
```

```
Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys Arg Gly Arg Lys Arg Arg Ser Gly Ser
465                 470                 475                 480

Gly Ala Thr Asn Phe Ser Leu Leu Lys Gln Ala Gly Asp Val Glu Glu
                485                 490                 495

Asn Pro Gly Pro Met Val Leu Gln Thr Gln Val Phe Ile Ser Leu Leu
            500                 505                 510

Leu Trp Ile Ser Gly Ala Tyr Gly Ala Ile Gln Met Thr Gln Ser Pro
        515                 520                 525

Ser Ser Leu Ser Ala Ser Val Gly Asp Arg Val Thr Ile Thr Cys Arg
    530                 535                 540

Ala Ser Gln Ser Val Pro Arg Asn Tyr Leu Gly Trp Tyr Gln Gln Lys
545                 550                 555                 560

Pro Gly Lys Ala Pro Lys Leu Leu Ile Tyr Gly Ala Ser Thr Leu Gln
                565                 570                 575

Ser Gly Val Pro Ser Arg Phe Ser Gly Ser Gly Ser Gly Thr Asp Phe
            580                 585                 590

Thr Leu Thr Ile Ser Ser Leu Gln Pro Glu Asp Phe Ala Thr Tyr Tyr
        595                 600                 605

Cys His Gln Tyr Asp Arg Leu Pro Tyr Thr Phe Gly Gln Gly Thr Lys
    610                 615                 620

Val Glu Ile Lys Arg Thr Val Ala Ala Pro Ser Val Phe Ile Phe Pro
625                 630                 635                 640

Pro Ser Asp Glu Gln Leu Lys Ser Gly Thr Ala Ser Val Val Cys Leu
                645                 650                 655

Leu Asn Asn Phe Tyr Pro Arg Glu Ala Lys Val Gln Trp Lys Val Asp
            660                 665                 670
```

Asn Ala Leu Gln Ser Gly Asn Ser Gln Glu Ser Val Thr Glu Gln Asp
        675                 680                 685

Ser Lys Asp Ser Thr Tyr Ser Leu Ser Asn Thr Leu Thr Leu Ser Lys
    690                 695                 700

Ala Asp Tyr Glu Lys His Lys Val Tyr Ala Cys Glu Val Thr His Gln
705                 710                 715                 720

Gly Leu Ser Ser Pro Val Thr Lys Ser Phe Asn Arg Gly Glu Cys
                725                 730                 735

<210> SEQ ID NO 19
<211> LENGTH: 1476
<212> TYPE: DNA
<213> ORGANISM: Artificial Sequence
<220> FEATURE:
<223> OTHER INFORMATION: Chemically Synthesized, pGX9330, Ebola Z5D2
      scFv-Fc

<400> SEQUENCE: 19

| | | |
|---|---|---|
| atggtgctgc agacccaggt gttcatttcc ctgctgctgt ggattagcgg agcctatgga | 60 |
| gatgtcgtgc tgacccagac cccactgacc ctgagcgtga ccatcggcca gccagcctcc | 120 |
| atctcttgca gtccagcca gtccctgctg gattctgacg gcaagaccta cctgaattgg | 180 |
| ctgctgcaga gacctggcca gagccctaag cggctgatct atctggtgtc taagctggat | 240 |
| tctggcgtga ccgatagatt caccggctcc ggctctggca ccgactttac cctgaagatc | 300 |
| tccagggtgg aggccgagga tctgggcgtg tattactgtt ggcagggcac ccactccccc | 360 |
| tttacattcg gcagcggcac aaagctggag atcaagggcg gcggcggctc cggcggcggc | 420 |
| ggctctggcg gcggcggctc tgaggtgcag ctgcaggaga gggcccagg cctggtgcgc | 480 |
| ccatcccaga gcctgtctct gacatgtacc gtgacaggct acagcatcac atccgattac | 540 |
| gcctggaact ggatcagaca gttcccaggc aacaagctgg agtggctggg ctatatcacc | 600 |
| aacaccggct ctacaggctt caaccttcc ctgaagtcca gaatctctat cacccgcgat | 660 |
| acatccaaga ccagttctt tctgcagctg atcagcgtga ccacagagga taccgccaca | 720 |
| tatcactgtg ccagaggcct ggcctactgg ggcagggca ccctggtgac cgtgtcctct | 780 |
| gagcccaagt cctgtgataa gacccacacc tgccccacctt gtcccgcccc agagctgctg | 840 |
| ggcggcccca gcgtgttcct gtttcctcca agcccaagg acaccctgat gatcagcagg | 900 |
| acaccagagg tgacatgcgt ggtggtggac gtgtctcacg aggacccaga ggtgaagttc | 960 |
| aactggtacg tggatggcgt ggaggtgcac aacgccaaga ccaagccacg ggaggagcag | 1020 |
| tacaacagca cctacagagt ggtgtccgtg ctgaccgtgc tgcaccagga ttggctgaac | 1080 |
| ggcaaggagt acaagtgtaa ggtgtctaac aaggccctgc cgcccccaat cgagaagacc | 1140 |
| atctccaagg ccaagggcca gcctagggag ccacaggtgt atacactgcc accctctaga | 1200 |
| gatgagctga caaagaatca ggtgtccctg acatgcctgg tgaagggctt ctatccatcc | 1260 |
| gacatcgccg tggagtggga gagcaatggc cagccagaga taactacaa gaccacacca | 1320 |
| cctgtgctgg attccgacgg ctcttttcttc ctgtactcca agctgaccgt ggataagtcc | 1380 |
| aggtggcagc agggcaacgt gttttcttgc agcgtcatgc acgaagcact gcacaaccat | 1440 |
| tacactcaga gagcctgtc actgtcacct tgataa | 1476 |

<210> SEQ ID NO 20
<211> LENGTH: 490
<212> TYPE: PRT
<213> ORGANISM: Artificial Sequence
<220> FEATURE:

<223> OTHER INFORMATION: Chemically Synthesized, pGX9330, Ebola Z5D2 scFv-Fc

<400> SEQUENCE: 20

```
Met Val Leu Gln Thr Gln Val Phe Ile Ser Leu Leu Trp Ile Ser
1               5                   10                  15

Gly Ala Tyr Gly Asp Val Val Leu Thr Gln Thr Pro Leu Thr Leu Ser
            20                  25                  30

Val Thr Ile Gly Gln Pro Ala Ser Ile Ser Cys Lys Ser Ser Gln Ser
                35                  40                  45

Leu Leu Asp Ser Asp Gly Lys Thr Tyr Leu Asn Trp Leu Leu Gln Arg
        50                  55                  60

Pro Gly Gln Ser Pro Lys Arg Leu Ile Tyr Leu Val Ser Lys Leu Asp
65                  70                  75                  80

Ser Gly Val Thr Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Ser Pro Phe Thr Phe Gly Ser Gly Thr Lys
                115                 120                 125

Leu Glu Ile Lys Gly Gly Gly Gly Ser Gly Gly Gly Gly Ser Gly Gly
130                 135                 140

Gly Gly Ser Glu Val Gln Leu Gln Glu Ser Gly Pro Gly Leu Val Arg
145                 150                 155                 160

Pro Ser Gln Ser Leu Ser Leu Thr Cys Thr Val Thr Gly Tyr Ser Ile
                165                 170                 175

Thr Ser Asp Tyr Ala Trp Asn Trp Ile Arg Gln Phe Pro Gly Asn Lys
            180                 185                 190

Leu Glu Trp Leu Gly Tyr Ile Thr Asn Thr Gly Ser Thr Gly Phe Asn
        195                 200                 205

Pro Ser Leu Lys Ser Arg Ile Ser Ile Thr Arg Asp Thr Ser Lys Asn
210                 215                 220

Gln Phe Phe Leu Gln Leu Ile Ser Val Thr Thr Glu Asp Thr Ala Thr
225                 230                 235                 240

Tyr His Cys Ala Arg Gly Leu Ala Tyr Trp Gly Gln Gly Thr Leu Val
                245                 250                 255

Thr Val Ser Ser Glu Pro Lys Ser Cys Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
370                 375                 380

Lys Gly Gln Pro Arg Glu Pro Gln Val Tyr Thr Leu Pro Pro Ser Arg
385                 390                 395                 400
```

```
Asp Glu Leu Thr Lys Asn Gln Val Ser Leu Thr Cys Leu Val Lys Gly
            405                 410                 415
Phe Tyr Pro Ser Asp Ile Ala Val Glu Trp Glu Ser Asn Gly Gln Pro
            420                 425                 430
Glu Asn Asn Tyr Lys Thr Thr Pro Pro Val Leu Asp Ser Asp Gly Ser
            435                 440                 445
Phe Phe Leu Tyr Ser Lys Leu Thr Val Asp Lys Ser Arg Trp Gln Gln
450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro
            485                 490

<210> SEQ ID NO 21
<211> LENGTH: 1488
<212> TYPE: DNA
<213> ORGANISM: Artificial Sequence
<220> FEATURE:
<223> OTHER INFORMATION: Chemically Synthesized, pGX9331, Ebola Z1H3
      scFv-Fc

<400> SEQUENCE: 21
atggactgga cctggagaat cctgttcctg gtcgccgccg ctactgggac tcacgccgaa      60
gtgcagctgc agcagagtgg agccgagctg gtgaagccag cgccagcgt gaagctgtcc      120 tgcacagcct ccggctttaa catcaaggat acctacatcc actgggtgaa gcagggccct      180
gagcagggcc tggagtggat cggcaggatc gatcccgcca acggcaatac aaagtacgat      240
ccaaagtttc agggcaaggc caccatcaca gccgacacct ctagcaatac agcctatctg      300
cagctgtctg gcctgacatc cgaggataca gccgtgtact attgtgcccg ggagtctaga      360
atcagcacaa tgctgaccac aggctacttt gactactggg gccagggcac caccctgacc      420
gtgagcagcg gcggcggcgg ctctggcggc ggcggctccg gcggcggcgg cagccagatc      480
gtgctgaccc agtccccagc catcatgagc gcctcccag gcgagaaggt gaccatgacc      540
tgctccgcct ctagctccgt gtcttatatg tactggtatc agcagaagcc aggctcctct      600
ccaagactgc tgatctatga taccagcaat ctggcctctg gcgtgccagt gagattctct      660
ggcagcggct ccggcaccag ctactccctg acaatcagca ggatggaggc cgaggatgcc      720
gccacatact attgccagca gtggtcttcc tatccctaca cctttggcgg cggcacaaag      780
ctggagatca aggagcctaa gtcctgcgat aagacccaca cctgtcctcc ctgcccagcc      840
cccgagctgc tgggcggccc atccgtgttt ctgttccctc caaagcccaa ggatacccctg     900 atgatctccc ggacaccaga ggtgacatgc gtggtggtgg atgtgagcca cgaggaccca      960
gaggtgaagt tcaactggta cgtggatggc gtggaggtgc acaatgccaa gaccaagcca     1020
agagaggagc agtacaacag cacatacagg gtggtgtctg tgctgacagt gctgcaccag     1080
gactggctga atggcaagga gtataagtgc aaggtgtcca ataaggccct gcctgccccct    1140 atcgagaaga ccatctccaa ggccaagggc cagcccaggg agccacaggt gtataccctg     1200
cctcccagcc gggatgagct gacaaagaac caggtgtccc tgacatgtct ggtgaagggc     1260
ttctacccta gcgatatcgc cgtggagtgg gagtccaacg gccagccaga gaacaattat     1320
aagacaaccc cacctgtgct ggattccgac ggcagcttct ttctgtattc caagctgaca     1380
gtggacaaga gcaggtggca gcagggcaac gtgtttagct gctccgtcat gcacgaagcc     1440
ctgcacaacc actacaccca gaagtcactg agcctgtcac cttgataa                  1488
```

<210> SEQ ID NO 22
<211> LENGTH: 494
<212> TYPE: PRT
<213> ORGANISM: Artificial Sequence
<220> FEATURE:
<223> OTHER INFORMATION: Chemically Synthesized, pGX9331, Ebola Z1H3 scFv-Fc

<400> SEQUENCE: 22

```
Met Asp Trp Thr Trp Arg Ile Leu Phe Leu Val Ala Ala Thr Gly
1               5                   10                  15

Thr His Ala Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
            35                  40                  45

Lys Asp Thr Tyr Ile His Trp Val Lys Gln Gly Pro Glu Gln Gly Leu
        50                  55                  60

Glu Trp Ile Gly Arg Ile Asp Pro Ala Asn Gly Asn Thr Lys Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Ser Gly Leu Thr Ser Glu Asp Thr Ala Val
            100                 105                 110

Tyr Tyr Cys Ala Arg Glu Ser Arg Ile Ser Thr Met Leu Thr Thr Gly
            115                 120                 125

Tyr Phe Asp Tyr Trp Gly Gln Gly Thr Thr Leu Thr Val Ser Ser Gly
        130                 135                 140

Gly Gly Ser Gly Gly Gly Gly Ser Gly Gly Gly Ser Gln Ile
145                 150                 155                 160

Val Leu Thr Gln Ser Pro Ala Ile Met Ser Ala Ser Pro Gly Glu Lys
                165                 170                 175

Val Thr Met Thr Cys Ser Ala Ser Ser Val Ser Tyr Met Tyr Trp
            180                 185                 190

Tyr Gln Gln Lys Pro Gly Ser Ser Pro Arg Leu Leu Ile Tyr Asp Thr
            195                 200                 205

Ser Asn Leu Ala Ser Gly Val Pro Val Arg Phe Ser Gly Ser Gly Ser
        210                 215                 220

Gly Thr Ser Tyr Ser Leu Thr Ile Ser Arg Met Glu Ala Glu Asp Ala
225                 230                 235                 240

Ala Thr Tyr Tyr Cys Gln Gln Trp Ser Ser Tyr Pro Tyr Thr Phe Gly
                245                 250                 255

Gly Gly Thr Lys Leu Glu Ile Lys Glu Pro Lys Ser Cys Asp Lys Thr
            260                 265                 270

His Thr Cys Pro Pro Cys Pro Ala Pro Glu Leu Leu Gly Gly Pro Ser
            275                 280                 285

Val Phe Leu Phe Pro Pro Lys Pro Lys Asp Thr Leu Met Ile Ser Arg
        290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
```

```
              355                 360                 365
Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro
                485                 490
```

<210> SEQ ID NO 23
<211> LENGTH: 1488
<212> TYPE: DNA
<213> ORGANISM: Artificial Sequence
<220> FEATURE:
<223> OTHER INFORMATION: Chemically Synthesized, pGX9332, Ebola ZBDBV223 scFv-Fc

<400> SEQUENCE: 23

```
atggattgga cttggaggat tctgtttctg gtcgccgccg ctacagggac tcacgctcag      60
gtgcagctgc agcagtgggg agccgggctg ctgaagccat ctgagaccct gtctctgaca     120
tgcgccgtgt acggcggctc cttcacaacc acctactgga actggatcag acagccaccc     180
ggcaagggcc tggagtggat cggcgaggtg aactacagcg gcaatgccaa ctacaatccc     240
tccctgaagg gcagggtggc catctccgtg gatacatcca agaaccagtt ttccctgcgg     300
ctgaatagcg tgacagccgc cgacaccgcc atctattact gcacaagccg gatcagaagc     360
cacatcgcct actcttggaa gggcgacgtg tggggcaagg gcacaaccgt gacagtgtcc     420
tctggcggcg gcggctccgg cggcggcggc agcggcggcg gcggcagcga gatcgtgatg     480
acccagtccc caggcacact gagcctgtcc ccaggcgaga gaccaccct gagctgtagg     540 gcctctcagt ccgtgccaag gaactatatc ggctggtttc agcagaagcc aggccaggcc     600
cctagactgc tgatctatgg cgccagctcc agagccgccg gcttccccga taggttttct     660
ggctccggct ctggcaccga cttcacactg accatcacaa gactggagcc agaggacttt     720
gccatgtatt actgccacca gtatgatcgg ctgccataca ccttcggcca gggcaccaag     780
ctggagatca aggagccaaa gagctgtgac aagacccaca cctgccctcc ctgcccagcc     840
ccagagctgc tgggcggccc atccgtgttc ctgttcccac aaagcccaa ggacaccctg     900 atgatctccc gcacaccaga ggtgacctgc gtggtggtgg acgtgtctca cgaggaccca     960
gaggtgaagt ttaactggta cgtggacggc gtggaggtgc acaacgccaa gacaaagccc    1020
agagaggagc agtacaattc cacatacaga gtggtgtctg tgctgacagt gctgcaccag    1080
gattggctga acggcaagga gtataagtgc aaggtgtcta caaggccct gcccgcccca    1140 atcgagaaga caatcagcaa ggccaagggc cagccaagag agcccaggt gtataccctg    1200 cctccatcta gagacgagct gaccaagaat caggtgtccc tgacatgtct ggtgaagggc    1260
```

```
ttctacccta gcgacatcgc cgtggagtgg gagtccaatg gccagccaga gaataactac   1320
aagaccaccc ctccagtgct ggattctgac ggcagctttt tcctgtattc taagctgacc   1380
gtggacaaga gcagatggca gcagggcaac gtgtttttcct gcagcgtcat gcacgaagcc   1440
ctgcacaacc attacaccca gaagagcctg tcactgagcc cctgataa                1488
```

<210> SEQ ID NO 24
<211> LENGTH: 494
<212> TYPE: PRT
<213> ORGANISM: Artificial Sequence
<220> FEATURE:
<223> OTHER INFORMATION: Chemically Synthesized, pGX9332, Ebola ZBDBV223 scFv-Fc

<400> SEQUENCE: 24

```
Met Asp Trp Thr Trp Arg Ile Leu Phe Leu Val Ala Ala Ala Thr Gly
1               5                   10                  15

Thr His Ala Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Thr Thr Thr Tyr Trp Asn Trp Ile Arg Gln Pro Pro Gly Lys Gly Leu
    50                  55                  60

Glu Trp Ile Gly Glu Val Asn Tyr Ser Gly Asn Ala Asn Tyr Asn Pro
65                  70                  75                  80

Ser Leu Lys Gly Arg Val Ala Ile Ser Val Asp Thr Ser Lys Asn Gln
                85                  90                  95

Phe Ser Leu Arg Leu Asn Ser Val Thr Ala Ala Asp Thr Ala Ile Tyr
            100                 105                 110

Tyr Cys Thr Ser Arg Ile Arg Ser His Ile Ala Tyr Ser Trp Lys Gly
        115                 120                 125

Asp Val Trp Gly Lys Gly Thr Thr Val Thr Val Ser Ser Gly Gly Gly
    130                 135                 140

Gly Ser Gly Gly Gly Gly Ser Gly Gly Gly Gly Ser Glu Ile Val Met
145                 150                 155                 160

Thr Gln Ser Pro Gly Thr Leu Ser Leu Ser Pro Gly Glu Arg Ala Thr
                165                 170                 175

Leu Ser Cys Arg Ala Ser Gln Ser Val Pro Arg Asn Tyr Ile Gly Trp
            180                 185                 190

Phe Gln Gln Lys Pro Gly Gln Ala Pro Arg Leu Leu Ile Tyr Gly Ala
        195                 200                 205

Ser Ser Arg Ala Ala Gly Phe Pro Asp Arg Phe Ser Gly Ser Gly Ser
    210                 215                 220

Gly Thr Asp Phe Thr Leu Thr Ile Thr Arg Leu Glu Pro Glu Asp Phe
225                 230                 235                 240

Ala Met Tyr Tyr Cys His Gln Tyr Asp Arg Leu Pro Tyr Thr Phe Gly
                245                 250                 255

Gln Gly Thr Lys Leu Glu Ile Lys Glu Pro Lys Ser Cys Asp Lys Thr
            260                 265                 270

His Thr Cys Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320
```

```
Glu Val Lys Phe Asn Trp Tyr Val Asp Gly Val Glu Val His Asn Ala
            325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
            370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
            405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
            450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro
            485                 490

<210> SEQ ID NO 25
<211> LENGTH: 1482
<212> TYPE: DNA
<213> ORGANISM: Artificial Sequence
<220> FEATURE:
<223> OTHER INFORMATION: Chemically Synthesized, pGX9345, EBV114_scFv-Fc

<400> SEQUENCE: 25
atggactgga cctggagaat cctgttcctg gtcgccgccg ctactgggac tcacgccgaa    60
gtgcagctgg tcgaatctgg gggaggcctg atccagccag gcggctccct gaggctgtct   120
tgcgccgcct ctggcttcgc cctgagaatg tacgatatgc actgggtgcg gcagacaatc   180
gacaagagac tggagtgggt gtctgccgtg ggccaagcg cgacaccta ttacgccgac    240 tctgtgaagg gccggttcgc cgtgtctaga gagaatgcca agaactccct gagcctgcag   300
atgaacagcc tgacagccgg cgacaccgcc atctattact gcgtgagaag cgacagggc    360 gtggccggcc tgttcgattc ctggggccag ggcatcctgg tgacagtgtc cagcggcggc   420
ggcggctctg gcggcggcgg ctccggcggc ggcggcagcg atatccagat gacccagagc   480
ccctcctccc tgagcgcctc cgtgggcgac agaatcacaa tcacctgtag agcctcccag   540 gccttttgata ttacgtggc ctggtatcag cagcggccag gcaaggtgcc aaagctgctg   600
atcagcgccg cctctgccct gcacgccggc gtgccaagca gattctctgg ctctggctcc   660 ggcaccact tcacactgac catctctagc ctgcagcccg aggatgtggc cacctattac   720
tgccagaact acaattccgc cccactgaca tttggcggcg gcacaaaggt ggagatcaag   780
gagccaaagt cttgcgacaa gacccacacc tgtccaccct gccccgcccc agagctgctg   840
ggcggccctt ccgtgttcct gtttcccccca agcctaagg atacctgat gatctccagg   900 acacccgagg tgacatgcgt ggtggtggat gtgagccacg aggacccaga ggtgaagttc   960
aattggtacg tggacggcgt ggaggtgcac aatgccaaga caaagcctag agaggagcag  1020
tataactcca cctataggt ggtgtccgtg ctgacagtgc tgcaccagga ttggctgaac  1080
```

```
ggcaaggagt acaagtgcaa ggtgtccaat aaggccctgc ccgcccctat cgagaagaca   1140
atctctaagg ccaagggcca gccaagagag ccacaggtgt acaccctgcc accctccaga   1200
gacgagctga caaagaacca ggtgtccctg acatgtctgg tgaagggctt ctatccctcc   1260
gatatcgccg tggagtggga gtctaatggc cagcccgaga caattacaa gacaacccca    1320 cctgtgctgg actccgacgg cagctttttc ctgtactcca agctgaccgt ggataagtcc   1380
cggtggcagc agggcaacgt gttttcctgc tccgtgatgc acgaagcact gcacaaccac   1440
tacactcaga aaagcctgtc cctgtcacct ggcaaatgat aa                      1482
```

<210> SEQ ID NO 26
<211> LENGTH: 492
<212> TYPE: PRT
<213> ORGANISM: Artificial Sequence
<220> FEATURE:
<223> OTHER INFORMATION: Chemically Synthesized, pGX9345, EBV114_scFv-Fc

<400> SEQUENCE: 26

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Ile Gln
            20                  25                  30

Pro Gly Gly Ser Leu Arg Leu Ser Cys Ala Ala Ser Gly Phe Ala Leu
        35                  40                  45

Arg Met Tyr Asp Met His Trp Val Arg Gln Thr Ile Asp Lys Arg Leu
    50                  55                  60

Glu Trp Val Ser Ala Val Gly Pro Ser Gly Asp Thr Tyr Tyr Ala Asp
65                  70                  75                  80

Ser Val Lys Gly Arg Phe Ala Val Ser Arg Glu Asn Ala Lys Asn Ser
                85                  90                  95

Leu Ser Leu Gln Met Asn Ser Leu Thr Ala Gly Asp Thr Ala Ile Tyr
            100                 105                 110

Tyr Cys Val Arg Ser Asp Arg Gly Val Ala Gly Leu Phe Asp Ser Trp
        115                 120                 125

Gly Gln Gly Ile Leu Val Thr Val Ser Ser Gly Gly Gly Gly Ser Gly
    130                 135                 140

Gly Gly Gly Ser Gly Gly Gly Ser Asp Ile Gln Met Thr Gln Ser
145                 150                 155                 160

Pro Ser Ser Leu Ser Ala Ser Val Gly Asp Arg Ile Thr Ile Thr Cys
                165                 170                 175

Arg Ala Ser Gln Ala Phe Asp Asn Tyr Val Ala Trp Tyr Gln Gln Arg
            180                 185                 190

Pro Gly Lys Val Pro Lys Leu Leu Ile Ser Ala Ala Ser Ala Leu His
        195                 200                 205

Ala Gly Val Pro Ser Arg Phe Ser Gly Ser Gly Ser Gly Thr His Phe
    210                 215                 220

Thr Leu Thr Ile Ser Ser Leu Gln Pro Glu Asp Val Ala Thr Tyr Tyr
225                 230                 235                 240

Cys Gln Asn Tyr Asn Ser Ala Pro Leu Thr Phe Gly Gly Gly Thr Lys
                245                 250                 255

Val Glu Ile Lys Glu Pro Lys Ser Cys Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
```

```
                290                 295                 300
Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
                340                 345                 350

Val Leu His Gln Asp Trp Leu Asn Gly Lys Glu Tyr Lys Cys Lys Val
            355                 360                 365

Ser Asn Lys Ala Leu Pro Ala Pro Ile Glu Lys Thr Ile Ser Lys Ala
370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
                420                 425                 430

Glu Asn Asn Tyr Lys Thr Thr Pro Pro Val Leu Asp Ser Asp Gly Ser
                435                 440                 445

Phe Phe Leu Tyr Ser Lys Leu Thr Val Asp Lys Ser Arg Trp Gln Gln
450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 27
<211> LENGTH: 1512
<212> TYPE: DNA
<213> ORGANISM: Artificial Sequence
<220> FEATURE:
<223> OTHER INFORMATION: Chemically Synthesized, pGX9346, 1A2_scFv-Fc

<400> SEQUENCE: 27
atggtgctgc agacccaggt gttcatctct ctgctgctgt ggatctctgg cgcctatggc      60
gatatcgtga tgacccagtc ccctagaagc ctgtccgtga cacccggcga gcctgccagc     120
atctcctgca gatcctctca gagcctgctg cacaggaatg gctacaacta cctggactgg     180
tatctgcaga gcctggccag tcccctcag ctgctgatct atctgggctc taatcgcgcc     240
agcggcgtgc ctgacaggtt ctccggcagc ggctctggca ccgacttcac actgaagatc     300
agcagagtgg aggccgagga cgtgggcgtg tactattgta tgcaggccct gcagacccct     360
tcctggacat tcggccaggg caccaaggtg gagatcaagg cggcggcgg ctccggcggc     420 ggcggctctg gcggcggcgg ctccgaggtg cagctggtgg agtctggcgg cggcctgatc     480
cagccaggcg gctccctgag actgtcttgc gccgcctctg gcttcgccgt gaggtccaac     540
tacctgtctt gggtgcgcca ggcccctggc aagggcctgg agtgggtgtc tctgatctac     600
tccggcggcc tgacagccta cgccgattcc gtggagggcc ggttcacaat ctccagagac     660
aattccaaga cacccctgta cctgcagatg aactccctga gagtggagga tacagccctg     720
tattactgtg ccagagtggc cagctccgcc ggcacattct attacggcat ggacgtgtgg     780
ggccagggca aaccgtgac cgtgtcttc gagcctaagt cctgtgacaa gacccacacc     840
tgtccaccct gtcctgcccc agagctgctg ggcggcccat ccgtgttcct gttccctcca     900
aagcccaagg atacactgat gatctctagg acccctgagg tgacctgcgt ggtggtggat     960
```

```
gtgagccacg aggaccctga ggtgaagttt aactggtacg tggatggcgt ggaggtgcac    1020
aatgccaaga caaagccaag agaggagcag tacaattcta catacagagt ggtgtctgtg    1080
ctgacagtgc tgcaccagga ctggctgaat ggcaaggagt acaagtgcaa ggtgtccaac    1140
aaggccctgc cagcccctat cgagaagacc atctccaagg ccaagggcca gccccgggag    1200
ccacaggtgt ataccctgcc accaagcaga gatgagctga ccaagaatca ggtgtccctg    1260
acatgtctgg tgaagggctt ctatcccagc gatatcgccg tggagtggga gagcaacggc    1320
cagcctgaga taactacaa gaccacacca cctgtgctgg attccgatgg cagcttcttt    1380
ctgtattcca agctgaccgt ggacaagtcc agatggcagc agggcaacgt gttcagctgc    1440
tccgtgatgc acgaggccct gcacaatcac tacacccaga gtctctgtc cctgtctcct    1500 ggcaagtgat aa                                                         1512
```

<210> SEQ ID NO 28
<211> LENGTH: 502
<212> TYPE: PRT
<213> ORGANISM: Artificial Sequence
<220> FEATURE:
<223> OTHER INFORMATION: Chemically Synthesized, pGX9346, 1A2_scFv-Fc

<400> SEQUENCE: 28

```
Met Val Leu Gln Thr Gln Val Phe Ile Ser Leu Leu Trp Ile Ser
1               5                   10                  15

Gly Ala Tyr Gly Asp Ile Val Met Thr Gln Ser Pro Arg Ser Leu Ser
            20                  25                  30

Val Thr Pro Gly Glu Pro Ala Ser Ile Ser Cys Arg Ser Gln Ser
        35                  40                  45

Leu Leu His Arg Asn Gly Tyr Asn Tyr Leu Asp Trp Tyr Leu Gln Lys
    50                  55                  60

Pro Gly Gln Ser Pro Gln Leu Leu Ile Tyr Leu Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Leu Gln Thr Pro Ser Trp Thr Phe Gly Gln Gly Thr
        115                 120                 125

Lys Val Glu Ile Lys Gly Gly Gly Ser Gly Gly Gly Gly Ser Gly
    130                 135                 140

Gly Gly Gly Ser Glu Val Gln Leu Val Glu Ser Gly Gly Gly Leu Ile
145                 150                 155                 160

Gln Pro Gly Gly Ser Leu Arg Leu Ser Cys Ala Ala Ser Gly Phe Ala
                165                 170                 175

Val Arg Ser Asn Tyr Leu Ser Trp Val Arg Gln Ala Pro Gly Lys Gly
            180                 185                 190

Leu Glu Trp Val Ser Leu Ile Tyr Ser Gly Gly Leu Thr Ala Tyr Ala
        195                 200                 205

Asp Ser Val Glu Gly Arg Phe Thr Ile Ser Arg Asp Asn Ser Lys Asn
    210                 215                 220

Thr Leu Tyr Leu Gln Met Asn Ser Leu Arg Val Glu Asp Thr Ala Leu
225                 230                 235                 240

Tyr Tyr Cys Ala Arg Val Ala Ser Ala Gly Thr Phe Tyr Tyr Gly
                245                 250                 255
```

Met Asp Val Trp Gly Gln Gly Thr Thr Val Thr Val Ser Ser Glu Pro
            260                 265                 270

Lys Ser Cys Asp Lys Thr His Thr Cys Pro Pro Cys Pro Ala Pro Glu
        275                 280                 285

Leu Leu Gly Gly Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Lys
            500

<210> SEQ ID NO 29
<211> LENGTH: 2226
<212> TYPE: DNA
<213> ORGANISM: Artificial Sequence
<220> FEATURE:
<223> OTHER INFORMATION: Chemically Synthesized, pGX9356,
      1A2_Full length_partial graft

<400> SEQUENCE: 29
atggactgga cctggagaat cctgttcctg gtggcagcag caaccggaac acacgcagag      60
gtgcagctgg tggagagcgg cggcggcctg atccagcccg gcggctctct gaggctgagc     120
tgcgcagcat ccggatttgc cgtgaggtct aactacctga gctgggtgcg ccaggcacct     180
ggcaagggcc tggagtgggt gtccctgatc tactctggcg gcctgaccgc atatgcagac     240
tccgtggagg gccggttcac catcagcaga gataactcca agaatacact gtatctgcag     300
atgaatagcc tgagggtgga ggacaccgcc ctgtactatt gcgcccgcgt ggccagctcc     360
gccggcacat tctactatgg catggacgtg tggggccagg gcaccacagt gaccgtgtct     420
agcgccagca aagggacc atccgtgttt ccactggcac cttcctctaa gtccacctct     480
ggcggcacag ccgccctggg ctgtctggtg aaggactact cccctgagcc agtgaccgtg     540
tcttggaaca gcggcgccct gacctctgga gtgcacacat tccagccgt gctgcagagc     600

```
tccggcctgt acagcctgtc tagcgtggtg accgtgccct cctctagcct gggcacccag    660
acatatatct gcaacgtgaa tcacaagcca tctaatacaa aggtggacaa gaaggtggag    720
cccaagagct gtgataagac ccacacatgc cctccctgtc cagcacctga gctgctgggc    780
ggcccaagcg tgttcctgtt tccacccaag cctaaggaca ccctgatgat ctccaggacc    840
cccgaggtga catgcgtggt ggtggacgtg tctcacgagg accccgaggt gaagtttaac    900
tggtacgtgg atggcgtgga ggtgcacaat gccaagacca gccccgggga ggagcagtac    960
aactctacct atagagtggt gagcgtgctg acagtgctgc accaggattg gctgaacggc   1020
aaggagtata agtgcaaggt gagcaataag gccctgccag cccccatcga aagaccatc    1080 tccaaggcaa agggacagcc acgggagcca caggtgtaca cactgcctcc aagcagagac   1140
gagctgacca gaaccaggt gtccctgaca tgtctggtga agggcttcta tccttccgat    1200
atcgccgtgg agtgggagtc taatggccag ccagagaaca attacaagac cacaccccct   1260
gtgctggact ccgatggctc tttctttctg tatagcaagc tgaccgtgga caagtcccgg   1320
tggcagcagg gcaacgtgtt tagctgctcc gtgatgcacg aggccctgca caatcactac   1380
acccagaagt ctctgagcct gtcccctggc aagaggggaa ggaagcggag atctggcagc   1440
ggagccacaa acttctccct gctgaagcag gccggcgatg tggaggagaa tcctggccca   1500
atggtgctgc agacccaggt gtttatctcc ctgctgctgt ggatctctgg cgcctacggc   1560
gccatccaga tgacacagag cccatcctct ctgtccgcct ctgtgggcga cagggtgacc   1620
atcacatgtc gcagctccca gtccctgctg cacagaaacg gctacaatta tctggattgg   1680
tacctgcaga agcctggcca gagcccacag ctgctgatct atctgggctc taacagggca   1740
agcggagtgc cagacagatt cagcggctcc ggctctggaa ccgacttcac cctgaagatc   1800
tcccgggtgg aggcagagga cgtgggcgtg tactattgca tgcaggccct gcagaccct   1860 agctggacat tcggccaggg caccaaggtg gagatcaaga aacagtggc cgccccaagc   1920 gtgttcatct ttccacccag cgacgagcag ctgaagtccg gcaccgcctc tgtggtgtgc   1980
ctgctgaaca acttctaccc tagggaggcc aaggtgcagt ggaaggtgga taacgccctg   2040
cagagcggca attcccagga gtctgtgacc gagcaggaca gcaaggattc cacatatagc   2100
ctgtccaaca ccctgacact gtccaaggcc gattacgaga agcacaaggt gtatgcctgc   2160
gaggtgaccc accagggcct gtctagccca gtgacaaaga gcttcaatcg cggcgagtgt   2220
tgataa                                                              2226
```

<210> SEQ ID NO 30
<211> LENGTH: 740
<212> TYPE: PRT
<213> ORGANISM: Artificial Sequence
<220> FEATURE:
<223> OTHER INFORMATION: Chemically Synthesized, pGX9356,
     1A2_Full length_partial graft

<400> SEQUENCE: 30

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Ile Gln
            20                  25                  30

Pro Gly Gly Ser Leu Arg Leu Ser Cys Ala Ala Ser Gly Phe Ala Val
        35                  40                  45

Arg Ser Asn Tyr Leu Ser Trp Val Arg Gln Ala Pro Gly Lys Gly Leu
    50                  55                  60
```

-continued

```
Glu Trp Val Ser Leu Ile Tyr Ser Gly Gly Leu Thr Ala Tyr Ala Asp
 65                  70                  75                  80

Ser Val Glu Gly Arg Phe Thr Ile Ser Arg Asp Asn Ser Lys Asn Thr
             85                  90                  95

Leu Tyr Leu Gln Met Asn Ser Leu Arg Val Glu Asp Thr Ala Leu Tyr
        100                 105                 110

Tyr Cys Ala Arg Val Ala Ser Ala Gly Thr Phe Tyr Tyr Gly Met
        115                 120                 125

Asp Val Trp Gly Gln Gly Thr Thr Val Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
        450                 455                 460

Leu Ser Leu Ser Pro Gly Lys Arg Gly Arg Lys Arg Arg Ser Gly Ser
465                 470                 475                 480

Gly Ala Thr Asn Phe Ser Leu Leu Lys Gln Ala Gly Asp Val Glu Glu
```

|     |     |     |     |     | 485 |     |     |     | 490 |     |     |     | 495 |     |
| --- | --- | --- | --- | --- | --- | --- | --- | --- | --- | --- | --- | --- | --- | --- |
| Asn | Pro | Gly | Pro | Met | Val | Leu | Gln | Thr | Gln | Val | Phe | Ile | Ser | Leu | Leu |
|     |     |     | 500 |     |     |     |     | 505 |     |     |     |     | 510 |     |     |
| Leu | Trp | Ile | Ser | Gly | Ala | Tyr | Gly | Ala | Ile | Gln | Met | Thr | Gln | Ser | Pro |
|     |     |     | 515 |     |     |     |     | 520 |     |     |     |     | 525 |     |     |
| Ser | Ser | Leu | Ser | Ala | Ser | Val | Gly | Asp | Arg | Val | Thr | Ile | Thr | Cys | Arg |
|     |     |     | 530 |     |     |     |     | 535 |     |     |     |     | 540 |     |     |
| Ser | Ser | Gln | Ser | Leu | Leu | His | Arg | Asn | Gly | Tyr | Asn | Tyr | Leu | Asp | Trp |
| 545 |     |     |     |     | 550 |     |     |     |     | 555 |     |     |     |     | 560 |
| Tyr | Leu | Gln | Lys | Pro | Gly | Gln | Ser | Pro | Gln | Leu | Leu | Ile | Tyr | Leu | Gly |
|     |     |     |     | 565 |     |     |     |     | 570 |     |     |     |     | 575 |     |
| Ser | Asn | Arg | Ala | Ser | Gly | Val | Pro | Asp | Arg | Phe | Ser | Gly | Ser | Gly | Ser |
|     |     |     | 580 |     |     |     |     | 585 |     |     |     |     | 590 |     |     |
| Gly | Thr | Asp | Phe | Thr | Leu | Lys | Ile | Ser | Arg | Val | Glu | Ala | Glu | Asp | Val |
|     |     |     | 595 |     |     |     |     | 600 |     |     |     |     | 605 |     |     |
| Gly | Val | Tyr | Tyr | Cys | Met | Gln | Ala | Leu | Gln | Thr | Pro | Ser | Trp | Thr | Phe |
|     |     |     | 610 |     |     |     |     | 615 |     |     |     |     | 620 |     |     |
| Gly | Gln | Gly | Thr | Lys | Val | Glu | Ile | Lys | Arg | Thr | Val | Ala | Ala | Pro | Ser |
| 625 |     |     |     |     | 630 |     |     |     |     | 635 |     |     |     |     | 640 |
| Val | Phe | Ile | Phe | Pro | Pro | Ser | Asp | Glu | Gln | Leu | Lys | Ser | Gly | Thr | Ala |
|     |     |     |     | 645 |     |     |     |     | 650 |     |     |     |     | 655 |     |
| Ser | Val | Val | Cys | Leu | Leu | Asn | Asn | Phe | Tyr | Pro | Arg | Glu | Ala | Lys | Val |
|     |     |     | 660 |     |     |     |     | 665 |     |     |     |     | 670 |     |     |
| Gln | Trp | Lys | Val | Asp | Asn | Ala | Leu | Gln | Ser | Gly | Asn | Ser | Gln | Glu | Ser |
|     |     |     | 675 |     |     |     |     | 680 |     |     |     |     | 685 |     |     |
| Val | Thr | Glu | Gln | Asp | Ser | Lys | Asp | Ser | Thr | Tyr | Ser | Leu | Ser | Asn | Thr |
|     |     |     | 690 |     |     |     |     | 695 |     |     |     |     | 700 |     |     |
| Leu | Thr | Leu | Ser | Lys | Ala | Asp | Tyr | Glu | Lys | His | Lys | Val | Tyr | Ala | Cys |
| 705 |     |     |     |     | 710 |     |     |     |     | 715 |     |     |     |     | 720 |
| Glu | Val | Thr | His | Gln | Gly | Leu | Ser | Ser | Pro | Val | Thr | Lys | Ser | Phe | Asn |
|     |     |     |     | 725 |     |     |     |     | 730 |     |     |     |     | 735 |     |
| Arg | Gly | Glu | Cys |
|     |     |     | 740 |

```
<210> SEQ ID NO 31
<211> LENGTH: 1512
<212> TYPE: DNA
<213> ORGANISM: Artificial Sequence
<220> FEATURE:
<223> OTHER INFORMATION: Chemically Synthesized, pGX9357,
      1A2_scFv-Fc_partial graft

<400> SEQUENCE: 31
atggtgctgc agacccaggt gttcatctct ctgctgctgt ggatctctgg cgcctatggc      60
gctatccaga tgacccagtc cccttcaagc ctgtccgcct ctgtgggcga cagggtgaca     120
atcacctgca gatcctctca gagcctgctg cacaggaatg gctacaacta cctggactgg     180
tatctgcaga agcctggcca gtcccctcag ctgctgatct atctgggctc taatcgcgcc     240
agcggcgtgc ctgacaggtt ctccggcagc ggctctggca ccgacttcac actgaagatc     300
agcagagtgg aggccgagga cgtgggcgtg tactattgta tgcaggccct gcagaccccc     360
tcctggacat tcggccaggg caccaaggtg gagatcaagg gcggcggcgg ctccggcggc     420
ggcggctctg gcggcggcgg ctccgaggtg cagctggtgg agtctggcgg cggcctgatc     480
cagccaggcg gctccctgag actgtcttgc gccgcctctg gcttcgccgt gaggtccaac     540
```

```
tacctgtctt gggtgcgcca ggcccctggc aagggcctgg agtgggtgtc tctgatctac    600
tccggcggcc tgacagccta cgccgattcc gtggagggcc ggttcacaat ctccagagac    660
aattccaaga acaccctgta cctgcagatg aactccctga gagtggagga tacagccctg    720
tattactgtg ccagagtggc cagctccgcc ggcacattct attacggcat ggacgtgtgg    780
ggccagggca aaccgtgac cgtgtcttcc gagcctaagt cctgtgacaa gacccacacc    840
tgtccaccct gtcctgcccc agagctgctg gcggcccat ccgtgttcct gttccctcca    900
aagcccaagg atacactgat gatctctagg acccctgagg tgacctgcgt ggtggtggat    960
gtgagccacg aggaccctga ggtgaagttt aactggtacg tggatggcgt ggaggtgcac   1020
aatgccaaga caaagccaag agaggagcag tacaattcta catacagagt ggtgtctgtg   1080
ctgacagtgc tgcaccagga ctggctgaat ggcaaggagt acaagtgcaa ggtgtccaac   1140
aaggccctgc cagcccctat cgagaagacc atctccaagg ccaagggcca gccccgggag   1200
ccacaggtgt ataccctgcc accaagcaga tgagctga ccaagaatca ggtgtccctg    1260
acatgtctgg tgaagggctt ctatcccagc gatatcgccg tggagtggga gagcaacggc   1320
cagcctgaga ataactacaa gaccacacca cctgtgctgg attccgatgg cagcttcttt   1380
ctgtattcca agctgaccgt ggacaagtcc agatggcagc agggcaacgt gttcagctgc   1440
tccgtgatgc acgaggccct gcacaataca tacacccaga gtctctgtc cctgtctcct   1500 ggcaagtgat aa                                                        1512
```

<210> SEQ ID NO 32
<211> LENGTH: 502
<212> TYPE: PRT
<213> ORGANISM: Artificial Sequence
<220> FEATURE:
<223> OTHER INFORMATION: Chemically Synthesized, pGX9357,
    1A2_scFv-Fc_partial graft

<400> SEQUENCE: 32

Met Val Leu Gln Thr Gln Val Phe Ile Ser Leu Leu Trp Ile Ser
1               5                   10                  15

Gly Ala Tyr Gly Ala Ile Gln Met Thr Gln Ser Pro Ser Ser Leu Ser
                20                  25                  30

Ala Ser Val Gly Asp Arg Val Thr Ile Thr Cys Arg Ser Gln Ser
            35                  40                  45

Leu Leu His Arg Asn Gly Tyr Asn Tyr Leu Asp Trp Tyr Leu Gln Lys
        50                  55                  60

Pro Gly Gln Ser Pro Gln Leu Leu Ile Tyr Leu Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Leu Gln Thr Pro Ser Trp Thr Phe Gly Gln Gly Thr
        115                 120                 125

Lys Val Glu Ile Lys Gly Gly Gly Ser Gly Gly Gly Ser Gly
        130                 135                 140

Gly Gly Gly Ser Glu Val Gln Leu Val Glu Ser Gly Gly Gly Leu Ile
145                 150                 155                 160

Gln Pro Gly Gly Ser Leu Arg Leu Ser Cys Ala Ala Ser Gly Phe Ala
                165                 170                 175

Val Arg Ser Asn Tyr Leu Ser Trp Val Arg Gln Ala Pro Gly Lys Gly

```
            180             185             190
Leu Glu Trp Val Ser Leu Ile Tyr Ser Gly Gly Leu Thr Ala Tyr Ala
            195                 200                 205
Asp Ser Val Glu Gly Arg Phe Thr Ile Ser Arg Asp Asn Ser Lys Asn
            210                 215                 220
Thr Leu Tyr Leu Gln Met Asn Ser Leu Arg Val Glu Asp Thr Ala Leu
225                 230                 235                 240
Tyr Tyr Cys Ala Arg Val Ala Ser Ser Ala Gly Thr Phe Tyr Tyr Gly
                245                 250                 255
Met Asp Val Trp Gly Gln Gly Thr Thr Val Thr Val Ser Ser Glu Pro
                260                 265                 270
Lys Ser Cys Asp Lys Thr His Thr Cys Pro Pro Cys Pro Ala Pro Glu
                275                 280                 285
Leu Leu Gly Gly Pro Ser Val Phe Leu Phe Pro Pro Lys Pro Lys Asp
                290                 295                 300
Thr Leu Met Ile Ser Arg Thr Pro Glu Val Thr Cys Val Val Val Asp
305                 310                 315                 320
Val Ser His Glu Asp Pro Glu Val Lys Phe Asn Trp Tyr Val Asp Gly
                325                 330                 335
Val Glu Val His Asn Ala Lys Thr Lys Pro Arg Glu Glu Gln Tyr Asn
                340                 345                 350
Ser Thr Tyr Arg Val Val Ser Val Leu Thr Val Leu His Gln Asp Trp
                355                 360                 365
Leu Asn Gly Lys Glu Tyr Lys Cys Lys Val Ser Asn Lys Ala Leu Pro
                370                 375                 380
Ala Pro Ile Glu Lys Thr Ile Ser Lys Ala Lys Gly Gln Pro Arg Glu
385                 390                 395                 400
Pro Gln Val Tyr Thr Leu Pro Pro Ser Arg Asp Glu Leu Thr Lys Asn
                405                 410                 415
Gln Val Ser Leu Thr Cys Leu Val Lys Gly Phe Tyr Pro Ser Asp Ile
                420                 425                 430
Ala Val Glu Trp Glu Ser Asn Gly Gln Pro Glu Asn Asn Tyr Lys Thr
                435                 440                 445
Thr Pro Pro Val Leu Asp Ser Asp Gly Ser Phe Phe Leu Tyr Ser Lys
                450                 455                 460
Leu Thr Val Asp Lys Ser Arg Trp Gln Gln Gly Asn Val Phe Ser Cys
465                 470                 475                 480
Ser Val Met His Glu Ala Leu His Asn His Tyr Thr Gln Lys Ser Leu
                485                 490                 495
Ser Leu Ser Pro Gly Lys
                500

<210> SEQ ID NO 33
<211> LENGTH: 2199
<212> TYPE: DNA
<213> ORGANISM: Artificial Sequence
<220> FEATURE:
<223> OTHER INFORMATION: Chemically Synthesized, pGX9362,
      EBV114_ Full length _partial graft

<400> SEQUENCE: 33
atggactgga cctggagaat cctgttcctg gtggcagcag caaccggaac acacgcagag      60
gtgcagctgg tggagagcgg cggcggcctg atccagccag cgggctccct gaggctgtct     120
tgcgcagcaa gcggatttgc actgaggatg tacgacatgc actgggtgcg gcagaccatc     180
```

```
gataagagac tggagtgggt gagcgccgtg ggaccatccg gcgacacata ctatgccgat    240
agcgtgaagg gcaggttcgc cgtgtcccgc gagaacgcca agaattctct gagcctgcag    300
atgaacagcc tgaccgccgg cgacacagcc atctactatt gcgtgcggtc cgacagaggc    360
gtggcaggcc tgttcgattc ttggggccag ggcatcctgg tgaccgtgag ctccgcctct    420
acaaagggac caagcgtgtt tccactggca ccttctagca agtccacctc tggcggcaca    480
gccgccctgg gctgtctggt gaaggattac ttccctgagc cagtgaccgt gtcttggaac    540
agcggcgccc tgacctctgg agtgcacaca tttcctgccg tgctgcagtc ctctggcctg    600
tacagcctga gctccgtggt gaccgtgcca tctagctccc tgggcaccca gacatatatc    660
tgcaacgtga atcacaagcc atctaataca aaggtggaca gaaggtgga gcccaagagc    720 tgtgataaga cccacacatg ccctccctgt ccagcacctg agctgctggg cggcccatcc    780
gtgttcctgt tccacccaa gcctaaggac accctgatga tctccaggac ccccgaggtg    840
acatgcgtgg tggtggacgt gtctcacgag gaccccgagg tgaagttcaa ctggtacgtg    900
gatggcgtgg aggtgcacaa tgccaagacc aagcccgg aggagcagta caattccacc    960
tatagagtgg tgtctgtgct gacagtgctg caccaggact ggctgaacgg caaggagtat    1020
aagtgcaagg tgagcaataa ggccctgcca gcccccatcg agaagaccat ctccaaggca    1080
aagggacagc cacgggagcc acaggtgtac acactgcctc caagcagaga cgagctgacc    1140
aagaaccagg tgtccctgac atgtctggtg aagggcttct atccttctga tatcgccgtg    1200
gagtgggaga gcaatggcca gccagagaac aattacaaga ccacaccccc tgtgctggac    1260
tccgatggct ctttctttct gtattctaag ctgaccgtgg acaagagccg ctggcagcag    1320
ggcaacgtgt ttagctgctc cgtgatgcac gaggccctgc acaatcacta cacccagaag    1380
tctctgagcc tgtcccctgg caagagggga aggaagcgga gatctggcag cggagccaca    1440
aacttcagcc tgctgaagca ggccggcgat gtggaggaga tcctggcc aatggtgctg    1500 cagacccagg tgtttatcag cctgctgctg tggatctccg gcgcctatgg cgccatccag    1560
atgacacagt ccccttctag cctgtccgcc tctgtgggcg acagggtgac catcacatgt    1620
cgcgccagcc aggccttcga taactacgtg gcctggtatc agcagaggcc tggcaaggtg    1680
ccaaagctgc tgatcagcgc cgcatccgcc ctgcacgcag gagtgccatc ccgcttcagc    1740
ggctccggct ctggaaccca ctttaccctg acaatctcct ctctgcagcc agaggacgtg    1800
gccacatact attgccagaa ctacaatagc gcacccctga ccttcggggg cgggacaaag    1860
gtggagatca gaggaccgt ggcagcacca tccgtgttca tctttccacc ctctgacgag    1920
cagctgaagt ccggcacagc ctctgtggtg tgcctgctga caacttcta ccctagagag    1980 gccaaggtgc agtggaaggt ggataacgcc ctgcagtctg gcaatagcca ggagtccgtg    2040
accgagcagg actctaagga tagcacatat agcctgtcca caccctgac actgtccaag    2100 gccgattacg agaagcacaa ggtgtatgca tgcgaggtga cccaccaggg cctgagctcc    2160
ccagtgacaa agagctttaa tagaggcgag tgttgataa                          2199
```

<210> SEQ ID NO 34
<211> LENGTH: 731
<212> TYPE: PRT
<213> ORGANISM: Artificial Sequence
<220> FEATURE:
<223> OTHER INFORMATION: Chemically Synthesized, pGX9362,
      EBV114_ Full length _partial graft

<400> SEQUENCE: 34

-continued

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Ile Gln
                20                  25                  30

Pro Gly Gly Ser Leu Arg Leu Ser Cys Ala Ala Ser Gly Phe Ala Leu
            35                  40                  45

Arg Met Tyr Asp Met His Trp Val Arg Gln Thr Ile Asp Lys Arg Leu
    50                  55                  60

Glu Trp Val Ser Ala Val Gly Pro Ser Gly Asp Thr Tyr Tyr Ala Asp
65                  70                  75                  80

Ser Val Lys Gly Arg Phe Ala Val Ser Arg Glu Asn Ala Lys Asn Ser
                85                  90                  95

Leu Ser Leu Gln Met Asn Ser Leu Thr Ala Gly Asp Thr Ala Ile Tyr
            100                 105                 110

Tyr Cys Val Arg Ser Asp Arg Gly Val Ala Gly Leu Phe Asp Ser Trp
        115                 120                 125

Gly Gln Gly Ile Leu Val Thr Val Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
```

```
            420             425             430
Val Asp Lys Ser Arg Trp Gln Gln Gly Asn Val Phe Ser Cys Ser Val
            435             440             445

Met His Glu Ala Leu His Asn His Tyr Thr Gln Lys Ser Leu Ser Leu
            450             455             460

Ser Pro Gly Lys Arg Gly Arg Lys Arg Arg Ser Gly Ser Gly Ala Thr
465             470             475             480

Asn Phe Ser Leu Leu Lys Gln Ala Gly Asp Val Glu Glu Asn Pro Gly
                485             490             495

Pro Met Val Leu Gln Thr Gln Val Phe Ile Ser Leu Leu Leu Trp Ile
            500             505             510

Ser Gly Ala Tyr Gly Ala Ile Gln Met Thr Gln Ser Pro Ser Ser Leu
            515             520             525

Ser Ala Ser Val Gly Asp Arg Val Thr Ile Thr Cys Arg Ala Ser Gln
            530             535             540

Ala Phe Asp Asn Tyr Val Ala Trp Tyr Gln Gln Arg Pro Gly Lys Val
545             550             555             560

Pro Lys Leu Leu Ile Ser Ala Ala Ser Ala Leu His Ala Gly Val Pro
                565             570             575

Ser Arg Phe Ser Gly Ser Gly Ser Gly Thr His Phe Thr Leu Thr Ile
            580             585             590

Ser Ser Leu Gln Pro Glu Asp Val Ala Thr Tyr Tyr Cys Gln Asn Tyr
            595             600             605

Asn Ser Ala Pro Leu Thr Phe Gly Gly Gly Thr Lys Val Glu Ile Lys
            610             615             620

Arg Thr Val Ala Ala Pro Ser Val Phe Ile Phe Pro Pro Ser Asp Glu
625             630             635             640

Gln Leu Lys Ser Gly Thr Ala Ser Val Val Cys Leu Leu Asn Asn Phe
                645             650             655

Tyr Pro Arg Glu Ala Lys Val Gln Trp Lys Val Asp Asn Ala Leu Gln
            660             665             670

Ser Gly Asn Ser Gln Glu Ser Val Thr Glu Gln Asp Ser Lys Asp Ser
            675             680             685

Thr Tyr Ser Leu Ser Asn Thr Leu Thr Leu Ser Lys Ala Asp Tyr Glu
            690             695             700

Lys His Lys Val Tyr Ala Cys Glu Val Thr His Gln Gly Leu Ser Ser
705             710             715             720

Pro Val Thr Lys Ser Phe Asn Arg Gly Glu Cys
                725             730

<210> SEQ ID NO 35
<211> LENGTH: 1485
<212> TYPE: DNA
<213> ORGANISM: Artificial Sequence
<220> FEATURE:
<223> OTHER INFORMATION: Chemically Synthesized, pGX9363,
      EBV114_scFv-Fc_partial graft

<400> SEQUENCE: 35
atggtgctgc agactcaggt gtttatttca ctgctgctgt ggatttcagg agcctatgga      60
gctattcaga tgactcagag cccaagcagc ctgtctgcct ccgtgggcga tagagtgaca     120
atcacctgta gagccagcca ggccttcgac aattacgtgg cctggtacca gcagagaccc     180
ggcaaggtgc caaagctgct gatcagcgcc gcctccgccc tgcacgccgg cgtgccttct     240
cgcttttccg gcagcggcag cggcacccac tttaccctga caatctccag cctgcagcct     300
```

```
gaggatgtgg ccacctacta ttgtcagaat tacaactctg ccccactgac cttcggcggc    360
ggcaccaagg tggagatcaa gggcggcggc ggcagcggcg gcggcggctc cggcggcggc    420
ggctctgagg tgcagctggt ggagtctggc ggcggcctga tccagcccgg cggctctctg    480
aggctgtcct gcgccgcctc cggctttgcc ctgcggatgt atgacatgca ctgggtgcgc    540
cagacaatcg acaagagact ggagtgggtg tctgccgtgg gccttccgg cgatacctac     600 tatgccgata gcgtgaaggg cagatttgcc gtgagcagag agaacgccaa gaactctctg    660
agcctgcaga tgaacagcct gaccgccggc gatacagcca tctactattg cgtgagaagc    720
gacagaggcg tggccggcct gttcgactct ggggccaggg catcctggt gacagtgtcc      780 agcgagccta agtcttgcga taagacccac acctgtcccc cttgcccagc ccctgagctg    840
ctgggcggcc ccagcgtgtt cctgttccca cctaagccta aggatacact gatgatctcc    900
aggacaccag aggtgacatg cgtggtggtg gacgtgtccc acgaggaccc tgaggtgaag    960
ttcaactggt acgtggatgg cgtggaggtg cacaacgcca agacaaagcc cagggaggag   1020
cagtacaaca gcacctatag agtggtgtcc gtgctgacag tgctgcacca ggattggctg   1080
aatggcaagg agtacaagtg caaggtgtcc aacaaggccc tgcccgcccc tatcgagaag   1140
accatctcca aggccaaggg ccagcctaga gagccccagg tgtataccct gcctccctct   1200
agggatgagc tgacaaagaa ccaggtgtcc ctgacctgtc tggtgaaggg cttctatcca   1260
agcgatatcg ccgtggagtg ggagtctaac ggccagcccg agaataacta caagacaacc   1320
cctccagtgc tggacagcga tggctccttc tttctgtaca gcaagctgac cgtggacaag   1380
tccaggtggc agcagggcaa cgtgtttagc tgttccgtga tgcacgaagc cctgcacaac   1440
cactacactc agaagtcact gtcactgtct cctgggaagt gataa                    1485
```

<210> SEQ ID NO 36
<211> LENGTH: 493
<212> TYPE: PRT
<213> ORGANISM: Artificial Sequence
<220> FEATURE:
<223> OTHER INFORMATION: Chemically Synthesized, pGX9363,
      EBV114_scFv-Fc_partial graft

<400> SEQUENCE: 36

```
Met Val Leu Gln Thr Gln Val Phe Ile Ser Leu Leu Trp Ile Ser
1               5                   10                  15

Gly Ala Tyr Gly Ala Ile Gln Met Thr Gln Ser Pro Ser Ser Leu Ser
            20                  25                  30

Ala Ser Val Gly Asp Arg Val Thr Ile Thr Cys Arg Ala Ser Gln Ala
        35                  40                  45

Phe Asp Asn Tyr Val Ala Trp Tyr Gln Gln Arg Pro Gly Lys Val Pro
    50                  55                  60

Lys Leu Leu Ile Ser Ala Ala Ser Ala Leu His Ala Gly Val Pro Ser
65                  70                  75                  80

Arg Phe Ser Gly Ser Gly Ser Gly Thr His Phe Thr Leu Thr Ile Ser
                85                  90                  95

Ser Leu Gln Pro Glu Asp Val Ala Thr Tyr Tyr Cys Gln Asn Tyr Asn
            100                 105                 110

Ser Ala Pro Leu Thr Phe Gly Gly Gly Thr Lys Val Glu Ile Lys Gly
        115                 120                 125

Gly Gly Gly Ser Gly Gly Gly Gly Ser Gly Gly Gly Gly Ser Glu Val
    130                 135                 140
```

Gln Leu Val Glu Ser Gly Gly Gly Leu Ile Gln Pro Gly Gly Ser Leu
145                 150                 155                 160

Arg Leu Ser Cys Ala Ala Ser Gly Phe Ala Leu Arg Met Tyr Asp Met
            165                 170                 175

His Trp Val Arg Gln Thr Ile Asp Lys Arg Leu Glu Trp Val Ser Ala
        180                 185                 190

Val Gly Pro Ser Gly Asp Thr Tyr Tyr Ala Asp Ser Val Lys Gly Arg
    195                 200                 205

Phe Ala Val Ser Arg Glu Asn Ala Lys Asn Ser Leu Ser Leu Gln Met
210                 215                 220

Asn Ser Leu Thr Ala Gly Asp Thr Ala Ile Tyr Tyr Cys Val Arg Ser
225                 230                 235                 240

Asp Arg Gly Val Ala Gly Leu Phe Asp Ser Trp Gly Gln Gly Ile Leu
                245                 250                 255

Val Thr Val Ser Ser Glu Pro Lys Ser Cys Asp Lys Thr His Thr Cys
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 37
<211> LENGTH: 2193
<212> TYPE: DNA
<213> ORGANISM: Artificial Sequence
<220> FEATURE:
<223> OTHER INFORMATION: Chemically Synthesized, pGX9224, Ebola Z5D2

<400> SEQUENCE: 37
atggattgga cttggaggat tctgtttctg gtcgccgccg ctactgggac acacgccgag      60
gtgcagctgc aggagagtgg gcctggactg gtgcgaccca gccagtccct gtctctgaca     120

```
tgcactgtga ccggctacag tatcacatca gactatgcct ggaactggat tcgccagttc      180
ccaggcaata agctggaatg gctgggatac atcacaaaca ctggcagcac cgggtttaat      240
cccagcctga agtcccgaat ctctattaca agggacactt ctaaaaacca gttctttctg      300
cagctgatta gtgtgaccac agaggatacc gcaacatacc actgcgcccg gggactggct      360
tattggggac aggggaccct ggtcacagtg agctccgcta gtacaaaggg gccttcagtg      420
ttccccctgg caccttctag taaaagtaca tcaggcggaa ctgccgctct gggctgtctg      480
gtgaaggatt acttccctga gccagtcacc gtgagttgga actcaggagc actgacctcc      540
ggggtccata catttcccgc cgtgctgcag tcaagcggcc tgtactctct gtcctctgtg      600
gtcactgtgc ctagttcaag cctgggaact cagacctata tctgcaacgt gaatcacaag      660
cctagcaata ccaaagtcga caagaaagtg aaccaaaga gctgtgataa aacacatact      720
tgcccacctt gtccagcacc tgagctgctg gaggaccaa gcgtgttcct gtttccaccc      780
aagcctaaag acacactgat gatctcccgc accccagaag tcacatgtgt ggtcgtggac      840
gtgtctcacg aggaccccga agtcaagttc aactggtacg tggatggcgt cgaggtgcat      900
aatgctaaga ccaaaccacg cgaggaacag tacaacagca catatcgagt cgtgtccgtc      960
ctgactgtgc tgcaccagga ctggctgaac ggcaaggagt ataagtgcaa agtgagcaat     1020
aaggctctgc cagcacccat cgagaaaaca attagcaagg caaaaggaca gccaagggaa     1080
ccccaggtgt acactctgcc tccatccaga gacgagctga ctaagaacca ggtctctctg     1140
acctgtctgg tgaaaggatt ctatcccagc gatatcgccg tggagtggga atccaatggg     1200
cagcctgaaa acaattacaa gactaccccc cctgtgctgg acagcgatgg gtccttcttt     1260
ctgtattcca agctgaccgt ggataaatct cggtggcagc agggcaacgt ctttagctgc     1320
tccgtgatgc atgaggccct gcacaatcat tacacacaga agtctctgag tctgtcacct     1380
ggcaagcggg gacgcaaaag gagaagcggc tccggagcaa ctaacttcag cctgctgaaa     1440
caggccgggg acgtggagga aaatcctggc ccaatggtcc tgcagaccca ggtgtttatc     1500
tctctgctgc tgtggattag tggggcctat ggcgatgtcg tgctgaccca gacaccactg     1560
actctgagcg tgaccatcgg acagcccgct tctattagtt gtaagtcctc tcagtctctg     1620
ctggacagtg atggcaaaac ctacctgaac tggctgctgc agagacctgg acagtcccca     1680
aagcggctga tctatctggt ctcaaaactg gacagcggcg tgacagatcg gttcactggg     1740
tcaggcagcg gaactgactt taccctgaag atttctcgcg tcgaggctga agatctggga     1800
gtgtactatt gctggcaggg gactcactca cctttcacct tgggagcggg cacaaagctg     1860
gaaatcaaaa ccgtcgcagc cccaagtgtg ttcatttttc caccctcaga cgagcagctg     1920
aagtccggga cagcatctgt cgtgtgtctg ctgaacaatt tctaccctag ggaggctaag     1980
gtccagtgga aagtggataa cgcactgcag tctggcaata gtcaggagtc agtgaccgaa     2040
caggacagca aggattccac atattccctg tctaacactc tgaccctgag caaagccgac     2100
tacgagaagc acaaagtcta tgcttgcgaa gtgactcatc aggggctgag ttcaccagtg     2160
accaagagct ttaatagagg cgagtgttga taa                                  2193
```

<210> SEQ ID NO 38
<211> LENGTH: 729
<212> TYPE: PRT
<213> ORGANISM: Artificial Sequence
<220> FEATURE:
<223> OTHER INFORMATION: Chemically Synthesized, pGX9224, Ebola Z5D2

-continued

```
<400> SEQUENCE: 38

Met Asp Trp Thr Trp Arg Ile Leu Phe Leu Val Ala Ala Ala Thr Gly
1               5                   10                  15

Thr His Ala Glu Val Gln Leu Gln Glu Ser Gly Pro Gly Leu Val Arg
            20                  25                  30

Pro Ser Gln Ser Leu Ser Leu Thr Cys Thr Val Thr Gly Tyr Ser Ile
        35                  40                  45

Thr Ser Asp Tyr Ala Trp Asn Trp Ile Arg Gln Phe Pro Gly Asn Lys
    50                  55                  60

Leu Glu Trp Leu Gly Tyr Ile Thr Asn Thr Gly Ser Thr Gly Phe Asn
65                  70                  75                  80

Pro Ser Leu Lys Ser Arg Ile Ser Ile Thr Arg Asp Thr Ser Lys Asn
                85                  90                  95

Gln Phe Phe Leu Gln Leu Ile Ser Val Thr Thr Glu Asp Thr Ala Thr
            100                 105                 110

Tyr His Cys Ala Arg Gly Leu Ala Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415
```

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Arg Gly
    450                 455                 460

Arg Lys Arg Arg Ser Gly Ser Ala Thr Asn Phe Ser Leu Leu Lys
465                 470                 475                 480

Gln Ala Gly Asp Val Glu Glu Asn Pro Gly Pro Met Val Leu Gln Thr
                485                 490                 495

Gln Val Phe Ile Ser Leu Leu Leu Trp Ile Ser Gly Ala Tyr Gly Asp
            500                 505                 510

Val Val Leu Thr Gln Thr Pro Leu Thr Leu Ser Val Thr Ile Gly Gln
        515                 520                 525

Pro Ala Ser Ile Ser Cys Lys Ser Ser Gln Ser Leu Leu Asp Ser Asp
    530                 535                 540

Gly Lys Thr Tyr Leu Asn Trp Leu Leu Gln Arg Pro Gly Gln Ser Pro
545                 550                 555                 560

Lys Arg Leu Ile Tyr Leu Val Ser Lys Leu Asp Ser Gly Val Thr Asp
                565                 570                 575

Arg Phe Thr Gly Ser Gly Ser Gly Thr Asp Phe Thr Leu Lys Ile Ser
            580                 585                 590

Arg Val Glu Ala Glu Asp Leu Gly Val Tyr Tyr Cys Trp Gln Gly Thr
        595                 600                 605

His Ser Pro Phe Thr Phe Gly Ser Gly Thr Lys Leu Glu Ile Lys Thr
    610                 615                 620

Val Ala Ala Pro Ser Val Phe Ile Phe Pro Pro Ser Asp Glu Gln Leu
625                 630                 635                 640

Lys Ser Gly Thr Ala Ser Val Val Cys Leu Leu Asn Asn Phe Tyr Pro
                645                 650                 655

Arg Glu Ala Lys Val Gln Trp Lys Val Asp Asn Ala Leu Gln Ser Gly
            660                 665                 670

Asn Ser Gln Glu Ser Val Thr Glu Gln Asp Ser Lys Asp Ser Thr Tyr
        675                 680                 685

Ser Leu Ser Asn Thr Leu Thr Leu Ser Lys Ala Asp Tyr Glu Lys His
    690                 695                 700

Lys Val Tyr Ala Cys Glu Val Thr His Gln Gly Leu Ser Ser Pro Val
705                 710                 715                 720

Thr Lys Ser Phe Asn Arg Gly Glu Cys
                725

<210> SEQ ID NO 39
<211> LENGTH: 2208
<212> TYPE: DNA
<213> ORGANISM: Artificial Sequence
<220> FEATURE:
<223> OTHER INFORMATION: Chemically Synthesized, pGX9225, Ebola Z1H3

<400> SEQUENCE: 39
atggattgga catggagaat cctgttcctg gtcgccgccg ctactgggac acacgccgaa      60
gtgcagctgc agcagagtgg agccgagctg gtcaaacctg ggcatccgt gaagctgtct     120 tgcactgcca gtggcttcaa catcaaagac acctacattc actgggtgaa gcagggccca     180
gagcagggac tggaatggat cggacggatt gacccagcaa acgggaatac caagtatgat     240

```
cccaaatttc agggggaaggc aaccatcaca gccgacacaa gctccaatac tgcctacctg      300
cagctgtcag gcctgaccag cgaggataca gccgtgtact attgcgccag ggagagcagg      360
atttccacca tgctgaccac aggatatttc gactactggg acaggggac taccctgacc       420 gtctctagtg ccagcacaaa agggccttcc gtgtttcccc tggctccttc aagcaagtct      480
actagtggag gaaccgcagc tctgggatgt ctggtgaagg attacttccc tgagccagtc      540
accgtgtctt ggaacagtgg ggctctgacc tccggcgtcc acacatttcc agcagtgctg      600
cagtcctctg ggctgtattc tctgagttca gtggtcaccg tgcccagctc ctctctgggc      660
actcagacct acatctgcaa cgtgaatcac aaaccctcca atacaaaggt cgacaagaaa      720
gtggaaccta atcttgtga taagacacat acttgcccac cttgtccagc acctgagctg      780
ctgggaggac ctagcgtgtt cctgtttcca cccaagccaa agacaccct gatgatcagc       840 cgcacacctg aagtcacttg tgtggtcgtg gacgtgtccc acgaggaccc cgaagtcaag      900
ttcaactggt acgtggatgg cgtcgaggtg cataatgcca agacaaaacc cagagaggaa     960
cagtataact ctacataccg ggtcgtgagt gtcctgactg tgctgcacca ggattggctg     1020
aacggcaagg agtacaagtg caaagtgtct aacaaggccc tgccagctcc catcgagaag     1080
accattagca aggccaaagg acagccacgc gaaccccagg tgtatacact gcctcccagc     1140
agggacgagc tgactaaaaa ccaggtcagc ctgacctgtc tggtgaaggg cttctaccca     1200
agcgatatcg ctgtggagtg ggaatccaat ggacagcccg aaaacaatta agacaact      1260 ccccctgtgc tggactcaga tggcagcttc tttctgtaca gtaaactgac cgtggacaag     1320
tcaagatggc agcagggaaa cgtcttttca tgcagcgtga tgcatgaggc cctgcacaat     1380
cattatactc agaagtccct gtctctgagt ccagggaaac ggggccgcaa gaggagatca     1440
ggcagcggag ctacaaactt cagcctgctg aagcaggcag cgatgtgga ggaaaatcct      1500 ggaccaatgg tcctgcagac tcaggtgttt atctcactgc tgctgtggat agcggagcc      1560 tacgacagat cgtgctgac ccagtcccca gctattatgt ccgcatctcc tggcgagaaa      1620
gtgaccatga catgttccgc tagttcaagc gtgtcttaca tgtattggta ccagcagaag     1680
cctggcagca gccaaggct gctgatctat gacacctcca acctggcttc tggggtcccc     1740
gtgagattca gtgggtcagg cagcggaact tcctactctc tgaccattc ccggatggag      1800 gcagaagatg cagccacata ctattgccag cagtggagtt catatcccta cactttgga     1860 gggggcacta aactggaaat caagacagtc gctgcacctt ctgtgttcat ttttccaccc     1920
agtgacgagc agctgaagag tggcactgcc tcagtcgtgt gtctgctgaa caatttctat     1980
ccccgcgagg ccaaagtcca gtggaaggtg gataacgctc tgcagtccgg caattctcag     2040
gagagtgtga ccgaacagga ctcaaaagat agcacataca gtctgtcaaa cactctgacc     2100
ctgagcaagg cagactatga aagcacaaa gtctacgcct gcgaagtgac acatcaggga     2160
ctgagctccc ctgtgactaa gtcctttaat cgaggggagt gttgataa              2208
```

<210> SEQ ID NO 40
<211> LENGTH: 734
<212> TYPE: PRT
<213> ORGANISM: Artificial Sequence
<220> FEATURE:
<223> OTHER INFORMATION: Chemically Synthesized, pGX9225, Ebola Z1H3

<400> SEQUENCE: 40

Met Asp Trp Thr Trp Arg Ile Leu Phe Leu Val Ala Ala Ala Thr Gly
1               5                   10                  15

Thr His Ala Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Thr Tyr Ile His Trp Val Lys Gln Gly Pro Glu Gln Gly Leu
 50                  55                  60

Glu Trp Ile Gly Arg Ile Asp Pro Ala Asn Gly Asn Thr Lys Tyr Asp
 65                  70                  75                  80

Pro Lys Phe Gln Gly Lys Ala Thr Ile Thr Ala Asp Thr Ser Ser Asn
                85                  90                  95

Thr Ala Tyr Leu Gln Leu Ser Gly Leu Thr Ser Glu Asp Thr Ala Val
            100                 105                 110

Tyr Tyr Cys Ala Arg Glu Ser Arg Ile Ser Thr Met Leu Thr Thr Gly
        115                 120                 125

Tyr Phe Asp Tyr Trp Gly Gln Gly Thr Thr Leu Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val

```
              435                 440                 445
Phe Ser Cys Ser Val Met His Glu Ala Leu His Asn His Tyr Thr Gln
        450                 455                 460
Lys Ser Leu Ser Leu Ser Pro Gly Lys Arg Gly Arg Lys Arg Arg Ser
465                 470                 475                 480
Gly Ser Gly Ala Thr Asn Phe Ser Leu Leu Lys Gln Ala Gly Asp Val
                    485                 490                 495
Glu Glu Asn Pro Gly Pro Met Val Leu Gln Thr Gln Val Phe Ile Ser
                500                 505                 510
Leu Leu Leu Trp Ile Ser Gly Ala Tyr Gly Gln Ile Val Leu Thr Gln
            515                 520                 525
Ser Pro Ala Ile Met Ser Ala Ser Pro Gly Glu Lys Val Thr Met Thr
        530                 535                 540
Cys Ser Ala Ser Ser Val Ser Tyr Met Tyr Trp Tyr Gln Gln Lys
545                 550                 555                 560
Pro Gly Ser Ser Pro Arg Leu Leu Ile Tyr Asp Thr Ser Asn Leu Ala
                565                 570                 575
Ser Gly Val Pro Val Arg Phe Ser Gly Ser Gly Ser Gly Thr Ser Tyr
                580                 585                 590
Ser Leu Thr Ile Ser Arg Met Glu Ala Glu Asp Ala Ala Thr Tyr Tyr
            595                 600                 605
Cys Gln Gln Trp Ser Ser Tyr Pro Tyr Thr Phe Gly Gly Gly Thr Lys
        610                 615                 620
Leu Glu Ile Lys Thr Val Ala Ala Pro Ser Val Phe Ile Phe Pro Pro
625                 630                 635                 640
Ser Asp Glu Gln Leu Lys Ser Gly Thr Ala Ser Val Val Cys Leu Leu
                645                 650                 655
Asn Asn Phe Tyr Pro Arg Glu Ala Lys Val Gln Trp Lys Val Asp Asn
                660                 665                 670
Ala Leu Gln Ser Gly Asn Ser Gln Glu Ser Val Thr Glu Gln Asp Ser
            675                 680                 685
Lys Asp Ser Thr Tyr Ser Leu Ser Asn Thr Leu Thr Leu Ser Lys Ala
        690                 695                 700
Asp Tyr Glu Lys His Lys Val Tyr Ala Cys Glu Val Thr His Gln Gly
705                 710                 715                 720
Leu Ser Ser Pro Val Thr Lys Ser Phe Asn Arg Gly Glu Cys
                    725                 730

<210> SEQ ID NO 41
<211> LENGTH: 2208
<212> TYPE: DNA
<213> ORGANISM: Artificial Sequence
<220> FEATURE:
<223> OTHER INFORMATION: Chemically Synthesized, pGX9228, Ebola ZBDBV223

<400> SEQUENCE: 41
atggattgga cttggagaat tctgtttctg gtggccgccg ctacaggaac tcacgctcag      60
gtgcagctgc agcagtgggg agccgggctg ctgaagccaa gcagacact gtccctgact      120 tgcgccgtgt acggcggaag cttcaccaca acttattgga attggatcag cagcccccct     180
ggcaagggac tggagtggat tggggaagtg aactacagcg gcaacgctaa ttataacccc     240
tccctgaagg gccgagtcgc aatctctgtg gacactagta aaaatcagtt tagtctgagg     300
ctgaactcag tgaccgccgc tgatacagca atctactatt gcaccagcag gatcaggagc     360
cacattgcct actcctggaa gggagacgtg tggggaaag gcaccacagt caccgtgagc      420
```

```
tccgccagca caaagggacc atccgtgttc ccactggctc cctctagtaa aagtacttca    480
gggggcaccg cagccctggg atgtctggtg aaggattact tccccgagcc tgtcaccgtg    540
tcctggaatt ctggcgcact gacctctgga gtccatacat ttccagccgt gctgcagtca    600
agcgggctgt acagcctgtc ctctgtggtc accgtcccca gttcaagcct gggcacacag    660
acttatatct gcaatgtgaa ccacaagccc tctaacacaa aagtcgacaa gaaagtggaa    720
cctaagagct gtgataaaac ccatacatgc ccaccctgtc cagcaccaga gctgctggga    780
gggcctagcg tgttcctgtt tcctccaaag ccaaaagaca cactgatgat tagcaggaca    840
cctgaagtca cttgcgtggt cgtggacgtg tcccacgagg accccgaagt caagtttaat    900
tggtacgtgg atggcgtcga ggtgcataac gctaagacca aacctaggga ggaacagtac    960
aactctacat atagagtcgt gagtgtcctg actgtgctgc accaggactg gctgaatggg   1020
aaggagtata agtgcaaagt gtctaacaag gcactgcctg ccccaatcga gaaaactatt   1080
agcaaggcta aggccagcc tcgggaacca caggtgtaca ccctgccccc tagccgcgac   1140
gagctgacta agaatcaggt ctccctgacc tgtctggtga aggcttcta tccatctgat   1200 atcgcagtgg agtgggaaag taacggacag cccgaaaaca attacaagac tacccccaccc   1260 gtcctggaca gtgatggctc attctttctg tattccaagc tgaccgtgga caaatctaga   1320
tggcagcagg gaaatgtctt tagctgctcc gtgatgcacg aggccctgca caaccattac   1380
actcagaagt ctctgagtct gtcaccaggg aagcgaggca ggaaaaggag aagcggcagc   1440
ggggcaacca attctctct gctgaaacag gccgagatg tggaggaaaa ccccgggcct   1500
atggtcctgc agacacaggt gtttatctca ctgctgctgt ggattagcgg agcctacggg   1560
gaaatcgtga tgactcagag cccaggcacc tgtctctga gtcccggaga gagagctaca   1620
ctgtcctgtc gggcatcaca gagcgtgccc agaaattaca tcggatggtt ccagcagaag   1680
ccaggacagg cccctcggct gctgatctac ggagcttcct ctcgcgctgc agggttccct   1740
gaccgatttt ccggctctgg aagtgggacc gatttcactc tgaccatcac acgcctggag   1800
cccgaagact tgccatgta ctattgccac cagtacgatc gactgcctta tacattcggc   1860
cagggaacta agctggaaat caaaacagtc gccgctccta gcgtgttcat ctttcctcca   1920
tcagacgagc agctgaagtc cggaactgct tctgtggtgt gcctgctgaa caacttctac   1980
ccacgcgaag ctaaggtcca gtggaaagtg ataatgcac tgcagagcgg caactcccag   2040
gagtctgtga ccgaacagga cagtaaggat tcaacatatt cactgagcaa cactctgacc   2100
ctgtccaaag ccgactacga gaagcataaa gtgtatgctt gcgaggtcac ccaccagggg   2160
ctgtcatctc cagtcactaa gtccttcaat agaggcgaat gttgataa    2208
```

<210> SEQ ID NO 42
<211> LENGTH: 734
<212> TYPE: PRT
<213> ORGANISM: Artificial Sequence
<220> FEATURE:
<223> OTHER INFORMATION: Chemically Synthesized, pGX9228, Ebola ZBDBV223

<400> SEQUENCE: 42

Met Asp Trp Thr Trp Arg Ile Leu Phe Leu Val Ala Ala Ala Thr Gly
1               5                   10                  15

Thr His Ala Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

```
Thr Thr Thr Tyr Trp Asn Trp Ile Arg Gln Pro Pro Gly Lys Gly Leu
         50              55                  60
Glu Trp Ile Gly Glu Val Asn Tyr Ser Gly Asn Ala Asn Tyr Asn Pro
 65              70                  75                      80
Ser Leu Lys Gly Arg Val Ala Ile Ser Val Asp Thr Ser Lys Asn Gln
                 85                  90                  95
Phe Ser Leu Arg Leu Asn Ser Val Thr Ala Ala Asp Thr Ala Ile Tyr
                100                 105                 110
Tyr Cys Thr Ser Arg Ile Arg Ser His Ile Ala Tyr Ser Trp Lys Gly
             115                 120                 125
Asp Val Trp Gly Lys Gly Thr Thr Val Thr Val Ser Ser Ala Ser Thr
        130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
        210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
        290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
        355                 360                 365
Glu Pro Gln Val Tyr Thr Leu Pro Pro Ser Arg Asp Glu Leu Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
        450                 455                 460
```

Leu Ser Leu Ser Pro Gly Lys Arg Gly Arg Lys Arg Ser Gly Ser
465                 470                 475                 480

Gly Ala Thr Asn Phe Ser Leu Leu Lys Gln Ala Gly Asp Val Glu Glu
            485                 490                 495

Asn Pro Gly Pro Met Val Leu Gln Thr Gln Val Phe Ile Ser Leu Leu
            500                 505                 510

Leu Trp Ile Ser Gly Ala Tyr Gly Glu Ile Val Met Thr Gln Ser Pro
        515                 520                 525

Gly Thr Leu Ser Leu Ser Pro Gly Glu Arg Ala Thr Leu Ser Cys Arg
530                 535                 540

Ala Ser Gln Ser Val Pro Arg Asn Tyr Ile Gly Trp Phe Gln Gln Lys
545                 550                 555                 560

Pro Gly Gln Ala Pro Arg Leu Leu Ile Tyr Gly Ala Ser Ser Arg Ala
            565                 570                 575

Ala Gly Phe Pro Asp Arg Phe Ser Gly Ser Gly Ser Gly Thr Asp Phe
            580                 585                 590

Thr Leu Thr Ile Thr Arg Leu Glu Pro Glu Asp Phe Ala Met Tyr Tyr
        595                 600                 605

Cys His Gln Tyr Asp Arg Leu Pro Tyr Thr Phe Gly Gln Gly Thr Lys
610                 615                 620

Leu Glu Ile Lys Thr Val Ala Ala Pro Ser Val Phe Ile Phe Pro Pro
625                 630                 635                 640

Ser Asp Glu Gln Leu Lys Ser Gly Thr Ala Ser Val Val Cys Leu Leu
            645                 650                 655

Asn Asn Phe Tyr Pro Arg Glu Ala Lys Val Gln Trp Lys Val Asp Asn
            660                 665                 670

Ala Leu Gln Ser Gly Asn Ser Gln Glu Ser Val Thr Glu Gln Asp Ser
        675                 680                 685

Lys Asp Ser Thr Tyr Ser Leu Ser Asn Thr Leu Thr Leu Ser Lys Ala
690                 695                 700

Asp Tyr Glu Lys His Lys Val Tyr Ala Cys Glu Val Thr His Gln Gly
705                 710                 715                 720

Leu Ser Ser Pro Val Thr Lys Ser Phe Asn Arg Gly Glu Cys
            725                 730

<210> SEQ ID NO 43
<211> LENGTH: 2223
<212> TYPE: DNA
<213> ORGANISM: Artificial Sequence
<220> FEATURE:
<223> OTHER INFORMATION: Chemically Synthesized, pGX9256, 1A2

<400> SEQUENCE: 43
atggactgga cctggagaat cctgttcctg gtggcagcag caaccggaac acacgcagag      60
gtgcagctgg tggagagcgg cggcggcctg atccagccag gcggcagcct gaggctgtcc     120
tgcgcagcat ctggatttgc cgtgaggagc aactacctgt cctgggtgag acaggcacca     180
ggcaagggac tggagtgggt gtctctgatc tacagcggcg gcctgaccgc atatgcagac     240
agcgtggagg gcaggttcac catctccaga gataactcta agaatacact gtatctgcag     300
atgaattccc tgcgggtgga ggacaccgcc ctgtactatt gcgcccgcgt ggccagctcc     360
gccggcacat tctactatgg catggacgtg tggggccagg gcaccacagt gaccgtgtct     420
agcgcctcca caagggacc aagcgtgttc ccactggcac cttcctctaa gtccacctct     480
ggcggcacag ccgccctggg ctgtctggtg aaggattact ccctgagcc agtgaccgtg     540

```
tcttggaaca gcggcgccct gaccagcgga gtgcacacat ttcctgccgt gctgcagagc    600
tccggcctgt actccctgtc tagcgtggtg accgtgccat cctctagcct gggcacccag    660
acatatatct gcaacgtgaa tcacaagcct agcaatacaa aggtggacaa gaaggtggag    720
ccaaagtcct gtgataagac ccacacatgc cctccctgtc cagcacctga gctgctgggc    780
ggcccaagcg tgttcctgtt tccacccaag cccaaggaca cactgatgat ctctaggacc    840
ccagaggtga catgcgtggt ggtggacgtg agccacgagg accccgaggt gaagtttaac    900
tggtacgtgg atggcgtgga ggtgcacaat gccaagacca gccaaggga ggagcagtac    960
aacagcacct atagagtggt gtccgtgctg acagtgctgc accaggactg gctgaacggc    1020
aaggagtata agtgcaaggt gtccaataag gccctgccag cccccatcga aagaccatc    1080
tctaaggcaa agggacagcc aagggagcca caggtgtaca cactgcctcc atccagagac    1140
gagctgacca agaaccaggt gtctctgaca tgtctggtga agggcttcta tccctctgat    1200
atcgccgtgg agtgggagag caatggccag cctgagaaca attacaagac cacacccct    1260
gtgctggact ccgatggctc tttctttctg tattccaagc tgaccgtgga taagtctcgg    1320
tggcagcagg gcaacgtgtt tagctgctcc gtgatgcacg aggccctgca caatcactac    1380
acccagaagt ctctgagcct gtcccctggc aagaggggaa ggaagaggag atctggcagc    1440
ggcgccacaa acttcagcct gctgaagcag gcaggcgacg tggaggagaa tcctggacca    1500
atggtgctgc agacccaggt gtttatctct ctgctgctgt ggatcagcgg cgcctacggc    1560
gatatcgtga tgacccagtc ccctcgctcc ctgtctgtga cacctggcga gccagccagc    1620
atctcctgtc ggtcctctca gtctctgctg caccgcaacg gctacaatta tctggactgg    1680
tacctgcaga gcccggcca gtcccctcag ctgctgatct atctgggcag caacagggca    1740
tccggagtgc cagaccgctt ctctggcagc ggctccggaa ccgacttcac cctgaagatc    1800
agcagggtgg aggccgagga tgtgggcgtg tactattgca tgcaggccct gcagaccccc    1860
tcctggacat tcggccaggg caccaaggtg gagatcaaga cagtgccgc ccctagcgtg    1920
ttcatctttc cacccctccga cgagcagctg aagtctggca ccgccagcgt ggtgtgcctg    1980
ctgaacaact tctaccccag agaggccaag gtgcagtgga aggtggataa cgccctgcag    2040
agcggcaatt cccaggagtc tgtgaccgag caggacagca aggattccac atattctctg    2100
agctccaccc tgacactgag caaggccgac tacgagaagc acaaggtgta tgcctgcgag    2160
gtgacccacc agggcctgtc tagccctgtg acaaagtcct tcaacagagg cgagtgttga    2220
taa                                                                 2223
```

<210> SEQ ID NO 44
<211> LENGTH: 739
<212> TYPE: PRT
<213> ORGANISM: Artificial Sequence
<220> FEATURE:
<223> OTHER INFORMATION: Chemically Synthesized, pGX9256, 1A2

<400> SEQUENCE: 44

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Ile Gln
            20                  25                  30

Pro Gly Gly Ser Leu Arg Leu Ser Cys Ala Ala Ser Gly Phe Ala Val
        35                  40                  45

Arg Ser Asn Tyr Leu Ser Trp Val Arg Gln Ala Pro Gly Lys Gly Leu
    50                  55                  60
```

```
Glu Trp Val Ser Leu Ile Tyr Ser Gly Gly Leu Thr Ala Tyr Ala Asp
 65                  70                  75                  80

Ser Val Glu Gly Arg Phe Thr Ile Ser Arg Asp Asn Ser Lys Asn Thr
                 85                  90                  95

Leu Tyr Leu Gln Met Asn Ser Leu Arg Val Glu Asp Thr Ala Leu Tyr
            100                 105                 110

Tyr Cys Ala Arg Val Ala Ser Ala Gly Thr Phe Tyr Tyr Gly Met
        115                 120                 125

Asp Val Trp Gly Gln Gly Thr Thr Val Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
        450                 455                 460

Leu Ser Leu Ser Pro Gly Lys Arg Gly Arg Lys Arg Arg Ser Gly Ser
465                 470                 475                 480
```

```
Gly Ala Thr Asn Phe Ser Leu Leu Lys Gln Ala Gly Asp Val Glu Glu
                485                 490                 495

Asn Pro Gly Pro Met Val Leu Gln Thr Gln Val Phe Ile Ser Leu Leu
            500                 505                 510

Leu Trp Ile Ser Gly Ala Tyr Gly Asp Ile Val Met Thr Gln Ser Pro
        515                 520                 525

Arg Ser Leu Ser Val Thr Pro Gly Glu Pro Ala Ser Ile Ser Cys Arg
    530                 535                 540

Ser Ser Gln Ser Leu Leu His Arg Asn Gly Tyr Asn Tyr Leu Asp Trp
545                 550                 555                 560

Tyr Leu Gln Lys Pro Gly Gln Ser Pro Gln Leu Leu Ile Tyr Leu Gly
                565                 570                 575

Ser Asn Arg Ala Ser Gly Val Pro Asp Arg Phe Ser Gly Ser Gly Ser
            580                 585                 590

Gly Thr Asp Phe Thr Leu Lys Ile Ser Arg Val Glu Ala Glu Asp Val
        595                 600                 605

Gly Val Tyr Tyr Cys Met Gln Ala Leu Gln Thr Pro Ser Trp Thr Phe
    610                 615                 620

Gly Gln Gly Thr Lys Val Glu Ile Lys Thr Val Ala Ala Pro Ser Val
625                 630                 635                 640

Phe Ile Phe Pro Pro Ser Asp Glu Gln Leu Lys Ser Gly Thr Ala Ser
                645                 650                 655

Val Val Cys Leu Leu Asn Asn Phe Tyr Pro Arg Glu Ala Lys Val Gln
            660                 665                 670

Trp Lys Val Asp Asn Ala Leu Gln Ser Gly Asn Ser Gln Glu Ser Val
        675                 680                 685

Thr Glu Gln Asp Ser Lys Asp Ser Thr Tyr Ser Leu Ser Ser Thr Leu
    690                 695                 700

Thr Leu Ser Lys Ala Asp Tyr Glu Lys His Lys Val Tyr Ala Cys Glu
705                 710                 715                 720

Val Thr His Gln Gly Leu Ser Ser Pro Val Thr Lys Ser Phe Asn Arg
                725                 730                 735

Gly Glu Cys

<210> SEQ ID NO 45
<211> LENGTH: 2196
<212> TYPE: DNA
<213> ORGANISM: Artificial Sequence
<220> FEATURE:
<223> OTHER INFORMATION: Chemically Synthesized, pGX9290, EBV114

<400> SEQUENCE: 45
atggactgga catggagaat cctgttcctg gtcgccgccg ctactgggac tcacgccgag      60
gtgcagctgg tcgaaagtgg aggggactg atccagccag gcggaagcct gcgactgtcc     120
tgcgcagctt ctggattcgc actgcgcatg tacgacatgc actgggtgcg ccagacaatt     180
gataagcgac tggaatgggt cagcgccgtg ggaccatccg ggacactta ctatgctgat     240 tctgtgaagg ggagatttgc tgtcagtcgg gagaacgcaa aaattctctc gagtctgcag     300
atgaactctc tgaccgcagg cgacacagcc atctactatt gcgtgcgatc cgacaggggc     360
gtcgcaggac tgttcgattc ttggggccag ggaattctgg tcacagtgag ctccgcctct     420
actaagggac caagcgtgtt cccactggct ccttctagta aatcaactag cgggggcacc     480
gcagccctgg gatgtctggt gaaggattac ttccctgagc cagtcaccgt gagttggaac     540
tcaggcgcac tgaccagcgg agtgcataca tttcctgccg tcctgcagtc aagcggcctg     600
```

```
tactccctgt cctctgtggt cacagtgcca agttcaagcc tgggaactca gacctatatc    660
tgcaacgtga atcacaagcc atctaatact aaagtcgaca agaaagtgga acccaagagc    720
tgtgataaaa cacatacttg ccctccctgt ccagcacctg agctgctggg agggccaagc    780
gtgttcctgt ttccacccaa gcctaaagac accctgatga ttagccggac acccgaagtg    840
acttgcgtgg tcgtggacgt gagccacgag gaccccgaag tgaagttcaa ctggtacgtg    900
gatggcgtcg aggtgcataa tgctaagaca aaaccccggg aggaacagta caattcaact    960
tatcgcgtcg tgagcgtcct gaccgtgctg caccaggact ggctgaacgg aaaggagtat   1020
aagtgcaaag tgtctaataa ggcactgcca gcccccatcg agaaaaccat tagcaaggcc   1080
aaagggcagc caagggaacc ccaggtgtac acactgcctc caagtagaga cgagctgacc   1140
aagaaccagg tgtccctgac atgtctggtc aaaggattct atccttcaga tatcgctgtg   1200
gagtgggaaa gcaatgggca gccagaaaac aattacaaga ccacaccccc tgtgctggac   1260
agcgatggca gcttcttcct gtatagtaag ctgaccgtgg ataaatcaag gtggcagcag   1320
gggaacgtct tttcctgctc tgtgatgcat gaggccctgc acaatcatta cacccagaag   1380
agtctgtcac tgagccctgg gaagcgagga cgaaaaagga gatccgggtc tggcgccaca   1440
aacttcagcc tgctgaagca ggctggggac gtggaggaaa atcctggccc aatggtcctg   1500
cagacccagg tgtttatctc cctgctgctg tggattctg gagcatatgg ggatatccag   1560
atgacacagt ctccttcctc tctgagtgct tcagtgggcg acaggatcac cattacatgt   1620
agagctagcc aggcattcga taactacgtg gcctggtatc agcagcggcc tgggaaggtg   1680
ccaaaactgc tgatctctgc tgcaagtgcc ctgcacgctg gagtgccaag ccgcttcagc   1740
ggcagcgggt ctggaactca cttcacccctg accattagtt cactgcagcc agaggacgtg   1800
gctacctact attgccagaa ctacaattcc gcaccctga ctttcggcgg agggaccaag   1860
gtcgaaatca aaactgtggc cgctcccagc gtcttcattt tccacccctc cgacgagcag   1920
ctgaagagtg gcaccgcctc agtggtgtgc ctgctgaaca acttctaccc tagagaagca   1980
aaggtccagt ggaaagtgga taacgccctg cagtcaggaa atagccagga gtccgtgaca   2040
gaacaggact ctaaggatag tacttattca ctgagctcca cactgactct gtccaaagct   2100
gactacgaga agcacaaagt gtatgcatgc gaagtgaccc accagggact gagcagcccc   2160
gtgaccaaga gctttaatag aggagaatgt tgataa   2196
```

<210> SEQ ID NO 46
<211> LENGTH: 730
<212> TYPE: PRT
<213> ORGANISM: Artificial Sequence
<220> FEATURE:
<223> OTHER INFORMATION: Chemically Synthesized, pGX9290, EBV114

<400> SEQUENCE: 46

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Ile Gln
            20                  25                  30

Pro Gly Gly Ser Leu Arg Leu Ser Cys Ala Ala Ser Gly Phe Ala Leu
        35                  40                  45

Arg Met Tyr Asp Met His Trp Val Arg Gln Thr Ile Asp Lys Arg Leu
    50                  55                  60

Glu Trp Val Ser Ala Val Gly Pro Ser Gly Asp Thr Tyr Tyr Ala Asp
65                  70                  75                  80
```

```
Ser Val Lys Gly Arg Phe Ala Val Ser Arg Glu Asn Ala Lys Asn Ser
                85                  90                  95

Leu Ser Leu Gln Met Asn Ser Leu Thr Ala Gly Asp Thr Ala Ile Tyr
                100                 105                 110

Tyr Cys Val Arg Ser Asp Arg Gly Val Ala Gly Leu Phe Asp Ser Trp
            115                 120                 125

Gly Gln Gly Ile Leu Val Thr Val Ser Ala Ser Thr Lys Gly Pro
        130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Gln Thr Tyr Ile Cys Asn Val Asn
                210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
                275                 280                 285

His Glu Asp Pro Glu Val Lys Phe Asn Trp Tyr Val Asp Gly Val Glu
                290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Asp Glu Leu Thr Lys Asn Gln Val
                370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
                450                 455                 460

Ser Pro Gly Lys Arg Gly Arg Lys Arg Arg Ser Gly Ser Gly Ala Thr
465                 470                 475                 480

Asn Phe Ser Leu Leu Lys Gln Ala Gly Asp Val Glu Glu Asn Pro Gly
                485                 490                 495
```

```
Pro Met Val Leu Gln Thr Gln Val Phe Ile Ser Leu Leu Trp Ile
            500                 505                 510
Ser Gly Ala Tyr Gly Asp Ile Gln Met Thr Gln Ser Pro Ser Ser Leu
            515                 520                 525
Ser Ala Ser Val Gly Asp Arg Ile Thr Ile Thr Cys Arg Ala Ser Gln
            530                 535                 540
Ala Phe Asp Asn Tyr Val Ala Trp Tyr Gln Gln Arg Pro Gly Lys Val
545                 550                 555                 560
Pro Lys Leu Leu Ile Ser Ala Ala Ser Leu His Ala Gly Val Pro
            565                 570                 575
Ser Arg Phe Ser Gly Ser Gly Ser Gly Thr His Phe Thr Leu Thr Ile
            580                 585                 590
Ser Ser Leu Gln Pro Glu Asp Val Ala Thr Tyr Tyr Cys Gln Asn Tyr
            595                 600                 605
Asn Ser Ala Pro Leu Thr Phe Gly Gly Gly Thr Lys Val Glu Ile Lys
            610                 615                 620
Thr Val Ala Ala Pro Ser Val Phe Ile Phe Pro Pro Ser Asp Glu Gln
625                 630                 635                 640
Leu Lys Ser Gly Thr Ala Ser Val Val Cys Leu Leu Asn Asn Phe Tyr
            645                 650                 655
Pro Arg Glu Ala Lys Val Gln Trp Lys Val Asp Asn Ala Leu Gln Ser
            660                 665                 670
Gly Asn Ser Gln Glu Ser Val Thr Glu Gln Asp Ser Lys Asp Ser Thr
            675                 680                 685
Tyr Ser Leu Ser Ser Thr Leu Thr Leu Ser Lys Ala Asp Tyr Glu Lys
            690                 695                 700
His Lys Val Tyr Ala Cys Glu Val Thr His Gln Gly Leu Ser Ser Pro
705                 710                 715                 720
Val Thr Lys Ser Phe Asn Arg Gly Glu Cys
            725                 730

<210> SEQ ID NO 47
<211> LENGTH: 108
<212> TYPE: PRT
<213> ORGANISM: Artificial Sequence
<220> FEATURE:
<223> OTHER INFORMATION: Chemically Synthesized

<400> SEQUENCE: 47

Glu Thr Thr Leu Thr Gln Ser Pro Gly Thr Leu Ser Leu Ser Pro Gly
1               5                   10                  15
Glu Arg Ala Thr Leu Ser Cys Arg Ala Ser Glu Asn Ile Tyr Ser Tyr
            20                  25                  30
Leu Ala Trp Tyr Gln Gln Lys Gln Gly Lys Ser Pro Gln Leu Leu Val
            35                  40                  45
Tyr Asn Ala Lys Thr Leu Ile Glu Gly Val Pro Ser Arg Phe Ser Gly
        50                  55                  60
Ser Gly Ser Gly Thr Gln Phe Ser Leu Lys Ile Asn Ser Leu Gln Pro
65                  70                  75                  80
Glu Asp Phe Gly Ser Tyr Phe Cys Gln His His Phe Gly Thr Pro Phe
            85                  90                  95
Thr Phe Gly Ser Gly Thr Lys Leu Glu Ile Lys Arg
            100                 105

<210> SEQ ID NO 48
<211> LENGTH: 107
```

```
<212> TYPE: PRT
<213> ORGANISM: Artificial Sequence
<220> FEATURE:
<223> OTHER INFORMATION: Chemically Synthesized

<400> SEQUENCE: 48

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ile Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Phe Cys Gln His His Phe Gly Thr Pro Phe
                85                  90                  95

Thr Phe Gly Ser Gly Thr Glu Leu Glu Ile Lys
            100                 105

<210> SEQ ID NO 49
<211> LENGTH: 107
<212> TYPE: PRT
<213> ORGANISM: Artificial Sequence
<220> FEATURE:
<223> OTHER INFORMATION: Chemically Synthesized

<400> SEQUENCE: 49

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ile Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Phe Cys Gln His His Phe Gly Thr Pro Phe
                85                  90                  95

Thr Phe Gly Ser Gly Thr Glu Leu Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: Chemically Synthesized

<400> SEQUENCE: 50

Asp Ile Gln Met Thr Gln Ser Pro Ala Ser Leu Ser Ala Ser Val Gly
1               5                   10                  15

Glu Thr Val Thr Ile Thr Cys Asn Ala Ser Glu Asn Ile Tyr Ser Tyr
            20                  25                  30

Leu Ala Trp Tyr Gln Gln Lys Gln Gly Gln Ser Pro Gln Leu Leu Val
        35                  40                  45

Tyr Asn Ala Lys Thr Leu Ile Glu Gly Val Pro Ser Arg Phe Ser Gly
```

```
                50                  55                  60
Ser Gly Ser Gly Thr Gln Phe Ser Leu Lys Ile Asn Ser Leu Gln Pro
 65                  70                  75                  80

Glu Asp Phe Gly Ser Tyr Trp Cys Gln His His Phe Gly Thr Pro Phe
                 85                  90                  95

Thr Phe Gly Ser Gly Thr Glu Leu Glu Ile Lys
                100                 105
```

<210> SEQ ID NO 51
<211> LENGTH: 119
<212> TYPE: PRT
<213> ORGANISM: Artificial Sequence
<220> FEATURE:
<223> OTHER INFORMATION: Chemically Synthesized

<400> SEQUENCE: 51

```
Gln Val Gln Leu Gln Gln Ser Gly Pro Glu Leu Glu Met Pro Gly Ala
 1               5                  10                  15

Ser Val Lys Ile Ser Cys Lys Ala Ser Gly Ser Ser Phe Thr Gly Phe
                20                  25                  30

Ser Met Asn Trp Val Lys Gln Ser Asn Gly Lys Ser Leu Glu Trp Ile
             35                  40                  45

Gly Asn Ile Asp Thr Tyr Tyr Gly Gly Thr Thr Tyr Asn Gln Lys Phe
 50                  55                  60

Lys Gly Lys Ala Thr Leu Thr Val Asp Lys Ser Ser Thr Ala Tyr
 65                  70                  75                  80

Met Gln Leu Lys Ser Leu Thr Ser Glu Asp Ser Ala Val Tyr Tyr Cys
                 85                  90                  95

Ala Arg Ser Ala Tyr Tyr Gly Ser Thr Phe Ala Tyr Trp Gly Gln Gly
                100                 105                 110

Thr Leu Val Thr Val Ser Ser
            115
```

<210> SEQ ID NO 52
<211> LENGTH: 119
<212> TYPE: PRT
<213> ORGANISM: Artificial Sequence
<220> FEATURE:
<223> OTHER INFORMATION: Chemically Synthesized

<400> SEQUENCE: 52

```
Gln Val Gln Leu Gln Gln Ser Gly Pro Glu Leu Glu Met Pro Gly Ala
 1               5                  10                  15

Ser Val Lys Ile Ser Cys Gln Ala Ser Gly Ser Ser Phe Thr Gly Phe
                20                  25                  30

Ser Met Asn Trp Val Lys Tyr Ser Asn Gly Lys Ser Leu Glu Trp Ile
             35                  40                  45

Gly Asn Ile Asp Thr Tyr Tyr Gly Gly Thr Thr Tyr Asn Gln Lys Phe
 50                  55                  60

Lys Gly Lys Ala Thr Leu Thr Val Asp Lys Ser Ser Thr Ala Tyr
 65                  70                  75                  80

Met Gln Leu Gln Ser Leu Thr Ser Glu Asp Ser Ala Val Tyr Tyr Cys
                 85                  90                  95

Ala Arg Ser Ala Tyr Tyr Gly Ser Thr Phe Ala Tyr Trp Gly Gln Gly
                100                 105                 110

Thr Leu Val Thr Val Ser Ser
            115
```

```
<210> SEQ ID NO 53
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 53

Gly Gly Gly Gly Ser Gly Gly Gly Gly Ser Gly Gly Gly Gly Ser
1               5                   10                  15

<210> SEQ ID NO 54
<211> LENGTH: 113
<212> TYPE: PRT
<213> ORGANISM: Artificial Sequence
<220> FEATURE:
<223> OTHER INFORMATION: Chemically Synthesized

<400> SEQUENCE: 54

Asp Ile Val Met Thr Gln Ser Pro Arg Ser Leu Ser Val Thr Pro Gly
1               5                   10                  15

Glu Pro Ala Ser Ile Ser Cys Arg Ala Ser Gln Ser Leu Leu His Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ser Trp Thr Phe Gly Gln Gly Thr Lys Val Glu Ile
            100                 105                 110

Lys

<210> SEQ ID NO 55
<211> LENGTH: 107
<212> TYPE: PRT
<213> ORGANISM: Artificial Sequence
<220> FEATURE:
<223> OTHER INFORMATION: Chemically Synthesized

<400> SEQUENCE: 55

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Ala Phe Asp Asn Tyr
            20                  25                  30

Val Ala Trp Tyr Gln Gln Arg Pro Gly Lys Val Pro Lys Leu Leu Ile
        35                  40                  45

Ser Ala Ala Ser Ala Leu His Ala Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Val Ala Thr Tyr Tyr Cys Gln Asn Tyr Asn Ser Ala Pro Leu
                85                  90                  95

Thr Phe Gly Gly Gly Thr Lys Val Glu Ile Lys
            100                 105

<210> SEQ ID NO 56
```

```
<211> LENGTH: 108
<212> TYPE: PRT
<213> ORGANISM: Artificial Sequence
<220> FEATURE:
<223> OTHER INFORMATION: Chemically Synthesized

<400> SEQUENCE: 56

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Ile Ala Trp Tyr Gln Gln Lys Pro Gly Gln Ala Pro Arg Leu Leu Met
        35                  40                  45

Phe Asp Ser Ser Thr Arg Ala Thr Gly Ile Pro Asp Arg Phe Ser Gly
    50                  55                  60

Ser Gly Ser Gly Thr Asp Phe Thr Leu Asn Ile Ser Ser Leu Glu Pro
65                  70                  75                  80

Glu Asp Phe Ala Val Tyr Tyr Cys Gln Gln Tyr Ser Ser Ser Pro Tyr
                85                  90                  95

Thr Phe Gly Gln Gly Thr Lys Leu Glu Ile Lys Arg
            100                 105

<210> SEQ ID NO 57
<211> LENGTH: 108
<212> TYPE: PRT
<213> ORGANISM: Artificial Sequence
<220> FEATURE:
<223> OTHER INFORMATION: Chemically Synthesized

<400> SEQUENCE: 57

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg
            100                 105

<210> SEQ ID NO 58
<211> LENGTH: 114
<212> TYPE: PRT
<213> ORGANISM: Artificial Sequence
<220> FEATURE:
<223> OTHER INFORMATION: Chemically Synthesized

<400> SEQUENCE: 58

Glu Thr Thr Leu Thr Gln Ser Pro Gly Thr Leu Ser Leu Ser Pro Gly
1               5                   10                  15

Glu Arg Ala Thr Leu Ser Cys Arg Ser Ser Gln Ser Leu Leu His Arg
            20                  25                  30

Asn Gly Tyr Asn Tyr Leu Asp Trp Tyr Leu Gln Lys Pro Gly Gln Ser
        35                  40                  45
```

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ser Trp Thr Phe Gly Gln Gly Thr Lys Leu Glu Ile
                100                 105                 110

Lys Arg

<210> SEQ ID NO 59
<211> LENGTH: 108
<212> TYPE: PRT
<213> ORGANISM: Artificial Sequence
<220> FEATURE:
<223> OTHER INFORMATION: Chemically Synthesized

<400> SEQUENCE: 59

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ala Phe Asp Asn Tyr
                20                  25                  30

Val Ala Trp Tyr Gln Gln Arg Pro Gly Lys Val Pro Lys Leu Leu Ile
            35                  40                  45

Ser Ala Ala Ser Ala Leu His Ala Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Val Ala Thr Tyr Tyr Cys Gln Asn Tyr Asn Ser Ala Pro Leu
                85                  90                  95

Thr Phe Gly Gly Gly Thr Lys Leu Glu Ile Lys Arg
                100                 105

<210> SEQ ID NO 60
<211> LENGTH: 114
<212> TYPE: PRT
<213> ORGANISM: Artificial Sequence
<220> FEATURE:
<223> OTHER INFORMATION: Chemically Synthesized

<400> SEQUENCE: 60

Ala Ile Gln Met Thr Gln Ser Pro Ser Leu Ser Ala Ser Val Gly
1               5                   10                  15

Asp Arg Val Thr Ile Thr Cys Arg Ser Ser Gln Ser Leu Leu His Arg
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ser Trp Thr Phe Gly Gln Gly Thr Lys Val Glu Ile
                100                 105                 110

Lys Arg

```
<210> SEQ ID NO 61
<211> LENGTH: 108
<212> TYPE: PRT
<213> ORGANISM: Artificial Sequence
<220> FEATURE:
<223> OTHER INFORMATION: Chemically Synthesized

<400> SEQUENCE: 61

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Phe Asp Asn Tyr
            20                  25                  30

Val Ala Trp Tyr Gln Gln Arg Pro Gly Lys Val Pro Lys Leu Leu Ile
        35                  40                  45

Ser Ala Ala Ser Ala Leu His Ala Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Val Ala Thr Tyr Tyr Cys Gln Asn Tyr Asn Ser Ala Pro Leu
                85                  90                  95

Thr Phe Gly Gly Gly Thr Lys Val Glu Ile Lys Arg
            100                 105

<210> SEQ ID NO 62
<211> LENGTH: 47
<212> TYPE: PRT
<213> ORGANISM: Artificial Sequence
<220> FEATURE:
<223> OTHER INFORMATION: Chemically Synthesized

<400> SEQUENCE: 62

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr Val Ile Val Ile
        35                  40                  45

<210> SEQ ID NO 63
<211> LENGTH: 2235
<212> TYPE: DNA
<213> ORGANISM: Artificial Sequence
<220> FEATURE:
<223> OTHER INFORMATION: Chemically Synthesized, pRD211,
      190-FP2A-mouse-GeneArt

<400> SEQUENCE: 63
atggattgga cttggagaat cctgttcctg gtggccgctg ctacaggcac acatgctcag    60
gtgcagctgg ttgaaagcgg aggcggagtt gtgcagcctg gcagatctct gagactgtct   120
tgtgccgcca gcggcttcac cttctctaag tacggaatgc actgggtccg acaggcccct   180
ggaaaaggac tggaatgggt cgccgtgatc agctacgagg cagcaacaa gtactacgcc    240 gacagcgtga aggcagatt caccatcagc agagacaaca gcaagaacac cctgtacctg   300
cagatgaaca gcctgagagc cgaggacacc gccgtgtact actgtgctaa gagcggcacc   360
cagtactacg acaccaccgg ctacgagtac agaggcctgg aatactttgg ctactgggc   420 cagggaaccc tggtcacagt tagctctgct agcacaaagg gcccagcgt tttcccactg    480 gctcctagct ctaagagcac atctggcgga acagctgctc tgggctgtct ggtcaaggac   540
tactttcctg agcctgtgac cgtgtcctgg aactctggtg ctctgacaag cggcgtgcac   600
```

-continued

```
acatttccag ctgtgctgca gtctagcggc ctgtactctc tgtctagcgt cgtgacagtg    660
cctagcagct ctctgggaac ccagacctac atctgcaacg tgaaccacaa gcctagcaac    720
accaaggtgg acaagagagt ggaacccaag agctgcgaca agacccacac ctgtcctcca    780
tgtcctgctc cagaagctgc aggcggaccc tctgtgttcc tgtttcctcc aaagcctaag    840
gacaccctga tgatcagcag aacccctgaa gtgacctgcg tggtggtgga tgtgtctcac    900
gaggaccccg aagtgaagtt caattggtac gtggacggcg tggaagtgca aacgccaag     960
accaagccta gagaggaaca gtacaacagc acctacagag tggtgtccgt gctgacagtg   1020
ctgcaccagg attggctgaa cggcaaagag tacaagtgca aggtgtccaa caaggccctg   1080
cctgctccta tcgaaaagac catctccaag gctaagggcc agcctaggga accccaggtt   1140
tacacactgc ctccaagcag agaagagatg accaagaacc aggtgtccct gacctgcctc   1200
gtgaagggat tctacccttc cgatatcgcc gtggaatggg agtctaacgg ccagccagag   1260
aacaactaca agacaacccc tcctgtgctg gacagcgacg gctcattctt cctgtacagc   1320
aagctgaccg tggacaagtc cagatggcag cagggcaacg tgttcagctg ttctgtgatg   1380
cacgaggccc tgcacaacca ctacacccag aagtctctgt ctctgagccc cggcaagcgc   1440
ggcagaaaga gaagatctgg aagcggcgcc accaacttca gtctgctgaa acaggctggc   1500
gacgtggaag agaaccctgg acctatggtg ctgcagaccc aggtgttcat tagcctgctg   1560
ctgtggatct ctggcgccta tggcgagatc gtgctgaccc agtctcctgg cacattgagc   1620
ctgtctccag cgagagagc cacactgagc tgtagagcct tcagagcgt gtcctctagc     1680
tacctggcct ggtatcagca aagagaggc caggctccta gactgctgat ctacgacgcc    1740
tcttccagag ccacaggcat ccctgataga ttcagcggct ctggcagcgg caccgacttc   1800
acactgacca tctctagact ggaacccgag gatttcgctg tgtactattg ccagcagtac   1860
ggcagatcca gatggacctt tggacagggc acaaaggtgg aaatcaagag aaccgtggcc   1920
gctcctagcg tgttcatctt tccaccaagc gacgagcagc tgaagtctgg cacagcttct   1980
gtcgtgtgcc tgctgaacaa cttctacccc agagaagcca aggtgcagtg gaaggtcgac   2040
aacgctctgc agtccggcaa cagccaagag agcgtgacag agcaggactc caaggacagc   2100
acatactccc tgagcagcac cctgacactg agcaaggccg actacgaaaa gcacaaggtg   2160
tacgcctgcg aagtgacaca ccagggactg agcagccctg tgaccaagtc tttcaacaga   2220
ggcgagtgct gatga                                                     2235
```

<210> SEQ ID NO 64
<211> LENGTH: 743
<212> TYPE: PRT
<213> ORGANISM: Artificial Sequence
<220> FEATURE:
<223> OTHER INFORMATION: Chemically Synthesized, pRD211, 190-FP2A-mouse-GeneArt

<400> SEQUENCE: 64

Met Asp Trp Thr Trp Arg Ile Leu Phe Leu Val Ala Ala Thr Gly
1               5                   10                  15

Thr His Ala Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Lys Tyr Gly Met His Trp Val Arg Gln Ala Pro Gly Lys Gly Leu
    50                  55                  60

```
Glu Trp Val Ala Val Ile Ser Tyr Glu Gly Ser Asn Lys Tyr Tyr Ala
 65                  70                  75                  80

Asp Ser Val Lys Gly Arg Phe Thr Ile Ser Arg Asp Asn Ser Lys Asn
             85                  90                  95

Thr Leu Tyr Leu Gln Met Asn Ser Leu Arg Ala Glu Asp Thr Ala Val
            100                 105                 110

Tyr Tyr Cys Ala Lys Ser Gly Thr Gln Tyr Tyr Asp Thr Thr Gly Tyr
        115                 120                 125

Glu Tyr Arg Gly Leu Glu Tyr Phe Gly Tyr Trp Gly Gln Gly Thr Leu
        130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
        210                 215                 220

Leu Gly Thr Gln Thr Tyr Ile Cys Asn Val Asn His Lys Pro Ser Asn
225                 230                 235                 240

Thr Lys Val Asp Lys Arg Val Glu Pro Lys Ser Cys Asp Lys Thr His
                245                 250                 255

Thr Cys Pro Pro Cys Pro Ala Pro Glu Ala Ala Gly Gly Pro Ser Val
                260                 265                 270

Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
        290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
        370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
        450                 455                 460

His Asn His Tyr Thr Gln Lys Ser Leu Ser Leu Ser Pro Gly Lys Arg
465                 470                 475                 480
```

```
Gly Arg Lys Arg Arg Ser Gly Ser Gly Ala Thr Asn Phe Ser Leu Leu
                485                 490                 495
Lys Gln Ala Gly Asp Val Glu Glu Asn Pro Gly Pro Met Val Leu Gln
            500                 505                 510
Thr Gln Val Phe Ile Ser Leu Leu Leu Trp Ile Ser Gly Ala Tyr Gly
        515                 520                 525
Glu Ile Val Leu Thr Gln Ser Pro Gly Thr Leu Ser Leu Ser Pro Gly
    530                 535                 540
Glu Arg Ala Thr Leu Ser Cys Arg Ala Ser Gln Ser Val Ser Ser Ser
545                 550                 555                 560
Tyr Leu Ala Trp Tyr Gln Gln Lys Arg Gly Gln Ala Pro Arg Leu Leu
                565                 570                 575
Ile Tyr Asp Ala Ser Ser Arg Ala Thr Gly Ile Pro Asp Arg Phe Ser
            580                 585                 590
Gly Ser Gly Ser Gly Thr Asp Phe Thr Leu Thr Ile Ser Arg Leu Glu
        595                 600                 605
Pro Glu Asp Phe Ala Val Tyr Tyr Cys Gln Gln Tyr Gly Arg Ser Arg
    610                 615                 620
Trp Thr Phe Gly Gln Gly Thr Lys Val Glu Ile Lys Arg Thr Val Ala
625                 630                 635                 640
Ala Pro Ser Val Phe Ile Phe Pro Pro Ser Asp Glu Gln Leu Lys Ser
                645                 650                 655
Gly Thr Ala Ser Val Val Cys Leu Leu Asn Asn Phe Tyr Pro Arg Glu
            660                 665                 670
Ala Lys Val Gln Trp Lys Val Asp Asn Ala Leu Gln Ser Gly Asn Ser
        675                 680                 685
Gln Glu Ser Val Thr Glu Gln Asp Ser Lys Asp Ser Thr Tyr Ser Leu
    690                 695                 700
Ser Ser Thr Leu Thr Leu Ser Lys Ala Asp Tyr Glu Lys His Lys Val
705                 710                 715                 720
Tyr Ala Cys Glu Val Thr His Gln Gly Leu Ser Ser Pro Val Thr Lys
                725                 730                 735
Ser Phe Asn Arg Gly Glu Cys
                740

<210> SEQ ID NO 65
<211> LENGTH: 2235
<212> TYPE: DNA
<213> ORGANISM: Artificial Sequence
<220> FEATURE:
<223> OTHER INFORMATION: Chemically Synthesized, pRD212,
      190-FP2A-mouse-Synbio

<400> SEQUENCE: 65
atggactgga cttggagaat cctgttcctg gtggcagcag ctacaggaac acacgctcag    60
gtgcagctgg tggaatcagg aggaggagtg gtgcagccag cagaagcct gagactgtct    120
tgcgccgcta gcggcttcac attcagcaag tacggcatgc attgggtccg acaggctcca    180
ggaaagggac tggagtgggt ggccgtgatt agctacgagg cagcaacaa gtactacgcc    240
gacagcgtga agggcaggtt caccatcagc cggacaacag caagaacac cctgtacctg    300
cagatgaaca gcctgagggc cgaggatacc gccgtgtact attgcgccaa gagcggaacc    360
cagtactacg acaccaccgg ctacgagtac aggggactgg agtacttcgg ctattgggc    420
cagggaacac tggtgaccgt gtctagcgct agcaccaagg gacctagcgt gttccctctg    480
gccccttcta gcaagtctac cagcggagga acagccgctc tgggttgtct ggtgaaggac    540
```

```
tacttcccag agcccgtgac cgtgtcttgg aatagcggag ctctgaccag cggagtgcac      600
acattcccag cagtgctgca gagcagcgga ctgtactctc tgagcagcgt ggtgaccgtg      660
ccttcttcta gcctgggcac ccagacctac atctgcaacg tgaaccacaa gcccagcaac      720
accaaggtgg acaagagggt ggagcccaag tcttgcgaca gacccacac ctgtcccct       780 tgtccagctc cagaagcagc aggaggacct agcgtgttcc tgttccctcc caagcccaag      840
gacaccctga tgatcagccg gacccccgaa gtgacttgcg tggtggtgga cgtgtctcac      900
gaggaccccg aggtcaagtt caattggtac gtggacggag tggaggtgca caacgctaag      960
accaagccca gggaggagca gtacaacagc acctacaggg tggtgtccgt gctgacagtg     1020
ctgcaccagg attggctgaa cggcaaggag tacaagtgca aggtgtccaa caaggctctg     1080
ccagccccca tcgagaagac catcagcaag gctaagggac agcctaggga acctcaggtg     1140
tacaccctgc ctcctagcag ggaggagatg accaagaacc aggtgtccct gacttgcctc     1200
gtgaagggct ctaccctagc gacatcgcc gtggagtggg aatctaacgg ccagccagag     1260
aacaactaca agaccacccc cccagtgctg gacagcgacg gcagcttctt cctgtacagc     1320
aagctgaccg tggacaagag ccgttggcag cagggcaacg tgttctcttg cagcgtgatg     1380
cacgaggccc tgcacaacca ctacacccag aagagcctga gcctgagccc aggaaagagg     1440
ggcagaaaga gaagaagcgg aagcggcgct accaacttca gcctgctgaa gcaggccgga     1500
gacgtggagg agaatccagg acccatggtg ctgcagaccc aggtgttcat cagcctcctc     1560
ctgtggatca gcggagctta cggcgagatc gtgctgacac agagcccagg aaccctgtct     1620
ctgtctccag gagagagagc cacccctgtct tgcagagcta gccagagcgt gtctagcagc     1680
tacctggctt ggtaccagca gaagaggggc caggctccta gactgctgat ctacgacgcc     1740
agctctagag ccaccggaat ccccgacaga ttcagcggaa gcggaagcgg aaccgacttc     1800
accctgacca tcagcagact ggagccagag gacttcgccg tctactactg ccagcagtac     1860
ggcagatctc gttggacctt cggacaggga accaaggtgg agatcaagcg gaccgtggca     1920 gccctagcg tgttcatctt ccctcctagc gacgagcagc tgaagagcgg aacagctagc     1980
gtcgtctgcc tgctgaacaa cttctacccc agggaggcca aggtccagtg gaaggtcgat     2040
aacgccctgc agagcggaaa ctctcaggag agcgtgaccg agcaggactc taaggacagc     2100
acctacagcc tgagcagcac actgaccctg agcaaggccg actacgagaa gcacaaggtg     2160
tacgcttgcg aagtgaccca ccagggactg tctagccccg tgaccaagag cttcaaccgg     2220
ggcgagtgtt gataa                                                      2235
```

<210> SEQ ID NO 66
<211> LENGTH: 743
<212> TYPE: PRT
<213> ORGANISM: Artificial Sequence
<220> FEATURE:
<223> OTHER INFORMATION: Chemically Synthesized, pRD212,
      190-FP2A-mouse-Synbio

<400> SEQUENCE: 66

Met Asp Trp Thr Trp Arg Ile Leu Phe Leu Val Ala Ala Ala Thr Gly
1               5                   10                  15

Thr His Ala Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

-continued

```
Ser Lys Tyr Gly Met His Trp Val Arg Gln Ala Pro Gly Lys Gly Leu
     50                  55                  60
Glu Trp Val Ala Val Ile Ser Tyr Glu Gly Ser Asn Lys Tyr Tyr Ala
 65                  70                  75                  80
Asp Ser Val Lys Gly Arg Phe Thr Ile Ser Arg Asp Asn Ser Lys Asn
                 85                  90                  95
Thr Leu Tyr Leu Gln Met Asn Ser Leu Arg Ala Glu Asp Thr Ala Val
            100                 105                 110
Tyr Tyr Cys Ala Lys Ser Gly Thr Gln Tyr Tyr Asp Thr Thr Gly Tyr
            115                 120                 125
Glu Tyr Arg Gly Leu Glu Tyr Phe Gly Tyr Trp Gly Gln Gly Thr Leu
        130                 135                 140
Val Thr Val Ser Ser Ala Ser Thr Lys Gly Pro Ser Val Phe Pro Leu
145                 150                 155                 160
Ala Pro Ser Ser Lys Ser Thr Ser Gly Gly Thr Ala Ala Leu Gly Cys
                165                 170                 175
Leu Val Lys Asp Tyr Phe Pro Glu Pro Val Thr Val Ser Trp Asn Ser
            180                 185                 190
Gly Ala Leu Thr Ser Gly Val His Thr Phe Pro Ala Val Leu Gln Ser
        195                 200                 205
Ser Gly Leu Tyr Ser Leu Ser Ser Val Val Thr Val Pro Ser Ser Ser
    210                 215                 220
Leu Gly Thr Gln Thr Tyr Ile Cys Asn Val Asn His Lys Pro Ser Asn
225                 230                 235                 240
Thr Lys Val Asp Lys Arg Val Glu Pro Lys Ser Cys Asp Lys Thr His
                245                 250                 255
Thr Cys Pro Pro Cys Pro Ala Pro Glu Ala Ala Gly Gly Pro Ser Val
            260                 265                 270
Phe Leu Phe Pro Pro Lys Pro Lys Asp Thr Leu Met Ile Ser Arg Thr
        275                 280                 285
Pro Glu Val Thr Cys Val Val Val Asp Val Ser His Glu Asp Pro Glu
290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
                325                 330                 335
Val Leu Thr Val Leu His Gln Asp Trp Leu Asn Gly Lys Glu Tyr Lys
            340                 345                 350
Cys Lys Val Ser Asn Lys Ala Leu Pro Ala Pro Ile Glu Lys Thr Ile
        355                 360                 365
Ser Lys Ala Lys Gly Gln Pro Arg Glu Pro Gln Val Tyr Thr Leu Pro
    370                 375                 380
Pro Ser Arg Glu Glu Met Thr Lys Asn Gln Val Ser Leu Thr Cys Leu
385                 390                 395                 400
Val Lys Gly Phe Tyr Pro Ser Asp Ile Ala Val Glu Trp Glu Ser Asn
                405                 410                 415
Gly Gln Pro Glu Asn Asn Tyr Lys Thr Thr Pro Pro Val Leu Asp Ser
            420                 425                 430
Asp Gly Ser Phe Phe Leu Tyr Ser Lys Leu Thr Val Asp Lys Ser Arg
        435                 440                 445
Trp Gln Gln Gly Asn Val Phe Ser Cys Ser Val Met His Glu Ala Leu
    450                 455                 460
His Asn His Tyr Thr Gln Lys Ser Leu Ser Leu Ser Pro Gly Lys Arg
```

Gly Arg Lys Arg Arg Ser Gly Ser Gly Ala Thr Asn Phe Ser Leu Leu
465                 470                 475                 480
                    485                 490                 495

Lys Gln Ala Gly Asp Val Glu Glu Asn Pro Gly Pro Met Val Leu Gln
                500                 505                 510

Thr Gln Val Phe Ile Ser Leu Leu Leu Trp Ile Ser Gly Ala Tyr Gly
                515                 520                 525

Glu Ile Val Leu Thr Gln Ser Pro Gly Thr Leu Ser Leu Ser Pro Gly
            530                 535                 540

Glu Arg Ala Thr Leu Ser Cys Arg Ala Ser Gln Ser Val Ser Ser Ser
545                 550                 555                 560

Tyr Leu Ala Trp Tyr Gln Lys Arg Gly Gln Ala Pro Arg Leu Leu
                565                 570                 575

Ile Tyr Asp Ala Ser Ser Arg Ala Thr Gly Ile Pro Asp Arg Phe Ser
                580                 585                 590

Gly Ser Gly Ser Gly Thr Asp Phe Thr Leu Thr Ile Ser Arg Leu Glu
            595                 600                 605

Pro Glu Asp Phe Ala Val Tyr Tyr Cys Gln Gln Tyr Gly Arg Ser Arg
        610                 615                 620

Trp Thr Phe Gly Gln Gly Thr Lys Val Glu Ile Lys Arg Thr Val Ala
625                 630                 635                 640

Ala Pro Ser Val Phe Ile Phe Pro Pro Ser Asp Glu Gln Leu Lys Ser
                645                 650                 655

Gly Thr Ala Ser Val Val Cys Leu Leu Asn Asn Phe Tyr Pro Arg Glu
                660                 665                 670

Ala Lys Val Gln Trp Lys Val Asp Asn Ala Leu Gln Ser Gly Asn Ser
                675                 680                 685

Gln Glu Ser Val Thr Glu Gln Asp Ser Lys Asp Ser Thr Tyr Ser Leu
            690                 695                 700

Ser Ser Thr Leu Thr Leu Ser Lys Ala Asp Tyr Glu Lys His Lys Val
705                 710                 715                 720

Tyr Ala Cys Glu Val Thr His Gln Gly Leu Ser Ser Pro Val Thr Lys
                725                 730                 735

Ser Phe Asn Arg Gly Glu Cys
            740

<210> SEQ ID NO 67
<211> LENGTH: 2235
<212> TYPE: DNA
<213> ORGANISM: Artificial Sequence
<220> FEATURE:
<223> OTHER INFORMATION: Chemically Synthesized, pRD213,
      190-FP2A-mouse-Genewiz

<400> SEQUENCE: 67
atggactgga cctggagaat cctgttcctc gtcgctgccg ctacaggcac ccatgcccag    60
gtgcagctgg tggaaagcgg cggaggcgtc gtgcagcctg gaaggagcct gagactgagc    120
tgcgccgcct ccggcttcac cttctccaaa tacggcatgc actgggtgag gcaggccccc    180
ggcaagggcc tggagtgggt cgctgtgatc agctacgaag cagcaacaa gtactacgcc    240 gacagcgtca agggcaggtt caccatctcc agagacaact ccaagaatac actgtacctg    300
cagatgaaca gcctgagggc tgaggacacc gctgtgtact actgcgccaa gagcggcacc    360
cagtactatg ataccaccgg ctatgagtac aggggcctgg aatacttcgg atattggggc    420
cagggcaccc tggtgacagt gagctccgct agcacaaagg gacccagcgt gttccctctc    480

```
gctcccagct ccaagtccac aagcggcgga acagccgctc tgggctgcct cgtgaaagac        540
tatttccctg agcccgtgac agtcagctgg aattccggcg ccctgacaag cggcgtccat        600
accttccctg ccgtcctcca agctccggc ctgtactccc tgtcctccgt ggtcacagtg         660
cccagctcct ccctgggaac ccagacctac atttgcaacg tcaatcacaa gcccagcaac        720
accaaggtcg acaaaagggt cgaacccaag agctgcgaca aacccacac ctgtcctccc         780 tgccctgctc ctgaagccgc tggaggacct agcgtgttcc tctttcctcc taagcccaag        840
gacaccctga tgatctccag gacccctgag gtgacctgtg tggtcgtgga cgtgagccac        900
gaagatcccg aggtcaagtt caactggtac gtggacggcg tcgaagtgca aatgccaaa        960 accaagccca gagaggagca atacaactcc acctacagag tggtgtccgt gctcacagtg       1020
ctgcaccagg actggctgaa tggcaaagag tacaagtgta aagtcagcaa taaggctctg       1080
cccgctccta ttgagaaaac catcagcaag ctaaaggac agcccaggga ccccaggtg        1140 tacacactgc ctcccagcag ggaggagatg acaaagaatc aggtgtccct gacatgcctg       1200
gtgaagggat tctacccctc cgatatcgct gtcgagtggg agtccaacgg ccaacccgaa       1260
aacaactata agaccacacc cccgtcctc gattccgacg gctccttctt tctgtattcc        1320
aagctgaccg tggacaagtc caggtggcag cagggcaacg tcttctcctg tagcgtgatg       1380
cacgaggctc tgcacaatca ctacacccag aaaagcctgt ccctgagccc tggcaagaga       1440
ggcaggaaga gaagatccgg aagcggagcc acaaacttct ccctgctgaa gcaggccgga       1500
gacgtcgaag agaaccctgg ccccatggtc ctgcagacac aggtgttcat ttccctgctg       1560
ctgtggatct ccggagccta cggcgagatc gtcctcaccc agagccctgg cacactgtcc       1620
ctgagccctg gcgagagagc cacccctgtcc tgtagagcca gccaaaagcgt ctccagcagc    1680 tatctggcct ggtaccagca aagagggggc caagctccca gactcctgat ctatgacgct      1740
tcctccaggg ctaccggcat ccccgatagg tttagcggca gcggcagcgg caccgatttc      1800
accctcacaa tctccaggct ggagcctgag gactttgctg tgtattactg ccagcagtac      1860
ggcaggagca ggtggacctt cggacaggga accaaggtgg agatcaaaag gaccgtcgct      1920
gctcccagcg tcttcatctt cccccccagc gatgagcagc tgaagtccgg cacagctagc      1980
gtcgtgtgcc tcctgaacaa tttctatccc agagaggcca agtccagtg gaaggtggat       2040 aacgccctgc agagcggaaa cagccaagaa tccgtcaccg aacaggacag caaggacagc      2100
acctacagcc tctcctccac actcacctc agcaaagccg actacgagaa gcacaaggtg       2160
tacgcttgcg aggtgaccca ccagggcctg agctcccctg tgaccaagag cttcaatagg      2220
ggcgagtgct gataa                                                        2235
```

<210> SEQ ID NO 68
<211> LENGTH: 743
<212> TYPE: PRT
<213> ORGANISM: Artificial Sequence
<220> FEATURE:
<223> OTHER INFORMATION: Chemically Synthesized, pRD213,
      190-FP2A-mouse-Genewiz

<400> SEQUENCE: 68

Met Asp Trp Thr Trp Arg Ile Leu Phe Leu Val Ala Ala Ala Thr Gly
1               5                   10                  15

Thr His Ala Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe

```
                    35                  40                  45
Ser Lys Tyr Gly Met His Trp Val Arg Gln Ala Pro Gly Lys Gly Leu
 50                  55                  60
Glu Trp Val Ala Val Ile Ser Tyr Glu Gly Ser Asn Lys Tyr Tyr Ala
 65                  70                  75                  80
Asp Ser Val Lys Gly Arg Phe Thr Ile Ser Arg Asp Asn Ser Lys Asn
                     85                  90                  95
Thr Leu Tyr Leu Gln Met Asn Ser Leu Arg Ala Glu Asp Thr Ala Val
                100                 105                 110
Tyr Tyr Cys Ala Lys Ser Gly Thr Gln Tyr Tyr Asp Thr Thr Gly Tyr
                115                 120                 125
Glu Tyr Arg Gly Leu Glu Tyr Phe Gly Tyr Trp Gly Gln Gly Thr Leu
                130                 135                 140
Val Thr Val Ser Ser Ala Ser Thr Lys Gly Pro Ser Val Phe Pro Leu
145                 150                 155                 160
Ala Pro Ser Ser Lys Ser Thr Ser Gly Gly Thr Ala Ala Leu Gly Cys
                165                 170                 175
Leu Val Lys Asp Tyr Phe Pro Glu Pro Val Thr Val Ser Trp Asn Ser
                180                 185                 190
Gly Ala Leu Thr Ser Gly Val His Thr Phe Pro Ala Val Leu Gln Ser
                195                 200                 205
Ser Gly Leu Tyr Ser Leu Ser Ser Val Val Thr Val Pro Ser Ser Ser
210                 215                 220
Leu Gly Thr Gln Thr Tyr Ile Cys Asn Val Asn His Lys Pro Ser Asn
225                 230                 235                 240
Thr Lys Val Asp Lys Arg Val Glu Pro Lys Ser Cys Asp Lys Thr His
                245                 250                 255
Thr Cys Pro Pro Cys Pro Ala Pro Glu Ala Ala Gly Gly Pro Ser Val
                260                 265                 270
Phe Leu Phe Pro Pro Lys Pro Lys Asp Thr Leu Met Ile Ser Arg Thr
                275                 280                 285
Pro Glu Val Thr Cys Val Val Val Asp Val Ser His Glu Asp Pro Glu
                290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
                325                 330                 335
Val Leu Thr Val Leu His Gln Asp Trp Leu Asn Gly Lys Glu Tyr Lys
                340                 345                 350
Cys Lys Val Ser Asn Lys Ala Leu Pro Ala Pro Ile Glu Lys Thr Ile
                355                 360                 365
Ser Lys Ala Lys Gly Gln Pro Arg Glu Pro Gln Val Tyr Thr Leu Pro
                370                 375                 380
Pro Ser Arg Glu Glu Met Thr Lys Asn Gln Val Ser Leu Thr Cys Leu
385                 390                 395                 400
Val Lys Gly Phe Tyr Pro Ser Asp Ile Ala Val Glu Trp Glu Ser Asn
                405                 410                 415
Gly Gln Pro Glu Asn Asn Tyr Lys Thr Thr Pro Pro Val Leu Asp Ser
                420                 425                 430
Asp Gly Ser Phe Phe Leu Tyr Ser Lys Leu Thr Val Asp Lys Ser Arg
                435                 440                 445
Trp Gln Gln Gly Asn Val Phe Ser Cys Ser Val Met His Glu Ala Leu
                450                 455                 460
```

His Asn His Tyr Thr Gln Lys Ser Leu Ser Leu Ser Pro Gly Lys Arg
465                 470                 475                 480

Gly Arg Lys Arg Arg Ser Gly Ser Gly Ala Thr Asn Phe Ser Leu Leu
            485                 490                 495

Lys Gln Ala Gly Asp Val Glu Glu Asn Pro Gly Pro Met Val Leu Gln
        500                 505                 510

Thr Gln Val Phe Ile Ser Leu Leu Leu Trp Ile Ser Gly Ala Tyr Gly
    515                 520                 525

Glu Ile Val Leu Thr Gln Ser Pro Gly Thr Leu Ser Leu Ser Pro Gly
530                 535                 540

Glu Arg Ala Thr Leu Ser Cys Arg Ala Ser Gln Ser Val Ser Ser Ser
545                 550                 555                 560

Tyr Leu Ala Trp Tyr Gln Gln Lys Arg Gly Gln Ala Pro Arg Leu Leu
                565                 570                 575

Ile Tyr Asp Ala Ser Ser Arg Ala Thr Gly Ile Pro Asp Arg Phe Ser
            580                 585                 590

Gly Ser Gly Ser Gly Thr Asp Phe Thr Leu Thr Ile Ser Arg Leu Glu
        595                 600                 605

Pro Glu Asp Phe Ala Val Tyr Tyr Cys Gln Gln Tyr Gly Arg Ser Arg
    610                 615                 620

Trp Thr Phe Gly Gln Gly Thr Lys Val Glu Ile Lys Arg Thr Val Ala
625                 630                 635                 640

Ala Pro Ser Val Phe Ile Phe Pro Pro Ser Asp Glu Gln Leu Lys Ser
                645                 650                 655

Gly Thr Ala Ser Val Val Cys Leu Leu Asn Asn Phe Tyr Pro Arg Glu
            660                 665                 670

Ala Lys Val Gln Trp Lys Val Asp Asn Ala Leu Gln Ser Gly Asn Ser
        675                 680                 685

Gln Glu Ser Val Thr Glu Gln Asp Ser Lys Asp Ser Thr Tyr Ser Leu
    690                 695                 700

Ser Ser Thr Leu Thr Leu Ser Lys Ala Asp Tyr Glu Lys His Lys Val
705                 710                 715                 720

Tyr Ala Cys Glu Val Thr His Gln Gly Leu Ser Ser Pro Val Thr Lys
                725                 730                 735

Ser Phe Asn Arg Gly Glu Cys
            740

<210> SEQ ID NO 69
<211> LENGTH: 2235
<212> TYPE: DNA
<213> ORGANISM: Artificial Sequence
<220> FEATURE:
<223> OTHER INFORMATION: Chemically Synthesized, pRD214,
      190-FP2A-mouse-Blue heron

<400> SEQUENCE: 69
atggactgga cctggcgaat tctgttcttg gttgcagcag cgactggtac acacgctcag      60
gtccagctgg tcgaatctgg gggcggcgtg gtacagccag ggagatcact gaggctgagt     120
tgcgctgcat ccggcttcac cttctccaaa tacggcatgc attgggtgcg gcaagctccc     180
gggaaaggct tggaatgggt ggccgtaatt tcatacgaag gtctaacaa gtattacgcc      240 gattctgtca agggccgctt tacaataagc cgcgataata gcaaaaacac gctttacctg     300
cagatgaact ctctgagagc agaggacact gctgtgtatt actgtgctaa atctgggacg     360
cagtactatg atacaactgg atacgagtac agaggcctcg aatacttcgg atactggggt     420

-continued

```
caggggaacac tggtcacggt tagtagcgcc tccactaagg gtccttcagt cttcccctg      480
gcacccagta gtaaatccac ctccggcggt actgcagctc ttggttgcct cgtgaaagac      540
tacttccctg aaccagtgac cgtctcctgg aactccggtg cactcaccag cggcgtacat      600
acattcccag ctgtgttgca aagttctggt ctgtatagct tgtcttccgt ggtgactgtc      660
cccagctcca gcctggggac ccaaacttac atttgtaatg tcaaccacaa gccgtctaat      720
acaaaggtgg acaagcgggt tgagccaaag agctgcgaca aaacgcacac ctgcccacct      780
tgccccgccc cagaagccgc ggggggaccc tcagtattcc tgttcccccc caagcccaag      840
gacactttga tgattagtcg cactcctgag gtcacctgcg tagtagtcga cgtgagccat      900
gaagatcctg aagtgaagtt taactggtac gtcgacggag tggaggtcca taacgccaaa      960
accaagccgc gcgaagaaca atacaactca acctacaggg tggtctctgt gcttacagtc     1020
ctccatcagg actggctcaa cggcaaagaa tacaagtgta aggtctccaa caaggcgctg     1080
cccgcgccca tcgagaagac aatcagcaag gccaaaggcc agcccaggga gccccaggtg     1140
tatactctgc cacccagtcg agaggagatg acaaaaaatc aagtgtccct cacatgcttg     1200
gtaaagggtt tctatccgtc tgacatagcc gtggagtggg agtctaatgg ccaaccagaa     1260
aacaactata agactacacc tcccgtcctt gactctgacg gcagttttt tctttactcc     1320
aaacttacag tcgataagag tcggtggcag caaggtaatg tgttcagctg cagcgttatg     1380
cacgaagcgc tgcacaatca ctacacgcag aagtccttga gtctgtctcc cggaaaacgg     1440
ggccgcaagc ggcgcagtgg ctcaggggcc acaaatttct cactcctcaa acaggctggc     1500
gacgtggagg aaaaccccgg gccaatggtg ctgcagaccc aagtcttcat aagcttgttg     1560
ctttggattt ccggggccta cggagaaatc gttctcactc agtctccagg cacactctca     1620
ctgtcacctg gagagcgcgc taccctcagt tgcagagcaa gtcaaagcgt gagctcttcc     1680
taccttgctt ggtaccaaca gaagagaggt caggccccgc gcttgctgat ctatgatgct     1740
tcatcccggg cgactggtat ccccgaccga ttctccggct ccggcagcgg taccgatttt     1800
actttgacta ttagccgcct tgaacctgag gacttcgccg tctactactg tcagcagtac     1860
ggaagaagcc gatggacatt cggcagggt accaaggtag agatcaagcg gactgtggca     1920
gccccatctg tgtttatctt ccctcctagc gatgaacaac ttaagtccgg aactgcctcc     1980
gtagtatgcc ttctgaacaa ttttttatcca cgcgaggcaa aggtgcagtg gaaagtggac     2040
aacgcccttc agtctggcaa ttcccaggaa agcgtcacag aacaggatag caaggactca     2100
acctactccc tctccagtac tctgacattg tccaaagccg attatgaaaa gcacaaagtg     2160
tatgcctgcg aagtaacaca ccaagggctg tcatctccag taaccaagag cttcaaccgc     2220
ggtgagtgtt gatga                                                      2235
```

<210> SEQ ID NO 70
<211> LENGTH: 743
<212> TYPE: PRT
<213> ORGANISM: Artificial Sequence
<220> FEATURE:
<223> OTHER INFORMATION: Chemically Synthesized, pRD214,
      190-FP2A-mouse-Blue heron

<400> SEQUENCE: 70

```
Met Asp Trp Thr Trp Arg Ile Leu Phe Leu Val Ala Ala Ala Thr Gly
1               5                   10                  15

Thr His Ala Gln Val Gln Leu Val Glu Ser Gly Gly Gly Val Val Gln
            20                  25                  30
```

```
Pro Gly Arg Ser Leu Arg Leu Ser Cys Ala Ala Ser Gly Phe Thr Phe
         35                  40                  45

Ser Lys Tyr Gly Met His Trp Val Arg Gln Ala Pro Gly Lys Gly Leu
 50                      55                  60

Glu Trp Val Ala Val Ile Ser Tyr Glu Gly Ser Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Lys Ser Gly Thr Gln Tyr Tyr Asp Thr Thr Gly Tyr
            115                 120                 125

Glu Tyr Arg Gly Leu Glu Tyr Phe Gly Tyr Trp Gly Gln Gly Thr Leu
        130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Arg Val Glu Pro Lys Ser Cys Asp Lys Thr His
                245                 250                 255

Thr Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445
```

```
Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Arg
465                 470                 475                 480

Gly Arg Lys Arg Arg Ser Gly Ser Gly Ala Thr Asn Phe Ser Leu Leu
                485                 490                 495

Lys Gln Ala Gly Asp Val Glu Glu Asn Pro Gly Pro Met Val Leu Gln
            500                 505                 510

Thr Gln Val Phe Ile Ser Leu Leu Leu Trp Ile Ser Gly Ala Tyr Gly
        515                 520                 525

Glu Ile Val Leu Thr Gln Ser Pro Gly Thr Leu Ser Leu Ser Pro Gly
530                 535                 540

Glu Arg Ala Thr Leu Ser Cys Arg Ala Ser Gln Ser Val Ser Ser Ser
545                 550                 555                 560

Tyr Leu Ala Trp Tyr Gln Gln Lys Arg Gly Gln Ala Pro Arg Leu Leu
                565                 570                 575

Ile Tyr Asp Ala Ser Ser Arg Ala Thr Gly Ile Pro Asp Arg Phe Ser
            580                 585                 590

Gly Ser Gly Ser Gly Thr Asp Phe Thr Leu Thr Ile Ser Arg Leu Glu
        595                 600                 605

Pro Glu Asp Phe Ala Val Tyr Tyr Cys Gln Gln Tyr Gly Arg Ser Arg
610                 615                 620

Trp Thr Phe Gly Gln Gly Thr Lys Val Glu Ile Lys Arg Thr Val Ala
625                 630                 635                 640

Ala Pro Ser Val Phe Ile Phe Pro Pro Ser Asp Glu Gln Leu Lys Ser
                645                 650                 655

Gly Thr Ala Ser Val Val Cys Leu Leu Asn Asn Phe Tyr Pro Arg Glu
            660                 665                 670

Ala Lys Val Gln Trp Lys Val Asp Asn Ala Leu Gln Ser Gly Asn Ser
        675                 680                 685

Gln Glu Ser Val Thr Glu Gln Asp Ser Lys Asp Ser Thr Tyr Ser Leu
690                 695                 700

Ser Ser Thr Leu Thr Leu Ser Lys Ala Asp Tyr Glu Lys His Lys Val
705                 710                 715                 720

Tyr Ala Cys Glu Val Thr His Gln Gly Leu Ser Ser Pro Val Thr Lys
                725                 730                 735

Ser Phe Asn Arg Gly Glu Cys
            740

<210> SEQ ID NO 71
<211> LENGTH: 2235
<212> TYPE: DNA
<213> ORGANISM: Artificial Sequence
<220> FEATURE:
<223> OTHER INFORMATION: Chemically Synthesized, pRD215,
      190-FP2A-mammal-DNA2.0

<400> SEQUENCE: 71
atggactgga cctggcgcat cctgtttctc gtcgctgccg ccactggtac ccatgcccag    60
gtgcaactgg tggagtccgg tgcggagtg gtgcaaccgg tcgcagcct gagactctca    120 tgcgccgcct caggcttcac cttctcgaag tacgggatgc actgggtcag acaggctccc    180
gggaaaggcc tggaatgggt ggccgtcatc tcgtacgagg gctcaaacaa gtactatgcc    240
gattccgtga agggacggtt caccatctcc cgggacaaca gcaagaacac cctgtacctc    300
caaatgaaca gcctgagggc cgaggacact gcagtgtact actgcgccaa gtcgggcact    360
```

```
cagtactacg acaccacggg atacgagtac aggggactcg aatacttcgg atactggggc    420
cagggcacac tcgtgaccgt cagctccgcc tccactaagg accttcagt gttccctctg    480
gcgccatcct ccaagtcgac cagcggtgga actgcagccc tgggatgtct cgtgaaggac    540
tacttccctg aacctgtcac cgtgtcctgg aacagcggag cactgacctc cggggtccac    600
actttccccg cggtgttgca gagctccggc ctgtactccc tgtcgtccgt cgtgacagtg    660
ccgtccagct cgttggggac ccagacttac atctgcaacg tgaaccacaa gccgtccaac    720
actaaagtgg acaaacgggt ggaacccaag tcgtgtgaca agactcatac ttgtccgcca    780
tgtcccgctc ctgaagcggc gggaggacct tccgtgttcc tcttcccccc gaagcctaag    840
gacacccctca tgattagcag gaccccggaa gtgacctgtg tcgtggtcga cgtgtcacac    900
gaggaccccg aagtgaagtt taattggtac gtggacggcg tcgaagtgca caacgccaag    960
accaagccac gcgaagaaca gtacaactcc acctaccggg tggtgtccgt gcttactgtg    1020
ctccatcagg actggctcaa cggaaaggag tacaagtgca aagtgtccaa caaagcgctc    1080
ccggctccta ttgaaaagac gatttccaag gccaagggac agcctcggga acctcaggtc    1140
tacacccctgc ctccttcgcg cgaggagatg accaagaatc aggtgtccct gacttgcctg    1200
gtcaagggat tctatccatc cgacatcgcc gtggagtggg agtccaacgg ccagccggaa    1260
aacaactaca agaccacccc acccgtcctg gacagcgacg gtccttctt cctgtactca    1320
aagctgactg tggataagtc ccgctggcaa cagggcaacg tgttctcctg ctccgtgatg    1380
cacgaggccc tgcacaacca ctacacccag aagtcgctta gcctctcgcc gggcaaacga    1440
ggaagaaagc gccggtccgg atcaggagcg actaacttct ccctcctgaa gcaggccggg    1500
gatgtggagg aaaatccagg acccatggtg ctgcaaaccc aggtgttcat cagcctcctc    1560
ctgtggatct ccggagccta cggcgaaatt gtgctgaccc agtcccctgg gaccctgtcc    1620
ctgtccccccg agagagagag cacccttttcc tgccgggcat cgcagagcgt cagctccagc    1680
tatctggcct ggtaccagca aaagcgcgga caagctccga actgctgat ctacgatgcc    1740
tcatcacgcg ccaccggaat cccggatagg ttctcaggat cgggctccgg tactgatttc    1800
accctgacca tcagccggct ggaacctgag gacttcgctg tgtattactg ccagcagtac    1860
ggccggtcca gatggacttt cggacagggc actaaggtcg aaatcaagcg gactgtcgct    1920
gcaccgagcg tgttcatttt cccaccctcc gacgagcagc ttaagagcgg aactgcttcc    1980
gtggtgtgcc ttctgaacaa tttctacccc cgggaagcca aggtccagtg gaaggtcgac    2040
aacgccctgc aatccgggaa ctcccaagaa tccgtcaccg aacaggactc caaggacagc    2100
acctactccc tctcatctac cctgaccctg tctaaggccg actacgagaa gcataaggtc    2160
tacgcctgcg aagtgacaca ccaaggcctt tcttcccccg tgaccaaatc cttcaaccgc    2220
ggagagtgct gataa                                                    2235
```

<210> SEQ ID NO 72  
<211> LENGTH: 743  
<212> TYPE: PRT  
<213> ORGANISM: Artificial Sequence  
<220> FEATURE:  
<223> OTHER INFORMATION: Chemically Synthesized, pRD215, 190-FP2A-mammal-DNA2.0

<400> SEQUENCE: 72

```
Met Asp Trp Thr Trp Arg Ile Leu Phe Leu Val Ala Ala Ala Thr Gly
1               5                   10                  15
```

-continued

```
Thr His Ala Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
        35                  40                  45

Ser Lys Tyr Gly Met His Trp Val Arg Gln Ala Pro Gly Lys Gly Leu
    50                  55                  60

Glu Trp Val Ala Val Ile Ser Tyr Glu Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Ser Gly Thr Gln Tyr Tyr Asp Thr Thr Gly Tyr
        115                 120                 125

Glu Tyr Arg Gly Leu Glu Tyr Phe Gly Tyr Trp Gly Gln Gly Thr Leu
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Arg Val Glu Pro Lys Ser Cys Asp Lys Thr His
                245                 250                 255

Thr Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
```

```
                    435                 440                 445
Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys Arg
465                 470                 475                 480

Gly Arg Lys Arg Arg Ser Gly Ser Gly Ala Thr Asn Phe Ser Leu Leu
                485                 490                 495

Lys Gln Ala Gly Asp Val Glu Glu Asn Pro Gly Pro Met Val Leu Gln
            500                 505                 510

Thr Gln Val Phe Ile Ser Leu Leu Leu Trp Ile Ser Gly Ala Tyr Gly
        515                 520                 525

Glu Ile Val Leu Thr Gln Ser Pro Gly Thr Leu Ser Leu Ser Pro Gly
    530                 535                 540

Glu Arg Ala Thr Leu Ser Cys Arg Ala Ser Gln Ser Val Ser Ser Ser
545                 550                 555                 560

Tyr Leu Ala Trp Tyr Gln Gln Lys Arg Gly Gln Ala Pro Arg Leu Leu
                565                 570                 575

Ile Tyr Asp Ala Ser Ser Arg Ala Thr Gly Ile Pro Asp Arg Phe Ser
            580                 585                 590

Gly Ser Gly Ser Gly Thr Asp Phe Thr Leu Thr Ile Ser Arg Leu Glu
        595                 600                 605

Pro Glu Asp Phe Ala Val Tyr Tyr Cys Gln Gln Tyr Gly Arg Ser Arg
    610                 615                 620

Trp Thr Phe Gly Gln Gly Thr Lys Val Glu Ile Lys Arg Thr Val Ala
625                 630                 635                 640

Ala Pro Ser Val Phe Ile Phe Pro Pro Ser Asp Glu Gln Leu Lys Ser
                645                 650                 655

Gly Thr Ala Ser Val Val Cys Leu Leu Asn Asn Phe Tyr Pro Arg Glu
            660                 665                 670

Ala Lys Val Gln Trp Lys Val Asp Asn Ala Leu Gln Ser Gly Asn Ser
        675                 680                 685

Gln Glu Ser Val Thr Glu Gln Asp Ser Lys Asp Ser Thr Tyr Ser Leu
    690                 695                 700

Ser Ser Thr Leu Thr Leu Ser Lys Ala Asp Tyr Glu Lys His Lys Val
705                 710                 715                 720

Tyr Ala Cys Glu Val Thr His Gln Gly Leu Ser Ser Pro Val Thr Lys
                725                 730                 735

Ser Phe Asn Arg Gly Glu Cys
            740

<210> SEQ ID NO 73
<211> LENGTH: 2235
<212> TYPE: DNA
<213> ORGANISM: Artificial Sequence
<220> FEATURE:
<223> OTHER INFORMATION: Chemically Synthesized, pRD216,
      190-FP2A-mouse-Genscript

<400> SEQUENCE: 73
atggactgga cttggcgcat cctctttctc gtcgcagccg caactggaac tcacgctcag      60
gtgcagctcg tcgaatcagg gggagggtg gtgcagccag gcaggagcct gaggctgagc     120
tgcgctgctt ccggcttcac cttttccaag tacggaatgc actgggtgag gcaggctcct     180
ggcaagggac tggagtgggt ggctgtgatc tcttacgagg gcagcaacaa gtactacgcc     240
gatagcgtga agggaaggtt caccatctcc agagacaact ctaagaacac actgtacctg     300
```

```
cagatgaact  ccctgagggc  cgaggatacc  gccgtgtact  actgcgctaa  gtctggcaca    360
cagtactacg  acaccacagg  atacgagtac  agaggcctgg  agtacttcgg  atactggggc    420
cagggaaccc  tggtgacagt  gagctccgcc  tctacaaagg  ccccagcgt   gtttcccctg    480 gctccttcta  gcaagagcac  ctccggcgga  acagccgctc  tgggatgtct  ggtgaaggac    540
tacttccctg  agccagtgac  cgtgtcctgg  aactctggcg  ccctgacctc  tggagtgcac    600
acatttcctg  ctgtgctgca  gtcctctggc  ctgtacagcc  tgagctccgt  ggtgaccgtg    660
ccatctagct  ccctgggaac  ccagacatac  atctgcaacg  tgaaccacaa  gccatccaac    720
acaaaggtgg  acaagagggt  ggagcccaag  tcttgtgata  gacccacac   atgccctccc    780 tgtccagctc  ctgaggctgc  tggcggacca  tccgtgttcc  tgtttccacc  caagcctaag    840
gatacactga  tgatcagcag  aaccccccgag gtgacatgcg  tggtggtgga  cgtgtcccac    900
gaggaccccg  aggtgaagtt  caactggtac  gtggacggcg  tggaggtgca  aacgccaag     960 accaagccta  gggaggagca  gtacaactcc  acctacagag  tggtgtctgt  gctgacagtg   1020
ctgcaccagg  attggctgaa  cggcaaggag  tacaagtgca  aggtgtctaa  caaggccctg   1080
ccagctccca  tcgagaagac  catcagcaag  gctaagggac  agccacggga  gccacaggtg   1140
tacacactgc  ctccatctcg  cgaggagatg  accaagaacc  aggtgagcct  gacatgtctg   1200
gtgaagggct  tctaccctag  cgatatcgct  gtggagtggg  agtccaacgg  acagccagag   1260
aacaactaca  agaccacacc  ccctgtgctg  gacagcgatg  gctccttctt  tctgtactct   1320
aagctgaccg  tggacaagag  ccggtggcag  caggaaaacg  tgttttcttg  cagcgtgatg   1380
cacgaggccc  tgcacaacca  ctacacccag  aagtccctgt  ctctgagccc  tggaaagagg   1440
ggaaggaaga  ggagatccgg  ctctggagcc  acaaacttct  ccctgctgaa  gcaggctggc   1500
gacgtggagg  agaaccctgg  accaatggtg  ctgcagaccc  aggtgtttat  cagcctgctg   1560
ctgtggatct  ccggagccta  cggcgagatc  gtgctgaccc  agagccctgg  cacactgagc   1620
ctgtccccag  gagagagggc  caccctgtcc  tgtagagctt  ctcagagcgt  gtctagctcc   1680
tacctggctt  ggtaccagca  gaagagggga  caggctccac  gcctgctgat  ctacgacgcc   1740
tctagccggg  ctaccggaat  ccccgatcgc  ttctccggct  ctggaagcgg  cacagacttt   1800
accctgacaa  tctcccggct  ggagccagag  gatttcgccg  tgtactactg  ccagcagtac   1860
ggcaggagca  gatggacctt  tggacagggc  acaaaggtgg  agatcaagcg  caccgtggcc   1920
gctccatccg  tgttcatctt  tccaccctct  gatgagcagc  tgaagagcgg  cacagcttcc   1980
gtggtgtgcc  tgctgaacaa  cttctacccc  agggaggcca  aggtgcagtg  gaaggtggac   2040
aacgctctgc  agtctggcaa  cagccaggag  tccgtgaccg  agcaggactc  taaggatagc   2100
acatactccc  tgtcctctac  cctgacactg  agcaaggccg  actacgagaa  gcacaaggtg   2160
tacgcttgcg  aagtgaccca  ccagggggctg agcagtccag  tgacaaagtc  cttcaataga   2220
ggggaatgct  gataa                                                        2235
```

<210> SEQ ID NO 74
<211> LENGTH: 743
<212> TYPE: PRT
<213> ORGANISM: Artificial Sequence
<220> FEATURE:
<223> OTHER INFORMATION: Chemically Synthesized, pRD216,
      190-FP2A-mouse-Genscript

<400> SEQUENCE: 74

Met Asp Trp Thr Trp Arg Ile Leu Phe Leu Val Ala Ala Ala Thr Gly

-continued

```
  1               5                  10                 15
Thr His Ala Gln Val Gln Leu Val Glu Ser Gly Gly Val Gln
             20                  25                 30
Pro Gly Arg Ser Leu Arg Leu Ser Cys Ala Ala Ser Gly Phe Thr Phe
             35                  40                 45
Ser Lys Tyr Gly Met His Trp Val Arg Gln Ala Pro Gly Lys Gly Leu
 50                  55                 60
Glu Trp Val Ala Val Ile Ser Tyr Glu Gly Ser Asn Lys Tyr Tyr Ala
 65                  70                 75                  80
Asp Ser Val Lys Gly Arg Phe Thr Ile Ser Arg Asp Asn Ser Lys Asn
             85                  90                 95
Thr Leu Tyr Leu Gln Met Asn Ser Leu Arg Ala Glu Asp Thr Ala Val
             100                 105                110
Tyr Tyr Cys Ala Lys Ser Gly Thr Gln Tyr Tyr Asp Thr Thr Gly Tyr
             115                 120                125
Glu Tyr Arg Gly Leu Glu Tyr Phe Gly Tyr Trp Gly Gln Gly Thr Leu
             130                 135                140
Val Thr Val Ser Ser Ala Ser Thr Lys Gly Pro Ser Val Phe Pro Leu
145                  150                155                160
Ala Pro Ser Ser Lys Ser Thr Ser Gly Gly Thr Ala Ala Leu Gly Cys
             165                 170                175
Leu Val Lys Asp Tyr Phe Pro Glu Pro Val Thr Val Ser Trp Asn Ser
             180                 185                190
Gly Ala Leu Thr Ser Gly Val His Thr Phe Pro Ala Val Leu Gln Ser
             195                 200                205
Ser Gly Leu Tyr Ser Leu Ser Ser Val Val Thr Val Pro Ser Ser Ser
             210                 215                220
Leu Gly Thr Gln Thr Tyr Ile Cys Asn Val Asn His Lys Pro Ser Asn
225                  230                235                240
Thr Lys Val Asp Lys Arg Val Glu Pro Lys Ser Cys Asp Lys Thr His
             245                 250                255
Thr Cys Pro Pro Cys Pro Ala Pro Glu Ala Ala Gly Gly Pro Ser Val
             260                 265                270
Phe Leu Phe Pro Pro Lys Pro Lys Asp Thr Leu Met Ile Ser Arg Thr
             275                 280                285
Pro Glu Val Thr Cys Val Val Val Asp Val Ser His Glu Asp Pro Glu
             290                 295                300
Val Lys Phe Asn Trp Tyr Val Asp Gly Val Glu Val His Asn Ala Lys
305                  310                315                320
Thr Lys Pro Arg Glu Glu Gln Tyr Asn Ser Thr Tyr Arg Val Val Ser
             325                 330                335
Val Leu Thr Val Leu His Gln Asp Trp Leu Asn Gly Lys Glu Tyr Lys
             340                 345                350
Cys Lys Val Ser Asn Lys Ala Leu Pro Ala Pro Ile Glu Lys Thr Ile
             355                 360                365
Ser Lys Ala Lys Gly Gln Pro Arg Glu Pro Gln Val Tyr Thr Leu Pro
             370                 375                380
Pro Ser Arg Glu Glu Met Thr Lys Asn Gln Val Ser Leu Thr Cys Leu
385                  390                395                400
Val Lys Gly Phe Tyr Pro Ser Asp Ile Ala Val Glu Trp Glu Ser Asn
             405                 410                415
Gly Gln Pro Glu Asn Asn Tyr Lys Thr Thr Pro Val Leu Asp Ser
             420                 425                430
```

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Arg
465                 470                 475                 480

Gly Arg Lys Arg Arg Ser Gly Ser Gly Ala Thr Asn Phe Ser Leu Leu
                485                 490                 495

Lys Gln Ala Gly Asp Val Glu Glu Asn Pro Gly Pro Met Val Leu Gln
            500                 505                 510

Thr Gln Val Phe Ile Ser Leu Leu Leu Trp Ile Ser Gly Ala Tyr Gly
        515                 520                 525

Glu Ile Val Leu Thr Gln Ser Pro Gly Thr Leu Ser Leu Ser Pro Gly
    530                 535                 540

Glu Arg Ala Thr Leu Ser Cys Arg Ala Ser Gln Ser Val Ser Ser Ser
545                 550                 555                 560

Tyr Leu Ala Trp Tyr Gln Gln Lys Arg Gly Gln Ala Pro Arg Leu Leu
                565                 570                 575

Ile Tyr Asp Ala Ser Ser Arg Ala Thr Gly Ile Pro Asp Arg Phe Ser
            580                 585                 590

Gly Ser Gly Ser Gly Thr Asp Phe Thr Leu Thr Ile Ser Arg Leu Glu
        595                 600                 605

Pro Glu Asp Phe Ala Val Tyr Tyr Cys Gln Gln Tyr Gly Arg Ser Arg
    610                 615                 620

Trp Thr Phe Gly Gln Gly Thr Lys Val Glu Ile Lys Arg Thr Val Ala
625                 630                 635                 640

Ala Pro Ser Val Phe Ile Phe Pro Pro Ser Asp Glu Gln Leu Lys Ser
                645                 650                 655

Gly Thr Ala Ser Val Val Cys Leu Leu Asn Asn Phe Tyr Pro Arg Glu
            660                 665                 670

Ala Lys Val Gln Trp Lys Val Asp Asn Ala Leu Gln Ser Gly Asn Ser
        675                 680                 685

Gln Glu Ser Val Thr Glu Gln Asp Ser Lys Asp Ser Thr Tyr Ser Leu
    690                 695                 700

Ser Ser Thr Leu Thr Leu Ser Lys Ala Asp Tyr Glu Lys His Lys Val
705                 710                 715                 720

Tyr Ala Cys Glu Val Thr His Gln Gly Leu Ser Ser Pro Val Thr Lys
                725                 730                 735

Ser Phe Asn Arg Gly Glu Cys
            740

<210> SEQ ID NO 75
<211> LENGTH: 2211
<212> TYPE: DNA
<213> ORGANISM: Artificial Sequence
<220> FEATURE:
<223> OTHER INFORMATION: Chemically Synthesized, pRD225,
      185-mouse-GeneArt

<400> SEQUENCE: 75
atggactgga cttggagaat cctgttcctg gtggccgctg ctacaggcac acatgctgaa     60
gtgcagctgg tgcagtctgg cgccgaagtg aagaaacctg gcgagagcct gagaatcagc    120
tgcaaaggca gcggctacag cttcaccagc tactggatca cctgggtccg acagatgcct    180
ggcaaaggcc tggaatggat ggccaagttc gaccctagcg acagccagac caactacagc    240

```
cctagctttc agggccacgt gaccatcagc gtggacaaga gcatcagcac agcctacctg      300
cagtggtcta gcctgaaggc cagcgacacc gccatgtact actgcgccag aagatactgc      360
agcagcagct cctgctacgt ggacaactgg ggacagggca ccctggtcac aatcttctct      420
gcctctacaa agggccccag cgtgttccct ctggctccta gctctaagag cacatctggc      480
ggaacagctg ctctgggctg tctggtcaag gactactttc ctgagcctgt gaccgtgtcc      540
tggaactctg gtgctctgac aagcggcgtg cacacattc cagcagtgct gcagtctagc      600
ggcctgtact ctctgtctag cgtggtcaca gtgcctagca gcagcctggg aacccagacc      660
tacatctgca acgtgaacca caagcctagc aacaccaagg tcgacaagaa ggtggaaccc      720
aagagctgcg acaagaccca cacctgtcct ccatgtcctg ctccagaagc tgctggcgga      780
ccctctgtgt tcctgtttcc tccaaagcct aaggacaccc tgatgatcag cagaaccccct      840
gaagtgacct gcgtggtggt ggatgtgtct cacgaggacc cagaagtgaa gttcaattgg      900
tacgtggacg gcgtggaagt gcacaacgcc aagaccaagc ctagagagga acagtacaac      960
agcacctaca gagtggtgtc cgtgctgacc gtgctgcacc aggattggct gaacggcaaa     1020
gagtacaagt gcaaggtgtc caacaaggcc ctgcctgctc ctatcgaaaa gaccatctcc     1080
aaggctaagg gccagccaag agaacccccag gtgtacacac tgcctccaag cagggacgag     1140
ctgaccaaga tcaggtgtc cctgacctgc ctcgtgaagg gcttctaccc ttccgatatc     1200
gccgtggaat gggagtctaa cggacagccc gagaacaact acaagacaac ccctcctgtg     1260
ctggacagcg acggctcatt cttcctgtac agcaagctga cagtggacaa gtccagatgg     1320
cagcagggca acgtgttcag ctgttctgtg atgcacgagg ccctgcacaa ccactacaca     1380
cagaagtccc tgtctctgag ccccggcaag aggggcagaa agagaagatc tggcagcggc     1440
gccacaaact tcagtctgct gaaacaggct ggcgacgtgg aagagaatcc cggacctatg     1500
gtgctgcaga cacaggtgtt catcagcctg ctgctgtgga tctctggcgc ctacggaagc     1560
agctatgagc tgacacagcc tcctagcgtg tccgtgtctc tggccagac cgccagaatc     1620
acatgtagcg gagatgccct gcctaacaag ttcgcctact ggtacaggca gaagtccgga     1680
caggctcccg tgctggtcat ctacgaggac aacaagaggc ctagcggcat ccctgagaga     1740
ttcagcggct ctagctctgg caccatggcc acactgacaa tcagtggcgc tcaggtggaa     1800
gatgaggccg actaccactg ttacagcacc gacagcagct ctaaccctct gggagtgttt     1860
ggcggcggaa caaagcttac agtgctgggc caacctaagg ctgccccttc tgtgacactg     1920
ttcccaccta gctctgagga actgcaggct aacaaggcca cactcgtgtg cctgatcagc     1980
gatttctacc ctggcgctgt gacagtggct tggaaggctg atagctctcc tgtgaaggcc     2040
ggcgtcgaga caacaacacc tagcaagcag agcaacaaca atacgccgc cagctcctat     2100
ctgagcctga cacctgagca gtggaagtcc cacagatcct acagctgcca agtgacccac     2160
gagggcagca ccgtggaaaa gactgtggct cctaccgagt gctcctgatg a              2211
```

<210> SEQ ID NO 76
<211> LENGTH: 735
<212> TYPE: PRT
<213> ORGANISM: Artificial Sequence
<220> FEATURE:
<223> OTHER INFORMATION: Chemically Synthesized, pRD225,
      185-mouse-GeneArt

<400> SEQUENCE: 76

Met Asp Trp Thr Trp Arg Ile Leu Phe Leu Val Ala Ala Ala Thr Gly

-continued

```
1               5                   10                  15
Thr His Ala Glu Val Gln Leu Val Gln Ser Gly Ala Glu Val Lys Lys
                20                  25                  30
Pro Gly Glu Ser Leu Arg Ile Ser Cys Lys Gly Ser Gly Tyr Ser Phe
                35                  40                  45
Thr Ser Tyr Trp Ile Thr Trp Val Arg Gln Met Pro Gly Lys Gly Leu
                50                  55                  60
Glu Trp Met Ala Lys Phe Asp Pro Ser Asp Ser Gln Thr Asn Tyr Ser
65                  70                  75                  80
Pro Ser Phe Gln Gly His Val Thr Ile Ser Val Asp Lys Ser Ile Ser
                85                  90                  95
Thr Ala Tyr Leu Gln Trp Ser Ser Leu Lys Ala Ser Asp Thr Ala Met
                100                 105                 110
Tyr Tyr Cys Ala Arg Arg Tyr Cys Ser Ser Ser Cys Tyr Val Asp
                115                 120                 125
Asn Trp Gly Gln Gly Thr Leu Val Thr Ile Phe Ser Ala Ser Thr Lys
                130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
                180                 185                 190
Phe Pro Ala Val Leu Gln Ser Ser Gly Leu Tyr Ser Leu Ser Ser Val
                195                 200                 205
Val Thr Val Pro Ser Ser Ser Leu Gly Thr Gln Thr Tyr Ile Cys Asn
                210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Ala Ala Gly Gly Pro Ser Val Phe Leu Phe Pro Pro Lys Pro Lys Asp
                260                 265                 270
Thr Leu Met Ile Ser Arg Thr Pro Glu Val Thr Cys Val Val Val Asp
                275                 280                 285
Val Ser His Glu Asp Pro Glu Val Lys Phe Asn Trp Tyr Val Asp Gly
                290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
                340                 345                 350
Ala Pro Ile Glu Lys Thr Ile Ser Lys Ala Lys Gly Gln Pro Arg Glu
                355                 360                 365
Pro Gln Val Tyr Thr Leu Pro Pro Ser Arg Asp Glu Leu Thr Lys Asn
                370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
                420                 425                 430
```

```
Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys Arg Gly Arg Lys Arg Arg Ser Gly Ser Gly
465                 470                 475                 480

Ala Thr Asn Phe Ser Leu Leu Lys Gln Ala Gly Asp Val Glu Glu Asn
                485                 490                 495

Pro Gly Pro Met Val Leu Gln Thr Gln Val Phe Ile Ser Leu Leu Leu
            500                 505                 510

Trp Ile Ser Gly Ala Tyr Gly Ser Ser Tyr Glu Leu Thr Gln Pro Pro
            515                 520                 525

Ser Val Ser Val Ser Pro Gly Gln Thr Ala Arg Ile Thr Cys Ser Gly
    530                 535                 540

Asp Ala Leu Pro Asn Lys Phe Ala Tyr Trp Tyr Arg Gln Lys Ser Gly
545                 550                 555                 560

Gln Ala Pro Val Leu Val Ile Tyr Glu Asp Asn Lys Arg Pro Ser Gly
                565                 570                 575

Ile Pro Glu Arg Phe Ser Gly Ser Ser Gly Thr Met Ala Thr Leu
            580                 585                 590

Thr Ile Ser Gly Ala Gln Val Glu Asp Glu Ala Asp Tyr His Cys Tyr
            595                 600                 605

Ser Thr Asp Ser Ser Ser Asn Pro Leu Gly Val Phe Gly Gly Gly Thr
610                 615                 620

Lys Leu Thr Val Leu Gly Gln Pro Lys Ala Ala Pro Ser Val Thr Leu
625                 630                 635                 640

Phe Pro Pro Ser Ser Glu Glu Leu Gln Ala Asn Lys Ala Thr Leu Val
                645                 650                 655

Cys Leu Ile Ser Asp Phe Tyr Pro Gly Ala Val Thr Val Ala Trp Lys
            660                 665                 670

Ala Asp Ser Ser Pro Val Lys Ala Gly Val Glu Thr Thr Thr Pro Ser
            675                 680                 685

Lys Gln Ser Asn Asn Lys Tyr Ala Ala Ser Ser Tyr Leu Ser Leu Thr
690                 695                 700

Pro Glu Gln Trp Lys Ser His Arg Ser Tyr Ser Cys Gln Val Thr His
705                 710                 715                 720

Glu Gly Ser Thr Val Glu Lys Thr Val Ala Pro Thr Glu Cys Ser
                725                 730                 735

<210> SEQ ID NO 77
<211> LENGTH: 2211
<212> TYPE: DNA
<213> ORGANISM: Artificial Sequence
<220> FEATURE:
<223> OTHER INFORMATION: Chemically Synthesized, pRD227,
      185-mouse-Synbio

<400> SEQUENCE: 77
atggactgga cttggagaat cctgttcctg gtggcagccg ctacaggaac acacgcagaa      60
gtgcagctgg tgcagagcgg agcagaagtg aagaagccag cgagagcct gcggatctct     120 tgcaagggaa gcggctacag cttcaccagc tactggatca cttgggtgcg ccagatgcca    180
ggcaagggac tggagtggat ggccaagttc gaccctagcg acagccagac caactacagc    240
cctagcttcc agggccacgt gacaatcagc gtggacaaga gcatcagcac cgcctacctc    300
```

```
cagtggtcta gcctgaaggc cagcgatacc gccatgtact attgcgcccg gcggtattgc    360
agcagcagct cttgctacgt ggacaattgg ggccagggaa cactggtgac catcttcagc    420
gccagcacca agggacctag cgtgtttcct ctggcccctt ctagcaagag cacaagcgga    480
ggaacagccg ctctgggctg tctggtgaaa gactacttcc ccgagccagt gaccgtgtct    540
tggaactcag gagccctgac aagcggagtg cacacatttc cagccgtgct gcagagcagc    600
ggactgtact ctctgagcag cgtggtgacc gtgccttctt cttctctggg cacccagacc    660
tacatctgca acgtgaacca caagcccagc aacaccaagg tggacaagaa ggtggagccc    720
aagtcttgcg acaagaccca cacttgcccc cctgtccag ctccagaagc agcaggagga    780
cctagcgtgt tcctgttccc tcctaagccc aaggacaccc tgatgatcag ccggacccca    840
gaagtgactt gcgtggtggt ggacgtgtcc cacgaagacc ccgaggtcaa gttcaattgg    900
tacgtggacg gagtggaggt gcacaacgct aagaccaagc cagggagga gcagtacaac    960
agcacctaca gggtggtgtc cgtgctgaca gtgctgcacc aggattggct gaacggcaag   1020
gagtacaagt gcaaggtgtc caacaaggcc ctgccagctc ccatcgagaa gaccatcagc   1080
aaggccaagg gacagcctag agagcctcag gtgtacaccc tgcctccttc tagggacgag   1140
ctgaccaaga accaggtgtc cctgacttgc ctcgtgaagg gcttctaccc cagcgacatc   1200
gcagtggagt gggaaagcaa cggtcagcca gagaacaact acaagaccac cccccagtg   1260
ctggacagcg acggcagctt cttcctgtac agcaagctga ccgtggacaa agccgctgg   1320
cagcagggca acgtgttctc ttgcagcgtg atgcacgagg ccctgcacaa ccactacacc   1380
cagaagagcc tgtctctgag cccaggcaag aggggcagaa agagaagaag cggcagcgga   1440
gccaccaact tcagcctgct gaagcaggca ggagacgtgg aggagaaccc aggacctatg   1500
gtgctgcaga cccaggtgtt catcagcctc tgctgtgga tcagcggagc ttacggaagc   1560
agctacgagc tgacacagcc tcctagcgtg tccgtgtctc aggacagac cgccagaatc   1620
acttgtagcg gcgacgccct gcctaacaag ttcgcctatt ggtaccggca aagagcggaa   1680
caggctccag tgctggtcat ctacgaggac aacaagaggc ctagcggcat cccagagagg   1740
ttcagcggat ctagcagcgg cacaatggcc acactgacca tcagcggagc tcaggtggag   1800
gacgaggccg actaccattg ctacagcacc gacagcagct ctaacccact gggcgtgttc   1860
ggaggaggaa caaagctgac cgtgctggga cagcctaagg cagctcctag cgtgacactg   1920
ttccctcctt ctagcgagga gctgcaggct aacaaggcca cactcgtctg cctgatcagc   1980
gacttctatc caggcgccgt gacagtggct tggaaggccg atagcagccc agtgaaagcc   2040
ggagtggaga caaccacccc tagcaagcag agcaacaaca agtacgccgc cagcagctac   2100
ctgagcctga caccagagca gtggaagagc cacaggagct actcttgcca ggtcaccca   2160
gagggaagca cagtggagaa gacagtggcc cctacagagt gctcctgata a           2211
```

<210> SEQ ID NO 78
<211> LENGTH: 735
<212> TYPE: PRT
<213> ORGANISM: Artificial Sequence
<220> FEATURE:
<223> OTHER INFORMATION: Chemically Synthesized, pRD227,
      185-mouse-Synbio

<400> SEQUENCE: 78

Met Asp Trp Thr Trp Arg Ile Leu Phe Leu Val Ala Ala Ala Thr Gly
1               5                   10                  15

Thr His Ala Glu Val Gln Leu Val Gln Ser Gly Ala Glu Val Lys Lys

-continued

```
               20                  25                  30
Pro Gly Glu Ser Leu Arg Ile Ser Cys Lys Gly Ser Gly Tyr Ser Phe
            35                  40                  45
Thr Ser Tyr Trp Ile Thr Trp Val Arg Gln Met Pro Gly Lys Gly Leu
        50                  55                  60
Glu Trp Met Ala Lys Phe Asp Pro Ser Asp Ser Gln Thr Asn Tyr Ser
 65                  70                  75                  80
Pro Ser Phe Gln Gly His Val Thr Ile Ser Val Asp Lys Ser Ile Ser
                85                  90                  95
Thr Ala Tyr Leu Gln Trp Ser Ser Leu Lys Ala Ser Asp Thr Ala Met
            100                 105                 110
Tyr Tyr Cys Ala Arg Arg Tyr Cys Ser Ser Ser Cys Tyr Val Asp
            115                 120                 125
Asn Trp Gly Gln Gly Thr Leu Val Thr Ile Phe Ser Ala Ser Thr Lys
            130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
            195                 200                 205
Val Thr Val Pro Ser Ser Ser Leu Gly Thr Gln Thr Tyr Ile Cys Asn
        210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Ala Ala Gly Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
            275                 280                 285
Val Ser His Glu Asp Pro Glu Val Lys Phe Asn Trp Tyr Val Asp Gly
        290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
            355                 360                 365
Pro Gln Val Tyr Thr Leu Pro Pro Ser Arg Asp Glu Leu Thr Lys Asn
        370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
            435                 440                 445
```

Ser Val Met His Glu Ala Leu His Asn His Tyr Thr Gln Lys Ser Leu
    450                 455                 460

Ser Leu Ser Pro Gly Lys Arg Gly Lys Arg Arg Ser Gly Ser Gly
465                 470                 475                 480

Ala Thr Asn Phe Ser Leu Leu Lys Gln Ala Gly Asp Val Glu Glu Asn
                    485                 490                 495

Pro Gly Pro Met Val Leu Gln Thr Gln Val Phe Ile Ser Leu Leu Leu
                500                 505                 510

Trp Ile Ser Gly Ala Tyr Gly Ser Ser Tyr Glu Leu Thr Gln Pro Pro
            515                 520                 525

Ser Val Ser Val Ser Pro Gly Gln Thr Ala Arg Ile Thr Cys Ser Gly
530                 535                 540

Asp Ala Leu Pro Asn Lys Phe Ala Tyr Trp Tyr Arg Gln Lys Ser Gly
545                 550                 555                 560

Gln Ala Pro Val Leu Val Ile Tyr Glu Asp Asn Lys Arg Pro Ser Gly
                565                 570                 575

Ile Pro Glu Arg Phe Ser Gly Ser Ser Ser Gly Thr Met Ala Thr Leu
                580                 585                 590

Thr Ile Ser Gly Ala Gln Val Glu Asp Glu Ala Asp Tyr His Cys Tyr
            595                 600                 605

Ser Thr Asp Ser Ser Ser Asn Pro Leu Gly Val Phe Gly Gly Gly Thr
        610                 615                 620

Lys Leu Thr Val Leu Gly Gln Pro Lys Ala Ala Pro Ser Val Thr Leu
625                 630                 635                 640

Phe Pro Pro Ser Ser Glu Glu Leu Gln Ala Asn Lys Ala Thr Leu Val
                645                 650                 655

Cys Leu Ile Ser Asp Phe Tyr Pro Gly Ala Val Thr Val Ala Trp Lys
                660                 665                 670

Ala Asp Ser Ser Pro Val Lys Ala Gly Val Glu Thr Thr Thr Pro Ser
            675                 680                 685

Lys Gln Ser Asn Asn Lys Tyr Ala Ala Ser Ser Tyr Leu Ser Leu Thr
        690                 695                 700

Pro Glu Gln Trp Lys Ser His Arg Ser Tyr Ser Cys Gln Val Thr His
705                 710                 715                 720

Glu Gly Ser Thr Val Glu Lys Thr Val Ala Pro Thr Glu Cys Ser
                725                 730                 735

<210> SEQ ID NO 79
<211> LENGTH: 2211
<212> TYPE: DNA
<213> ORGANISM: Artificial Sequence
<220> FEATURE:
<223> OTHER INFORMATION: Chemically Synthesized, pRD229,
      185-mouse-GeneWiz

<400> SEQUENCE: 79
atggactgga catggagaat cctcttcctg gtggccgccg ctaccggcac acatgctgag      60
gtgcagctgg tgcagtccgg cgctgaagtg aagaaacccg agagagcct gagaatctcc     120 tgtaaaggct ccggctacag cttcacctcc tactggatta cctgggtgag acagatgccc    180
ggcaaaggac tggagtggat ggccaagttc gatccctccg acagccagac caactacagc    240
cccagctttc agggacatgt gaccatcagc gtgataaga gcatctccac cgcttatctg    300
cagtggagca gcctcaaggc cagcgatacc gccatgtact actgcgccag gaggtattgc   360
tccagctcca gctgctacgt cgacaactgg ggccagggaa cactggtcac aatcttctcc   420

```
gcctccacca agggcccctc cgtgtttcct ctggctccta gcagcaagtc cacctccgga      480
ggaacagctg ccctcggctg cctcgtgaaa gactacttcc ccgagcccgt gaccgtgtcc      540
tggaactccg gagccctgac ctccggagtc cataccttcc ctgccgtgct ccagagcagc      600
ggcctctaca gcctgagctc cgtggtgacc gtcccttcca gcagcctggg cacccagaca      660
tatatctgca acgtgaacca taagcctagc aacacaaagg tggacaagaa ggtcgaaccc      720
aagagctgtg acaagaccca cacctgtcct ccttgtcccg cccctgaagc tgctggcgga      780
cctagcgtgt tcctgttccc tcctaagccc aaggacaccc tcatgatctc cagaacccct      840
gaagtgacct gcgtggtcgt ggacgtgagc acgaggaccc cgaggtcaa gttcaattgg      900 tatgtggacg gcgtcgaggt gcacaatgcc aagaccaaac ccagagagga gcaatacaac      960
agcacctaca gtggtgtc cgtgctgaca gtgctgcacc aggattggct caatggcaag     1020
gagtacaaat gcaaagtgtc caacaaggcc ctgcccgctc ccatcgaaaa gacaatcagc     1080
aaggccaagg gccagcccag ggaacctcag gtctataccc tccctcccag cagggatgag     1140
ctcaccaaga accaagtgtc cctgacctgt ctggtcaaag gattctaccc ctccgatatt     1200
gctgtcgagt gggagagcaa cggccagccc gaaaacaact acaagacaac ccctcctgtg     1260
ctggatagcg acggttcttt cttcctgtac tccaagctca cagtggacaa atccaggtgg     1320
cagcagggca acgtgttctc ctgctccgtc atgcatgagg ccctgcacaa ccactatacc     1380
cagaagtccc tgtccctgag ccccggaaaa agaggcagaa aagaaggtc cggctccggc     1440 gccacaaact tctccctgct gaagcaggct ggcgacgtgg aggagaaccc cggccctatg     1500
gtcctccaga cccaggtgtt tattagcctg ctgctgtgga tcagcggcgc ctatggcagc     1560
tcctacgaac tgacacagcc ccctagcgtg agcgtgagcc ctggacgac cgccagaatt     1620 acctgcagcg gcgatgccct gcccaacaag tttgcttact ggtacaggca gaaatccggc     1680
caagcccctg tgctggtcat ttacgaggac aacaagaggc ccagcggcat tcctgagagg     1740
ttcagcggca gcagcagcgg aaccatggcc accctgacaa tcagcggcgc ccaagtggaa     1800
gacgaggctg actaccactg ttacagcaca gactcctcct ccaatcctct cggcgtgttc     1860
ggcggcggca caaactgac agtgctcgga cagcctaagg ccgcccctag cgtgacactg     1920
tttcctcctt cctccgagga actgcaggcc aacaaggcca cactggtgtg tctgatctcc     1980
gacttctacc ccggcgctgt gaccgtggct tggaaggccg attccagccc cgtgaaggct     2040
ggcgtcgaga ccacaacccc cagcaagcag agcaacaaca gtatgctgc ctcctcctac     2100 ctgtccctca cacccgaaca gtggaagagc ataggtcct acagctgcca ggtgacacac     2160
gaaggcagca cagtggaaaa gaccgtggcc cctaccgaat gctcctgata a           2211
```

<210> SEQ ID NO 80
<211> LENGTH: 735
<212> TYPE: PRT
<213> ORGANISM: Artificial Sequence
<220> FEATURE:
<223> OTHER INFORMATION: Chemically Synthesized, pRD229,
      185-mouse-GeneWiz

<400> SEQUENCE: 80

Met Asp Trp Thr Trp Arg Ile Leu Phe Leu Val Ala Ala Ala Thr Gly
1               5                   10                  15

Thr His Ala Glu Val Gln Leu Val Gln Ser Gly Ala Glu Val Lys Lys
                20                  25                  30

Pro Gly Glu Ser Leu Arg Ile Ser Cys Lys Gly Ser Gly Tyr Ser Phe

```
            35                  40                  45
Thr Ser Tyr Trp Ile Thr Trp Val Arg Gln Met Pro Gly Lys Gly Leu
 50                  55                  60

Glu Trp Met Ala Lys Phe Asp Pro Ser Asp Ser Gln Thr Asn Tyr Ser
 65                  70                  75                  80

Pro Ser Phe Gln Gly His Val Thr Ile Ser Val Asp Lys Ser Ile Ser
                     85                  90                  95

Thr Ala Tyr Leu Gln Trp Ser Ser Leu Lys Ala Ser Asp Thr Ala Met
                100                 105                 110

Tyr Tyr Cys Ala Arg Arg Tyr Cys Ser Ser Ser Cys Tyr Val Asp
                115                 120                 125

Asn Trp Gly Gln Gly Thr Leu Val Thr Ile Phe Ser Ala Ser Thr Lys
                130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Leu Gly Thr Gln Thr Tyr Ile Cys Asn
                210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
                290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
                370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460
```

Ser Leu Ser Pro Gly Lys Arg Gly Arg Lys Arg Ser Gly Ser Gly
465                 470                 475                 480

Ala Thr Asn Phe Ser Leu Leu Lys Gln Ala Gly Asp Val Glu Glu Asn
            485                 490                 495

Pro Gly Pro Met Val Leu Gln Thr Gln Val Phe Ile Ser Leu Leu Leu
            500                 505                 510

Trp Ile Ser Gly Ala Tyr Gly Ser Ser Tyr Glu Leu Thr Gln Pro Pro
        515                 520                 525

Ser Val Ser Val Ser Pro Gly Gln Thr Ala Arg Ile Thr Cys Ser Gly
530                 535                 540

Asp Ala Leu Pro Asn Lys Phe Ala Tyr Trp Tyr Arg Gln Lys Ser Gly
545                 550                 555                 560

Gln Ala Pro Val Leu Val Ile Tyr Glu Asp Asn Lys Arg Pro Ser Gly
            565                 570                 575

Ile Pro Glu Arg Phe Ser Gly Ser Ser Ser Gly Thr Met Ala Thr Leu
            580                 585                 590

Thr Ile Ser Gly Ala Gln Val Glu Asp Glu Ala Asp Tyr His Cys Tyr
        595                 600                 605

Ser Thr Asp Ser Ser Asn Pro Leu Gly Val Phe Gly Gly Gly Thr
610                 615                 620

Lys Leu Thr Val Leu Gly Gln Pro Lys Ala Ala Pro Ser Val Thr Leu
625                 630                 635                 640

Phe Pro Pro Ser Ser Glu Glu Leu Gln Ala Asn Lys Ala Thr Leu Val
            645                 650                 655

Cys Leu Ile Ser Asp Phe Tyr Pro Gly Ala Val Thr Val Ala Trp Lys
            660                 665                 670

Ala Asp Ser Ser Pro Val Lys Ala Gly Val Glu Thr Thr Thr Pro Ser
        675                 680                 685

Lys Gln Ser Asn Asn Lys Tyr Ala Ala Ser Ser Tyr Leu Ser Leu Thr
            690                 695                 700

Pro Glu Gln Trp Lys Ser His Arg Ser Tyr Ser Cys Gln Val Thr His
705                 710                 715                 720

Glu Gly Ser Thr Val Glu Lys Thr Val Ala Pro Thr Glu Cys Ser
                725                 730                 735

<210> SEQ ID NO 81
<211> LENGTH: 2211
<212> TYPE: DNA
<213> ORGANISM: Artificial Sequence
<220> FEATURE:
<223> OTHER INFORMATION: Chemically Synthesized, pRD231,
      185-mouse-GenScript

<400> SEQUENCE: 81
atggattgga catggaggat tctgtttctg gtcgccgccg ctactggaac tcacgccgaa      60
gtgcagctgg tgcagtcagg agccgaagtg aagaagccag gcgagagcct gcggatctcc    120
tgtaagggaa gcggctactc ctttacatct tactggatca cctgggtgcg ccagatgcca    180
ggaaagggcc tggagtggat ggccaagttc gaccccttctg atagccagac aaactactcc    240
ccatcttttc agggccacgt gacaatcagc gtggacaaga gcatctccac cgcctacctg    300
cagtggagct ccctgaaggc ctccgatacc gctatgtact actgcgctag agatactgt    360 tctagctcct cttgctacgt ggacaactgg ggacagggca cactggtgac catcttctct    420
gccagcacaa agggacccag cgtgttccca ctggctccca gctccaagtc cacatctggc    480

```
ggaaccgccg ctctgggatg tctggtgaag gattacttcc ccgagcctgt gaccgtgagc      540
tggaactccg gagccctgac aagcggcgtg cacacctttc ccgctgtgct gcagtctagc      600
ggactgtact ccctgtcctc tgtggtgaca gtgcctagct cctctctggg cacacagacc      660
tacatctgta acgtgaacca caagccttcc aacaccaagg tggacaagaa ggtggagcca      720
aagtcttgcg ataagacaca cacctgccct ccctgtccag ctccagaggc tgctggcgga      780
ccatccgtgt tcctgtttcc acccaagcct aaggacaccc tgatgatcag caggacacca      840
gaggtgacct gcgtggtggt ggacgtgtcc cacgaggacc ccgaggtgaa gttcaactgg      900
tacgtggatg gcgtggaggt gcacaacgcc aagacaaagc caagggagga gcagtacaac      960
tctacataca gagtggtgag cgtgctgacc gtgctgcacc aggactggct gaacggaaag     1020
gagtacaagt gtaaggtgtc taacaaggcc ctgcctgctc caatcgagaa gacaatcagc     1080
aaggctaagg gacagcctcg ggagccacag gtgtacaccc tgcctccatc tcgcgacgag     1140
ctgacaaaga accaggtgag cctgacctgc ctggtgaagg gcttctaccc ctccgatatc     1200
gctgtggagt gggagtctaa cggccagcct gagaacaact acaagaccac ccccctgtg      1260 ctggactctg atggaagctt ctttctgtac agcaagctga ccgtggacaa gtccagatgg     1320
cagcagggca acgtgttcag ctgttccgtg atgcacgagg ccctgcacaa ccactacaca     1380
cagaagtctc tgagcctgtc ccctggaaag aggggaagaa agcggcgctc tggaagcgga     1440
gccaccaact ttagcctgct gaagcaggct ggagatgtgg aggagaaccc cggccctatg     1500
gtgctgcaga cacaggtgtt catctccctg ctgctgtgga tctctggagc ctacggcagc     1560
tcctacagcc tgacccagcc accctccgtg tctgtgagcc ctggacagac agctaggatc     1620
acctgctctg gcgacgccct gccaaacaag tttgcttact ggtacagaca gaagtccgga     1680
caggcccccg tgctggtcat ctacgaggat aacaagcggc cctctggcat ccctgagagg     1740
ttcagcggat ctagctccgg cacaatggct acactgacca tctccggagc tcaggtggag     1800
gacgaggctg attaccactg ttactctacc gactctagtc caacccctct gggagtgttc     1860
ggcggaggca aaagctgac cgtgctggga cagccaaagg ctgctccaag cgtgaccctg     1920
tttcctccat ctagcgagga gctgcaggcc aacaaggcta cactggtgtg cctgatctcc     1980
gacttctacc ctggagctgt gaccgtggct tggaaggctg attcctctcc agtgaaggct     2040
ggcgtggaga acaacccc ctccaagcag tctaacaaca gtacgccgc tagctcctac     2100 ctgagcctga ccccagagca gtggaagtcc caccggtcct actcttgcca ggtcactcac     2160
gaaggaagca ctgtggaaaa aactgtcgcc cctaccgaat gttcttgata a              2211
```

<210> SEQ ID NO 82
<211> LENGTH: 735
<212> TYPE: PRT
<213> ORGANISM: Artificial Sequence
<220> FEATURE:
<223> OTHER INFORMATION: Chemically Synthesized, pRD231,
      185-mouse-GenScript

<400> SEQUENCE: 82

Met Asp Trp Thr Trp Arg Ile Leu Phe Leu Val Ala Ala Ala Thr Gly
1               5                   10                  15

Thr His Ala Glu Val Gln Leu Val Gln Ser Gly Ala Glu Val Lys Lys
            20                  25                  30

Pro Gly Glu Ser Leu Arg Ile Ser Cys Lys Gly Ser Gly Tyr Ser Phe
        35                  40                  45

Thr Ser Tyr Trp Ile Thr Trp Val Arg Gln Met Pro Gly Lys Gly Leu

-continued

```
                50                  55                  60
Glu Trp Met Ala Lys Phe Asp Pro Ser Asp Ser Gln Thr Asn Tyr Ser
 65                  70                  75                  80

Pro Ser Phe Gln Gly His Val Thr Ile Ser Val Asp Lys Ser Ile Ser
                 85                  90                  95

Thr Ala Tyr Leu Gln Trp Ser Ser Leu Lys Ala Ser Asp Thr Ala Met
            100                 105                 110

Tyr Tyr Cys Ala Arg Arg Tyr Cys Ser Ser Ser Cys Tyr Val Asp
        115                 120                 125

Asn Trp Gly Gln Gly Thr Leu Val Thr Ile Phe Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys Arg Gly Arg Lys Arg Arg Ser Gly Ser Gly
465                 470                 475                 480
```

```
Ala Thr Asn Phe Ser Leu Leu Lys Gln Ala Gly Asp Val Glu Glu Asn
                485                 490                 495

Pro Gly Pro Met Val Leu Gln Thr Gln Val Phe Ile Ser Leu Leu Leu
            500                 505                 510

Trp Ile Ser Gly Ala Tyr Gly Ser Ser Tyr Glu Leu Thr Gln Pro Pro
            515                 520                 525

Ser Val Ser Val Ser Pro Gly Gln Thr Ala Arg Ile Thr Cys Ser Gly
            530                 535                 540

Asp Ala Leu Pro Asn Lys Phe Ala Tyr Trp Tyr Arg Gln Lys Ser Gly
545                 550                 555                 560

Gln Ala Pro Val Leu Val Ile Tyr Glu Asp Asn Lys Arg Pro Ser Gly
                565                 570                 575

Ile Pro Glu Arg Phe Ser Gly Ser Ser Ser Gly Thr Met Ala Thr Leu
            580                 585                 590

Thr Ile Ser Gly Ala Gln Val Glu Asp Glu Ala Asp Tyr His Cys Tyr
            595                 600                 605

Ser Thr Asp Ser Ser Ser Asn Pro Leu Gly Val Phe Gly Gly Gly Thr
            610                 615                 620

Lys Leu Thr Val Leu Gly Gln Pro Lys Ala Ala Pro Ser Val Thr Leu
625                 630                 635                 640

Phe Pro Pro Ser Ser Glu Glu Leu Gln Ala Asn Lys Ala Thr Leu Val
                645                 650                 655

Cys Leu Ile Ser Asp Phe Tyr Pro Gly Ala Val Thr Val Ala Trp Lys
            660                 665                 670

Ala Asp Ser Ser Pro Val Lys Ala Gly Val Glu Thr Thr Thr Pro Ser
            675                 680                 685

Lys Gln Ser Asn Asn Lys Tyr Ala Ala Ser Ser Tyr Leu Ser Leu Thr
            690                 695                 700

Pro Glu Gln Trp Lys Ser His Arg Ser Tyr Ser Cys Gln Val Thr His
705                 710                 715                 720

Glu Gly Ser Thr Val Glu Lys Thr Val Ala Pro Thr Glu Cys Ser
                725                 730                 735

<210> SEQ ID NO 83
<211> LENGTH: 2211
<212> TYPE: DNA
<213> ORGANISM: Artificial Sequence
<220> FEATURE:
<223> OTHER INFORMATION: Chemically Synthesized, pRD233,
      185-mouse-Blue Heron

<400> SEQUENCE: 83
atggactgga cctggaggat actgtttctg gtggctgccg caaccggaac acatgccgaa    60
gtacagctgg ttcagtctgg agcggaggtc aagaagcccg ggaaagtct gaggatctct    120 tgcaagggt caggttatag tttcacaagt tattggatca cttgggtcag acaaatgccg    180
gggaagggac tggagtggat ggctaagttt gatcctccg attctcagac taattactcc    240
ccgtcatttc agggtcatgt gactatcagc gtcgataaat ctatttcaac tgcctacctg    300
caatggagca gcttgaaggc ttccgatacc gccatgtatt actgtgcacg gaggtattgt    360
tccagctcct cttgttacgt ggataactgg gggcagggga cattggtaac gatttttta    420 gcttctacaa agggcccctc tgtctttcct ctcgctcctt ctagcaaatc cacttctggg    480
ggaaccgctg cactgggatg cctcgtgaaa gactacttcc ccgaaccgt gaccgtgtca    540 tggaactcag gtgcccttac cagcggagtc cacacgttcc cggctgtgct tcagagttcc    600
```

```
ggtctgtatt ccctctcctc tgtggtgacg gtgccctcca gctcactggg aacgcagaca    660
tatatctgta acgtgaacca caaaccctcc aataccaagg tcgacaagaa ggtggagccg    720
aaatcctgtg ataagaccca tacctgtcct ccatgccccg ccccagaagc agctggagga    780
ccctctgtgt tcttgtttcc ccccaaaccg aaagatactt tgatgatctc ccggacccca    840
gaagtcacgt gtgtagtggt cgatgttagt catgaagacc ccgaagtgaa attcaactgg    900
tacgtagacg gcgtggaggt ccataatgct aagacgaagc cacgagaaga acagtataat    960
tccacctacc gggttgtcag cgtgcttacc gttttgcatc aggattggtt gaatggaaag   1020
gaatacaaat gcaaggtgtc caataaggcc ctgcccgctc ctatcgagaa gacaattagt   1080
aaggcaaaag gccaacctcg cgagccccag gtgtataccc tccctccctc cagggacgaa   1140
ctgacaaaga accaagtgag cctgacatgt ctggtcaagg gattttatcc ttcagatatc   1200
gctgtggagt gggaaagcaa tggccagcca gaaaacaact acaaaacaac tccgcccgtc   1260
ctggactctg acggttcctt tttcctgtac tctaagctga ctgtggataa gtcaagatgg   1320
cagcagggga atgtgttttc ttgtagcgtt atgcacgagg ctctgcacaa ccattatacg   1380
cagaagagtt tgagcctgag tcctggtaaa aggggccgga aacgcaggtc tggatctggg   1440
gctactaact tcagccttt gaaacaagcc ggggatgtgg aggaaaaccc agggcccatg   1500
gtcctgcaga ctcaggtttt tatcagtctg ctgctctgga tttcaggcgc ttacggtagc   1560
agctacgagc tgacccagcc cccttcagtg tccgtctcac aggacagac cgcgaggatc   1620 acttgcagtg gggatgccct gccgaataag tttgcgtatt ggtacagaca aaagtccggt   1680
caggcaccag tcctggtgat ttatgaagac aacaagcgac aagcggcat ccctgagcgc   1740 ttctccggtt ccagcagcgg gaccatggcc acactgacaa tcagtggggc ccaggtcgag   1800
gacgaggccg actaccactg ctattctacc gatagctctt caaatccatt gggagtgttt   1860
ggcggtggaa caaaactcac cgtgctgggg cagccaaagg cagctccaag tgtcactctt   1920
tttccaccta gcagtgaaga gctccaggcc aacaaagcaa ccctggtgtg tcttatcagc   1980 gattttacc ctgggcgt gacagtggc tggaaagccg attccagccc cgtgaaagcc   2040
ggtgtcgaaa ccactactcc tagcaagcag agcaacaata aatatgccgc gagttcctac   2100
ctgagcctta ctccagagca gtggaagtca caccggtcct atagttgtca ggttacacac   2160
gaaggaagta ctgttgaaaa gactgttgct ccgacagaat gcagctgata a            2211
```

<210> SEQ ID NO 84
<211> LENGTH: 735
<212> TYPE: PRT
<213> ORGANISM: Artificial Sequence
<220> FEATURE:
<223> OTHER INFORMATION: Chemically Synthesized, pRD233,
      185-mouse-Blue Heron

<400> SEQUENCE: 84

Met Asp Trp Thr Trp Arg Ile Leu Phe Leu Val Ala Ala Ala Thr Gly
1               5                   10                  15

Thr His Ala Glu Val Gln Leu Val Gln Ser Gly Ala Glu Val Lys Lys
                20                  25                  30

Pro Gly Glu Ser Leu Arg Ile Ser Cys Lys Gly Ser Gly Tyr Ser Phe
            35                  40                  45

Thr Ser Tyr Trp Ile Thr Trp Val Arg Gln Met Pro Gly Lys Gly Leu
        50                  55                  60

Glu Trp Met Ala Lys Phe Asp Pro Ser Asp Ser Gln Thr Asn Tyr Ser

```
                65                  70                  75                  80
            Pro Ser Phe Gln Gly His Val Thr Ile Ser Val Asp Lys Ser Ile Ser
                            85                  90                  95

Thr Ala Tyr Leu Gln Trp Ser Ser Leu Lys Ala Ser Asp Thr Ala Met
                            100                 105                 110

Tyr Tyr Cys Ala Arg Arg Tyr Cys Ser Ser Ser Cys Tyr Val Asp
                            115                 120                 125

Asn Trp Gly Gln Gly Thr Leu Val Thr Ile Phe Ser Ala Ser Thr Lys
                            130                 135                 140

Gly Pro Ser Val Phe Pro Leu Ala Pro Ser Ser Lys Ser Thr Ser Gly
            145                 150                 155                 160

Gly Thr Ala Ala Leu Gly Cys Leu Val Lys Asp Tyr Phe Pro Glu Pro
                            165                 170                 175

Val Thr Val Ser Trp Asn Ser Gly Ala Leu Thr Ser Gly Val His Thr
                            180                 185                 190

Phe Pro Ala Val Leu Gln Ser Ser Gly Leu Tyr Ser Leu Ser Ser Val
                            195                 200                 205

Val Thr Val Pro Ser Ser Leu Gly Thr Gln Thr Tyr Ile Cys Asn
            210                 215                 220

Val Asn His Lys Pro Ser Asn Thr Lys Val Asp Lys Lys Val Glu Pro
            225                 230                 235                 240

Lys Ser Cys Asp Lys Thr His Thr Cys Pro Pro Cys Pro Ala Pro Glu
                            245                 250                 255

Ala Ala Gly Gly Pro Ser Val Phe Leu Phe Pro Pro Lys Pro Lys Asp
                            260                 265                 270

Thr Leu Met Ile Ser Arg Thr Pro Glu Val Thr Cys Val Val Val Asp
                            275                 280                 285

Val Ser His Glu Asp Pro Glu Val Lys Phe Asn Trp Tyr Val Asp Gly
                            290                 295                 300

Val Glu Val His Asn Ala Lys Thr Lys Pro Arg Glu Glu Gln Tyr Asn
            305                 310                 315                 320

Ser Thr Tyr Arg Val Val Ser Val Leu Thr Val Leu His Gln Asp Trp
                            325                 330                 335

Leu Asn Gly Lys Glu Tyr Lys Cys Lys Val Ser Asn Lys Ala Leu Pro
                            340                 345                 350

Ala Pro Ile Glu Lys Thr Ile Ser Lys Ala Lys Gly Gln Pro Arg Glu
                            355                 360                 365

Pro Gln Val Tyr Thr Leu Pro Pro Ser Arg Asp Glu Leu Thr Lys Asn
                            370                 375                 380

Gln Val Ser Leu Thr Cys Leu Val Lys Gly Phe Tyr Pro Ser Asp Ile
            385                 390                 395                 400

Ala Val Glu Trp Glu Ser Asn Gly Gln Pro Glu Asn Asn Tyr Lys Thr
                            405                 410                 415

Thr Pro Pro Val Leu Asp Ser Asp Gly Ser Phe Phe Leu Tyr Ser Lys
                            420                 425                 430

Leu Thr Val Asp Lys Ser Arg Trp Gln Gln Gly Asn Val Phe Ser Cys
                            435                 440                 445

Ser Val Met His Glu Ala Leu His Asn His Tyr Thr Gln Lys Ser Leu
            450                 455                 460

Ser Leu Ser Pro Gly Lys Arg Gly Arg Lys Arg Ser Gly Ser Gly
            465                 470                 475                 480

Ala Thr Asn Phe Ser Leu Leu Lys Gln Ala Gly Asp Val Glu Glu Asn
                            485                 490                 495
```

```
Pro Gly Pro Met Val Leu Gln Thr Gln Val Phe Ile Ser Leu Leu Leu
            500                 505                 510
Trp Ile Ser Gly Ala Tyr Gly Ser Tyr Glu Leu Thr Gln Pro Pro
            515                 520                 525
Ser Val Ser Val Ser Pro Gly Gln Thr Ala Arg Ile Thr Cys Ser Gly
530                 535                 540
Asp Ala Leu Pro Asn Lys Phe Ala Tyr Trp Tyr Arg Gln Lys Ser Gly
545                 550                 555                 560
Gln Ala Pro Val Leu Val Ile Tyr Glu Asp Asn Lys Arg Pro Ser Gly
                565                 570                 575
Ile Pro Glu Arg Phe Ser Gly Ser Ser Gly Thr Met Ala Thr Leu
                580                 585                 590
Thr Ile Ser Gly Ala Gln Val Glu Asp Glu Ala Asp Tyr His Cys Tyr
            595                 600                 605
Ser Thr Asp Ser Ser Ser Asn Pro Leu Gly Val Phe Gly Gly Gly Thr
            610                 615                 620
Lys Leu Thr Val Leu Gly Gln Pro Lys Ala Ala Pro Ser Val Thr Leu
625                 630                 635                 640
Phe Pro Pro Ser Ser Glu Glu Leu Gln Ala Asn Lys Ala Thr Leu Val
                645                 650                 655
Cys Leu Ile Ser Asp Phe Tyr Pro Gly Ala Val Thr Val Ala Trp Lys
                660                 665                 670
Ala Asp Ser Ser Pro Val Lys Ala Gly Val Glu Thr Thr Pro Ser
            675                 680                 685
Lys Gln Ser Asn Asn Lys Tyr Ala Ala Ser Ser Tyr Leu Ser Leu Thr
            690                 695                 700
Pro Glu Gln Trp Lys Ser His Arg Ser Tyr Ser Cys Gln Val Thr His
705                 710                 715                 720
Glu Gly Ser Thr Val Glu Lys Thr Val Ala Pro Thr Glu Cys Ser
                725                 730                 735

<210> SEQ ID NO 85
<211> LENGTH: 2211
<212> TYPE: DNA
<213> ORGANISM: Artificial Sequence
<220> FEATURE:
<223> OTHER INFORMATION: Chemically Synthesized, pRD234,
      185-mammal-DNA2.0

<400> SEQUENCE: 85
atggactgga cttggcggat tttgttcctg gtggcggcgg ctactggaac tcatgcagaa    60
gtgcagcttg tgcagtccgg cgctgaagtc aagaagcctg gagagtccct gagaatcagc   120
tgcaagggca gcggctactc cttcaccctc gtactggatca cttgggtcag acaaatgccg   180
ggaaagggac tggaatggat ggctaaattc gacccgtcgg acagccagac taactacagc   240
ccgtcgttcc aaggacatgt caccatctcc gtggacaaat cgatcagcac cgcgtacctc   300
cagtggagct cactcaaagc atccgacacc gcgatgtact actgcgcccg ccgctactgc   360
tcgtcctcgt cctgctacgt ggacaattgg ggacagggta ctcttgtgac aatcttctcc   420
gcctccacca agggcccctc agtgttcccc ctggcaccat cctctaagtc cacctccgga   480
ggcaccgccg ccttgggttg cctggtcaag gactacttcc cggaacctgt gaccgtgtcc   540
tggaacagcg gggcactgac ctccggcgtg catacttttc ccgccgtcct gcaatcttcc   600
ggcctgtact cactgtcatc agtggtcacc gtgccctcgt cctccctggg cacccagact   660
```

```
tacatctgta acgtgaacca taagccctcc aacaccaaag tggacaagaa agtggagcca    720
aagtcgtgtg acaagactca cacttgcccg ccgtgcccgg ccccggaagc cgccggtgga    780
ccgagcgtgt ttctcttccc acccaagccg aaggatacccc tgatgatttc gcggacccct   840
gaagtgacct gtgtggtggt cgacgtgtcc cacgaggacc ccgaagtcaa gttcaattgg    900
tacgtggacg gtgtcgaagt gcacaacgcc aagacgaagc ctcgcgagga acagtacaac    960
agcacttacc gggtcgtgtc cgtcctcacc gtgctgcacc aagattggct caacgggaag    1020
gagtacaagt gcaaagtgtc aaataaggcc ctgccggccc cgattgaaaa gaccattagc    1080
aaggccaagg gacagcctag ggaaccctcaa gtgtacacgc tgcccccgtc gcgggacgag   1140
ctgaccaaga accaagtgtc gctgacttgc cttgtgaagg gattctaccc gtccgacatt    1200
gccgtggagt gggagtccaa cggacagccc gaaaacaact acaagaccac ccctcctgtg    1260
ctggactctg atggatcatt cttcctttac tcgaaactca ccgtggacaa gtcccgctgg    1320
caacagggaa acgtgttcag ctgctccgtg atgcacgagg ccctgcacaa ccactatacc    1380
cagaagtccc tgtcactgag ccccgggaag cgcggcagga gcggagaag cggaagcgga    1440
gctacaaaact tttcgctgct gaagcaggcc ggcgatgtgg aagaaaaccc agggcctatg    1500
gtgctgcaga ctcaagtgtt tatctccctg ctcctgtgga tctccggagc gtatgggtcc    1560
agctacgagc tcacccagcc tccttccgtg tcggtgtcac caggacagac cgcccggatt    1620
acctgttccg gggatgccct ccccaacaag ttcgcctact ggtaccgcca gaagtccggc    1680
caggctccag tgcttgtgat ctacgaggac aacaagcggc cttctggcat ccccgagcgg    1740
ttctccgggt cctcctccgg caccatggca accctgacca tctcgggagc tcaggtcgaa    1800
gatgaagccg actatcactg ctactcgacc gatagctcct caaacccgtt gggggtctttt   1860
ggcggaggaa ccaagctgac tgtgctggga cagccgaagg ccgcgccgtc cgtcaccctg    1920
ttcccgccga gcagcgagga actccaggcc aacaaggcca ctctcgtgtg cctgatttcc    1980
gacttctacc ctggtgccgt gactgtggcg tggaaggccg actcgtcgcc ggtcaaggcc    2040
ggcgtggaga ctaccacccc gtcaaaacag agcaacaata gtacgccgc tcctcctat     2100
ttgtcactga ctcccgagca gtggaagtcc accggtcct actcatgcca agtcaccccat   2160
gaagggtcca ccgtggaaaa gactgtggcc cccactgagt gttcgtaatg a            2211
```

<210> SEQ ID NO 86
<211> LENGTH: 735
<212> TYPE: PRT
<213> ORGANISM: Artificial Sequence
<220> FEATURE:
<223> OTHER INFORMATION: Chemically Synthesized, pRD234,
      185-mammal-DNA2.0

<400> SEQUENCE: 86

Met Asp Trp Thr Trp Arg Ile Leu Phe Leu Val Ala Ala Ala Thr Gly
1               5                   10                  15

Thr His Ala Glu Val Gln Leu Val Gln Ser Gly Ala Glu Val Lys Lys
            20                  25                  30

Pro Gly Glu Ser Leu Arg Ile Ser Cys Lys Gly Ser Gly Tyr Ser Phe
        35                  40                  45

Thr Ser Tyr Trp Ile Thr Trp Val Arg Gln Met Pro Gly Lys Gly Leu
    50                  55                  60

Glu Trp Met Ala Lys Phe Asp Pro Ser Asp Ser Gln Thr Asn Tyr Ser
65                  70                  75                  80

Pro Ser Phe Gln Gly His Val Thr Ile Ser Val Asp Lys Ser Ile Ser

```
                      85                  90                  95
Thr Ala Tyr Leu Gln Trp Ser Ser Leu Lys Ala Ser Asp Thr Ala Met
                100                 105                 110
Tyr Tyr Cys Ala Arg Arg Tyr Cys Ser Ser Ser Cys Tyr Val Asp
            115                 120                 125
Asn Trp Gly Gln Gly Thr Leu Val Thr Ile Phe Ser Ala Ser Thr Lys
    130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
                180                 185                 190
Phe Pro Ala Val Leu Gln Ser Ser Gly Leu Tyr Ser Leu Ser Ser Val
                195                 200                 205
Val Thr Val Pro Ser Ser Ser Leu Gly Thr Gln Thr Tyr Ile Cys Asn
                210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Ala Ala Gly Gly Pro Ser Val Phe Leu Phe Pro Pro Lys Pro Lys Asp
                260                 265                 270
Thr Leu Met Ile Ser Arg Thr Pro Glu Val Thr Cys Val Val Val Asp
                275                 280                 285
Val Ser His Glu Asp Pro Glu Val Lys Phe Asn Trp Tyr Val Asp Gly
                290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
                340                 345                 350
Ala Pro Ile Glu Lys Thr Ile Ser Lys Ala Lys Gly Gln Pro Arg Glu
                355                 360                 365
Pro Gln Val Tyr Thr Leu Pro Pro Ser Arg Asp Glu Leu Thr Lys Asn
                370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
                420                 425                 430
Leu Thr Val Asp Lys Ser Arg Trp Gln Gln Gly Asn Val Phe Ser Cys
                435                 440                 445
Ser Val Met His Glu Ala Leu His Asn His Tyr Thr Gln Lys Ser Leu
                450                 455                 460
Ser Leu Ser Pro Gly Lys Arg Gly Arg Lys Arg Arg Ser Gly Ser Gly
465                 470                 475                 480
Ala Thr Asn Phe Ser Leu Leu Lys Gln Ala Gly Asp Val Glu Glu Asn
                485                 490                 495
Pro Gly Pro Met Val Leu Gln Thr Gln Val Phe Ile Ser Leu Leu Leu
                500                 505                 510
```

```
Trp Ile Ser Gly Ala Tyr Gly Ser Ser Tyr Glu Leu Thr Gln Pro Pro
        515                 520                 525

Ser Val Ser Val Ser Pro Gly Gln Thr Ala Arg Ile Thr Cys Ser Gly
    530                 535                 540

Asp Ala Leu Pro Asn Lys Phe Ala Tyr Trp Tyr Arg Gln Lys Ser Gly
545                 550                 555                 560

Gln Ala Pro Val Leu Val Ile Tyr Glu Asp Asn Lys Arg Pro Ser Gly
                565                 570                 575

Ile Pro Glu Arg Phe Ser Gly Ser Ser Ser Gly Thr Met Ala Thr Leu
            580                 585                 590

Thr Ile Ser Gly Ala Gln Val Glu Asp Glu Ala Asp Tyr His Cys Tyr
        595                 600                 605

Ser Thr Asp Ser Ser Ser Asn Pro Leu Gly Val Phe Gly Gly Gly Thr
    610                 615                 620

Lys Leu Thr Val Leu Gly Gln Pro Lys Ala Ala Pro Ser Val Thr Leu
625                 630                 635                 640

Phe Pro Pro Ser Ser Glu Glu Leu Gln Ala Asn Lys Ala Thr Leu Val
                645                 650                 655

Cys Leu Ile Ser Asp Phe Tyr Pro Gly Ala Val Thr Val Ala Trp Lys
            660                 665                 670

Ala Asp Ser Ser Pro Val Lys Ala Gly Val Glu Thr Thr Thr Pro Ser
        675                 680                 685

Lys Gln Ser Asn Asn Lys Tyr Ala Ala Ser Ser Tyr Leu Ser Leu Thr
    690                 695                 700

Pro Glu Gln Trp Lys Ser His Arg Ser Tyr Ser Cys Gln Val Thr His
705                 710                 715                 720

Glu Gly Ser Thr Val Glu Lys Thr Val Ala Pro Thr Glu Cys Ser
                725                 730                 735

<210> SEQ ID NO 87
<211> LENGTH: 2235
<212> TYPE: DNA
<213> ORGANISM: Artificial Sequence
<220> FEATURE:
<223> OTHER INFORMATION: Chemically Synthesized, pGX9382, 190

<400> SEQUENCE: 87
atggattgga cctggagaat cctgttcctg gtggcagcag caaccggaac acacgcacag    60
gtgcagctgg tggagagcgg cggcggcgtg gtgcagccag ccggtccct gaggctgtct   120 tgcgcagcaa gcggcttcac ctttagcaag tacggaatgc actgggtgag acaggcacct   180
ggcaagggcc tggagtgggt ggccgtgatc tcctatgagg ctctaacaa gtactatgcc   240 gattccgtga agggcaggtt taccatcagc agagacaact ccaagaatac actgtacctg   300
cagatgaata gcctgagggc cgaggatacc gccgtgtact attgcgccaa gtccggcaca   360
cagtactatg acaccacagg ctacgagtat agaggcctgg agtacttcgg ctattgggc   420 cagggcaccc tggtgacagt gagctccgcc tccacaaagg gaccaagcgt gttcccactg   480
gcaccttcta gcaagtctac cagcggcggc acagccgccc tgggatgtct ggtgaaggat   540
tacttccctg agccagtgac cgtgagctgg aactccggcg ccctgacctc cggagtgcac   600
acatttcctg ccgtgctgca gtcctctggc ctgtactctc tgagctccgt ggtgaccgtg   660
ccatctagct ccctgggcac ccagacatat atctgcaacg tgaatcacaa gccaagcaat   720
acaaaggtgg acaagagggt ggagcccaag tcctgtgata agacccacac atgccctccc   780
```

```
tgtccagcac ctgaggcagc cggcggccca agcgtgttcc tgtttccacc caagcctaag      840
gatacactga tgatctctag aaccccgag gtgacatgcg tggtggtgga cgtgagccac      900
gaggaccccg aggtgaagtt caactggtac gtggacggcg tggaggtgca caatgccaag      960
accaagccca gggaggagca gtacaacagc acctatagag tggtgtccgt gctgacagtg     1020
ctgcaccagg actggctgaa cggcaaggag tataagtgca aggtgtccaa taaggccctg     1080
ccagccccca tcgagaagac catctctaag gcaaagggac agccacggga gccacaggtg     1140
tacacactgc ctccatcccg cgaggagatg accaagaacc aggtgtctct gacatgtctg     1200
gtgaagggct tctatccttc tgatatcgcc gtggagtggg agagcaatgg ccagccagag     1260
aacaattaca agaccacacc ccctgtgctg gactctgatg gcagcttctt tctgtattcc     1320
aagctgaccg tggacaagtc taggtggcag cagggcaacg tgttttcctg ctctgtgatg     1380
cacgaggccc tgcacaatca ctacacccag aagagcctgt ccctgtctcc tggcaagagg     1440
ggaaggaaga ggagaagcgg ctccggcgcc acaaacttca gcctgctgaa gcaggcaggc     1500
gacgtggagg agaatcctgg accaatggtg ctgcagaccc aggtgtttat ctctctgctg     1560
ctgtggatca gcggagcata cggagagatc gtgctgaccc agtctcctgg cacactgtct     1620
ctgagcccag agagagggc caccctgagc tgtagagcc cccagagcgt gagcagcagc     1680
tacctggcct ggtatcagca gaagagggga caggccccac gcctgctgat ctacgacgcc     1740
tctagccggg ccaccggcat ccccgatcgc ttcagcggct ccggctctgg cacagacttt     1800
accctgacaa tctcccggct ggagcctgag gatttcgccg tgtactattg ccagcagtat     1860
ggcaggagca gatggacctt tggccagggc acaaaggtgg agatcaagag gaccgtggca     1920
gcaccaagcg tgttcatctt tccaccctcc gatgagcagc tgaagtctgg cacagccagc     1980
gtggtgtgcc tgctgaacaa tttctacccc agggaggcca aggtgcagtg gaaggtggac     2040
aacgccctgc agtccggcaa ttctcaggag agcgtgaccg agcaggactc caaggattct     2100
acatatagcc tgtcctctac cctgacactg tccaaggccg actacgagaa gcacaaggtg     2160
tatgcatgcg aggtgaccca ccagggcctg agctccccag tgacaaagag ctttaaccgc     2220
ggcgagtgtt gataa                                                     2235
```

<210> SEQ ID NO 88
<211> LENGTH: 743
<212> TYPE: PRT
<213> ORGANISM: Artificial Sequence
<220> FEATURE:
<223> OTHER INFORMATION: Chemically Synthesized, pGX9382, 190

<400> SEQUENCE: 88

Met Asp Trp Thr Trp Arg Ile Leu Phe Leu Val Ala Ala Ala Thr Gly
1               5                   10                  15

Thr His Ala Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Lys Tyr Gly Met His Trp Val Arg Gln Ala Pro Gly Lys Gly Leu
    50                  55                  60

Glu Trp Val Ala Val Ile Ser Tyr Glu Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val

```
                100                 105                 110
Tyr Tyr Cys Ala Lys Ser Gly Thr Gln Tyr Tyr Asp Thr Thr Gly Tyr
            115                 120                 125

Glu Tyr Arg Gly Leu Glu Tyr Phe Gly Tyr Trp Gly Gln Gly Thr Leu
130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
            165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
            195                 200                 205

Ser Gly Leu Tyr Ser Leu Ser Ser Val Val Thr Val Pro Ser Ser Ser
            210                 215                 220

Leu Gly Thr Gln Thr Tyr Ile Cys Asn Val Asn His Lys Pro Ser Asn
225                 230                 235                 240

Thr Lys Val Asp Lys Arg Val Glu Pro Lys Ser Cys Asp Lys Thr His
            245                 250                 255

Thr Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
            290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
            325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
            370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
            450                 455                 460

His Asn His Tyr Thr Gln Lys Ser Leu Ser Leu Ser Pro Gly Lys Arg
465                 470                 475                 480

Gly Arg Lys Arg Arg Ser Gly Ser Gly Ala Thr Asn Phe Ser Leu Leu
            485                 490                 495

Lys Gln Ala Gly Asp Val Glu Glu Asn Pro Gly Pro Met Val Leu Gln
            500                 505                 510

Thr Gln Val Phe Ile Ser Leu Leu Leu Trp Ile Ser Gly Ala Tyr Gly
            515                 520                 525
```

```
Glu Ile Val Leu Thr Gln Ser Pro Gly Thr Leu Ser Leu Ser Pro Gly
    530                 535                 540

Glu Arg Ala Thr Leu Ser Cys Arg Ala Ser Gln Ser Val Ser Ser Ser
545                 550                 555                 560

Tyr Leu Ala Trp Tyr Gln Gln Lys Arg Gly Gln Ala Pro Arg Leu Leu
                565                 570                 575

Ile Tyr Asp Ala Ser Ser Arg Ala Thr Gly Ile Pro Asp Arg Phe Ser
            580                 585                 590

Gly Ser Gly Ser Gly Thr Asp Phe Thr Leu Thr Ile Ser Arg Leu Glu
        595                 600                 605

Pro Glu Asp Phe Ala Val Tyr Tyr Cys Gln Gln Tyr Gly Arg Ser Arg
    610                 615                 620

Trp Thr Phe Gly Gln Gly Thr Lys Val Glu Ile Lys Arg Thr Val Ala
625                 630                 635                 640

Ala Pro Ser Val Phe Ile Phe Pro Pro Ser Asp Glu Gln Leu Lys Ser
                645                 650                 655

Gly Thr Ala Ser Val Val Cys Leu Leu Asn Asn Phe Tyr Pro Arg Glu
            660                 665                 670

Ala Lys Val Gln Trp Lys Val Asp Asn Ala Leu Gln Ser Gly Asn Ser
        675                 680                 685

Gln Glu Ser Val Thr Glu Gln Asp Ser Lys Asp Ser Thr Tyr Ser Leu
    690                 695                 700

Ser Ser Thr Leu Thr Leu Ser Lys Ala Asp Tyr Glu Lys His Lys Val
705                 710                 715                 720

Tyr Ala Cys Glu Val Thr His Gln Gly Leu Ser Ser Pro Val Thr Lys
                725                 730                 735

Ser Phe Asn Arg Gly Glu Cys
            740

<210> SEQ ID NO 89
<211> LENGTH: 1518
<212> TYPE: DNA
<213> ORGANISM: Artificial Sequence
<220> FEATURE:
<223> OTHER INFORMATION: Chemically Synthesized, pGX93100,
      190.scFv_Fc.VH.G4S3.VL

<400> SEQUENCE: 89
atggattgga cctggagaat cctgttcctg gtggcagcag caaccggaac acacgcacag     60
gtgcagctgg tggagagcgg cggcggcgtg gtgcagccag ccggtccct gaggctgtct    120 tgcgcagcaa gcggcttcac ctttagcaag tacggaatgc actgggtgag acaggcacct    180
ggcaagggcc tggagtgggt ggccgtgatc tcctatgagg gctctaacaa gtactatgcc    240
gattccgtga agggcaggtt taccatcagc agagacaact ccaagaatac actgtacctg    300
cagatgaata gcctgagggc cgaggatacc gccgtgtact attgcgccaa gtccggcaca    360
cagtactatg acaccacagg ctacgagtat agaggcctgg agtacttcgg ctattgggc    420 cagggcaccc tggtgacagt gagctccggc ggcggcggct ccggcggcgg cggcagcggc    480
ggcggcggca gcgagatcgt gctgacccag tctcctggca cactgtctct gagcccagga    540
gagagggcca ccctgagctg tagagcctcc cagagcgtga gcagcagcta cctggcctgg    600
tatcagcaga gaggggacag gccccacgc ctgctgatct acgacgcctc tagccgggcc    660
accggcatcc ccgatcgctt cagcggctcc ggctctggca cagactttac cctgacaatc    720
tcccggctgg agcctgagga tttcgccgtg tactattgcc agcagtatgg caggagcaga    780
```

```
tggacctttg gccagggcac aaaggtggag atcaaggagc ccaagtcctg tgataagacc    840
cacacatgcc ctccctgtcc agcacctgag gcagccggcg gcccaagcgt gttcctgttt    900
ccacccaagc ctaaggatac actgatgatc tctagaaccc ccgaggtgac atgcgtggtg    960
gtggacgtga gccacgagga ccccgaggtg aagttcaact ggtacgtgga cggcgtggag   1020
gtgcacaatg ccaagaccaa gccagggag gagcagtaca acagcaccta tagagtggtg   1080
tccgtgctga cagtgctgca ccaggactgg ctgaacggca aggagtataa gtgcaaggtg   1140
tccaataagg ccctgccagc ccccatcgag aagaccatct ctaaggcaaa gggacagcca   1200
cgggagccac aggtgtacac actgcctcca tcccgcgagg agatgaccaa gaaccaggtg   1260
tctctgacat gtctggtgaa gggcttctat ccttctgata tcgccgtgga gtgggagagc   1320
aatggccagc cagagaacaa ttacaagacc acaccccctg tgctggactc tgatggcagc   1380
ttctttctgt attccaagct gaccgtggac aagtctaggt ggcagcaggg caacgtgttt   1440
tcctgctctg tgatgcacga ggccctgcac aatcactaca cccagaagag cctgtccctg   1500
tctcctggca agtgataa                                                 1518
```

<210> SEQ ID NO 90
<211> LENGTH: 504
<212> TYPE: PRT
<213> ORGANISM: Artificial Sequence
<220> FEATURE:
<223> OTHER INFORMATION: Chemically Synthesized, pGX93100,
      190.scFv_Fc.VH.G4S3.VL

<400> SEQUENCE: 90

```
Met Asp Trp Thr Trp Arg Ile Leu Phe Leu Val Ala Ala Thr Gly
1               5                   10                  15

Thr His Ala Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Lys Tyr Gly Met His Trp Val Arg Gln Ala Pro Gly Lys Gly Leu
    50                  55                  60

Glu Trp Val Ala Val Ile Ser Tyr Glu Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Ser Gly Thr Gln Tyr Tyr Asp Thr Thr Gly Tyr
        115                 120                 125

Glu Tyr Arg Gly Leu Glu Tyr Phe Gly Tyr Trp Gly Gln Gly Thr Leu
    130                 135                 140

Val Thr Val Ser Ser Gly Gly Gly Gly Ser Gly Gly Gly Gly Ser Gly
145                 150                 155                 160

Gly Gly Gly Ser Glu Ile Val Leu Thr Gln Ser Pro Gly Thr Leu Ser
                165                 170                 175

Leu Ser Pro Gly Glu Arg Ala Thr Leu Ser Cys Arg Ala Ser Gln Ser
            180                 185                 190

Val Ser Ser Ser Tyr Leu Ala Trp Tyr Gln Gln Lys Arg Gly Gln Ala
        195                 200                 205

Pro Arg Leu Leu Ile Tyr Asp Ala Ser Ser Arg Ala Thr Gly Ile Pro
    210                 215                 220
```

Asp Arg Phe Ser Gly Ser Gly Ser Gly Thr Asp Phe Thr Leu Thr Ile
225                 230                 235                 240

Ser Arg Leu Glu Pro Glu Asp Phe Ala Val Tyr Tyr Cys Gln Gln Tyr
            245                 250                 255

Gly Arg Ser Arg Trp Thr Phe Gly Gln Gly Thr Lys Val Glu Ile Lys
        260                 265                 270

Glu Pro Lys Ser Cys Asp Lys Thr His Thr Cys Pro Pro Cys Pro Ala
    275                 280                 285

Pro Glu Ala Ala Gly Gly Pro Ser Val Phe Leu Phe Pro Pro Lys Pro
290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
            325                 330                 335

Asp Gly Val Glu Val His Asn Ala Lys Thr Lys Pro Arg Glu Glu Gln
        340                 345                 350

Tyr Asn Ser Thr Tyr Arg Val Val Ser Val Leu Thr Val Leu His Gln
    355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
            405                 410                 415

Lys Asn Gln Val Ser Leu Thr Cys Leu Val Lys Gly Phe Tyr Pro Ser
        420                 425                 430

Asp Ile Ala Val Glu Trp Glu Ser Asn Gly Gln Pro Glu Asn Asn Tyr
    435                 440                 445

Lys Thr Thr Pro Pro Val Leu Asp Ser Asp Gly Ser Phe Phe Leu Tyr
450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
            485                 490                 495

Ser Leu Ser Leu Ser Pro Gly Lys
            500

<210> SEQ ID NO 91
<211> LENGTH: 1521
<212> TYPE: DNA
<213> ORGANISM: Artificial Sequence
<220> FEATURE:
<223> OTHER INFORMATION: Chemically Synthesized, pGX93101,
      190.scFv_Fc.VL.G4S3.VH

<400> SEQUENCE: 91
atggtgctgc agacccaggt gtttatctct ctgctgctgt ggatcagcgg agcatacgga     60
gagatcgtgc tgacccagtc tcctggcaca ctgtctctga gcccaggaga gagggccacc    120
ctgagctgta gagcctccca gagcgtgagc agcagctacc tggcctggta tcagcagaag    180
aggggacagg ccccacgcct gctgatctac gacgcctcta gccgggccac cggcatcccc    240
gatcgcttca gcggctccgg ctctggcaca gactttaccc tgacaatctc ccggctggag    300
cctgaggatt tcgccgtgta ctattgccag cagtatggca ggagcagatg gacctttggc    360
cagggcacaa aggtggagat caagggcggc ggcggctccg gcggcggcgg cagcggcggc    420

```
ggcggcagcc aggtgcagct ggtggagagc ggcggcggcg tggtgcagcc aggccggtcc      480
ctgaggctgt cttgcgcagc aagcggcttc acctttagca agtacggaat gcactgggtg      540
agacaggcac ctggcaaggg cctggagtgg gtggccgtga tctcctatga gggctctaac      600
aagtactatg ccgattccgt gaagggcagg tttaccatca gcagagacaa ctccaagaat      660
acactgtacc tgcagatgaa tagcctgagg gccgaggata ccgccgtgta ctattgcgcc      720
aagtccggca cacagtacta tgacaccaca ggctacgagt atagaggcct ggagtacttc      780
ggctattggg ccagggcac cctggtgaca gtgagctccg agcccaagtc ctgtgataag      840
acccacacat gccctcctg tccagcacct gaggcagccg gcggcccaag cgtgttcctg      900
tttccaccca gcctaagga tacactgatg atctctagaa cccccgaggt gacatgcgtg      960
gtggtggacg tgagccacga ggaccccgag gtgaagttca actggtacgt ggacggcgtg      1020
gaggtgcaca atgccaagac caagccagg gaggagcagt acaacagcac ctatagagtg      1080
gtgtccgtgc tgacagtgct gcaccaggac tggctgaacg gcaaggagta taagtgcaag      1140
gtgtccaata aggccctgcc agcccccatc gagaagacca tctctaaggc aaagggacag      1200
ccacgggagc cacaggtgta cactgcct ccatcccgcg aggagatgac caagaaccag      1260
gtgtctctga catgtctggt gaagggcttc tatccttctg atatcgccgt ggagtgggag      1320
agcaatggcc agccagagaa caattacaag accacccc ctgtgctgga ctctgatggc      1380
agcttctttc tgtattccaa gctgaccgtg gacaagtcta ggtggcagca gggcaacgtg      1440
ttttcctgct ctgtgatgca cgaggccctg cacaatcact acacccagaa gagcctgtcc      1500
ctgtctcctg gcaagtgata a                                                1521
```

<210> SEQ ID NO 92
<211> LENGTH: 505
<212> TYPE: PRT
<213> ORGANISM: Artificial Sequence
<220> FEATURE:
<223> OTHER INFORMATION: Chemically Synthesized, pGX93101,
      190.scFv_Fc.VL.G4S3.VH

<400> SEQUENCE: 92

```
Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Arg Gly Gln Ala
    50                  55                  60

Pro Arg Leu Leu Ile Tyr Asp Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Arg Ser Arg Trp Thr Phe Gly Gln Gly Thr Lys Val Glu Ile Lys
        115                 120                 125

Gly Gly Gly Gly Ser Gly Gly Gly Ser Gly Gly Gly Ser Gln
    130                 135                 140

Val Gln Leu Val Glu Ser Gly Gly Gly Val Val Gln Pro Gly Arg Ser
145                 150                 155                 160
```

```
Leu Arg Leu Ser Cys Ala Ala Ser Gly Phe Thr Phe Ser Lys Tyr Gly
                165                 170                 175

Met His Trp Val Arg Gln Ala Pro Gly Lys Gly Leu Glu Trp Val Ala
            180                 185                 190

Val Ile Ser Tyr Glu Gly Ser Asn Lys Tyr Tyr Ala Asp Ser Val Lys
        195                 200                 205

Gly Arg Phe Thr Ile Ser Arg Asp Asn Ser Lys Asn Thr Leu Tyr Leu
    210                 215                 220

Gln Met Asn Ser Leu Arg Ala Glu Asp Thr Ala Val Tyr Tyr Cys Ala
225                 230                 235                 240

Lys Ser Gly Thr Gln Tyr Tyr Asp Thr Thr Gly Tyr Glu Tyr Arg Gly
                245                 250                 255

Leu Glu Tyr Phe Gly Tyr Trp Gly Gln Gly Thr Leu Val Thr Val Ser
            260                 265                 270

Ser Glu Pro Lys Ser Cys Asp Lys Thr His Thr Cys Pro Pro Cys Pro
        275                 280                 285

Ala Pro Glu Ala Ala Gly Gly Pro Ser Val Phe Leu Phe Pro Pro Lys
    290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
370                 375                 380

Ala Leu Pro Ala Pro Ile Glu Lys Thr Ile Ser Lys Ala Lys Gly Gln
                385                 390                 395                 400

Pro Arg Glu Pro Gln Val Tyr Thr Leu Pro Pro Ser Arg Glu Glu Met
            405                 410                 415

Thr Lys Asn Gln Val Ser Leu Thr Cys Leu Val Lys Gly Phe Tyr Pro
        420                 425                 430

Ser Asp Ile Ala Val Glu Trp Glu Ser Asn Gly Gln Pro Glu Asn Asn
    435                 440                 445

Tyr Lys Thr Thr Pro Pro Val Leu Asp Ser Asp Gly Ser Phe Phe Leu
450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
            500                 505

<210> SEQ ID NO 93
<211> LENGTH: 1527
<212> TYPE: DNA
<213> ORGANISM: Artificial Sequence
<220> FEATURE:
<223> OTHER INFORMATION: Chemically Synthesized, pGX93102,
      190.scFv_Fc VH.Whitlow.VL

<400> SEQUENCE: 93
atggattgga cctggagaat cctgttcctg gtggcagcag caaccggaac acacgcacag      60
```

```
gtgcagctgg tggagagcgg cggcggcgtg gtgcagccag gccggtccct gaggctgtct    120
tgcgcagcaa gcggcttcac ctttagcaag tacggaatgc actgggtgag acaggcacct    180
ggcaagggcc tggagtgggt ggccgtgatc tcctatgagg gctctaacaa gtactatgcc    240
gattccgtga agggcaggtt taccatcagc agagacaact ccaagaatac actgtacctg    300
cagatgaata gcctgagggc cgaggatacc gccgtgtact attgcgccaa gtccggcaca    360
cagtactatg acaccacagg ctacgagtat agaggcctgg agtacttcgg ctattggggc    420
cagggcaccc tggtgacagt gagctccggc agcacctctg ctccggcaa gcccggctct    480 ggcgagggca gcaccaaggg cgagatcgtg ctgacccagt ctcctggcac actgtctctg    540
agcccaggag agagggccac cctgagctgt agagcctccc agagcgtgag cagcagctac    600
ctggcctggt atcagcagaa gaggggacag gcccccacgcc tgctgatcta cgacgcctct    660
agccgggcca ccggcatccc cgatcgcttc agcggctccg gctctggcac agactttacc    720
ctgacaatct cccggctgga gcctgaggat ttcgccgtgt actattgcca gcagtatggc    780
aggagcagat ggacctttgg ccagggcaca aaggtggaga tcaaggagcc caagtcctgt    840
gataagaccc acacatgccc tccctgtcca gcacctgagg cagccggcgg cccaagcgtg    900
ttcctgtttc cacccaagcc taaggataca ctgatgatct ctagaacccc cgaggtgaca    960
tgcgtggtgg tggacgtgag ccacgaggac cccgaggtga agttcaactg gtacgtggac   1020
ggcgtggagg tgcacaatgc caagaccaag cccagggagg agcagtacaa cagcacctat   1080
agagtggtgt ccgtgctgac agtgctgcac caggactggc tgaacggcaa ggagtataag   1140
tgcaaggtgt ccaataaggc cctgccagcc cccatcgaga agaccatctc taaggcaaag   1200
ggacagccac gggagccaca ggtgtacaca ctgcctccat cccgcgagga gatgaccaag   1260
aaccaggtgt ctctgacatg tctggtgaag ggcttctatc cttctgatat cgccgtggag   1320
tgggagagca atggccagcc agagaacaat tacaagacca cccccctgt gctggactct   1380 gatggcagct tctttctgta ttccaagctg accgtggaca gtctaggtg gcagcagggc   1440 aacgtgtttt cctgctctgt gatgcacgag gccctgcaca atcactacac ccagaagagc   1500
ctgtccctgt ctcctggcaa gtgataa                                        1527
```

<210> SEQ ID NO 94
<211> LENGTH: 507
<212> TYPE: PRT
<213> ORGANISM: Artificial Sequence
<220> FEATURE:
<223> OTHER INFORMATION: Chemically Synthesized, pGX93102,
      190.scFv_Fc VH.Whitlow.VL

<400> SEQUENCE: 94

Met Asp Trp Thr Trp Arg Ile Leu Phe Leu Val Ala Ala Thr Gly
1               5                   10                  15

Thr His Ala Gln Val Gln Leu Val Glu Ser Gly Gly Gly Val Gln
                20                  25                  30

Pro Gly Arg Ser Leu Arg Leu Ser Cys Ala Ala Ser Gly Phe Thr Phe
            35                  40                  45

Ser Lys Tyr Gly Met His Trp Val Arg Gln Ala Pro Gly Lys Gly Leu
        50                  55                  60

Glu Trp Val Ala Val Ile Ser Tyr Glu Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

```
Thr Leu Tyr Leu Gln Met Asn Ser Leu Arg Ala Glu Asp Thr Ala Val
            100                 105                 110

Tyr Tyr Cys Ala Lys Ser Gly Thr Gln Tyr Tyr Asp Thr Thr Gly Tyr
        115                 120                 125

Glu Tyr Arg Gly Leu Glu Tyr Phe Gly Tyr Trp Gly Gln Gly Thr Leu
130                 135                 140

Val Thr Val Ser Ser Gly Ser Thr Ser Gly Ser Gly Lys Pro Gly Ser
145                 150                 155                 160

Gly Glu Gly Ser Thr Lys Gly Glu Ile Val Leu Thr Gln Ser Pro Gly
                165                 170                 175

Thr Leu Ser Leu Ser Pro Gly Glu Arg Ala Thr Leu Ser Cys Arg Ala
            180                 185                 190

Ser Gln Ser Val Ser Ser Ser Tyr Leu Ala Trp Tyr Gln Gln Lys Arg
        195                 200                 205

Gly Gln Ala Pro Arg Leu Leu Ile Tyr Asp Ala Ser Ser Arg Ala Thr
    210                 215                 220

Gly Ile Pro Asp Arg Phe Ser Gly Ser Gly Ser Gly Thr Asp Phe Thr
225                 230                 235                 240

Leu Thr Ile Ser Arg Leu Glu Pro Glu Asp Phe Ala Val Tyr Tyr Cys
                245                 250                 255

Gln Gln Tyr Gly Arg Ser Arg Trp Thr Phe Gly Gln Gly Thr Lys Val
            260                 265                 270

Glu Ile Lys Glu Pro Lys Ser Cys Asp Lys Thr His Thr Cys Pro Pro
        275                 280                 285

Cys Pro Ala Pro Glu Ala Ala Gly Gly Pro Ser Val Phe Leu Phe Pro
    290                 295                 300

Pro Lys Pro Lys Asp Thr Leu Met Ile Ser Arg Thr Pro Glu Val Thr
305                 310                 315                 320

Cys Val Val Val Asp Val Ser His Glu Asp Pro Glu Val Lys Phe Asn
                325                 330                 335

Trp Tyr Val Asp Gly Val Glu Val His Asn Ala Lys Thr Lys Pro Arg
            340                 345                 350

Glu Glu Gln Tyr Asn Ser Thr Tyr Arg Val Val Ser Val Leu Thr Val
        355                 360                 365

Leu His Gln Asp Trp Leu Asn Gly Lys Glu Tyr Lys Cys Lys Val Ser
    370                 375                 380

Asn Lys Ala Leu Pro Ala Pro Ile Glu Lys Thr Ile Ser Lys Ala Lys
385                 390                 395                 400

Gly Gln Pro Arg Glu Pro Gln Val Tyr Thr Leu Pro Pro Ser Arg Glu
                405                 410                 415

Glu Met Thr Lys Asn Gln Val Ser Leu Thr Cys Leu Val Lys Gly Phe
            420                 425                 430

Tyr Pro Ser Asp Ile Ala Val Glu Trp Glu Ser Asn Gly Gln Pro Glu
        435                 440                 445

Asn Asn Tyr Lys Thr Thr Pro Pro Val Leu Asp Ser Asp Gly Ser Phe
    450                 455                 460

Phe Leu Tyr Ser Lys Leu Thr Val Asp Lys Ser Arg Trp Gln Gln Gly
465                 470                 475                 480

Asn Val Phe Ser Cys Ser Val Met His Glu Ala Leu His Asn His Tyr
                485                 490                 495

Thr Gln Lys Ser Leu Ser Leu Ser Pro Gly Lys
            500                 505
```

<210> SEQ ID NO 95
<211> LENGTH: 1530
<212> TYPE: DNA
<213> ORGANISM: Artificial Sequence
<220> FEATURE:
<223> OTHER INFORMATION: Chemically Synthesized, pGX93103,
190.scFv_Fc.VL.Whitlow.VH

<400> SEQUENCE: 95

```
atggtgctgc agacccaggt gtttatctct ctgctgctgt ggatcagcgg agcatacgga      60
gagatcgtgc tgacccagtc tcctggcaca ctgtctctga gcccaggaga gagggccacc     120
ctgagctgta gagcctccca gagcgtgagc agcagctacc tggcctggta tcagcagaag     180
aggggacagg ccccacgcct gctgatctac gacgcctcta ccgggccac cggcatcccc      240
gatcgcttca gcggctccgg ctctggcaca gactttaccc tgacaatctc ccggctggag     300
cctgaggatt tcgccgtgta ctattgccag cagtatggca ggagcagatg gacctttggc     360
cagggcacaa aggtggagat caagggcagc acctctggct ccggcaagcc cggctctggc     420
gagggcagca ccaagggcca ggtgcagctg gtggagagcg gcggcggcgt ggtgcagcca     480
ggccggtccc tgaggctgtc ttgcgcagca agcggcttca cctttagcaa gtacggaatg     540
cactgggtga cacaggcacc tggcaagggc ctggagtggg tggccgtgat ctcctatgag     600
ggctctaaca gtactatgc cgattccgtg aagggcaggt ttaccatcag cagagacaac      660
tccaagaata cactgtacct gcagatgaat agcctgaggg ccgaggatac cgccgtgtac     720
tattgcgcca gtccggcac acagtactat gacaccacag gctacgagta tagaggcctg      780
gagtacttcg ctattgggg ccagggcacc ctggtgacag tgagctccga gcccaagtcc      840
tgtgataaga cccacacatg ccctcctgt ccagcacctg aggcagccgg cggcccaagc      900
gtgttcctgt ttcacccaa gcctaaggat acactgatga tctctagaac ccccgaggtg      960
acatgcgtgg tggtggacgt gagccacgag acccccgagg tgaagttcaa ctggtacgtg    1020
gacggcgtgg aggtgcacaa tgccaagacc aagcccaggg aggagcagta caacagcacc    1080
tatagagtgg tgtccgtgct gacagtgctg caccaggact ggctgaacgg caaggagtat    1140
aagtgcaagg tgtccaataa ggccctgcca gcccccatcg agaagaccat ctctaaggca    1200
aagggacagc cacgggagcc acaggtgtac acactgcctc catcccgcga ggagatgacc    1260
aagaaccagg tgtctctgac atgtctggtg aagggcttct atccttctga tatcgccgtg    1320
gagtgggaga gcaatggcca gccagagaac aattacaaga ccacacccc tgtgctggac    1380
tctgatggca gcttctttct gtattccaag ctgaccgtgg acaagtctag gtggcagcag    1440
ggcaacgtgt tttcctgctc tgtgatgcac gaggccctgc acaatcacta cacccagaag    1500
agcctgtccc tgtctcctgg caagtgataa                                     1530
```

<210> SEQ ID NO 96
<211> LENGTH: 508
<212> TYPE: PRT
<213> ORGANISM: Artificial Sequence
<220> FEATURE:
<223> OTHER INFORMATION: Chemically Synthesized, pGX93103,
190.scFv_Fc.VL.Whitlow.VH

<400> SEQUENCE: 96

```
Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Gly Thr Leu Ser
            20                  25                  30
```

```
Leu Ser Pro Gly Glu Arg Ala Thr Leu Ser Cys Arg Ala Ser Gln Ser
             35                  40                  45

Val Ser Ser Ser Tyr Leu Ala Trp Tyr Gln Gln Lys Arg Gly Gln Ala
 50                  55                  60

Pro Arg Leu Leu Ile Tyr Asp Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
                100                 105                 110

Gly Arg Ser Arg Trp Thr Phe Gly Gln Gly Thr Lys Val Glu Ile Lys
            115                 120                 125

Gly Ser Thr Ser Gly Ser Gly Lys Pro Gly Ser Gly Glu Gly Ser Thr
        130                 135                 140

Lys Gly Gln Val Gln Leu Val Glu Ser Gly Gly Val Val Gln Pro
145                 150                 155                 160

Gly Arg Ser Leu Arg Leu Ser Cys Ala Ala Ser Gly Phe Thr Phe Ser
                165                 170                 175

Lys Tyr Gly Met His Trp Val Arg Gln Ala Pro Gly Lys Gly Leu Glu
            180                 185                 190

Trp Val Ala Val Ile Ser Tyr Glu Gly Ser Asn Lys Tyr Tyr Ala Asp
        195                 200                 205

Ser Val Lys Gly Arg Phe Thr Ile Ser Arg Asp Asn Ser Lys Asn Thr
    210                 215                 220

Leu Tyr Leu Gln Met Asn Ser Leu Arg Ala Glu Asp Thr Ala Val Tyr
225                 230                 235                 240

Tyr Cys Ala Lys Ser Gly Thr Gln Tyr Tyr Asp Thr Thr Gly Tyr Glu
                245                 250                 255

Tyr Arg Gly Leu Glu Tyr Phe Gly Tyr Trp Gly Gln Gly Thr Leu Val
            260                 265                 270

Thr Val Ser Ser Glu Pro Lys Ser Cys Asp Lys Thr His Thr Cys Pro
        275                 280                 285

Pro Cys Pro Ala Pro Glu Ala Ala Gly Gly Pro Ser Val Phe Leu Phe
    290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
            340                 345                 350

Arg Glu Glu Gln Tyr Asn Ser Thr Tyr Arg Val Val Ser Val Leu Thr
        355                 360                 365

Val Leu His Gln Asp Trp Leu Asn Gly Lys Glu Tyr Lys Cys Lys Val
    370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
                405                 410                 415

Glu Glu Met Thr Lys Asn Gln Val Ser Leu Thr Cys Leu Val Lys Gly
            420                 425                 430

Phe Tyr Pro Ser Asp Ile Ala Val Glu Trp Glu Ser Asn Gly Gln Pro
        435                 440                 445
```

```
Glu Asn Asn Tyr Lys Thr Thr Pro Pro Val Leu Asp Ser Asp Gly Ser
    450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
            485                 490                 495

Tyr Thr Gln Lys Ser Leu Ser Leu Ser Pro Gly Lys
            500                 505

<210> SEQ ID NO 97
<211> LENGTH: 2211
<212> TYPE: DNA
<213> ORGANISM: Artificial Sequence
<220> FEATURE:
<223> OTHER INFORMATION: Chemically Synthesized, pGX93134, 185

<400> SEQUENCE: 97
atggactgga cttggagaat cctgttcctg gtcgccgcag caaccgggac ccacgccgag     60
gtgcagctgg tgcagagcgg ggcagaagtg aagaagccag cgagagcct gcggatctcc    120 tgtaagggca gcggctactc ctttacatct tattggatca cctgggtgcg ccagatgcca    180
ggcaagggcc tggagtggat ggccaagttc gacccttctg atagccagac aaactactcc    240
ccatcttttc agggccacgt gacaatcagc gtggacaaga gcatctccac cgcctatctg    300
cagtggagct ccctgaaggc ctccgatacc gccatgtact attgcgccag agatactgt    360 tctagctcct cttgctatgt ggacaattgg ggccagggca cactggtgac catcttctct    420
gccagcacaa agggaccaag cgtgtttcca ctggcaccca gctccaagtc cacatctggc    480
ggcaccgccg ccctgggatg tctggtgaag gattacttcc ccgagcctgt gaccgtgagc    540
tggaactccg gcgccctgac aagcggagtg cacacctttc cagccgtgct gcagtctagc    600
ggcctgtact ccctgtcctc tgtggtgaca gtgcctagct cctctctggg cacacagacc    660
tatatctgta acgtgaatca caagccttcc aataccaagg tggacaagaa ggtgagccac    720
aagtcttgcg ataagacaca cacctgccct ccctgtccag caccagaggc agccggcgga    780
ccatccgtgt tcctgtttcc acccaagcct aaggacaccc tgatgatcag caggacacca    840
gaggtgacct gcgtggtggt ggacgtgtcc cacgaggacc ccgaggtgaa gttcaactgg    900
tacgtggatg gcgtggaggt gcacaatgcc aagacaaagc caaggagga gcagtacaac    960 tctacatata gagtggtgag cgtgctgacc gtgctgcacc aggactggct gaacggcaag   1020
gagtataagt gtaaggtgtc taataaggcc ctgcctgccc caatcgagaa gacaatcagc   1080
aaggcaaagg gacagcctcg ggagccacag gtgtacaccc tgcctccatc tcgcgacgag   1140
ctgacaaaga accaggtgag cctgacctgc ctggtgaagg gcttttatcc ctccgatatc   1200
gccgtggagt gggagtctaa tggccagcct gagaacaatt acaagaccac accccctgtg   1260
ctggactctg atggcagctt ctttctgtat agcaagctga ccgtggacaa gtccggtgg   1320 cagcagggca acgtgttcag ctgttccgtg atgcacgagg ccctgcacaa tcactacaca   1380
cagaagtctc tgagcctgtc cctggcaag aggggaagaa agcggcgctc tggcagcgga   1440
gcaaccaact ttagcctgct gaagcaggca ggcgatgtgg aggagaatcc aggacctatg   1500
gtgctgcaga cacaggtgtt catctccctg ctgctgtgga tctctggcgc ctacggcagc   1560
tcctatgagc tgacccagcc accctccgtg tctgtgagcc tggccagac agcaaggatc   1620 acctgcagcg gcgacgcact gccaaacaag tttgcctact ggtatagaca gaagtccgga   1680
caggcacccg tgctggtcat ctacgaggat aataagcggc cctctggcat ccctgagagg   1740
```

-continued

| | |
|---|---|
| ttcagcggct ctagctccgg cacaatggcc acactgacca tctccggagc acaggtggag | 1800 |
| gacgaggcag attaccactg ttattctacc gactctagct ccaaccctct gggcgtgttc | 1860 |
| ggcggcggaa caaagctgac cgtgctggga cagccaaagg cagcaccaag cgtgaccctg | 1920 |
| tttcctccat ctagcgagga gctgcaggcc aataaggcca cactggtgtg cctgatctcc | 1980 |
| gacttctacc ctggagcagt gaccgtggca tggaaggccg attcctctcc agtgaaggcc | 2040 |
| ggcgtggaga caacaacccc ctccaagcag tctaacaata agtacgccgc cagctcctat | 2100 |
| ctgagcctga ccccagagca gtggaagtcc cacaggtcct attcttgtca ggtcacccat | 2160 |
| gaaggctcaa cagtggagaa aacagtcgcc cctacagaat gctcatgata a | 2211 |

<210> SEQ ID NO 98
<211> LENGTH: 735
<212> TYPE: PRT
<213> ORGANISM: Artificial Sequence
<220> FEATURE:
<223> OTHER INFORMATION: Chemically Synthesized, pGX93134, 185

<400> SEQUENCE: 98

```
Met Asp Trp Thr Trp Arg Ile Leu Phe Leu Val Ala Ala Ala Thr Gly
1               5                   10                  15

Thr His Ala Glu Val Gln Leu Val Gln Ser Gly Ala Glu Val Lys Lys
                20                  25                  30

Pro Gly Glu Ser Leu Arg Ile Ser Cys Lys Gly Ser Gly Tyr Ser Phe
            35                  40                  45

Thr Ser Tyr Trp Ile Thr Trp Val Arg Gln Met Pro Gly Lys Gly Leu
        50                  55                  60

Glu Trp Met Ala Lys Phe Asp Pro Ser Asp Ser Gln Thr Asn Tyr Ser
65                  70                  75                  80

Pro Ser Phe Gln Gly His Val Thr Ile Ser Val Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Arg Tyr Cys Ser Ser Ser Cys Tyr Val Asp
        115                 120                 125

Asn Trp Gly Gln Gly Thr Leu Val Thr Ile Phe Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
```

-continued

```
                275                 280                 285
Val Ser His Glu Asp Pro Glu Val Lys Phe Asn Trp Tyr Val Asp Gly
        290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
            355                 360                 365
Pro Gln Val Tyr Thr Leu Pro Pro Ser Arg Asp Glu Leu Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
Ser Leu Ser Pro Gly Lys Arg Gly Arg Lys Arg Arg Ser Gly Ser Gly
465                 470                 475                 480
Ala Thr Asn Phe Ser Leu Leu Lys Gln Ala Gly Asp Val Glu Glu Asn
                485                 490                 495
Pro Gly Pro Met Val Leu Gln Thr Gln Val Phe Ile Ser Leu Leu Leu
            500                 505                 510
Trp Ile Ser Gly Ala Tyr Gly Ser Ser Tyr Glu Leu Thr Gln Pro Pro
        515                 520                 525
Ser Val Ser Val Ser Pro Gly Gln Thr Ala Arg Ile Thr Cys Ser Gly
    530                 535                 540
Asp Ala Leu Pro Asn Lys Phe Ala Tyr Trp Tyr Arg Gln Lys Ser Gly
545                 550                 555                 560
Gln Ala Pro Val Leu Val Ile Tyr Glu Asp Asn Lys Arg Pro Ser Gly
                565                 570                 575
Ile Pro Glu Arg Phe Ser Gly Ser Ser Ser Gly Thr Met Ala Thr Leu
            580                 585                 590
Thr Ile Ser Gly Ala Gln Val Glu Asp Glu Ala Asp Tyr His Cys Tyr
        595                 600                 605
Ser Thr Asp Ser Ser Asn Pro Leu Gly Val Phe Gly Gly Gly Thr
    610                 615                 620
Lys Leu Thr Val Leu Gly Gln Pro Lys Ala Ala Pro Ser Val Thr Leu
625                 630                 635                 640
Phe Pro Pro Ser Ser Glu Glu Leu Gln Ala Asn Lys Ala Thr Leu Val
                645                 650                 655
Cys Leu Ile Ser Asp Phe Tyr Pro Gly Ala Val Thr Val Ala Trp Lys
            660                 665                 670
Ala Asp Ser Ser Pro Val Lys Ala Gly Val Glu Thr Thr Thr Pro Ser
        675                 680                 685
Lys Gln Ser Asn Asn Lys Tyr Ala Ala Ser Ser Tyr Leu Ser Leu Thr
    690                 695                 700
```

```
Pro Glu Gln Trp Lys Ser His Arg Ser Tyr Ser Cys Gln Val Thr His
705                 710                 715                 720

Glu Gly Ser Thr Val Glu Lys Thr Val Ala Pro Thr Glu Cys Ser
                725                 730                 735
```

<210> SEQ ID NO 99
<211> LENGTH: 1497
<212> TYPE: DNA
<213> ORGANISM: Artificial Sequence
<220> FEATURE:
<223> OTHER INFORMATION: Chemically Synthesized, pGX93129,
      185.scFv_Fc.VH.G4S3.VL

<400> SEQUENCE: 99

```
atggattgga catggagaat cctgttcctg gtcgccgccg caactgggac ccacgccgaa      60
gtgcagctgg tgcagtctgg agccgaagtg aagaagccag gcgagtctct gagaatcagc     120
tgcaagggca gcggctactc tttcacatcc tactggatca cctgggtgcg ccagatgcca     180
ggcaagggcc tggagtggat ggccaagttc gacccatctg atagccagac aaactacagc     240
ccctccttcc agggccacgt gacaatctcc gtggacaagt ccatcagcac agcctatctg     300
cagtggtctt ccctgaaggc ctctgacacc gccatgtact attgcgcccg agatattgc      360
agctcttcca gctgttacgt ggacaactgg ggccagggca ccctggtgac aatcttctct     420
ggcggcggcg gctctggcgg cggcggcagc ggcggcggcg gctccagctc ctatgagctg     480
acccagcccc catccgtgag cgtgtctcca ggccagacag cccggatcac atgtagcggc     540
gacgccctgc ctaataagtt tgcctactgg tacaggcaga gagcggcca ggccccagtg      600
ctggtaatct acgaggacaa caagcgccca tctggcatcc ccgagagatt ttctggctct     660
tccagcggca ccatggccac cctgacaatc tccggcgccc aggtggagga tgaggccgat     720
tatcactgct acagcacaga ttccagctcc aatcccctgg gcgtgtttgg cggcggcacc     780
aagctgaccg tgctggagcc aaagagctcc gataagaccc acacctgtcc accttgcccc     840
gccccagagg ccgccggcgg cccaagcgtg ttcctgttcc cacctaagcc caaggacacc     900
ctgatgatct ccagaacccc tgaggtgaca tgcgtggtgg tggacgtgtc tcacgaggac     960
ccagaggtga agttcaactg gtatgtggac ggcgtggagg tgcacaacgc caagacaaag    1020
cctagagagg agcagtacaa cagcacctac agagtggtgt ctgtgctgac agtgctgcac    1080
caggactggc tgaacggcaa ggagtacaag tgtaaggtgt ccaataaggc cctgccagcc    1140
cctatcgaga gaccatctc taaggccaag ggccagccaa gagagccaca ggtgtatacc     1200
ctgccaccct ctagagacga gctgacaaag aaccaggtgt ctctgacatg tctggtgaag    1260
ggcttctacc cctctgatat cgccgtggag tgggagtcta atggccagcc agagaataac    1320
tacaagacca caccacctgt gctggactcc gatggcagct ttttcctgta cagcaagctg    1380
acagtggata gtccagatg gcagcaggg aacgtgttta gctgctccgt gatgcacgaa      1440
gcactgcaca accactacac ccagaagtcc ctgagcctgt cacccggcaa gtgataa       1497
```

<210> SEQ ID NO 100
<211> LENGTH: 497
<212> TYPE: PRT
<213> ORGANISM: Artificial Sequence
<220> FEATURE:
<223> OTHER INFORMATION: Chemically Synthesized, pGX93129,
      185.scFv_Fc.VH.G4S3.VL

<400> SEQUENCE: 100

```
Met Asp Trp Thr Trp Arg Ile Leu Phe Leu Val Ala Ala Ala Thr Gly
1               5                   10                  15

Thr His Ala Glu Val Gln Leu Val Gln Ser Gly Ala Glu Val Lys Lys
            20                  25                  30

Pro Gly Glu Ser Leu Arg Ile Ser Cys Lys Gly Ser Gly Tyr Ser Phe
            35                  40                  45

Thr Ser Tyr Trp Ile Thr Trp Val Arg Gln Met Pro Gly Lys Gly Leu
50                  55                  60

Glu Trp Met Ala Lys Phe Asp Pro Ser Asp Ser Gln Thr Asn Tyr Ser
65                  70                  75                  80

Pro Ser Phe Gln Gly His Val Thr Ile Ser Val Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Arg Tyr Cys Ser Ser Ser Cys Tyr Val Asp
            115                 120                 125

Asn Trp Gly Gln Gly Thr Leu Val Thr Ile Phe Ser Gly Gly Gly Gly
    130                 135                 140

Ser Gly Gly Gly Gly Ser Gly Gly Gly Ser Ser Ser Tyr Glu Leu
145                 150                 155                 160

Thr Gln Pro Pro Ser Val Ser Val Ser Pro Gly Gln Thr Ala Arg Ile
                165                 170                 175

Thr Cys Ser Gly Asp Ala Leu Pro Asn Lys Phe Ala Tyr Trp Tyr Arg
            180                 185                 190

Gln Lys Ser Gly Gln Ala Pro Val Leu Val Ile Tyr Glu Asp Asn Lys
    195                 200                 205

Arg Pro Ser Gly Ile Pro Glu Arg Phe Ser Gly Ser Ser Ser Gly Thr
210                 215                 220

Met Ala Thr Leu Thr Ile Ser Gly Ala Gln Val Glu Asp Glu Ala Asp
225                 230                 235                 240

Tyr His Cys Tyr Ser Thr Asp Ser Ser Asn Pro Leu Gly Val Phe
            245                 250                 255

Gly Gly Gly Thr Lys Leu Thr Val Leu Glu Pro Lys Ser Ser Asp Lys
            260                 265                 270

Thr His Thr Cys Pro Pro Cys Pro Ala Pro Glu Ala Ala Gly Gly Pro
    275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
            325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
            355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
```

420             425             430
Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
            450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
            485                 490                 495

Lys

<210> SEQ ID NO 101
<211> LENGTH: 1500
<212> TYPE: DNA
<213> ORGANISM: Artificial Sequence
<220> FEATURE:
<223> OTHER INFORMATION: Chemically Synthesized, pGX93130,
      185.scFv_Fc.VL.G4S3.VH

<400> SEQUENCE: 101
atggtcctgc agactcaggt gtttatttca ctgctgctgt ggatttccgg cgcttatggg        60
tcatcttacg aactgactca gcctccttcc gtgagcgtgt ctccaggcca gacagccaga      120
atcacatgct ccggcgacgc cctgccaaac aagtttgcct actggtatag cagaagtcc       180 ggccaggccc cagtgctggt aatctatgag acaacaagc ggccaagcgg catcccagag       240
cggtttagcg gctccagctc tggcaccatg gccaccctga caatctccgg cgcccaggtg      300
gaggatgagg ccgattatca ctgttactcc acagatagc cctccaatcc actgggcgtg       360
ttcggcggcg gcaccaagct gaccgtgctg ggcggcggcg gctccggcgg cggcggctct      420
ggcggcggcg gctccgaggt gcagctggtg cagtctggcg ccgaggtgaa gaagccaggc      480
gagtccctgc gcatcagctg caagggctct ggctatagct tcacaagcta ctggatcacc      540
tgggtgcggc agatgccagg caagggcctg gagtggatgg ccaagtttga ccctctgat      600 agccagacca attactctcc cagcttccag ggccacgtga caatcagcgt ggacaagtcc      660
atcagcacag cctacctgca gtggtctagc ctgaaggcca cgatacagc catgtattat      720 tgcgccccga gatactgttc cagctctagc tgttacgtgg acaattgggg ccagggcaca      780
ctggtgacaa tcttttccga gccaaagtct tccgataaga cccacacctg tccaccctgt      840
cctgccccag aggccgccgg cggccccagc gtgttcctgt tcctccaaa gcccaaggac      900 accctgatga tctccagaac accagaggtg acctgcgtgg tggtggacgt gtctcacgag      960
gacccagagg tgaagtttaa ctggtacgtg gacggcgtgg aggtgcacaa cgccaagaca     1020
aagcctagag aggagcagta caatagcacc tacagagtg tgtctgtgct gacagtgctg     1080
caccaggatt ggctgaacgg caaggagtac aagtgtaagg tgtccaataa ggccctgccc     1140
gcccctatcg agaagaccat ctctaaggcc aagggccagc ctagagagcc acaggtgtat     1200
acactgcccc catccaggga cgagctgacc aagaaccagg tgtccctgac atgtctggtg     1260
aagggctttt accctagcga tatcgccgtg gagtgggagt ctaacggcca gcctgagaat     1320
aactacaaga ccacaccacc tgtgctggac tctgacggca gcttttttcct gtacagcaag     1380 ctgacagtgg acaagagcag gtggcagcag ggcaacgtgt tcagctgctc cgtgatgcac     1440
gaagcactgc acaaccacta cactcagaaa tccctgtcac tgtcccctgg aaaatgataa    1500

<210> SEQ ID NO 102

<211> LENGTH: 498
<212> TYPE: PRT
<213> ORGANISM: Artificial Sequence
<220> FEATURE:
<223> OTHER INFORMATION: Chemically Synthesized, pGX93130,
      185.scFv_Fc.VL.G4S3.VH

<400> SEQUENCE: 102

```
Met Val Leu Gln Thr Gln Val Phe Ile Ser Leu Leu Trp Ile Ser
1               5                   10                  15

Gly Ala Tyr Gly Ser Ser Tyr Glu Leu Thr Gln Pro Pro Ser Val Ser
            20                  25                  30

Val Ser Pro Gly Gln Thr Ala Arg Ile Thr Cys Ser Gly Asp Ala Leu
        35                  40                  45

Pro Asn Lys Phe Ala Tyr Trp Tyr Arg Gln Lys Ser Gly Gln Ala Pro
    50                  55                  60

Val Leu Val Ile Tyr Glu Asp Asn Lys Arg Pro Ser Gly Ile Pro Glu
65                  70                  75                  80

Arg Phe Ser Gly Ser Ser Ser Gly Thr Met Ala Thr Leu Thr Ile Ser
                85                  90                  95

Gly Ala Gln Val Glu Asp Glu Ala Asp Tyr His Cys Tyr Ser Thr Asp
            100                 105                 110

Ser Ser Ser Asn Pro Leu Gly Val Phe Gly Gly Gly Thr Lys Leu Thr
        115                 120                 125

Val Leu Gly Gly Gly Gly Ser Gly Gly Gly Gly Ser Gly Gly Gly Gly
    130                 135                 140

Ser Glu Val Gln Leu Val Gln Ser Gly Ala Glu Val Lys Lys Pro Gly
145                 150                 155                 160

Glu Ser Leu Arg Ile Ser Cys Lys Gly Ser Gly Tyr Ser Phe Thr Ser
                165                 170                 175

Tyr Trp Ile Thr Trp Val Arg Gln Met Pro Gly Lys Gly Leu Glu Trp
            180                 185                 190

Met Ala Lys Phe Asp Pro Ser Asp Ser Gln Thr Asn Tyr Ser Pro Ser
        195                 200                 205

Phe Gln Gly His Val Thr Ile Ser Val Asp Lys Ser Ile Ser Thr Ala
    210                 215                 220

Tyr Leu Gln Trp Ser Ser Leu Lys Ala Ser Asp Thr Ala Met Tyr Tyr
225                 230                 235                 240

Cys Ala Arg Arg Tyr Cys Ser Ser Ser Cys Tyr Val Asp Asn Trp
                245                 250                 255

Gly Gln Gly Thr Leu Val Thr Ile Phe Ser Glu Pro Lys Ser Ser Asp
            260                 265                 270

Lys Thr His Thr Cys Pro Pro Cys Pro Ala Pro Glu Ala Ala Gly Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
```

| | | | | | | | | | | |
|---|---|---|---|---|---|---|---|---|---|---|
| | | 370 | | | 375 | | | 380 | | |
| Lys | Thr | Ile | Ser | Lys | Ala | Lys | Gly | Gln | Pro | Arg | Glu | Pro | Gln | Val | Tyr |
| 385 | | | | 390 | | | | 395 | | | | | | 400 | |
| Thr | Leu | Pro | Pro | Ser | Arg | Asp | Glu | Leu | Thr | Lys | Asn | Gln | Val | Ser | Leu |
| | | | 405 | | | | | 410 | | | | | 415 | | |
| Thr | Cys | Leu | Val | Lys | Gly | Phe | Tyr | Pro | Ser | Asp | Ile | Ala | Val | Glu | Trp |
| | | 420 | | | | | 425 | | | | | 430 | | | |
| Glu | Ser | Asn | Gly | Gln | Pro | Glu | Asn | Asn | Tyr | Lys | Thr | Thr | Pro | Pro | Val |
| | | 435 | | | | 440 | | | | 445 | | | | | |
| Leu | Asp | Ser | Asp | Gly | Ser | Phe | Phe | Leu | Tyr | Ser | Lys | Leu | Thr | Val | Asp |
| 450 | | | | | 455 | | | | | 460 | | | | | |
| Lys | Ser | Arg | Trp | Gln | Gln | Gly | Asn | Val | Phe | Ser | Cys | Ser | Val | Met | His |
| 465 | | | | 470 | | | | | 475 | | | | | 480 | |
| Glu | Ala | Leu | His | Asn | His | Tyr | Thr | Gln | Lys | Ser | Leu | Ser | Leu | Ser | Pro |
| | | | 485 | | | | | 490 | | | | | 495 | | |
| Gly | Lys |

<210> SEQ ID NO 103
<211> LENGTH: 1506
<212> TYPE: DNA
<213> ORGANISM: Artificial Sequence
<220> FEATURE:
<223> OTHER INFORMATION: Chemically Synthesized, pGX93131,
    185.scFv_Fc VH.Whitlow.VL

<400> SEQUENCE: 103

```
atggactgga catggagaat cctgttcctg gtcgccgccg ctaccgggac ccacgcagaa    60
gtgcagctgg tgcagagtgg agccgaagtg aagaagccag gcgagtctct gagaatcagc   120
tgcaagggca gcggctattc ctttacaagc tactggatca cctgggtgcg gcagatgccc   180
ggcaagggcc tggagtggat ggccaagttc gatccatccg atagccagac caattacagc   240
ccttctttcc agggccacgt gacaatctcc gtggacaagt ccatcagcac agcctacctg   300
cagtggtcct ctctgaaggc cagcgacacc gccatgtact actgtgcccg agatattgc   360
tcctcttcca gctgctatgt ggacaattgg ggccagggca ccctggtgac catcttcagc   420
ggctctacaa gcggctctgg caagccaggc tctggcgagg gctctaccaa gggctccagc   480
tatgagctga cccagcctcc atccgtgagc gtgtccccag ccagacagc cagaatcacc   540
tgtagcggcg acgccctgcc taacaagttt gcctactggt ataggcagaa gtctggccag   600
gcccctgtgc tggtaatcta cgaggataac aagaggccat ccggcatccc tgagagattt   660
tctggctcct ctagcggcac catggccacc ctgacaatct ctggcgccca ggtggaggat   720
gaggccgact accactgcta ctccacagac tcttccagca accctctggg cgtgttcggc   780
ggcggcacca agctgacagt gctggagccc aagagctctg acaagaccca cacctgccct   840
ccatgtccag ccccgaggc cgccggcggc ccaagcgtgt tcctgtttcc acctaagcca   900
aaggacaccc tgatgatctc tcggacccca gaggtgacat gcgtggtggt ggacgtgtcc   960
cacgaggacc ctgaggtgaa gtttaattgg tatgtggatg gcgtggaggt gcacaatgcc  1020
aagaccaagc cacgggagga gcagtataac agcacctaca gtggtgtc tgtgctgacc  1080
gtgctgcacc aggactggct gaacggcaag gagtacaagt gtaaggtgtc caacaaggcc  1140
ctgcccgccc ctatcgagaa gaccatctct aaggccaagg ccagccaag agagccacag  1200
gtgtataccc tgccaccctc cagagatgag ctgacaaaga tcaggtgtc tctgacctgt  1260
ctggtgaagg gcttctaccc aagcgatatc gccgtggagt gggagtctaa cggccagcct  1320
```

```
gagaacaaact ataagaccac acctcccgtg ctggattccg acggctcttt cttcctgtac    1380
agcaagctga ccgtggataa gagcagatgg cagcagggca acgtgttctc ctgtagcgtg    1440
atgcacgaag cactgcacaa ccattacacc cagaagtccc tgagcctgag ccctggcaaa    1500
tgataa                                                                1506

<210> SEQ ID NO 104
<211> LENGTH: 500
<212> TYPE: PRT
<213> ORGANISM: Artificial Sequence
<220> FEATURE:
<223> OTHER INFORMATION: Chemically Synthesized, pGX93131,
      185.scFv_Fc VH.Whitlow.VL

<400> SEQUENCE: 104

Met Asp Trp Thr Trp Arg Ile Leu Phe Leu Val Ala Ala Thr Gly
1               5                   10                  15

Thr His Ala Glu Val Gln Leu Val Gln Ser Gly Ala Glu Val Lys Lys
                20                  25                  30

Pro Gly Glu Ser Leu Arg Ile Ser Cys Lys Gly Ser Gly Tyr Ser Phe
            35                  40                  45

Thr Ser Tyr Trp Ile Thr Trp Val Arg Gln Met Pro Gly Lys Gly Leu
        50                  55                  60

Glu Trp Met Ala Lys Phe Asp Pro Ser Asp Ser Gln Thr Asn Tyr Ser
65                  70                  75                  80

Pro Ser Phe Gln Gly His Val Thr Ile Ser Val Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Arg Tyr Cys Ser Ser Ser Cys Tyr Val Asp
        115                 120                 125

Asn Trp Gly Gln Gly Thr Leu Val Thr Ile Phe Ser Gly Ser Thr Ser
130                 135                 140

Gly Ser Gly Lys Pro Gly Ser Gly Glu Gly Ser Thr Lys Gly Ser Ser
145                 150                 155                 160

Tyr Glu Leu Thr Gln Pro Pro Ser Val Ser Val Ser Pro Gly Gln Thr
                165                 170                 175

Ala Arg Ile Thr Cys Ser Gly Asp Ala Leu Pro Asn Lys Phe Ala Tyr
            180                 185                 190

Trp Tyr Arg Gln Lys Ser Gly Gln Ala Pro Val Leu Val Ile Tyr Glu
        195                 200                 205

Asp Asn Lys Arg Pro Ser Gly Ile Pro Glu Arg Phe Ser Gly Ser Ser
    210                 215                 220

Ser Gly Thr Met Ala Thr Leu Thr Ile Ser Gly Ala Gln Val Glu Asp
225                 230                 235                 240

Glu Ala Asp Tyr His Cys Tyr Ser Thr Asp Ser Ser Ser Asn Pro Leu
                245                 250                 255

Gly Val Phe Gly Gly Gly Thr Lys Leu Thr Val Leu Glu Pro Lys Ser
            260                 265                 270

Ser Asp Lys Thr His Thr Cys Pro Pro Cys Pro Ala Pro Glu Ala Ala
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320
```

```
His Glu Asp Pro Glu Val Lys Phe Asn Trp Tyr Val Asp Gly Val Glu
            325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
            405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
            485                 490                 495

Ser Pro Gly Lys
            500

<210> SEQ ID NO 105
<211> LENGTH: 1509
<212> TYPE: DNA
<213> ORGANISM: Artificial Sequence
<220> FEATURE:
<223> OTHER INFORMATION: Chemically Synthesized, pGX93132,
      185.scFv_Fc.VL.Whitlow.VH

<400> SEQUENCE: 105
atggtcctgc agactcaggt gtttatttca ctgctgctgt ggatttccgg ggcatacggg      60
tcctcatacg aactgactca gcctcccagc gtgtccgtgt ctcctggcca gaccgccagg     120
atcacctgca gcggcgatgc cctgccaaac aagttcgcct attggtacag cagaagtcc      180 ggccaggccc cagtgctggt aatctacgag gacaataagc ggccttctgg catccctgag     240
aggttcagcg gctcttcctc tggcacaatg ccacactga ccatctctgg cgcccaggtg      300
gaggatgagg ccgactacca ctgctacagc accgattcct ctagcaatcc tctgggcgtg     360
tttggcggcg gcaccaagct gacagtgctg ggctccacct ctggctccgg caagccaggc     420
tctggcgagg gctctacaaa gggcgaggtg cagctggtgc agtccggcgc cgaggtgaag     480
aagcctggcg agtctctgcg gatcagctgc aagggcagcg gctactcctt cacctcttac     540
tggatcacct gggtgcggca gatgccaggc aagggcctgg agtggatggc caagttcgac     600
cctagcgaca gccagaccaa ctacagccct cttttcagg gccacgtgac aatcagcgtg      660
gataagtcta tctccaccgc ctatctgcag tggagctccc tgaaggcctc tgataccgcc     720
atgtattact gcgccagacg ctactgttct agcagctcct gctatgtgga caactggggc     780
cagggcacac tggtgaccat cttcagcgag cctaagagct ccgataagac ccacacctgc     840
cctccctgcc cagcccccga ggccgccggc ggcccatccg tgtttctgtt ccctccaaag     900
cccaaggata ccctgatgat cagccgcacc cctgaggtga catgcgtggt ggtggacgtg     960
```

```
tctcacgagg acccagaggt gaagttcaac tggtacgtgg atggcgtgga ggtgcacaat    1020
gccaagacca agcccagaga ggagcagtac aattccacct acagagtggt gtctgtgctg    1080
accgtgctgc accaggattg gctgaacggc aaggagtaca gtgtaaggt gtccaataag     1140 gccctgccag cccccatcga gaagaccatc agcaaggcca agggccagcc aagagagcct    1200
caggtgtata ccctgccccc atctcgggac gagctgacca agaaccaggt gtccctgaca    1260
tgtctggtga agggcttta tccatccgac atcgccgtgg agtgggagag caatggccag     1320
cccgagaaca attacaagac aaccccctcca gtgctggata gcgacggctc cttttttcctg 1380 tattccaagc tgaccgtgga taagtccaga tggcagcagg gcaacgtgtt ctcctgctct    1440
gtgatgcacg aagccctgca caaccattac acccagaaat ccctgtccct gtcccccgga   1500
aaatgataa                                                           1509
```

<210> SEQ ID NO 106
<211> LENGTH: 501
<212> TYPE: PRT
<213> ORGANISM: Artificial Sequence
<220> FEATURE:
<223> OTHER INFORMATION: Chemically Synthesized, pGX93132,
      185.scFv_Fc.VL.Whitlow.VH

<400> SEQUENCE: 106

```
Met Val Leu Gln Thr Gln Val Phe Ile Ser Leu Leu Trp Ile Ser
1               5                   10                  15

Gly Ala Tyr Gly Ser Ser Tyr Glu Leu Thr Gln Pro Pro Ser Val Ser
            20                  25                  30

Val Ser Pro Gly Gln Thr Ala Arg Ile Thr Cys Ser Gly Asp Ala Leu
        35                  40                  45

Pro Asn Lys Phe Ala Tyr Trp Tyr Arg Gln Lys Ser Gly Gln Ala Pro
    50                  55                  60

Val Leu Val Ile Tyr Glu Asp Asn Lys Arg Pro Ser Gly Ile Pro Glu
65                  70                  75                  80

Arg Phe Ser Gly Ser Ser Ser Gly Thr Met Ala Thr Leu Thr Ile Ser
                85                  90                  95

Gly Ala Gln Val Glu Asp Glu Ala Asp Tyr His Cys Tyr Ser Thr Asp
            100                 105                 110

Ser Ser Ser Asn Pro Leu Gly Val Phe Gly Gly Gly Thr Lys Leu Thr
        115                 120                 125

Val Leu Gly Ser Thr Ser Gly Ser Gly Lys Pro Gly Ser Gly Glu Gly
    130                 135                 140

Ser Thr Lys Gly Glu Val Gln Leu Val Gln Ser Gly Ala Glu Val Lys
145                 150                 155                 160

Lys Pro Gly Glu Ser Leu Arg Ile Ser Cys Lys Gly Ser Gly Tyr Ser
                165                 170                 175

Phe Thr Ser Tyr Trp Ile Thr Trp Val Arg Gln Met Pro Gly Lys Gly
            180                 185                 190

Leu Glu Trp Met Ala Lys Phe Asp Pro Ser Asp Ser Gln Thr Asn Tyr
        195                 200                 205

Ser Pro Ser Phe Gln Gly His Val Thr Ile Ser Val Asp Lys Ser Ile
    210                 215                 220

Ser Thr Ala Tyr Leu Gln Trp Ser Ser Leu Lys Ala Ser Asp Thr Ala
225                 230                 235                 240

Met Tyr Tyr Cys Ala Arg Arg Tyr Cys Ser Ser Ser Cys Tyr Val
                245                 250                 255
```

```
Asp Asn Trp Gly Gln Gly Thr Leu Val Thr Ile Phe Ser Glu Pro Lys
            260                 265                 270
Ser Ser Asp Lys Thr His Thr Cys Pro Pro Cys Pro Ala Pro Glu Ala
        275                 280                 285
Ala Gly Gly Pro Ser Val Phe Leu Phe Pro Pro Lys Pro Lys Asp Thr
    290                 295                 300
Leu Met Ile Ser Arg Thr Pro Glu Val Thr Cys Val Val Val Asp Val
305                 310                 315                 320
Ser His Glu Asp Pro Glu Val Lys Phe Asn Trp Tyr Val Asp Gly Val
                325                 330                 335
Glu Val His Asn Ala Lys Thr Lys Pro Arg Glu Glu Gln Tyr Asn Ser
            340                 345                 350
Thr Tyr Arg Val Val Ser Val Leu Thr Val Leu His Gln Asp Trp Leu
        355                 360                 365
Asn Gly Lys Glu Tyr Lys Cys Lys Val Ser Asn Lys Ala Leu Pro Ala
    370                 375                 380
Pro Ile Glu Lys Thr Ile Ser Lys Ala Lys Gly Gln Pro Arg Glu Pro
385                 390                 395                 400
Gln Val Tyr Thr Leu Pro Pro Ser Arg Asp Glu Leu Thr Lys Asn Gln
                405                 410                 415
Val Ser Leu Thr Cys Leu Val Lys Gly Phe Tyr Pro Ser Asp Ile Ala
            420                 425                 430
Val Glu Trp Glu Ser Asn Gly Gln Pro Glu Asn Asn Tyr Lys Thr Thr
        435                 440                 445
Pro Pro Val Leu Asp Ser Asp Gly Ser Phe Phe Leu Tyr Ser Lys Leu
    450                 455                 460
Thr Val Asp Lys Ser Arg Trp Gln Gln Gly Asn Val Phe Ser Cys Ser
465                 470                 475                 480
Val Met His Glu Ala Leu His Asn His Tyr Thr Gln Lys Ser Leu Ser
                485                 490                 495
Leu Ser Pro Gly Lys
            500

<210> SEQ ID NO 107
<211> LENGTH: 1497
<212> TYPE: DNA
<213> ORGANISM: Artificial Sequence
<220> FEATURE:
<223> OTHER INFORMATION: Chemically Synthesized, pGX93141, DVSF3 LALA
      scFv-Fc VH.G4S3.VL

<400> SEQUENCE: 107
atggactgga cttggagaat cctgtttctg gtcgcagcag ccactggaac ccacgccgag      60
gtgcagctgg tcgagagcgg gggaggcctg gtgcagccag gcagatccct gaggctgtct    120
tgtgccgcct ctggcttcac atttgatgac tacgccatgt ctgggtgcg gcaggcccca    180 ggcaagggcc tggagtggat ctccggcatc agctggaact ctgccaccat cggctatgcc    240
gactccgtga agggcaggtt caccatctcc cgggacaatg ccaagaagtc tctggacctg    300
cagatgaaca gcctgagacc cgacgatacc gccctgtact attgtgccaa gggcggccca    360
agaggcctgc agctgctgtc ctcttgggtg gattactggg gccagggcac cctggtgaca    420
gtgtcttccg gcggcggcgg ctctggcggc ggcggcagcg gcggcggcgg ctccgatatc    480
cagatgaccc agtctccctc ttccctgagc gcctccgtgg gcgatcgggt gacaatcacc    540
tgcagagcca gccaggatat ccggagatac ctgaactggt accagcagag gcctggcaga    600
```

```
gtgccacagc tgctgatcta caccacatcc accctgcagt ctggcgtgcc aagcagattt    660
tccggcagcg gctccgtgac agacttcacc ctgacaatct ccagcctgca gccagaggat    720
ttcggcacat attactgcca gcagagctac tccccacctc acacctttgg ccagggcaca    780
aagctggaga tcaaggagcc caagtcttcc gacaagaccc acacctgtcc accttgtccc    840
gccccagagg ccgccggcgg ccctagcgtg tttctgttcc ctccaaagcc taaggatacc    900
ctgatgatct ccagaacccc agaggtgaca tgcgtggtgg tggacgtgtc tcacgaggac    960
cccgaggtga agtttaactg gtacgtggat ggcgtggagg tgcacaatgc caagaccaag   1020
ccaagggagg agcagtacaa cagcacctac agagtggtgt ccgtgctgac agtgctgcac   1080
caggactggc tgaatggcaa ggagtataag tgcaaggtgt ccaacaaggc cctgccagcc   1140
cccatcgaga agaccatcag caaggccaag ggccagccta gggagccaca ggtgtacacc   1200
ctgccaccct ccagagacga gctgacaaag aatcaggtgt ctctgacatg cctggtgaag   1260
ggcttctacc cttccgacat cgccgtggag tgggagtcta acggccagcc cgagaacaat   1320
tacaagacca caccacctgt gctggactcc gatggcagct tcttcctgta tagcaagctg   1380
accgtggata gtctagatg gcagcagggc aacgtgttct cctgttccgt gatgcacgaa   1440
gcactgcaca accactacac tcagaagagc ctgtccctgt cccctggaaa atgataa      1497
```

<210> SEQ ID NO 108
<211> LENGTH: 497
<212> TYPE: PRT
<213> ORGANISM: Artificial Sequence
<220> FEATURE:
<223> OTHER INFORMATION: Chemically Synthesized, pGX93141, DVSF3 LALA
      scFv-Fc VH.G4S3.VL

<400> SEQUENCE: 108

```
Met Asp Trp Thr Trp Arg Ile Leu Phe Leu Val Ala Ala Thr Gly
1               5                   10                  15

Thr His Ala Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met Phe Trp Val Arg Gln Ala Pro Gly Lys Gly Leu
    50                  55                  60

Glu Trp Ile Ser Gly Ile Ser Trp Asn Ser Ala Thr Ile Gly Tyr Ala
65                  70                  75                  80

Asp Ser Val Lys Gly Arg Phe Thr Ile Ser Arg Asp Asn Ala Lys Lys
                85                  90                  95

Ser Leu Asp Leu Gln Met Asn Ser Leu Arg Pro Asp Asp Thr Ala Leu
            100                 105                 110

Tyr Tyr Cys Ala Lys Gly Gly Pro Arg Gly Leu Gln Leu Leu Ser Ser
        115                 120                 125

Trp Val Asp Tyr Trp Gly Gln Gly Thr Leu Val Thr Val Ser Ser Gly
    130                 135                 140

Gly Gly Ser Gly Gly Gly Gly Ser Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Arg Ala Ser Gln Asp Ile Arg Arg Tyr Leu Asn
            180                 185                 190

Trp Tyr Gln Gln Arg Pro Gly Arg Val Pro Gln Leu Leu Ile Tyr Thr
```

```
                195                 200                 205
Thr Ser Thr Leu Gln Ser Gly Val Pro Ser Arg Phe Ser Gly Ser Gly
    210                 215                 220

Ser Val Thr Asp Phe Thr Leu Thr Ile Ser Ser Leu Gln Pro Glu Asp
225                 230                 235                 240

Phe Gly Thr Tyr Tyr Cys Gln Gln Ser Tyr Ser Pro Pro His Thr Phe
                245                 250                 255

Gly Gln Gly Thr Lys Leu Glu Ile Lys Glu Pro Lys Ser Ser Asp Lys
            260                 265                 270

Thr His Thr Cys Pro Pro Cys Pro Ala Pro Glu Ala Ala Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 109
<211> LENGTH: 18
<212> TYPE: PRT
<213> ORGANISM: Artificial Sequence
<220> FEATURE:
<223> OTHER INFORMATION: Chemically Synthesized

<400> SEQUENCE: 109

Gly Ser Thr Ser Gly Ser Gly Lys Pro Gly Ser Gly Glu Gly Ser Thr
1               5                   10                  15

Lys Gly

<210> SEQ ID NO 110
<211> LENGTH: 2199
<212> TYPE: DNA
<213> ORGANISM: Artificial Sequence
<220> FEATURE:
```

<223> OTHER INFORMATION: Chemically Synthesized, gene optimized
anti-RSV, pGX9368

<400> SEQUENCE: 110

```
atggactgga catggagaat cctgttcctg gtggcagcag caaccggaac acacgcacag     60
gtgaccctga gagagtccgg accagccctg gtgaagccaa cccagacact gaccctgaca    120
tgcaccttct ccggcttttc tctgagcacc tccggcatgt ctgtgggatg gatcaggcag    180
ccccctggca aggccctgga gtggctggcc gacatctggt gggacgataa gaaggattac    240
aaccctagcc tgaagtcccg cctgacaatc agcaaggaca cctccaagaa ccaggtggtg    300
ctgaaggtga caaatatgga cccagccgat acagccacct actattgcgc ccggagcatg    360
atcaccaatt ggtatttcga cgtgtggggc gccggaacca cagtgacagt gagctccgcc    420
tccaccaagg gaccaagcgt gttcccactg gcaccctcta gcaagtctac aagcggcggc    480
accgccgccc tgggatgtct ggtgaaggac tacttccccg agcctgtgac cgtgtcttgg    540
aacagcggcg ccctgacatc cggagtgcac acctttccag ccgtgctgca gtcctctggc    600
ctgtacagcc tgagctccgt ggtgacagtg ccctctagct ccctgggcac acagacctat    660
atctgcaacg tgaatcacaa gccctctaat accaaggtgg acaagaaggt ggagcctaag    720
agctgtgata agacacacac ctgcccaccc tgtccagcac cagagctgct gggcggccct    780
agcgtgttcc tgtttcctcc aaagccaaag gacaccctga tgatctccag aacacctgag    840
gtgacctgcg tggtggtgga cgtgtctcac gaggaccccg aggtgaagtt caactggtac    900
gtggatggcg tggaggtgca caatgccaag accaagcctc gggaggagca gtacaacagc    960
acatatagag tggtgtccgt gctgaccgtg ctgcaccagg attggctgaa cggcaaggag   1020
tataagtgca aggtgtccaa taaggccctg cctgccccaa tcgagaagac aatcagcaag   1080
gccaagggcc agcctaggga gccacaggtg tacaccctgc cccctagccg cgacgagctg   1140
acaaagaacc aggtgtccct gacctgtctg gtgaagggct tctatccatc tgatatcgcc   1200
gtggagtggg agagcaatgg ccagcccgag aacaattaca agaccacacc acccgtgctg   1260
gactccgatg gctctttctt tctgtattcc aagctgaccg tggacaagtc taggtggcag   1320
cagggcaacg tgttttcctg ttctgtgatg cacgaggccc tgcacaatca ctacacacag   1380
aagagcctgt ccctgtctcc aggcaagagg ggaaggaagc ggagaagcgg ctccggagca   1440
accaacttct ccctgctgaa gcaggcaggc gatgtggagg agaatccagg acctatggtg   1500
ctgcagaccc aggtgtttat ctctctgctg ctgtggatca gcggcgccta cggcgacatc   1560
cagatgacac agtctccaag caccctgtcc gcctctgtgg gcgatagggt gacaatcacc   1620
tgcaagtgtc agctgagcgt gggctacatg cactggtatc agcagaagcc cggcaaggcc   1680
cctaagctgc tgatctacga cacctctaag ctggcaagcg gagtgccctc ccgcttcagc   1740
ggctccggct ctggaacaga gtttacactg accatctcta gcctgcagcc cgacgatttc   1800
gccacctact attgctttca gggcagcggc tatcccttca ccttcggcgg cggcaccaag   1860
ctggagatca agcggacagt ggccgccccc agcgtgttca tctttcctcc atccgacgag   1920
cagctgaagt ctggcaccgc cagcgtggtg tgcctgctga acaatttcta ccctagagag   1980
gccaaggtgc agtggaaggt ggataacgcc ctgcagagcg gcaattccca ggagtctgtg   2040
acagagcagg acagcaagga ttccacctat tctctgtcct ctacactgac cctgtccaag   2100
gccgattacg agaagcacaa ggtgtatgcc tgcgaggtga cacaccaggg cctgagctcc   2160
cctgtgacca agagctttaa cagaggcgag tgttgataa                           2199
```

```
<210> SEQ ID NO 111
<211> LENGTH: 731
<212> TYPE: PRT
<213> ORGANISM: Artificial Sequence
<220> FEATURE:
<223> OTHER INFORMATION: Chemically Synthesized, gene optimized
      anti-RSV, pGX9368

<400> SEQUENCE: 111
```

| | | | | | | | | | | | | | | |
|---|---|---|---|---|---|---|---|---|---|---|---|---|---|---|
| Met | Asp | Trp | Thr | Trp | Arg | Ile | Leu | Phe | Leu | Val | Ala | Ala | Ala | Thr | Gly |
| 1 | | | | 5 | | | | | 10 | | | | | 15 | |
| Thr | His | Ala | Gln | Val | Thr | Leu | Arg | Glu | Ser | Gly | Pro | Ala | Leu | Val | Lys |
| | | | 20 | | | | | 25 | | | | | 30 | | |
| Pro | Thr | Gln | Thr | Leu | Thr | Leu | Thr | Cys | Thr | Phe | Ser | Gly | Phe | Ser | Leu |
| | | | 35 | | | | | 40 | | | | | 45 | | |
| Ser | Thr | Ser | Gly | Met | Ser | Val | Gly | Trp | Ile | Arg | Gln | Pro | Pro | Gly | Lys |
| 50 | | | | | 55 | | | | | 60 | | | | | |
| Ala | Leu | Glu | Trp | Leu | Ala | Asp | Ile | Trp | Trp | Asp | Asp | Lys | Lys | Asp | Tyr |
| 65 | | | | | 70 | | | | | 75 | | | | | 80 |
| Asn | Pro | Ser | Leu | Lys | Ser | Arg | Leu | Thr | Ile | Ser | Lys | Asp | Thr | Ser | Lys |
| | | | | 85 | | | | | 90 | | | | | 95 | |
| Asn | Gln | Val | Val | Leu | Lys | Val | Thr | Asn | Met | Asp | Pro | Ala | Asp | Thr | Ala |
| | | | | 100 | | | | | 105 | | | | | 110 | |
| Thr | Tyr | Tyr | Cys | Ala | Arg | Ser | Met | Ile | Thr | Asn | Trp | Tyr | Phe | Asp | Val |
| | | | 115 | | | | | 120 | | | | | 125 | | |
| Trp | Gly | Ala | Gly | Thr | Thr | Val | Thr | Val | Ser | Ser | Ala | Ser | Thr | Lys | Gly |
| 130 | | | | | 135 | | | | | 140 | | | | | |
| Pro | Ser | Val | Phe | Pro | Leu | Ala | Pro | Ser | Ser | Lys | Ser | Thr | Ser | Gly | Gly |
| 145 | | | | | 150 | | | | | 155 | | | | | 160 |
| Thr | Ala | Ala | Leu | Gly | Cys | Leu | Val | Lys | Asp | Tyr | Phe | Pro | Glu | Pro | Val |
| | | | | 165 | | | | | 170 | | | | | 175 | |
| Thr | Val | Ser | Trp | Asn | Ser | Gly | Ala | Leu | Thr | Ser | Gly | Val | His | Thr | Phe |
| | | | 180 | | | | | 185 | | | | | 190 | | |
| Pro | Ala | Val | Leu | Gln | Ser | Ser | Gly | Leu | Tyr | Ser | Leu | Ser | Ser | Val | Val |
| | | | 195 | | | | | 200 | | | | | 205 | | |
| Thr | Val | Pro | Ser | Ser | Ser | Leu | Gly | Thr | Gln | Thr | Tyr | Ile | Cys | Asn | Val |
| 210 | | | | | 215 | | | | | 220 | | | | | |
| Asn | His | Lys | Pro | Ser | Asn | Thr | Lys | Val | Asp | Lys | Lys | Val | Glu | Pro | Lys |
| 225 | | | | | 230 | | | | | 235 | | | | | 240 |
| Ser | Cys | Asp | Lys | Thr | His | Thr | Cys | Pro | Pro | Cys | Pro | Ala | Pro | Glu | Leu |
| | | | | 245 | | | | | 250 | | | | | 255 | |
| Leu | Gly | Gly | Pro | Ser | Val | Phe | Leu | Phe | Pro | Pro | Lys | Pro | Lys | Asp | Thr |
| | | | 260 | | | | | 265 | | | | | 270 | | |
| Leu | Met | Ile | Ser | Arg | Thr | Pro | Glu | Val | Thr | Cys | Val | Val | Val | Asp | Val |
| | | | 275 | | | | | 280 | | | | | 285 | | |
| Ser | His | Glu | Asp | Pro | Glu | Val | Lys | Phe | Asn | Trp | Tyr | Val | Asp | Gly | Val |
| | | | 290 | | | | | 295 | | | | | 300 | | |
| Glu | Val | His | Asn | Ala | Lys | Thr | Lys | Pro | Arg | Glu | Glu | Gln | Tyr | Asn | Ser |
| 305 | | | | | 310 | | | | | 315 | | | | | 320 |
| Thr | Tyr | Arg | Val | Val | Ser | Val | Leu | Thr | Val | Leu | His | Gln | Asp | Trp | Leu |
| | | | | 325 | | | | | 330 | | | | | 335 | |
| Asn | Gly | Lys | Glu | Tyr | Lys | Cys | Lys | Val | Ser | Asn | Lys | Ala | Leu | Pro | Ala |
| | | | | 340 | | | | | 345 | | | | | 350 | |
| Pro | Ile | Glu | Lys | Thr | Ile | Ser | Lys | Ala | Lys | Gly | Gln | Pro | Arg | Glu | Pro |
| | | | | 355 | | | | | 360 | | | | | 365 | |

```
Gln Val Tyr Thr Leu Pro Pro Ser Arg Asp Glu Leu Thr Lys Asn Gln
        370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
450                 455                 460
Leu Ser Pro Gly Lys Arg Gly Arg Lys Arg Arg Ser Gly Ser Gly Ala
465                 470                 475                 480
Thr Asn Phe Ser Leu Leu Lys Gln Ala Gly Asp Val Glu Glu Asn Pro
                485                 490                 495
Gly Pro Met Val Leu Gln Thr Gln Val Phe Ile Ser Leu Leu Leu Trp
            500                 505                 510
Ile Ser Gly Ala Tyr Gly Asp Ile Gln Met Thr Gln Ser Pro Ser Thr
515                 520                 525
Leu Ser Ala Ser Val Gly Asp Arg Val Thr Ile Thr Cys Lys Cys Gln
530                 535                 540
Leu Ser Val Gly Tyr Met His Trp Tyr Gln Gln Lys Pro Gly Lys Ala
545                 550                 555                 560
Pro Lys Leu Leu Ile Tyr Asp Thr Ser Lys Leu Ala Ser Gly Val Pro
                565                 570                 575
Ser Arg Phe Ser Gly Ser Gly Ser Gly Thr Glu Phe Thr Leu Thr Ile
            580                 585                 590
Ser Ser Leu Gln Pro Asp Asp Phe Ala Thr Tyr Tyr Cys Phe Gln Gly
        595                 600                 605
Ser Gly Tyr Pro Phe Thr Phe Gly Gly Gly Thr Lys Leu Glu Ile Lys
610                 615                 620
Arg Thr Val Ala Ala Pro Ser Val Phe Ile Phe Pro Pro Ser Asp Glu
625                 630                 635                 640
Gln Leu Lys Ser Gly Thr Ala Ser Val Val Cys Leu Leu Asn Asn Phe
                645                 650                 655
Tyr Pro Arg Glu Ala Lys Val Gln Trp Lys Val Asp Asn Ala Leu Gln
            660                 665                 670
Ser Gly Asn Ser Gln Glu Ser Val Thr Glu Gln Asp Ser Lys Asp Ser
        675                 680                 685
Thr Tyr Ser Leu Ser Ser Thr Leu Thr Leu Ser Lys Ala Asp Tyr Glu
690                 695                 700
Lys His Lys Val Tyr Ala Cys Glu Val Thr His Gln Gly Leu Ser Ser
705                 710                 715                 720
Pro Val Thr Lys Ser Phe Asn Arg Gly Glu Cys
                725                 730
```

<210> SEQ ID NO 112
<211> LENGTH: 1485
<212> TYPE: DNA
<213> ORGANISM: Artificial Sequence
<220> FEATURE:
<223> OTHER INFORMATION: Chemically Synthesized, scFv-Fc anti-RSV, pGX9369

<400> SEQUENCE: 112

```
atggtgctgc agacccaggt gtttatttca ctgctgctgt ggatttcagg agcctacggg      60
gacattcaga tgacccagag cccttcaaca ctgtccgcca gcgtgggcga cagagtgaca     120
atcacctgta agtgccagct gagcgtgggc tatatgcact ggtatcagca gaagcctggc     180
aaggccccaa agctgctgat ctatgacacc agcaagctgg cctctggcgt gccatccaga     240
ttctccggct ctggcagcgg caccgagttt acactgacca ctccagcct gcagccagat      300
gacttcgcca cctactattg cttccagggc agcggctatc ccttcacctt ggcggcggc      360
acaaagctgg agatcaaggg cggcggcggc tccggcggcg gcggctctgg cggcggcggc     420
tctcaggtga ccctgagaga gtccggccca gccctggtga agccaaccca gaccctgaca     480
ctgacatgca ccttctccgg cttcagcctg tccaccagcg gcatgtccgt gggctggatc     540
aggcagcccc caggcaaggc cctggagtgg ctggccgata tctggtggga cgataagaag     600
gactacaacc cctccctgaa gagcagactg accatcagca aggataccag caagaaccag     660
gtggtgctga aggtgacaaa tatggaccca gccgataccg ccacatacta ctgtgccaga     720
tccatgatca caaattggta cttcgacgtg tggggcgccg gcacaaccgt gacagtgagc     780
tctgagccaa agtcctgcga caagacccac acctgtcctc cttgtccagc cccgagctg      840
ctgggcggcc aagcgtgtt cctgtttccc cctaagccaa aggatccct gatgatctcc      900
agaacccag aggtgacatg cgtggtggtg gacgtgagcc acgaggaccc cgaggtgaag     960
ttcaattggt acgtggatgg cgtggaggtg cacaatgcca agaccaagcc aagagaggag    1020
cagtataact ctacatatcg cgtggtgtcc gtgctgacag tgctgcacca ggactggctg    1080
aatggcaagg agtacaagtg caaggtgtcc aataaggccc tgccagcccc tatcgagaag    1140
acaatctcca aggccaaggg ccagcccaga gagccacagg tgtatacact gccaccctcc    1200
agagatgagc tgacaaagaa tcaggtgtcc ctgacatgtc tggtgaaggg cttttatccc    1260
tccgatatcg ccgtggagtg gggagtctaat ggccagcccg agaataacta aagacaacc    1320
cctccagtgc tggactccga tggctccttt ttcctgtatt ccaagctgac cgtggataag    1380
agcaggtggc agcagggcaa cgtgttctct tgttccgtga tgcacgaagc actgcacaac    1440
cactacaccc agaagtcact gtcactgtca ccaggaaaat gataa                    1485
```

<210> SEQ ID NO 113
<211> LENGTH: 493
<212> TYPE: PRT
<213> ORGANISM: Artificial Sequence
<220> FEATURE:
<223> OTHER INFORMATION: Chemically Synthesized, scFv-Fc anti-RSV, pGX9369

<400> SEQUENCE: 113

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Thr Leu Ser
            20                  25                  30

Ala Ser Val Gly Asp Arg Val Thr Ile Thr Cys Lys Cys Gln Leu Ser
        35                  40                  45

Val Gly Tyr Met His Trp Tyr Gln Gln Lys Pro Gly Lys Ala Pro Lys
    50                  55                  60

Leu Leu Ile Tyr Asp Thr Ser Lys Leu Ala Ser Gly Val Pro Ser Arg
65                  70                  75                  80

Phe Ser Gly Ser Gly Ser Gly Thr Glu Phe Thr Leu Thr Ile Ser Ser
```

```
                          85                  90                  95
Leu Gln Pro Asp Asp Phe Ala Thr Tyr Tyr Cys Phe Gln Gly Ser Gly
                100                 105                 110

Tyr Pro Phe Thr Phe Gly Gly Gly Thr Lys Leu Glu Ile Lys Gly Gly
                115                 120                 125

Gly Gly Ser Gly Gly Gly Gly Ser Gly Gly Gly Gly Ser Gln Val Thr
            130                 135                 140

Leu Arg Glu Ser Gly Pro Ala Leu Val Lys Pro Thr Gln Thr Leu Thr
145                 150                 155                 160

Leu Thr Cys Thr Phe Ser Gly Phe Ser Leu Ser Thr Ser Gly Met Ser
                165                 170                 175

Val Gly Trp Ile Arg Gln Pro Pro Gly Lys Ala Leu Glu Trp Leu Ala
                180                 185                 190

Asp Ile Trp Trp Asp Asp Lys Lys Asp Tyr Asn Pro Ser Leu Lys Ser
                195                 200                 205

Arg Leu Thr Ile Ser Lys Asp Thr Ser Lys Asn Gln Val Val Leu Lys
                210                 215                 220

Val Thr Asn Met Asp Pro Ala Asp Thr Ala Thr Tyr Tyr Cys Ala Arg
225                 230                 235                 240

Ser Met Ile Thr Asn Trp Tyr Phe Asp Val Trp Gly Ala Gly Thr Thr
                245                 250                 255

Val Thr Val Ser Ser Glu Pro Lys Ser Cys Asp Lys Thr His Thr Cys
                260                 265                 270

Pro Pro Cys Pro Ala Pro Glu Leu Leu Gly Gly Pro Ser Val Phe Leu
                275                 280                 285

Phe Pro Pro Lys Pro Lys Asp Thr Leu Met Ile Ser Arg Thr Pro Glu
                290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
                340                 345                 350

Thr Val Leu His Gln Asp Trp Leu Asn Gly Lys Glu Tyr Lys Cys Lys
                355                 360                 365

Val Ser Asn Lys Ala Leu Pro Ala Pro Ile Glu Lys Thr Ile Ser Lys
                370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
                420                 425                 430

Pro Glu Asn Asn Tyr Lys Thr Thr Pro Pro Val Leu Asp Ser Asp Gly
                435                 440                 445

Ser Phe Phe Leu Tyr Ser Lys Leu Thr Val Asp Lys Ser Arg Trp Gln
                450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 114
```

<211> LENGTH: 2199
<212> TYPE: DNA
<213> ORGANISM: Artificial Sequence
<220> FEATURE:
<223> OTHER INFORMATION: Chemically Synthesized, gene optimized
anti-RSV, pGX9370

<400> SEQUENCE: 114

```
atggactgga cctggagaat cctgttcctg gtggcagcag caaccggaac acacgcacag      60
gtgacactga gggagagcgg acctgccctg gtgaagccaa cccagacact gaccctgaca     120
tgcaccttct ctggcttttc cctgtctacc agcggcatga gcgtgggatg gatcaggcag     180
ccccctggca aggccctgga gtggctggcc gacatctggt gggacgataa gaaggattac     240
aacccctctc tgaagagccg cctgaccatc agcaaggata catccaagaa ccaggtggtg     300
ctgaaggtga ccaatatgga ccctgccgat acagccacct actattgtgc ccggagcatg     360
atcaccaatt ggtactttga cgtgtggggc gccggcacca cagtgacagt gagctccgcc     420
aagaccacag ccccttccgt gtatcctctg gccccagtgt gcggcgatac cacaggctct     480
agcgtgaccc tgggctgtct ggtgaagggc tacttcccag agcccgtgac actgacctgg     540
aactccggct ctctgtcctc tggcgtgcac acctttccag ccgtgctgca gagcgacctg     600
tacacactga gctcctctgt gacagtgacc agctccacct ggccaagcca gtccatcaca     660
tgcaacgtgg cccaccccgc ctctagcacc aaggtggata agaagatcga gcccagaggc     720
cctacaatca agccctgtcc accctgcaag tgtcctgccc caaatctgct gggcggccct     780
tccgtgttca tctttcctcc aaagatcaag gacgtgctga tgatctctct gagccctatc     840
gtgacctgcg tggtggtgga cgtgtccgag gacgatccag atgtgcagat ctcttggttc     900
gtgaacaatg tggaggtgca caccgcccag acacagaccc accgggagga ttataacagc     960
acactgagag tggtgtccgc cctgccaatc cagcaccagg actggatgag cggcaaggag    1020
tttaagtgca aggtgaacaa taaggatctg cccgccccta tcgagcggac catctccaag    1080
cccaagggct ctgtgagagc cctcaggtg tacgtgctgc cccctccaga ggaggagatg    1140
accaagaagc aggtgacact gacctgtatg gtgacagact tcatgcctga ggatatctac    1200
gtggagtgga ccaacaatgg caagacagag ctgaactata agaataccga gccagtgctg    1260
gactccgatg gctcttactt tatgtatagc aagctgaggg tggagaagaa gaactgggtg    1320
gagcgcaatt cctattcttg tagcgtggtg cacgagggcc tgcacaatca ccacaccaca    1380
aagtccttct ctagaacccc aggcaagagg ggaaggaagc ggagaagcgg ctccggagcc    1440
acaaactttt ccctgctgaa gcaggcaggc gacgtggagg agaatccagg acccatggtg    1500
ctgcagaccc aggtgttcat ctctctgctg ctgtggatca gcggcgccta cggcgacatc    1560
cagatgaccc agtctcccag cacactgtcc gcctctgtgg gcgatcgggt gacaatcacc    1620
tgcaagtgtc agctgtccgt gggctacatg cactggtatc agcagaagcc aggcaaggcc    1680
cccaagctgc tgatctatga cacctctaag ctggccagcg gcgtgccttc cagattcagc    1740
ggctccggct ctggcaccga gtttacactg accatctcct ctctgcagcc agacgatttc    1800
gccacatact attgctttca gggcagcgga taccccttca ccttcggcgg cggcacaaag    1860
ctggagatca agagggccga tgccgcccca accgtgtcca tcttccctcc cagcagcgag    1920
cagctgacat ctggcggcgc cagcgtggtg tgcttcctga acaacttcta ccccaaggac    1980
atcaacgtga agtggaagat cgatggcagc gagcgccaga acggcgtgct gaattcctgg    2040
accgaccagg atagcaagga ctccacatac tctatgtcta gcacactgac cctgacaaag    2100
```

```
gatgagtacg agcggcacaa ttcctatacc tgcgaggcca cacacaagac cagcacatcc    2160
cctatcgtga agtctttaa cagaaatgag tgttgataa                            2199
```

<210> SEQ ID NO 115
<211> LENGTH: 731
<212> TYPE: PRT
<213> ORGANISM: Artificial Sequence
<220> FEATURE:
<223> OTHER INFORMATION: Chemically Synthesized, gene optimized
      anti-RSV, pGX9370

<400> SEQUENCE: 115

Met Asp Trp Thr Trp Arg Ile Leu Phe Leu Val Ala Ala Ala Thr Gly
1               5                   10                  15

Thr His Ala Gln Val Thr Leu Arg Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Ser Thr Ser Gly Met Ser Val Gly Trp Ile Arg Gln Pro Pro Gly Lys
    50                  55                  60

Ala Leu Glu Trp Leu Ala Asp Ile Trp Trp Asp Asp Lys Lys Asp Tyr
65                  70                  75                  80

Asn Pro Ser Leu Lys Ser Arg Leu Thr Ile Ser Lys Asp Thr Ser Lys
                85                  90                  95

Asn Gln Val Val Leu Lys Val Thr Asn Met Asp Pro Ala Asp Thr Ala
            100                 105                 110

Thr Tyr Tyr Cys Ala Arg Ser Met Ile Thr Asn Trp Tyr Phe Asp Val
        115                 120                 125

Trp Gly Ala Gly Thr Thr Val Thr Val Ser Ser Ala Lys Thr Thr Ala
    130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
    210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
                245                 250                 255

Leu Gly Gly Pro Ser Val Phe Ile Phe Pro Pro Lys Ile Lys Asp Val
            260                 265                 270

Leu Met Ile Ser Leu Ser Pro Ile Val Thr Cys Val Val Val Asp Val
        275                 280                 285

Ser Glu Asp Asp Pro Asp Val Gln Ile Ser Trp Phe Val Asn Asn Val
    290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Pro Ala

```
                340             345             350
Pro Ile Glu Arg Thr Ile Ser Lys Pro Lys Gly Ser Val Arg Ala Pro
            355                 360                 365

Gln Val Tyr Val Leu Pro Pro Glu Glu Met Thr Lys Lys Gln
    370                 375             380

Val Thr Leu Thr Cys Met Val Thr Asp Phe Met Pro Glu Asp Ile Tyr
385                 390                 395                 400

Val Glu Trp Thr Asn Asn Gly Lys Thr Glu Leu Asn Tyr Lys Asn Thr
                405                 410                 415

Glu Pro Val Leu Asp Ser Asp Gly Ser Tyr Phe Met Tyr Ser Lys Leu
            420                 425                 430

Arg Val Glu Lys Lys Asn Trp Val Glu Arg Asn Ser Tyr Ser Cys Ser
            435                 440                 445

Val Val His Glu Gly Leu His Asn His His Thr Thr Lys Ser Phe Ser
            450                 455                 460

Arg Thr Pro Gly Lys Arg Gly Arg Lys Arg Ser Gly Ser Gly Ala
465                 470                 475                 480

Thr Asn Phe Ser Leu Leu Lys Gln Ala Gly Asp Val Glu Glu Asn Pro
                485                 490                 495

Gly Pro Met Val Leu Gln Thr Gln Val Phe Ile Ser Leu Leu Leu Trp
            500                 505                 510

Ile Ser Gly Ala Tyr Gly Asp Ile Gln Met Thr Gln Ser Pro Ser Thr
            515                 520                 525

Leu Ser Ala Ser Val Gly Asp Arg Val Thr Ile Thr Cys Lys Cys Gln
            530                 535                 540

Leu Ser Val Gly Tyr Met His Trp Tyr Gln Gln Lys Pro Gly Lys Ala
545                 550                 555                 560

Pro Lys Leu Leu Ile Tyr Asp Thr Ser Lys Leu Ala Ser Gly Val Pro
                565                 570                 575

Ser Arg Phe Ser Gly Ser Gly Ser Gly Thr Glu Phe Thr Leu Thr Ile
            580                 585                 590

Ser Ser Leu Gln Pro Asp Asp Phe Ala Thr Tyr Tyr Cys Phe Gln Gly
            595                 600                 605

Ser Gly Tyr Pro Phe Thr Phe Gly Gly Gly Thr Lys Leu Glu Ile Lys
            610                 615                 620

Arg Ala Asp Ala Ala Pro Thr Val Ser Ile Phe Pro Pro Ser Ser Glu
625                 630                 635                 640

Gln Leu Thr Ser Gly Gly Ala Ser Val Val Cys Phe Leu Asn Asn Phe
                645                 650                 655

Tyr Pro Lys Asp Ile Asn Val Lys Trp Lys Ile Asp Gly Ser Glu Arg
            660                 665                 670

Gln Asn Gly Val Leu Asn Ser Trp Thr Asp Gln Asp Ser Lys Asp Ser
            675                 680                 685

Thr Tyr Ser Met Ser Ser Thr Leu Thr Leu Thr Lys Asp Glu Tyr Glu
            690                 695                 700

Arg His Asn Ser Tyr Thr Cys Glu Ala Thr His Lys Thr Ser Thr Ser
705                 710                 715                 720

Pro Ile Val Lys Ser Phe Asn Arg Asn Glu Cys
                725                 730

<210> SEQ ID NO 116
<211> LENGTH: 1488
<212> TYPE: DNA
<213> ORGANISM: Artificial Sequence
```

<220> FEATURE:
<223> OTHER INFORMATION: Chemically Synthesized, scFv-Fc anti-RSV, pGX9371

<400> SEQUENCE: 116

```
atggtgctgc agactcaggt gtttatttca ctgctgctgt ggatttccgg cgcttacggc      60
gacattcaga tgacccagag ccctccaca ctgagcgcct ccgtgggcga cagagtgaca     120
atcacatgca agtgtcagct gtctgtgggc tatatgcact ggtatcagca gaagcccggc    180
aaggccccaa agctgctgat ctatgacacc tctaagctgg cctctggcgt gccaagcaga    240
ttctccggca gcggctccgg caccgagttc accctgacaa tctcctctct gcagccagac    300
gatttcgcca catactactg ctttcaggge tccggctacc cattcacatt tggcggcggc    360
acaaagctgg agatcaaggg cggcggcggc tccggcggcg gcggctctgg cggcggcggc    420
tctcaggtga cactgcggga gtccggccca gccctggtga agccaaccca gacactgaca    480
ctgacctgta cattttccgg cttctctctg tccaccagcg gcatgagcgt gggctggatc    540
agacagcccc ctggcaaggc cctggagtgg ctggccgata tctggtggga cgataagaag    600
gactacaatc cttccctgaa gtctagactg accatctcca aggataccte caagaatcag    660
gtggtgctga aggtgaccaa catggaccct gccgatacag ccacctatta ctgcgccaga    720
agcatgatca ccaactggta ctttgacgtg tggggcgccg gcacaaccgt gacagtgtct    780
tccgagccta gaggccccaac catcaagcca tgcccaccct gtaagtgtcc cgccccaaac    840
ctgctgggcg gccatccgt gttcatcttt ccccctaaga tcaaggacgt gctgatgatc    900
agcctgagcc caatcgtgac atgcgtggtg gtggacgtgt ccgaggatga cccagatgtg    960
cagatctctt ggttcgtgaa taacgtggag gtgcacaccg cccagaccca gacccacaga   1020
gaggattaca attccacact gagagtggtg tccgccctgc ctatccagca ccaggattgg   1080
atgagcggca aggagtttaa gtgcaaggtg aacaataagg acctgccgc cccaatcgag   1140
agaaccatct ccaagccaaa gggctctgtg agggccccac aggtgtacgt gctgcctcct   1200
ccagaggagg agatgacaaa gaagcaggtg acactgacct gcatggtgac cgacttcatg   1260
cccgaggaca tctacgtgga gtggacaaac aatggcaaga cagagctgaa ctataagaac   1320
accgagccag tgctggattc cgacggctct tacttcatgt actccaagct gagagtggag   1380
aagaagaact gggtggagcg gaatagctac tcctgttccg tggtccacga agggctgcat   1440
aaccaccaca ccactaagtc attttcaaga acccaggca atgataa                  1488
```

<210> SEQ ID NO 117
<211> LENGTH: 494
<212> TYPE: PRT
<213> ORGANISM: Artificial Sequence
<220> FEATURE:
<223> OTHER INFORMATION: Chemically Synthesized, scFv-Fc anti-RSV, pGX9371

<400> SEQUENCE: 117

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Thr Leu Ser
            20                  25                  30

Ala Ser Val Gly Asp Arg Val Thr Ile Thr Cys Lys Cys Gln Leu Ser
        35                  40                  45

Val Gly Tyr Met His Trp Tyr Gln Gln Lys Pro Gly Lys Ala Pro Lys
    50                  55                  60
```

-continued

```
Leu Leu Ile Tyr Asp Thr Ser Lys Leu Ala Ser Gly Val Pro Ser Arg
 65                  70                  75                  80

Phe Ser Gly Ser Gly Ser Gly Thr Glu Phe Thr Leu Thr Ile Ser Ser
                 85                  90                  95

Leu Gln Pro Asp Asp Phe Ala Thr Tyr Tyr Cys Phe Gln Gly Ser Gly
            100                 105                 110

Tyr Pro Phe Thr Phe Gly Gly Gly Thr Lys Leu Glu Ile Lys Gly Gly
        115                 120                 125

Gly Gly Ser Gly Gly Gly Gly Ser Gly Gly Gly Gly Ser Gln Val Thr
    130                 135                 140

Leu Arg Glu Ser Gly Pro Ala Leu Val Lys Pro Thr Gln Thr Leu Thr
145                 150                 155                 160

Leu Thr Cys Thr Phe Ser Gly Phe Ser Leu Ser Thr Ser Gly Met Ser
                165                 170                 175

Val Gly Trp Ile Arg Gln Pro Pro Gly Lys Ala Leu Glu Trp Leu Ala
            180                 185                 190

Asp Ile Trp Trp Asp Asp Lys Lys Asp Tyr Asn Pro Ser Leu Lys Ser
        195                 200                 205

Arg Leu Thr Ile Ser Lys Asp Thr Ser Lys Asn Gln Val Val Leu Lys
    210                 215                 220

Val Thr Asn Met Asp Pro Ala Asp Thr Ala Thr Tyr Tyr Cys Ala Arg
225                 230                 235                 240

Ser Met Ile Thr Asn Trp Tyr Phe Asp Val Trp Gly Ala Gly Thr Thr
                245                 250                 255

Val Thr Val Ser Ser Glu Pro Arg Gly Pro Thr Ile Lys Pro Cys Pro
            260                 265                 270

Pro Cys Lys Cys Pro Ala Pro Asn Leu Leu Gly Gly Pro Ser Val Phe
        275                 280                 285

Ile Phe Pro Pro Lys Ile Lys Asp Val Leu Met Ile Ser Leu Ser Pro
    290                 295                 300

Ile Val Thr Cys Val Val Val Asp Val Ser Glu Asp Asp Pro Asp Val
305                 310                 315                 320

Gln Ile Ser Trp Phe Val Asn Asn Val Glu Val His Thr Ala Gln Thr
                325                 330                 335

Gln Thr His Arg Glu Asp Tyr Asn Ser Thr Leu Arg Val Val Ser Ala
            340                 345                 350

Leu Pro Ile Gln His Gln Asp Trp Met Ser Gly Lys Glu Phe Lys Cys
        355                 360                 365

Lys Val Asn Asn Lys Asp Leu Pro Ala Pro Ile Glu Arg Thr Ile Ser
    370                 375                 380

Lys Pro Lys Gly Ser Val Arg Ala Pro Gln Val Tyr Val Leu Pro Pro
385                 390                 395                 400

Pro Glu Glu Glu Met Thr Lys Lys Gln Val Thr Leu Thr Cys Met Val
                405                 410                 415

Thr Asp Phe Met Pro Glu Asp Ile Tyr Val Glu Trp Thr Asn Asn Gly
            420                 425                 430

Lys Thr Glu Leu Asn Tyr Lys Asn Thr Glu Pro Val Leu Asp Ser Asp
        435                 440                 445

Gly Ser Tyr Phe Met Tyr Ser Lys Leu Arg Val Glu Lys Lys Asn Trp
    450                 455                 460

Val Glu Arg Asn Ser Tyr Ser Cys Ser Val Val His Glu Gly Leu His
465                 470                 475                 480

Asn His His Thr Thr Lys Ser Phe Ser Arg Thr Pro Gly Lys
```

485 490

<210> SEQ ID NO 118
<211> LENGTH: 2220
<212> TYPE: DNA
<213> ORGANISM: Artificial Sequence
<220> FEATURE:
<223> OTHER INFORMATION: Chemically Synthesized, gene optimized
anti-RSV, pGX9283

<400> SEQUENCE: 118

```
atggactgga cttggagaat cctgttcctg gtcgccgccg caactgggac tcatgctcag 60
gtgcagctgg tgcagagcgg ggcagaggtg aagaagccag gcagctccgt gaaggtgtct 120
tgcaaggcaa gcggcggctc tctgagcacc tacggcatcc actgggtgag gcaggcacca 180
ggacagggcc tggagtgggt gggcggcgtg atgaccgtgt acggcaagac cacatatggc 240
cagaacttcc agggcagggt gacaatcgcc gtggaccgct ctaccaatac agcctacatg 300
gagctgtcta gcctgaccag cgacgatacc ggcacatact attgcgccac cgactcttac 360
tacgtgtgga caggcagcta tccccctcca ttcgatctgt ggggccaggg caccctggtg 420
acagtgtcct ctgcctctac aaagggacca agcgtgtttc cactggcacc tagctccaag 480
tccacctctg gcggcacagc cgccctgggc tgtctggtga aggattactt ccctgagcca 540
gtgaccgtgt cctggaactc tggcgccctg accagcggag tgcacacatt cccgccgtg 600
ctgcagtcta gcggcctgta ctccctgtcc tctgtggtga ccgtgcctag ctcctctctg 660
ggcacccaga catatatctg caacgtgaat cacaagccta gcaatacaaa ggtggacaag 720
aaggtggagc caaagtcctg tgataagacc cacacatgcc ctccctgtcc agcacctgag 780
ctgctgggcg gcccaagcgt gttcctgttt ccacccaagc ccaaggacac cctgatgatc 840
tccagaaccc cagaggtgac atgcgtggtg gtggacgtgt ctcacgagga ccccgaggtg 900
aagtttaact ggtacgtgga tggcgtggag gtgcacaatg ccaagaccaa gccccgggag 960
gagcagtaca actccaccta tagagtggtg tctgtgctga cagtgctgca ccaggactgg 1020
ctgaacggca aggagtataa gtgcaaggtg agcaataagg ccctgccagc ccccatcgag 1080
aagaccatct ccaaggcaaa gggacagcca agggagccac aggtgtacac actgcctcca 1140
tcccgcgacg agctgaccaa gaaccaggtg tctctgacat gtctggtgaa gggcttctat 1200
ccctctgata tcgccgtgga gtgggagagc aatggccagc ctgagaacaa ttacaagacc 1260
acacccccctg tgctggacag cgatggctcc ttctttctgt attccaagct gaccgtggac 1320
aagtctcggt ggcagcaggg caacgtgttt agctgctccg tgatgcacga ggccctgcac 1380
aatcactaca cccagaagtc tctgagcctg tccccaggca agaggggaag aaagcggaga 1440
tctggcagcg gcgccacaaa cttcagcctg ctgaagcagg ccggcgatgt ggaggagaat 1500
cctggcccaa tggtgctgca gacccaggtg tttatcagcc tgctgctgtg gatctccgga 1560
gcatacggag agatcgtgct gacccagaca ccaggaaccc agtccctgtc tcctggacag 1620
tccgccacac tgtcttgtag agccagccac tccgtgggca atgactacct ggcctggtat 1680
cagcagaagc ctggacagag cccacggctg ctgatccacg gagcatacag gagggactcc 1740
ggcatccctg atagattcat cggctctggc agcggcaccg actttaccct gacaatcgat 1800
agcctggagc ctgacgattg cgccgtgtac tattgtcagc agtatggctc ctggccactg 1860
accttcggcg gcggcacaaa ggtggacatc aagaggaccg tggccgcccc tagcgtgttc 1920
atctttccac cctccgatga gcagctgaag agcggcacag cctccgtggt gtgcctgctg 1980
```

-continued

```
aacaacttct acccacgcga ggccaaggtg cagtggaagg tggacaacgc cctgcagtct    2040
ggcaatagcc aggagtccgt gaccgagcag gactctaagg atagcacata ttccctgagc    2100
tccaccctga cactgtccaa ggccgattac gagaagcaca aggtgtatgc ctgtgaggtc    2160
acccaccagg gactgtcttc acccgtcaca aaatccttca atagggga ga atgctgataa    2220
```

<210> SEQ ID NO 119
<211> LENGTH: 738
<212> TYPE: PRT
<213> ORGANISM: Artificial Sequence
<220> FEATURE:
<223> OTHER INFORMATION: Chemically Synthesized, gene optimized
      anti-RSV, pGX9283

<400> SEQUENCE: 119

```
Met Asp Trp Thr Trp Arg Ile Leu Phe Leu Val Ala Ala Ala Thr Gly
1               5                   10                  15

Thr His Ala Gln Val Gln Leu Val Gln Ser Gly Ala Glu Val Lys Lys
                20                  25                  30

Pro Gly Ser Ser Val Lys Val Ser Cys Lys Ala Ser Gly Gly Ser Leu
            35                  40                  45

Ser Thr Tyr Gly Ile His Trp Val Arg Gln Ala Pro Gly Gln Gly Leu
        50                  55                  60

Glu Trp Val Gly Val Met Thr Val Tyr Gly Lys Thr Thr Tyr Gly
65                  70                  75                  80

Gln Asn Phe Gln Gly Arg Val Thr Ile Ala Val Asp Arg Ser Thr Asn
                85                  90                  95

Thr Ala Tyr Met Glu Leu Ser Ser Leu Thr Ser Asp Asp Thr Gly Thr
            100                 105                 110

Tyr Tyr Cys Ala Thr Asp Ser Tyr Tyr Val Trp Thr Gly Ser Tyr Pro
        115                 120                 125

Pro Pro Phe Asp Leu Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320
```

-continued

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys Arg Gly Arg Lys Arg Arg
465                 470                 475                 480

Ser Gly Ser Gly Ala Thr Asn Phe Ser Leu Leu Lys Gln Ala Gly Asp
                485                 490                 495

Val Glu Glu Asn Pro Gly Pro Met Val Leu Gln Thr Gln Val Phe Ile
            500                 505                 510

Ser Leu Leu Leu Trp Ile Ser Gly Ala Tyr Gly Glu Ile Val Leu Thr
        515                 520                 525

Gln Thr Pro Gly Thr Gln Ser Leu Ser Pro Gly Gln Ser Ala Thr Leu
    530                 535                 540

Ser Cys Arg Ala Ser His Ser Val Gly Asn Asp Tyr Leu Ala Trp Tyr
545                 550                 555                 560

Gln Gln Lys Pro Gly Gln Ser Pro Arg Leu Leu Ile His Gly Ala Tyr
                565                 570                 575

Arg Arg Asp Ser Gly Ile Pro Asp Arg Phe Ile Gly Ser Gly Ser Gly
            580                 585                 590

Thr Asp Phe Thr Leu Thr Ile Asp Ser Leu Glu Pro Asp Asp Cys Ala
        595                 600                 605

Val Tyr Tyr Cys Gln Gln Tyr Gly Ser Trp Pro Leu Thr Phe Gly Gly
    610                 615                 620

Gly Thr Lys Val Asp Ile Lys Arg Thr Val Ala Ala Pro Ser Val Phe
625                 630                 635                 640

Ile Phe Pro Pro Ser Asp Glu Gln Leu Lys Ser Gly Thr Ala Ser Val
                645                 650                 655

Val Cys Leu Leu Asn Asn Phe Tyr Pro Arg Glu Ala Lys Val Gln Trp
            660                 665                 670

Lys Val Asp Asn Ala Leu Gln Ser Gly Asn Ser Gln Glu Ser Val Thr
        675                 680                 685

Glu Gln Asp Ser Lys Asp Ser Thr Tyr Ser Leu Ser Ser Thr Leu Thr
    690                 695                 700

Leu Ser Lys Ala Asp Tyr Glu Lys His Lys Val Tyr Ala Cys Glu Val
705                 710                 715                 720

Thr His Gln Gly Leu Ser Ser Pro Val Thr Lys Ser Phe Asn Arg Gly
                725                 730                 735

Glu Cys

<210> SEQ ID NO 120
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 120

Ala Met Glu Lys Ile Val Ile Leu
1               5

<210> SEQ ID NO 121
<211> LENGTH: 5153
<212> TYPE: DNA
<213> ORGANISM: Artificial Sequence
<220> FEATURE:
<223> OTHER INFORMATION: Chemically Synthesized, pGX9368 full plasmid
      sequence

<400> SEQUENCE: 121

| | |
|---|---|
| gctgcttcgc gatgtacggg ccagatatac gcgttgacat tgattattga ctagttatta | 60 |
| atagtaatca attacggggt cattagttca tagcccatat atggagttcc gcgttacata | 120 |
| acttacggta aatggcccgc ctggctgacc gcccaacgac ccccgcccat tgacgtcaat | 180 |
| aatgacgtat gttcccatag taacgccaat agggactttc cattgacgtc aatgggtgga | 240 |
| gtatttacgg taaactgccc acttggcagt acatcaagtg tatcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |
| aaaatgtcgt aacaactccg ccccattgac gcaaatgggc ggtaggcgtg tacggtggga | 600 |
| ggtctatata agcagagctc tctggctaac tagagaaccc actgcttact ggcttatcga | 660 |
| aattaatacg actcactata gggagaccca agctggctag cgtttaaact taagcttggt | 720 |
| accgagctcg gatccgccac catggactgg acatggagaa tcctgttcct ggtggcagca | 780 |
| gcaaccggaa cacacgcaca ggtgaccctg agagagtccg gaccagccct ggtgaagcca | 840 |
| acccagacac tgaccctgac atgcaccttc tccggctttt ctctgagcac ctccggcatg | 900 |
| tctgtgggat ggatcaggca gccccctggc aaggccctgg agtggctggc gacatctgg | 960 |
| tgggacgata gaaggattca acccctagc ctgaagtccc gcctgacaat cagcaaggac | 1020 |
| acctccaaga accaggtggt gctgaaggtg acaaatatgg acccagccga tacagccacc | 1080 |
| tactattgcg cccggagcat gatcaccaat tggtatttcg acgtgtgggg cgccggaacc | 1140 |
| acagtgacag tgagctccgc ctccaccaag ggaccaagcg tgttcccact ggcaccctct | 1200 |
| agcaagtcta agcggcgg caccgccgcc ctggatgtc tggtgaagga ctacttcccc | 1260 |
| gagcctgtga ccgtgtcttg aacagcggc gccctgacat ccggagtgca cctttcca | 1320 |
| gccgtgctgc agtcctctgg cctgtacagc ctgagctccg tggtgacagt gccctctagc | 1380 |
| tccctgggca cacagaccta tatctgcaac gtgaatcaca gccctctaa taccaaggtg | 1440 |
| gacaagaagg tggagcctaa gagctgtgat aagacacaca cctgcccacc ctgtccagca | 1500 |
| ccagagctgc tgggcggccc tagcgtgttc ctgtttcctc caaagccaaa ggacaccctg | 1560 |
| atgatctcca gaacacctga ggtgacctgc gtggtggtgg acgtgtctca cgaggacccc | 1620 |

```
gaggtgaagt tcaactggta cgtggatggc gtggaggtgc acaatgccaa gaccaagcct      1680
cgggaggagc agtacaacag cacatataga gtggtgtccg tgctgaccgt gctgcaccag      1740
gattggctga acggcaagga gtataagtgc aaggtgtcca ataaggccct gcctgcccca      1800
atcgagaaga caatcagcaa ggccaagggc cagcctaggg agccacaggt gtacaccctg      1860 cccccctagcc gcgacgagct gacaaagaac caggtgtccc tgacctgtct ggtgaagggc      1920
ttctatccat ctgatatcgc cgtggagtgg gagagcaatg ccagcccga gaacaattac       1980 aagaccacac cacccgtgct ggactccgat ggctctttct ttctgtattc caagctgacc      2040
gtggacaagt ctaggtggca gcagggcaac gtgttttcct gttctgtgat gcacgaggcc      2100
ctgcacaatc actacacaca gaagagcctg tccctgtctc caggcaagag gggaaggaag      2160
cggagaagcg gctccggagc aaccaacttc tccctgctga gcaggcagg cgatgtggag       2220 gagaatccag gacctatggt gctgcagacc caggtgttta tctctctgct gctgtggatc      2280
agcggcgcct acggcgacat ccagatgaca cagtctccaa gcaccctgtc cgcctctgtg      2340
ggcgataggg tgacaatcac ctgcaagtgt cagctgagcg tgggctacat gcactggtat      2400
cagcagaagc ccggcaaggc ccctaagctg ctgatctacg acacctctaa gctggcaagc      2460
ggagtgccct cccgcttcag cggctccggc tctggaacag agtttacact gaccatctct      2520
agcctgcagc ccgacgattt cgccacctac tattgctttc agggcagcgg ctatcccttc      2580
accttcggcg gcggcaccaa gctggagatc aagcggacag tggccgcccc cagcgtgttc      2640
atctttcctc catccgacga gcagctgaag tctggcaccg ccagcgtggt gtgcctgctg      2700
aacaatttct accctagaga ggccaaggtg cagtggaagg tggataacgc cctgcagagc      2760
ggcaattccc aggagtctgt gacagagcag gacagcaagg attccaccta ttctctgtcc      2820
tctacactga ccctgtccaa ggccgattac gagaagcaca aggtgtatgc ctgcgaggtg      2880
acacaccagg gcctgagctc ccctgtgacc aagagcttta acagaggcga gtgttgataa      2940
ctcgagtcta gagggcccgt ttaaacccgc tgatcagcct cgactgtgcc ttctagttgc      3000
cagccatctg ttgtttgccc ctcccccgtg ccttccttga ccctggaagg tgccactccc      3060
actgtccttt cctaataaaa tgaggaaatt gcatcgcatt gtctgagtag gtgtcattct      3120
attctggggg gtggggtggg gcaggacagc aagggggagg attgggaaga caatagcagg      3180
catgctgggg atgcggtggg ctctatggct tctactgggc ggttttatgg acagcaagcg      3240
aaccggaatt gccagctggg gcgccctctg gtaaggttgg aagccctgc aaagtaaact       3300 ggatggcttt cttgccgcca aggatctgat ggcgcagggg atcaagctct gatcaagaga      3360
caggatgagg atcgtttcgc atgattgaac aagatggatt gcacgcaggt tctccggccg      3420
cttgggtgga gaggctattc ggctatgact gggcacaaca gacaatcggc tgctctgatg      3480
ccgccgtgtt ccggctgtca gcgcaggggc gcccggttct ttttgtcaag accgacctgt      3540
ccggtgccct gaatgaactg caagacgagg cagcgcggct atcgtggctg gccacgacgg      3600
gcgttccttg cgcagctgtg ctcgacgttg tcactgaagc gggaagggac tggctgctat      3660
tgggcgaagt gccggggcag gatctcctgt catctcacct tgctcctgcc gagaaagtat      3720
ccatcatggc tgatgcaatg cggcggctgc atacgcttga tccggctacc tgcccattcg      3780
accaccaagc gaaacatcgc atcgagcgag cacgtactcg gatggaagcc ggtcttgtcg      3840
atcaggatga tctggacgaa gagcatcagg ggctcgcgcc agccgaactg ttcgccaggc      3900
tcaaggcgag catgcccgac ggcgaggatc tcgtcgtgac ccatggcgat gcctgcttgc      3960
cgaatatcat ggtggaaaat ggccgctttt ctggattcat cgactgtggc cggctgggtg      4020
```

```
tggcggaccg ctatcaggac atagcgttgg ctacccgtga tattgctgaa gagcttggcg    4080
gcgaatgggc tgaccgcttc ctcgtgcttt acggtatcgc cgctcccgat tcgcagcgca    4140
tcgccttcta tcgccttctt gacgagttct tctgaattat taacgcttac aatttcctga    4200
tgcggtattt tctccttacg catctgtgcg gtatttcaca ccgcatcagg tggcactttt    4260
cggggaaatg tgcgcggaac ccctatttgt ttatttttct aaatacattc aaatatgtat    4320
ccgctcatga caataaacc ctgataaatg cttcaataat agcacgtgct aaaacttcat    4380
ttttaattta aaaggatcta ggtgaagatc ctttttgata atctcatgac caaaatccct    4440
taacgtgagt tttcgttcca ctgagcgtca gaccccgtag aaaagatcaa aggatcttct    4500
tgagatcctt ttttctgcg cgtaatctgc tgcttgcaaa caaaaaaacc accgctacca    4560
gcggtggttt gtttgccgga tcaagagcta ccaactcttt ttccgaaggt aactggcttc    4620
agcagagcgc agataccaaa tactgttctt ctagtgtagc cgtagttagg ccaccacttc    4680
aagaactctg tagcaccgcc tacatacctc gctctgctaa tcctgttacc agtggctgct    4740
gccagtggcg ataagtcgtg tcttaccggg ttggactcaa gacgatagtt accggataag    4800
gcgcagcggt cgggctgaac ggggggttcg tgcacacagc ccagcttgga gcgaacgacc    4860
tacaccgaac tgagatacct acagcgtgag ctatgagaaa gcgccacgct tcccgaaggg    4920
agaaaggcgg acaggtatcc ggtaagcggc agggtcggaa caggagagcg cacgagggag    4980
cttccagggg gaaacgcctg gtatctttat agtcctgtcg ggtttcgcca cctctgactt    5040
gagcgtcgat ttttgtgatg ctcgtcaggg gggcggagcc tatggaaaaa cgccagcaac    5100
gcggcctttt tacggttcct ggccttttgc tggccttttg ctcacatgtt ctt           5153

<210> SEQ ID NO 122
<211> LENGTH: 4439
<212> TYPE: DNA
<213> ORGANISM: Artificial Sequence
<220> FEATURE:
<223> OTHER INFORMATION: Chemically Synthesized, pGX9369 full plasmid
      sequence

<400> SEQUENCE: 122
gctgcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catggtgctg cagacccagg tgtttatttc actgctgctg    780 tggattcag gagcctacgg ggacattcag atgacccaga gccttcaac actgtccgcc    840 agcgtgggcg acagagtgac aatcacctgt aagtgccagc tgagcgtggg ctatatgcac    900
```

```
tggtatcagc agaagcctgg caaggcccca aagctgctga tctatgacac cagcaagctg    960
gcctctggcg tgccatccag attctccggc tctggcagcg gcaccgagtt tacactgacc   1020
atctccagcc tgcagccaga tgacttcgcc acctactatt gcttccaggg cagcggctat   1080
cccttcacct ttggcggcgg cacaaagctg gagatcaagg cggcggcgg ctccggcggc    1140 ggcggctctg cggcggcgg ctctcaggtg accctgagag agtccggccc agccctggtg    1200
aagccaaccc agaccctgac actgacatgc accttctccg gcttcagcct gtccaccagc   1260
ggcatgtccg tgggctggat caggcagccc ccaggcaagg ccctggagtg gctggccgat   1320
atctggtggg acgataagaa ggactacaac ccctccctga gagcagact gaccatcagc    1380 aaggatacca gcaagaacca ggtggtgctg aaggtgacaa atatggaccc agccgatacc   1440
gccacatact actgtgccag atccatgatc acaaattggt acttcgacgt gtggggcgcc   1500
ggcacaaccg tgacagtgag ctctgagcca aagtcctgcg acaagaccca cacctgtcct   1560
ccttgtccag cccccgagct gctgggcggc ccaagcgtgt tcctgtttcc ccctaagcca   1620 aaggatacccc tgatgatctc cagaacccca gaggtgacat gcgtggtggt ggacgtgagc   1680
cacgaggacc ccgaggtgaa gttcaattgg tacgtggatg gcgtggaggt gcacaatgcc   1740
aagaccaagc caagagagga gcagtataac tctacatatc gcgtggtgtc cgtgctgaca   1800
gtgctgcacc aggactggct gaatggcaag gagtacaagt gcaaggtgtc caataaggcc   1860
ctgccagccc ctatcgagaa gacaatctcc aaggccaagg ccagcccag agagccacag    1920 gtgtatacac tgccaccctc cagagatgag ctgacaaaga tcaggtgtc cctgacatgt    1980 ctggtgaagg cttttatcc ctccgatatc gccgtggagt gggagtctaa tggccagccc    2040
gagaataact ataagacaac ccctccagtg ctggactccg atggctcctt tttcctgtat   2100
tccaagctga ccgtggataa gagcaggtgg cagcagggca cgtgttctc ttgttccgtg    2160 atgcacgaag cactgcacaa ccactacacc cagaagtcac tgtcactgtc caggaaaaa    2220 tgataactcg agtctagagg gcccgtttaa acccgctgat cagcctcgac tgtgccttct   2280
agttgccagc catctgttgt ttgccccctcc ccgtgccctt ccttgaccct ggaaggtgcc   2340
actcccactg tccttcccta ataaaatgag gaaattgcat cgcattgtct gagtaggtgt   2400
cattctattc tggggggtgg ggtggggcag gacagcaagg gggaggattg gaagacaat    2460 agcaggcatg ctgggatgc ggtgggctct atggcttcta ctgggcggtt ttatggacag    2520
caagcgaacc ggaattgcca gctggggcgc cctctggtaa ggttgggaag ccctgcaaag   2580
taaactggat ggctttcttg ccgccaagga tctgatggcg caggggatca agctctgatc   2640
aagagacagg atgaggatcg tttcgcatga ttgaacaaga tggattgcac gcaggttctc   2700
cggccgcttg ggtggagagg ctattcggct atgactgggc acaacagaca atcggctgct   2760
ctgatgccgc cgtgttccgg ctgtcagcgc aggggcgccc ggttctttt gtcaagaccg   2820 acctgtccgg tgccctgaat gaactgcaag acgaggcagc gcggctatcg tggctggcca   2880
cgacgggcgt tccttgcgca gctgtgctcg acgttgtcac tgaagcggga agggactggc   2940
tgctattggg cgaagtgccg gggcaggatc tcctgtcatc tcaccttgct cctgccgaga   3000
aagtatccat catggctgat gcaatgcggc ggctgcatac gcttgatccg gctacctgcc   3060
cattcgacca ccaagcgaaa catcgcatcg agcgagcacg tactcggatg aagccggtc    3120 ttgtcgatca ggatgatctg gacgaagagc atcaggggct cgcgccagcc gaactgttcg   3180
ccaggctcaa ggcgagcatg cccgacggcg aggatctcgt cgtgacccat ggcgatgcct   3240
```

```
gcttgccgaa tatcatggtg gaaaatggcc gcttttctgg attcatcgac tgtggccggc   3300
tgggtgtggc ggaccgctat caggacatag cgttggctac ccgtgatatt gctgaagagc   3360
ttggcggcga atgggctgac cgcttcctcg tgctttacgg tatcgccgct cccgattcgc   3420
agcgcatcgc cttctatcgc cttcttgacg agttcttctg aattattaac gcttacaatt   3480
tcctgatgcg gtattttctc cttacgcatc tgtgcggtat ttcacaccgc atcaggtggc   3540
acttttcggg gaaatgtgcg cggaacccct atttgtttat ttttctaaat acattcaaat   3600
atgtatccgc tcatgagaca ataaccctga taaatgcttc aataatagca cgtgctaaaa   3660
cttcattttt aatttaaaag gatctaggtg aagatccttt ttgataatct catgaccaaa   3720
atcccttaac gtgagttttc gttccactga gcgtcagacc ccgtagaaaa gatcaaagga   3780
tcttcttgag atcctttttt tctgcgcgta atctgctgct tgcaaacaaa aaaaccaccg   3840
ctaccagcgg tggtttgttt gccggatcaa gagctaccaa ctcttttttcc gaaggtaact   3900
ggcttcagca gagcgcagat accaaatact gttcttctag tgtagccgta gttaggccac   3960
cacttcaaga actctgtagc accgcctaca tacctcgctc tgctaatcct gttaccagtg   4020
gctgctgcca gtggcgataa gtcgtgtctt accgggttgg actcaagacg atagttaccg   4080
gataaggcgc agcggtcggg ctgaacgggg gttcgtgca cacagcccag cttggagcga   4140
acgacctaca ccgaactgag atacctacag cgtgagctat gagaaagcgc cacgcttccc   4200
gaagggagaa aggcggacag gtatccggta agcggcaggg tcggaacagg agagcgcacg   4260
agggagcttc caggggggaaa cgcctggtat ctttatagtc ctgtcgggtt tcgccacctc   4320
tgacttgagc gtcgattttt gtgatgctcg tcagggggggc ggagcctatg gaaaaacgcc   4380
agcaacgcgg ccttttttacg gttcctggcc ttttgctggc cttttgctca catgttcctt   4439
```

<210> SEQ ID NO 123
<211> LENGTH: 5153
<212> TYPE: DNA
<213> ORGANISM: Artificial Sequence
<220> FEATURE:
<223> OTHER INFORMATION: Chemically Synthesized, pGX9370 full plasmid sequence

<400> SEQUENCE: 123

```
gctgcttcgc gatgtacggg ccagatatac gcgttgacat tgattattga ctagttatta    60
atagtaatca attacggggt cattagttca tagcccatat atggagttcc gcgttacata   120
acttacggta aatggcccgc ctggctgacc gcccaacgac ccccgcccat tgacgtcaat   180
aatgacgtat gttcccatag taacgccaat agggactttc cattgacgtc aatgggtgga   240
gtatttacgg taaactgccc acttggcagt acatcaagtg tatcatatgc caagtacgcc   300
ccctattgac gtcaatgacg gtaaatggcc cgcctggcat tatgcccagt acatgacctt   360
atgggacttt cctacttggc agtacatcta cgtattagtc atcgctatta ccatggtgat   420
gcggttttgg cagtacatca atgggcgtgg atagcggttt gactcacggg gatttccaag   480
tctccacccc attgacgtca atgggagttt gttttggcac caaaatcaac gggactttcc   540
aaaatgtcgt aacaactccg ccccattgac gcaaatgggc ggtaggcgtg tacggtggga   600
ggtctatata agcagagctc tctggctaac tagagaaccc actgcttact ggcttatcga   660
aattaatacg actcactata gggagaccca agctggctag cgtttaaact taagcttggt   720
accgagctcg gatccgccac catgactggg acctggagaa tcctgttcct ggtgcagcca   780
gcaaccggaa cacacgcaca ggtgcacactg agggagagcg gacctgccct ggtgaagcca   840
```

```
acccagacac tgaccctgac atgcaccttc tctggctttt ccctgtctac cagcggcatg    900
agcgtgggat ggatcaggca gcccctggc aaggccctgg agtggctggc cgacatctgg    960
tgggacgata agaaggatta caaccccctct ctgaagagcc gcctgaccat cagcaaggat   1020
acatccaaga accaggtggt gctgaaggtg accaatatgg accctgccga tacagccacc   1080
tactattgtg cccggagcat gatcaccaat tggtactttg acgtgtgggg cgccggcacc   1140
acagtgacag tgagctccgc caagaccaca gccccttccg tgtatcctct ggccccagtg   1200
tgcggcgata ccacaggctc tagcgtgacc ctgggctgtc tggtgaaggg ctacttccca   1260
gagcccgtga cactgacctg gaactccggc tctctgtcct ctggcgtgca cacctttcca   1320
gccgtgctgc agagcgacct gtacacactg agctcctctg tgacagtgac cagctccacc   1380
tggccaagcc agtccatcac atgcaacgtg gcccaccccg cctctagcac caaggtggat   1440
aagaagatcg agcccagagg ccctacaatc aagccctgtc caccctgcaa gtgtcctgcc   1500
ccaaatctgc tgggcggccc ttccgtgttc atctttcctc caaagatcaa ggacgtgctg   1560
atgatctctc tgagccctat cgtgacctgc gtggtggtgg acgtgtccga ggacgatcca   1620
gatgtgcaga tctcttggtt cgtgaacaat gtggaggtgc acaccgccca gacacagacc   1680
caccgggagg attataacag cacactgaga gtggtgtccg ccctgccaat ccagcaccag   1740
gactggatga gcggcaagga gtttaagtgc aaggtgaaca ataaggatct gcccgcccct   1800
atcgagcgga ccatctccaa gcccaagggc tctgtgagag cccctcaggt gtacgtgctg   1860
ccccctccag aggaggagat gaccaagaag caggtgacac tgacctgtat ggtgacagac   1920
ttcatgcctg aggatatcta cgtggagtgg accaacaatg gcaagacaga gctgaactat   1980
aagaataccg agccagtgct ggactccgat ggctcttact ttatgtatag caagctgagg   2040
gtggagaaga gaactgggt ggagcgcaat tcctattctt gtagcgtggt gcacgagggc   2100
ctgcacaatc accacaccac aaagtccttc tctagaaccc caggcaagag gggaaggaag   2160
cggagaagcg gctccggagc cacaaacttt ccctgctga agcaggcagg cgacgtggag   2220
gagaatccag accccatggt gctgcagacc caggtgttca tctctctgct gctgtggatc   2280
agcggcgcct acgcgacat ccagatgacc cagtctccca gcacactgtc cgcctctgtg   2340
ggcgatcggg tgacaatcac ctgcaagtgt cagctgtccg tgggctacat gcactggtat   2400
cagcagaagc caggcaaggc ccccaagctg ctgatctatg acacctctaa gctgccagc   2460 ggcgtgcctt ccagattcag cggctccggc tctggcaccg agtttacact gaccatctcc   2520
tctctgcagc cagacgattt cgccacatac tattgctttc agggcagcgg ataccccttc   2580
accttcggcg gcggcacaaa gctggagatc aagagggccg atgccgcccc aaccgtgtcc   2640
atcttccctc ccagcagcga gcagctgaca tctggcggcg ccagcgtggt gtgcttcctg   2700
aacaacttct accccaagga catcaacgtg aagtggaaga tcgatggcag cgagcgccag   2760
aacggcgtgc tgaattcctg gaccgaccag gatagcaagg actccacata ctctatgtct   2820
agcacactga cctgacaaa ggatgagtac gagcggcaca attcctatac ctgcgaggcc   2880
acacacaaga ccagcacatc ccctatcgtg aagtctttta acagaaatga gtgttgataa   2940
ctcgagtcta gagggcccgt ttaaacccgc tgatcagcct cgactgtgcc ttctagttgc   3000
cagccatctg ttgtttgccc ctcccccgtg ccttccttga ccctggaagg tgccactccc   3060
actgtccttt cctaataaaa tgaggaaatt gcatcgcatt gtctgagtag gtgtcattct   3120
attctggggg gtggggtggg gcaggacagc aaggggggagg attgggaaga caatagcagg   3180
catgctgggg atgcggtggg ctctatggct tctactgggc ggttttatgg acagcaagcg   3240
```

```
aaccggaatt gccagctggg gcgccctctg gtaaggttgg gaagccctgc aaagtaaact    3300
ggatggcttt cttgccgcca aggatctgat ggcgcagggg atcaagctct gatcaagaga    3360
caggatgagg atcgtttcgc atgattgaac aagatggatt gcacgcaggt tctccggccg    3420
cttgggtgga gaggctattc ggctatgact gggcacaaca gacaatcggc tgctctgatg    3480
ccgccgtgtt ccggctgtca gcgcaggggc gcccggttct ttttgtcaag accgacctgt    3540
ccggtgccct gaatgaactg caagacgagg cagcgcggct atcgtggctg gccacgacgg    3600
gcgttccttg cgcagctgtg ctcgacgttg tcactgaagc gggaagggac tggctgctat    3660
tgggcgaagt gccggggcag gatctcctgt catctcacct tgctcctgcc gagaaagtat    3720
ccatcatggc tgatgcaatg cggcggctgc atacgcttga tccggctacc tgcccattcg    3780
accaccaagc gaaacatcgc atcgagcgag cacgtactcg gatggaagcc ggtcttgtcg    3840
atcaggatga tctggacgaa gagcatcagg ggctcgcgcc agccgaactg ttcgccaggc    3900
tcaaggcgag catgcccgac ggcgaggatc tcgtcgtgac ccatggcgat gcctgcttgc    3960
cgaatatcat ggtggaaaat ggccgctttt ctggattcat cgactgtggc cggctgggtg    4020
tggcggaccg ctatcaggac atagcgttgg ctacccgtga tattgctgaa gagcttggcg    4080
gcgaatgggc tgaccgcttc ctcgtgcttt acggtatcgc cgctcccgat tcgcagcgca    4140
tcgccttcta tcgccttctt gacgagttct tctgaattat taacgcttac aatttcctga    4200
tgcggtattt tctccttacg catctgtgcg gtatttcaca ccgcatcagg tggcacttt     4260 cggggaaatg tgcgcggaac ccctatttgt ttatttttct aaatacattc aaatatgtat    4320
ccgctcatga gacaataacc ctgataaatg cttcaataat agcacgtgct aaaacttcat    4380
ttttaattta aaaggatcta ggtgaagatc ctttttgata atctcatgac caaaatccct    4440
taacgtgagt tttcgttcca ctgagcgtca ccccgtag aaaagatcaa aggatcttct    4500
tgagatcctt ttttttctgcg cgtaatctgc tgcttgcaaa caaaaaaacc accgctacca    4560
gcggtggttt gtttgccgga tcaagagcta ccaactcttt ttccgaaggt aactggcttc    4620
agcagagcgc agataccaaa tactgttctt ctagtgtagc cgtagttagg ccaccacttc    4680
aagaactctg tagcaccgcc tacatacctc gctctgctaa tcctgttacc agtggctgct    4740
gccagtggcg ataagtcgtg tcttaccggg ttggactcaa gacgatagtt accggataag    4800
gcgcagcggt cgggctgaac ggggggttcg tgcacacagc ccagcttgga gcgaacgacc    4860
tacaccgaac tgagatacct acagcgtgag ctatgagaaa gcgccacgct tcccgaaggg    4920
agaaaggcgg acaggtatcc ggtaagcggc agggtcggaa caggagagcg cacgagggag    4980
cttccagggg gaaacgcctg gtatctttat agtcctgtcg gtttcgccac cctctgactt    5040
gagcgtcgat ttttgtgatg ctcgtcaggg ggcggagcc tatggaaaaa cgccagcaac    5100
gcggcctttt tacggttcct ggccttttgc tggccttttg ctcacatgtt ctt           5153
```

<210> SEQ ID NO 124
<211> LENGTH: 4442
<212> TYPE: DNA
<213> ORGANISM: Artificial Sequence
<220> FEATURE:
<223> OTHER INFORMATION: Chemically Synthesized, pGX371 full plasmid
      sequence

<400> SEQUENCE: 124

```
gctgcttcgc gatgtacggg ccagatatac gcgttgacat tgattattga ctagttatta     60
atagtaatca attacggggt cattagttca tagcccatat atggagttcc gcgttacata    120
```

-continued

```
acttacggta aatggcccgc ctggctgacc gcccaacgac ccccgcccat tgacgtcaat    180
aatgacgtat gttcccatag taacgccaat agggactttc cattgacgtc aatgggtgga    240
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catggtgctg cagactcagg tgtttatttc actgctgctg    780
tggatttccg gcgcttacgg cgacattcag atgacccaga gcccctccac actgagcgcc    840
tccgtgggcg acagagtgac aatcacatgc aagtgtcagc tgtctgtggg ctatatgcac    900
tggtatcagc agaagcccgg caaggcccca agctgctga tctatgacac ctctaagctg    960
gcctctggcg tgccaagcag attctccggc agcggctccg gcaccgagtt caccctgaca    1020
atctcctctc tgcagccaga cgatttcgcc acatactact gctttcaggg ctccggctac    1080
ccattcacat ttggcggcgg cacaaagctg gagatcaagg gcggcggcgg ctccggcggc    1140
ggcggctctg gcgcggcgg ctctcaggtg acactgcggg agtccggccc agccctggtg    1200
aagccaaccc agacactgac actgacctgt acattttccg gcttctctct gtccaccagc    1260
ggcatgagcg tgggctggat cagacagccc cctggcaagg ccctggagtg gctggccgat    1320
atctggtggg acgataagaa ggactacaat ccttccctga agtctagact gaccatctcc    1380
aaggatacct ccaagaatca ggtggtgctg aaggtgacca acatggaccc tgccgataca    1440
gccacctatt actgcgccag aagcatgatc accaactggt actttgacgt gtggggcgcc    1500
ggcacaaccg tgacagtgtc ttccgagcct agaggcccaa ccatcaagcc atgcccaccc    1560
tgtaagtgtc ccgccccaaa cctgctgggc ggcccatccg tgttcatctt tccccctaag    1620
atcaaggacg tgctgatgat cagcctgagc ccaatcgtga catgcgtggt ggtggacgtg    1680
tccgaggatg acccagatgt gcagatctct tggttcgtga taacgtgga ggtgcacacc    1740 gcccagaccc agacccacag agaggattac aattccacac tgagagtggt gtccgccctg    1800
cctatccagc accaggattg gatgagcggc aaggagttta gtgcaaggt gaacaataag    1860 gacctgcccg ccccaatcga gagaaccatc tccaagccaa agggctctgt gagggcccca    1920
caggtgtacg tgctgcctcc tccagaggag gagatgacaa agaagcaggt gacactgacc    1980
tgcatggtga ccgacttcat gcccgaggac atctacgtgg agtggacaaa caatggcaag    2040
acagagctga actataagaa caccgagcca gtgctggatt ccgacggctc ttacttcatg    2100
tactccaagc tgagagtgga aagaagaac tgggtggagc ggaatagcta ctcctgttcc    2160
gtggtccacg aagggctgca taaccaccac accactaagt cattttcaag aaccccaggc    2220 aaaatgataac tcgagtctag agggcccgtt taaacccgct gatcagcctc gactgtgcct    2280
tctagttgcc agccatctgt tgtttgcccc tcccccgtgc cttccttgac cctggaaggt    2340
gccactccca ctgtcctttc ctaataaaat gaggaaattg catcgcattg tctgagtagg    2400
tgtcattcta ttctggggggg tggggtgggg caggacagca agggggagga ttgggaagac    2460
```

| | |
|---|---|
| aatagcaggc atgctgggga tgcggtgggc tctatggctt ctactgggcg gttttatgga | 2520 |
| cagcaagcga accggaattg ccagctgggg cgccctctgg taaggttggg aagccctgca | 2580 |
| aagtaaactg gatggctttc ttgccgccaa ggatctgatg gcgcagggga tcaagctctg | 2640 |
| atcaagagac aggatgagga tcgtttcgca tgattgaaca agatggattg cacgcaggtt | 2700 |
| ctccggccgc ttgggtggag aggctattcg gctatgactg ggcacaacag acaatcggct | 2760 |
| gctctgatgc cgccgtgttc cggctgtcag cgcaggggcg cccggttctt tttgtcaaga | 2820 |
| ccgacctgtc cggtgccctg aatgaactgc aagacgaggc agcgcggcta tcgtggctgg | 2880 |
| ccacgacggg cgttccttgc gcagctgtgc tcgacgttgt cactgaagcg ggaagggact | 2940 |
| ggctgctatt gggcgaagtg ccggggcagg atctcctgtc atctcacctt gctcctgccg | 3000 |
| agaaagtatc catcatggct gatgcaatgc ggcggctgca tacgcttgat ccggctacct | 3060 |
| gcccattcga ccaccaagcg aaacatcgca tcgagcgagc acgtactcgg atggaagccg | 3120 |
| gtcttgtcga tcaggatgat ctggacgaag agcatcaggg gctcgcgcca gccgaactgt | 3180 |
| tcgccaggct caaggcgagc atgcccgacg gcgaggatct cgtcgtgacc catggcgatg | 3240 |
| cctgcttgcc gaatatcatg gtggaaaatg gccgcttttc tggattcatc gactgtggcc | 3300 |
| ggctgggtgt ggcggaccgc tatcaggaca tagcgttggc tacccgtgat attgctgaag | 3360 |
| agcttggcgg cgaatgggct gaccgcttcc tcgtgcttta cggtatcgcc gctcccgatt | 3420 |
| cgcagcgcat cgccttctat cgccttcttg acgagttctt ctgaattatt aacgcttaca | 3480 |
| atttcctgat gcggtatttt ctccttacgc atctgtgcgg tatttcacac cgcatcaggt | 3540 |
| ggcacttttc ggggaaatgt gcgcggaacc cctatttgtt tatttttcta aatacattca | 3600 |
| aatatgtatc cgctcatgag acaataaccc tgataaatgc ttcaataata gcacgtgcta | 3660 |
| aaacttcatt tttaatttaa aaggatctag gtgaagatcc ttttttgataa tctcatgacc | 3720 |
| aaaatccctt aacgtgagtt ttcgttccac tgagcgtcag accccgtaga aaagatcaaa | 3780 |
| ggatcttctt gagatccttt ttttctgcgc gtaatctgct gcttgcaaac aaaaaaacca | 3840 |
| ccgctaccag cggtggtttg tttgccggat caagagctac caactctttt tccgaaggta | 3900 |
| actggcttca gcagagcgca gataccaaat actgttcttc tagtgtagcc gtagttaggc | 3960 |
| caccacttca agaactctgt agcaccgcct acatacctcg ctctgctaat cctgttacca | 4020 |
| gtggctgctg ccagtggcga taagtcgtgt cttaccgggt tggactcaag acgatagtta | 4080 |
| ccggataagg cgcagcggtc gggctgaacg gggggttcgt gcacacagcc cagcttggag | 4140 |
| cgaacgacct acaccgaact gagataccta cagcgtgagc tatgagaaag cgccacgctt | 4200 |
| cccgaaggga gaaaggcgga caggtatccg gtaagcggca gggtcggaac aggagagcgc | 4260 |
| acgagggagc ttccaggggg aaacgcctgg tatctttata gtcctgtcgg gtttcgccac | 4320 |
| ctctgacttg agcgtcgatt tttgtgatgc tcgtcagggg gcggagcct atggaaaaac | 4380 |
| gccagcaacg cggccttttt acggttcctg gccttttgct ggccttttgc tcacatgttc | 4440 |
| tt | 4442 |

<210> SEQ ID NO 125
<211> LENGTH: 5174
<212> TYPE: DNA
<213> ORGANISM: Artificial Sequence
<220> FEATURE:
<223> OTHER INFORMATION: Chemically Synthesized, pGX9283 full plasmid
      sequence

<400> SEQUENCE: 125

```
gctgcttcgc gatgtacggg ccagatatac gcgttgacat tgattattga ctagttatta    60
atagtaatca attacggggt cattagttca tagcccatat atggagttcc gcgttacata   120
acttacggta aatggcccgc ctggctgacc gcccaacgac ccccgcccat tgacgtcaat   180
aatgacgtat gttcccatag taacgccaat agggactttc cattgacgtc aatgggtgga   240
gtatttacgg taaactgccc acttggcagt acatcaagtg tatcatatgc caagtacgcc   300
ccctattgac gtcaatgacg gtaaatggcc cgcctggcat tatgcccagt acatgacctt   360
atgggacttt cctacttggc agtacatcta cgtattagtc atcgctatta ccatggtgat   420
gcggttttgg cagtacatca atgggcgtgg atagcggttt gactcacggg gatttccaag   480
tctccacccc attgacgtca atgggagttt gttttggcac caaaatcaac gggactttcc   540
aaaatgtcgt aacaactccg ccccattgac gcaaatgggc ggtaggcgtg tacggtggga   600
ggtctatata agcagagctc tctggctaac tagagaaccc actgcttact ggcttatcga   660
aattaatacg actcactata gggagaccca agctggctag cgtttaaact taagcttggt   720
accgagctcg gatccgccac catgactgg acttggagaa tcctgttcct ggtcgccgcc   780
gcaactggga ctcatgctca ggtgcagctg gtgcagagcg gggcagaggt gaagaagcca   840
ggcagctccg tgaaggtgtc ttgcaaggca agcggcggct ctctgagcac ctacggcatc   900
cactgggtga ggcaggcacc aggacagggc ctggagtggg tgggcggcgt gatgaccgtg   960
tacggcaaga ccacatatgg ccagaacttc cagggcaggt tgacaatcgc cgtggaccgc  1020
tctaccaata cagcctacat ggagctgtct agcctgacca gcgacgatac cggcacatac  1080
tattgcgcca ccgactctta ctacgtgtgg acaggcagct atcccctcc attcgatctg  1140
tgggggccagg gcaccctggt gacagtgtcc tctgcctcta caagggacc aagcgtgttt  1200
ccactggcac ctagctccaa gtccacctct ggcggcacag ccgccctggg ctgtctggtg  1260
aaggattact cccctgagcc agtgaccgtg tcctggaact ctggcgccct gaccagcgga  1320
gtgcacacat ttcccgccgt gctgcagtct agcggcctgt actccctgtc ctctgtggtg  1380
accgtgccta gctcctctct gggcacccag acatatatct gcaacgtgaa tcacaagcct  1440
agcaatacaa aggtggacaa gaaggtggag ccaaagtcct gtgataagac ccacacatgc  1500
cctcctgtc cagcacctga gctgctgggc ggcccaagcg tgttcctgtt tccacccaag  1560
cccaaggaca ccctgatgat ctccagaacc ccagaggtga catgcgtggt ggtggacgtg  1620
tctcacgagg accccgaggt gaagtttaac tggtacgtgg atggcgtgga ggtgcacaat  1680
gccaagacca gccccggga ggagcagtac aactccacct atagagtggt gtctgtgctg  1740
acagtgctgc accaggactg gctgaacggc aaggagtata agtgcaaggt gagcaataag  1800
gccctgccag cccccatcga gaagaccatc tccaaggcaa agggacagcc aagggagcca  1860
caggtgtaca cactgcctcc atcccgcgac gagctgacca agaaccaggt gtctctgaca  1920
tgtctggtga agggcttcta tccctctgat atcgccgtgg agtgggagag caatggccag  1980
cctgagaaca attacaagac cacaccccct gtgctggaca gcgatggctc cttctttctg  2040
tattccaagc tgaccgtgga caagtctcgg tggcagcagg gcaacgtgtt tagctgctcc  2100
gtgatgcacg aggccctgca caatcactac acccagaagt ctctgagcct gtccccaggc  2160
aagaggggaa gaaagcggag atctggcagc ggcgccacaa acttcagcct gctgaagcag  2220
gccggcgatg tggaggagaa tcctggccca atggtgctgc agaccaggt gtttatcagc  2280
ctgctgctgt ggatctccgg agcatacgga gagatcgtgc tgacccagac accaggaacc  2340
cagtccctgt ctcctggaca gtccgccaca ctgtcttgta gagccagcca ctccgtgggc  2400
```

```
aatgactacc tggcctggta tcagcagaag cctggacaga gcccacggct gctgatccac   2460
ggagcataca ggagggactc cggcatccct gatagattca tcggctctgg cagcggcacc   2520
gactttaccc tgacaatcga tagcctggag cctgacgatt gcgccgtgta ctattgtcag   2580
cagtatggct cctggccact gaccttcggc ggcggcacaa aggtggacat caagaggacc   2640
gtggccgccc ctagcgtgtt catctttcca ccctccgatg agcagctgaa gagcggcaca   2700
gcctccgtgg tgtgcctgct gaacaacttc tacccacgcg aggccaaggt gcagtggaag   2760
gtggacaacg ccctgcagtc tggcaatagc caggagtccg tgaccgagca ggactctaag   2820
gatagcacat attccctgag ctccaccctg acactgtcca aggccgatta cgagaagcac   2880
aaggtgtatg cctgtgaggt cacccaccag ggactgtctt cacccgtcac aaaatccttc   2940
aataggggag aatgctgata actcgagtct agagggcccg tttaaacccg ctgatcagcc   3000
tcgactgtgc cttctagttg ccagccatct gttgtttgcc cctcccccgt gccttccttg   3060
accctggaag gtgccactcc cactgtcctt tcctaataaa atgaggaaat tgcatcgcat   3120
tgtctgagta ggtgtcattc tattctgggg ggtggggtgg ggcaggacag caagggggag   3180
gattgggaag acaatagcag gcatgctggg gatgcggtgg gctctatggc ttctactggg   3240
cggttttatg gacagcaagc gaaccggaat tgccagctgg ggcgccctct ggtaaggttg   3300
ggaagccctg caaagtaaac tggatggctt tcttgccgcc aaggatctga tggcgcaggg   3360
gatcaagctc tgatcaagag acaggatgag gatcgtttcg catgattgaa caagatggat   3420
tgcacgcagg ttctccggcc gcttgggtgg agaggctatt cggctatgac tgggcacaac   3480
agacaatcgg ctgctctgat gccgccgtgt tccggctgtc agcgcagggg cgcccggttc   3540
tttttgtcaa gaccgacctg tccggtgccc tgaatgaact gcaagacgag gcagcgcggc   3600
tatcgtggct ggccacgacg ggcgttcctt gcgcagctgt gctcgacgtt gtcactgaag   3660
cgggaaggga ctggctgcta ttgggcgaag tgccggggca ggatctcctg tcatctcacc   3720
ttgctcctgc cgagaaagta tccatcatgg ctgatgcaat gcggcggctg catacgcttg   3780
atccggctac ctgcccattc gaccaccaag cgaaacatcg catcgagcga gcacgtactc   3840
ggatggaagc cggtcttgtc gatcaggatg atctggacga agagcatcag gggctcgcgc   3900
cagccgaact gttcgccagg ctcaaggcga gcatgcccga cggcgaggat ctcgtcgtga   3960
cccatggcga tgcctgcttg ccgaatatca tggtggaaaa tggccgcttt tctggattca   4020
tcgactgtgg ccggctgggt gtggcggacc gctatcagga catagcgttg gctacccgtg   4080
atattgctga agagcttggc ggcgaatggg ctgaccgctt cctcgtgctt tacggtatcg   4140
ccgctcccga ttcgcagcgc atcgccttct atcgccttct tgacgagttc ttctgaatta   4200
ttaacgctta caatttcctg atgcggtatt ttctccttac gcatctgtgc ggtatttcac   4260
accgcatcag gtggcacttt tcggggaaat gtgcgcggaa cccctatttg tttatttttc   4320
taaatacatt caaatatgta tccgctcatg agacaataac cctgataaat gcttcaataa   4380
tagcacgtgc taaaacttca ttttaatttt aaaaggatct aggtgaagat cctttttgat   4440
aatctcatga ccaaaatccc ttaacgtgag ttttcgttcc actgagcgtc agaccccgta   4500
gaaaagatca aaggatcttc ttgagatcct tttttctgc gcgtaatctg ctgcttgcaa   4560
acaaaaaaac caccgctacc agcggtggtt tgtttgccgg atcaagagct accaactctt   4620
tttccgaagg taactggctt cagcagagcg cagataccaa atactgttct tctagtgtag   4680
ccgtagttag gccaccactt caagaactct gtagcaccgc ctacatacct cgctctgcta   4740
```

```
atcctgttac cagtggctgc tgccagtggc gataagtcgt gtcttaccgg gttggactca    4800
agacgatagt taccggataa ggcgcagcgg tcgggctgaa cggggggttc gtgcacacag    4860
cccagcttgg agcgaacgac ctacaccgaa ctgagatacc tacagcgtga gctatgagaa    4920
agcgccacgc ttcccgaagg gagaaaggcg gacaggtatc cggtaagcgg cagggtcgga    4980
acaggagagc gcacgaggga gcttccaggg ggaaacgcct ggtatcttta tagtcctgtc    5040
gggtttcgcc acctctgact tgagcgtcga ttttttgtgat gctcgtcagg ggggcggagc    5100
ctatggaaaa acgccagcaa cgcggccttt ttacggttcc tggccttttg ctggccttt     5160 gctcacatgt tctt                                                       5174
```

<210> SEQ ID NO 126
<211> LENGTH: 6990
<212> TYPE: DNA
<213> ORGANISM: Artificial Sequence
<220> FEATURE:
<223> OTHER INFORMATION: Chemically Synthesized, pRD245 full plasmid
      sequence

<400> SEQUENCE: 126

```
gctgcttcgc gatgtacggg ccagatatac gcttaccaca tttgtagagg ttttacttgc      60
tttaaaaaac ctcccacatc tcccctgaa cctgaaacat aaaatgaatg caattgttgt     120
tgttaacttg tttattgcag cttataatgg ttacaaataa agcaatagca tcacaaattt    180
cacaaataaa gcatttttt cactgcattc tagttgtggt ttgtccaaac tcatcaatgt    240
atcttatcat gtctgtcagt cagtcacttg ccaggtgaca gtgacagtga cttctgagtg    300
taatggttgt gcagtgcctc gtgcatcacg ctgcaggaga acacgttgcc ctgctgccac    360
cggctcttat ccactgtcag cttgctgtac aggaaaaagg agccatcaga atccagcacg    420
ggtggtgtgg tcttgtagtt gttctctggc tggccattgc tctcccactc cacggcgatg    480
tcgctagggt aaaagccctt caccagacag gtcagagaca cctggttctt ggtcagctca    540
tctctgcttg gaggcagggt atacacctga ggctctcttg gctggccctt ggccttggag    600
atggtcttct cgataggggc tggcagggcc ttattggaca ccttgcactt gtactccttg    660
ccgttcagcc aatcctggtg cagcactgtc agcacggaca ccactctgta ggtggagttg    720
tactgctcct ctctgggctt tgtcttggca ttgtgcacct ccacgccgtc cacgtaccag    780
ttgaacttca cctcggggtc ctcgtggctc acatccacca ccacgcaggt cacctctggt    840
gttctggaga tcatcagggt gtccttaggc tttggtggaa acaggaacac ggatgggccg    900
ccggcggcct ctggggcggg gcatggagga catgtgtggg tcttatcgct ggacttaggc    960
tccttgatct ccagctttgt gccctggcca aggtgtgag gtggggaata gctctgctgg   1020
caatagtagg tgccgaagtc ctctggctgc aggctagaga tggtcagtgt gaagtctgtc   1080
acagagccgc tgccagaaaa ccgggatggc acgccagact gcagggtgct tgtggtgtag   1140
atcagcagct gaggcactct gcctggtctc tgctggtacc agttcaggta gcgtctgatg   1200
tcctggctgg ctctgcaggt gattgtcacc ctgtcgccca cgctggcgga cagagaagat   1260
ggggactggg tcatctggat gtcggagccg ccgccgccgc tgccgccgcc gccagagccg   1320
ccgccgccgg aagacacggt caccagtgtg ccctggcccc aatagtccac ccaggagctc   1380
agcagctgca ggcctctggg gccgcccttg gcgcagtagt acagggcggt atcgtcaggt   1440
ctcagggagt tcatctgcag gtccagggac ttccttggcgt tatccctgct gatggtgaat   1500
ctgcccttca cggagtcggc gtagccgatt gtggcggagt tccaagagat gccgctgatc   1560
```

```
cactccaggc ccttgcctgg ggcctgccgc acccaaaaca tggcgtaatc gtcgaatgta    1620
aagccgctgg cggcacagga cagtctcagg cttctgcctg gctgcaccag cccgcctccg    1680 cttttcgacca gctggaccctc tgcgtgagtg ccggtggctg ctgcgaccag gaacaggatg    1740
cgccaagtcc aatccatggt ggcggctccg agctctgtgg agagaaaggc aaagtggatg    1800
tcagtaagac caataggtgc ctatcagaaa cgcaagagtc ttctctgtct cgacaagccc    1860
agtttctatt ggtctcctta aacctgtctt gtaaccttga tacttacctg cccagtgcct    1920
cacgaccaac ttctgtagct taatcggccg ccagcttatc ggtaccgtta tcagatcggc    1980
ttcgagggga ggctggatcg gtcccggtgt cttctatgga ggtcaaaaca gcgtggatgg    2040
cgtctccagg cgatctgacg gttcactaaa cgagctctgc ttatatagac ctcccaccgt    2100
acacgcctac cgcccatttg cgtcaatggg gcggagttgt tacgacattt tggaaagtcc    2160
cgttgatttt ggtgccaaaa caaactccca ttgacgtcaa tggggtggag acttggaaat    2220
ccccgtgagt caaaccgcta tccacgccca ttgatgtact gccaaaaccg catcaccatc    2280
aatattggcc attagccata ttattcattg gttatatagc ataaatcaat attggctatt    2340
ggccattgca tacgttgtat ctatatcata atatgtacat ttatattggc tcatgtccaa    2400
tatgaccgcc atgttggcat tgattattga ctagttatta atagtaatca attacggggt    2460
cattagttca tagcccatat atggagttcc gcgttacata acttacggta aatggcccgc    2520
ctggctgacc gcccaacgac ccccgcccat tgacgtcaat aatgacgtat gttcccatag    2580
taacgccaat agggactttc cattgacgtc aatgggtgga gtatttacgg taaactgccc    2640
acttggcagt acatcaagtg tatcatatgc caagtccgcc ccctattgac gtcaatgacg    2700
gtaaatggcc cgcctggcat tatgcccagt acatgacctt acgggacttt cctacttggc    2760
agtacatcta cgtattagtc atcgctatta ccacatggtc tttcctattg acgtcatatg    2820
ggcggtccta ttgacgtata tggcgcctcc cccattgacg tcaattacgg taaatggccc    2880
gcctggctca atgcccattg acgtcaatag gaccacccac cattgacgtc aatgggatgg    2940
ctcattgccc attcatatcc gttctcacgc cccctattga cgtcaatgac ggtaaatggc    3000
ccacttggca gtacatcaat atctattaat agtaacttgg caagtacatt actattggaa    3060
gtacgccagg gtacattggc agtactccca ttgacgtcaa tggcggtaaa tggcccgcga    3120
tggctgccaa gtacatcccc attgacgtca atggggaggg gcaatgacgc aaatgggcgt    3180
tccattgacg taaatgggcg gtaggcgtgc ctaacgggag gtctatataa gcaatgctcg    3240
tttagggaac cgccattctg cctggggacg tcggaggagc agctcggagc cgccaccatg    3300
gactggactt ggcgcattct gtttctggtc gcagccgcta ctggaaccca cgctcaggtg    3360
cagctggtcg aatcaggagg aggggtggtc cagccaggca gatccctgag actgtcttgc    3420
gccgccagcg gcttcacatt ctccaagtac ggcatgcact gggtgcggca ggcccccggc    3480
aagggcctgg agtgggtggc cgtgatctct tacgagggca gcaacaagta ctatgccgac    3540
tctgtgaagg gcagattcac aatcagcaga gacaatagca gaacaccct gtacctgcag    3600 atgaactccc tgagagccga ggacaccgcc gtgtactatt gcgccaagtc cggcacccag    3660
tactatgaca ccacaggcta cgagtataga ggcctggagt actttggcta ttggggccag    3720
ggcacactgg tgacagtgtc ctctggcggc ggcggctccg gcggcggcgg cagcggcggc    3780
ggcggctctg agatcgtgct gacacagagc ccaggcacac tgtccctgag cccaggcgag    3840
agagccacac tgtcctgtag agcctctcag tccgtgagct cctcttacct ggcctggtat    3900
cagcagaaga gaggccaggc ccccagactg ctgatctatg acgcctccag cagagccaca    3960
```

```
ggcatccctg atcggttctc tggcagcggc tccggcaccg atttcaccct gacaatctct    4020
agactggagc ctgaggactt tgccgtgtac tactgccagc agtatggcag atctcggtgg    4080
acatttggcc agggcaccaa ggtggagatc aaggagccaa agagctgtga caagacccac    4140
acctgtccac cctgcccagc ccctgaggcc gccggcggcc ctagcgtgtt cctgttccca    4200
cctaagccca aggacaccct gatgatcagc cggacacctg aggtgacctg cgtggtggtg    4260
gacgtgagcc acgaggaccc tgaggtgaag ttcaactggt atgtggatgg cgtggaggtg    4320
cacaacgcca agacaaagcc agagaggag cagtacaatt ccacctacag agtggtgtcc    4380
gtgctgaccg tgctgcacca ggactggctg aatggcaagg agtacaagtg caaggtgtcc    4440
aacaaggccc tgcccgcccc aatcgagaag accatcagca aggccaaggg ccagcccaga    4500
gagccacagg tgtataccct gcctccatcc agagaggaga tgaccaagaa tcaggtgtct    4560
ctgacctgtc tggtgaaggg cttctatcca agcgatatcg ccgtggagtg ggagtccaat    4620
ggccagcctg agaataatta caagaccaca ccccctgtgc tggatagcga tggctccttc    4680
tttctgtact ccaagctgac cgtggacaag tccagatggc agcagggcaa cgtgtttttcc    4740 tgctctgtga tgcatgaagc cctgcataac cattcaccc agaaatccct gtccctgagc    4800
cccggaaaat gactgactga ctgtgccttc tagttgccag ccatctgttg tttgcccctc    4860
ccccgtgcct tccttgaccc tggaaggtgc cactcccact gtcctttcct aataaaatga    4920
ggaaattgca tcgcattgtc tgagtaggtg tcattctatt ctgggggtg gggtggggca    4980 ggacagcaag ggggaggatt gggaagacaa tagcaggcat gctggggatg cggtgggctc    5040
tatggcttct actgggcggt tttatggaca gcaagcgaac cggaattgcc agctggggcg    5100
ccctctggta aggttgggaa gccctgcaaa gtaaactgga tggctttctt gccgccaagg    5160
atctgatggc gcagggatc aagctctgat caagagacag gatgaggatc gtttcgcatg    5220
attgaacaag atggattgca cgcaggttct ccggccgctt gggtggagag gctattcggc    5280
tatgactggg cacaacagac aatcggctgc tctgatgccg ccgtgttccg gctgtcagcg    5340
caggggcgcc cggttctttt tgtcaagacc gacctgtccg gtgccctgaa tgaactgcaa    5400
gacgaggcag cgcggctatc gtggctggcc acgacgggcg ttccttgcgc agctgtgctc    5460
gacgttgtca ctgaagcggg aagggactgg ctgctattgg gcgaagtgcc ggggcaggat    5520
ctcctgtcat ctcaccttgc tcctgccgag aaagtatcca tcatggctga tgcaatgcgg    5580
cggctgcata cgcttgatcc ggctacctgc ccattcgacc accaagcgaa acatcgcatc    5640
gagcgagcac gtactcggat ggaagccggt cttgtcgatc aggatgatct ggacgaagag    5700 catcagggc tcgcgccagc cgaactgttc gccaggctca aggcgagcat gcccgacggc    5760
gaggatctcg tcgtgaccca tggcgatgcc tgcttgccga atatcatggt ggaaaatggc    5820
cgcttttctg gattcatcga ctgtggccgg ctgggtgtgg cggaccgcta tcaggacata    5880
gcgttggcta cccgtgatat tgctgaagag cttggcggcg aatgggctga ccgcttcctc    5940
gtgctttacg gtatcgccgc tcccgattcg cagcgcatcg ccttctatcg ccttcttgac    6000
gagttcttct gaattattaa cgcttacaat ttcctgatgc ggtattttct ccttacgcat    6060
ctgtgcggta tttcacaccg catcaggtgg cacttttcgg ggaaatgtgc gcggaacccc    6120
tatttgttta ttttttctaaa tacattcaaa tatgtatccg ctcatgagac aataaccctg    6180
ataaatgctt caataatagc acgtgctaaa acttcatttt taatttaaaa ggatctaggt    6240
gaagatcctt tttgataatc tcatgaccaa atcccttaa cgtgagtttt cgttccactg    6300
```

```
agcgtcagac cccgtagaaa agatcaaagg atcttcttga gatccttttt ttctgcgcgt    6360
aatctgctgc ttgcaaacaa aaaaaccacc gctaccagcg gtggtttgtt tgccggatca    6420
agagctacca actcttttc cgaaggtaac tggcttcagc agagcgcaga taccaaatac    6480
tgttcttcta gtgtagccgt agttaggcca ccacttcaag aactctgtag caccgcctac    6540 ataccctcgct ctgctaatcc tgttaccagt ggctgctgcc agtggcgata gtcgtgtct    6600 taccggttg gactcaagac gatagttacc ggataaggcg cagcggtcgg gctgaacggg    6660
gggttcgtgc acacagccca gcttggagcg aacgacctac accgaactga gatacctaca    6720
gcgtgagcta tgagaaagcg ccacgcttcc cgaagggaga aaggcggaca ggtatccggt    6780
aagcggcagg gtcggaacag gagagcgcac gagggagctt ccaggggaa acgcctggta    6840 tctttatagt cctgtcgggt ttcgccacct ctgacttgag cgtcgatttt tgtgatgctc    6900
gtcagggggg cggagcctat ggaaaaacgc cagcaacgcg gcctttttac ggttcctggc    6960
cttttgctgg ccttttgctc acatgttctt                                     6990
```

<210> SEQ ID NO 127
<211> LENGTH: 4472
<212> TYPE: DNA
<213> ORGANISM: Artificial Sequence
<220> FEATURE:
<223> OTHER INFORMATION: Chemically Synthesized, pGX 93100 full plasmid sequence

<400> SEQUENCE: 127

```
gctgcttcgc gatgtacggg ccagatatac gcgttgacat tgattattga ctagttatta      60
atagtaatca attacggggt cattagttca tagcccatat atggagttcc gcgttacata     120
acttacggta atggcccgc ctggctgacc gcccaacgac ccccgcccat tgacgtcaat     180
aatgacgtat gttcccatag taacgccaat agggactttc cattgacgtc aatgggtgga     240
gtatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccgccac catggattgg acctggagaa tcctgttcct ggtggcagca     780
gcaaccggaa cacacgcaca ggtgcagctg gtggagagcg gcggcggcgt ggtgcagcca     840
ggccggtccc tgaggctgtc ttgcgcagca agcggcttca cctttagcaa gtacggaatg     900
cactgggtga caggcacc tggcaaggc ctggagtggg tggccgtgat ctcctatgag     960
ggctctaaca gtactatgc cgattccgtg aagggcaggt ttaccatcag cagagacaac    1020
tccaagaata cactgtacct gcagatgaat agcctgaggg ccgaggatac cgccgtgtac    1080
tattgcgcca agtccggcac acagtactat gacaccacag ctacgagta tagaggcctg    1140 gagtacttcg gctattgggg ccagggcacc ctggtgacag tgagctccgg cggcggcggc    1200
tccggcggcg gcggcagcgg cggcggcggc agcgagatcg tgctgaccca gtctcctggc    1260
acactgtctc tgagcccagg agagagggcc accctgagct gtagagcctc ccagagcgtg    1320
```

```
agcagcagct acctggcctg gtatcagcag aagaggggac aggccccacg cctgctgatc    1380
tacgacgcct ctagccgggc caccggcatc cccgatcgct tcagcggctc cggctctggc    1440
acagacttta ccctgacaat ctcccggctg gagcctgagg atttcgccgt gtactattgc    1500
cagcagtatg gcaggagcag atggaccttt ggccagggca caaggtggag gatcaaggag    1560
cccaagtcct gtgataagac ccacacatgc cctccctgtc cagcacctga ggcagccggc    1620
ggcccaagcg tgttcctgtt tccacccaag cctaaggata cactgatgat ctctagaacc    1680
cccgaggtga catgcgtggt ggtggacgtg agccacgagg accccgaggt gaagttcaac    1740
tggtacgtgg acggcgtgga ggtgcacaat gccaagacca gcccaggga ggagcagtac    1800
aacagcacct atagagtggt gtccgtgctg acagtgctgc accaggactg gctgaacggc    1860
aaggagtata gtgcaaggt gtccaataag gccctgccag cccccatcga gaagaccatc    1920
tctaaggcaa agggacagcc acgggagcca caggtgtaca cactgcctcc atcccgcgag    1980
gagatgacca gaaccaggt gtctctgaca tgtctggtga agggcttcta tccttctgat    2040
atcgccgtgg agtgggagag caatggccag ccagagaaca attacaagac cacacccct     2100
gtgctggact ctgatggcag cttctttctg tattccaagc tgaccgtgga caagtctagg    2160
tggcagcagg gcaacgtgtt ttcctgctct gtgatgcacg aggccctgca caatcactac    2220
acccagaaga gcctgtccct gtctcctggc aagtgataac tcgagtctag agggcccgtt    2280
taaacccgct gatcagcctc gactgtgcct tctagttgcc agccatctgt tgtttgcccc    2340
tcccccgtgc cttccttgac cctggaaggt gccactccca ctgtcctttc ctaataaaat    2400
gaggaaattg catcgcattg tctgagtagg tgtcattcta ttctgggggg tggggtgggg    2460
caggacagca agggggagga ttgggaagac aatagcaggc atgctgggga tgcggtgggc    2520
tctatggctt ctactgggcg gttttatgga cagcaagcga accggaattg ccagctgggg    2580
cgccctctgg taaggttggg aagccctgca agtaaactg gatggctttc ttgccgccaa    2640
ggatctgatg cgcaggggga tcaagctctg atcaagagac aggatgagga tcgtttcgca    2700
tgattgaaca agatggattg cacgcaggtt ctccggccgc ttgggtggag aggctattcg    2760
gctatgactg ggcacaacag acaatcggct gctctgatgc cgccgtgttc cggctgtcag    2820
cgcaggggcg cccggttctt tttgtcaaga ccgacctgtc cggtgccctg aatgaactgc    2880
aagacgaggc agcgcggcta tcgtggctgg ccacgacggg cgttccttgc gcagctgtgc    2940
tcgacgttgt cactgaagcg ggaagggact ggctgctatt gggcgaagtg ccggggcagg    3000
atctcctgtc atctcacctt gctcctgccg agaaagtatc catcatggct gatgcaatgc    3060
ggcggctgca tacgcttgat ccggctacct gcccattcga ccaccaagcg aaacatcgca    3120
tcgagcgagc acgtactcgg atggaagccg gtcttgtcga tcaggatgat ctggacgaag    3180
agcatcaggg gctcgcgcca gccgaactgt tcgccaggct caaggcgagc atgcccgacg    3240
gcgaggatct cgtcgtgacc catggcgatg cctgcttgcc gaatatcatg gtggaaaatg    3300
gccgcttttc tggattcatc gactgtggcc ggctgggtgt ggcggaccgc tatcaggaca    3360
tagcgttggc tacccgtgat attgctgaag agcttggcgg cgaatgggct gaccgcttcc    3420
tcgtgcttta cggtatcgcc gctcccgatt cgcagcgcat cgccttctat cgccttcttg    3480
acgagttctt ctgaattatt aacgcttaca atttcctgat gcggtatttt ctccttacgc    3540
atctgtgcgg tatttcacac cgcatcaggt ggcactttc ggggaaatgt gcgcggaacc    3600
cctatttgtt tatttttcta aatacattca aatatgtatc cgctcatgag acaataaccc    3660
tgataaatgc ttcaataata gcacgtgcta aaacttcatt tttaatttaa aaggatctag    3720
```

```
gtgaagatcc tttttgataa tctcatgacc aaaatccctt aacgtgagtt ttcgttccac    3780
tgagcgtcag accccgtaga aaagatcaaa ggatcttctt gagatccttt ttttctgcgc    3840
gtaatctgct gcttgcaaac aaaaaaacca ccgctaccag cggtggtttg tttgccggat    3900
caagagctac caactctttt tccgaaggta actggcttca gcagagcgca gataccaaat    3960
actgttcttc tagtgtagcc gtagttaggc caccacttca agaactctgt agcaccgcct    4020
acatacctcg ctctgctaat cctgttacca gtggctgctg ccagtggcga taagtcgtgt    4080
cttaccgggt tggactcaag acgatagtta ccggataagg cgcagcggtc gggctgaacg    4140
gggggttcgt gcacacagcc cagcttggag cgaacgacct acaccgaact gagataccta    4200
cagcgtgagc tatgagaaag cgccacgctt cccgaaggga gaaaggcgga caggtatccg    4260
gtaagcggca gggtcggaac aggagagcgc acgagggagc ttccaggggg aaacgcctgg    4320
tatctttata gtcctgtcgg gtttcgccac ctctgacttg agcgtcgatt tttgtgatgc    4380
tcgtcagggg gcggagcct atggaaaaac gccagcaacg cggccttttt acggttcctg    4440
gccttttgct ggccttttgc tcacatgttc tt                                4472
```

<210> SEQ ID NO 128
<211> LENGTH: 4451
<212> TYPE: DNA
<213> ORGANISM: Artificial Sequence
<220> FEATURE:
<223> OTHER INFORMATION: Chemically Synthesized, pGX 93141 full plasmid
      sequence

<400> SEQUENCE: 128

```
gctgcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
gtatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag cgtttaaact taagcttggt     720
accgagctcg gatccgccac catggactgg acttggagaa tcctgtttct ggtcgcagca     780
gccactggaa cccacgccga ggtgcagctg gtcgagagcg ggggaggcct ggtgcagcca     840
ggcagatccc tgaggctgtc ttgtgccgcc tctggcttca catttgatga ctacgccatg     900
ttctgggtgc ggcaggcccc aggcaagggc ctggagtgga tctccggcat cagctggaac     960
tctgccacca tcggctatgc cgactccgtg aagggcaggt tcaccatctc ccgggacaat    1020
gccaagaagt ctctggacct gcagatgaac agcctgagac ccgacgatac cgccctgtac    1080
tattgtgcca agggcggccc aagaggcctg cagctgctgt cctcttgggt ggattactgg    1140
ggccagggca ccctggtgac agtgtcttcc ggcggcggcg gctctggcgg cggcggcagc    1200
ggcggcggcg gctccgatat ccagatgacc cagtctccct cttccctgag cgcctccgtg    1260
```

```
ggcgatcggg tgacaatcac ctgcagagcc agccaggata tccggagata cctgaactgg    1320
taccagcaga ggcctggcag agtgccacag ctgctgatct acaccacatc caccctgcag    1380
tctggcgtgc caagcagatt ttccggcagc ggctccgtga cagacttcac cctgacaatc    1440
tccagcctgc agccagagga tttcggcaca tattactgcc agcagagcta ctccccacct    1500
cacacctttg gccagggcac aaagctggag atcaaggagc ccaagtcttc cgacaagacc    1560
cacacctgtc caccttgtcc cgccccagag gcgccggcg ccctagcgt gtttctgttc    1620 cctccaaagc ctaaggatac cctgatgatc tccagaaccc cagaggtgac atgcgtggtg    1680
gtggacgtgt ctcacgagga ccccgaggtg aagtttaact ggtacgtgga tggcgtggag    1740
gtgcacaatg ccaagaccaa gccaagggag gagcagtaca acagcaccta cagagtggtg    1800
tccgtgctga cagtgctgca ccaggactgg ctgaatggca aggagtataa gtgcaaggtg    1860
tccaacaagg ccctgccagc ccccatcgag aagaccatca gcaaggccaa gggccagcct    1920
agggagccac aggtgtacac cctgccaccc tccagagacg agctgacaaa gaatcaggtg    1980
tctctgacat gcctggtgaa gggcttctac ccttccgaca tcgccgtgga gtgggagtct    2040
aacggccagc ccgagaacaa ttacaagacc acaccacctg tgctggactc cgatggcagc    2100
ttcttcctgt atagcaagct gaccgtggat aagtctagat ggcagcaggg caacgtgttc    2160
tcctgttccg tgatgcacga agcactgcac aaccactaca ctcagaagag cctgtccctg    2220
tcccctggaa aatgataact cgagtctaga gggcccgttt aaacccgctg atcagcctcg    2280
actgtgcctt ctagttgcca gccatctgtt gtttgcccct cccccgtgcc ttccttgacc    2340
ctggaaggtg ccactcccac tgtcctttcc taataaaatg aggaaattgc atcgcattgt    2400
ctgagtaggt gtcattctat tctggggggt ggggtgggc aggacagcaa ggggaggat    2460 tgggaagaca atagcaggca tgctgggat gcggtgggct ctatggcttc tactgggcgg    2520
ttttatggac agcaagcgaa ccggaattgc cagctgggc gccctctggt aaggttggga    2580
agccctgcaa agtaaactgg atggctttct tgccgccaag gatctgatgg cgcaggggat    2640
caagctctga tcaagagaca ggatgaggat cgtttcgcat gattgaacaa gatggattgc    2700
acgcaggttc tccggccgct tgggtggaga ggctattcgg ctatgactgg gcacaacaga    2760
caatcggctg ctctgatgcc gccgtgttcc ggctgtcagc gcaggggcgc ccggttcttt    2820
ttgtcaagac cgacctgtcc ggtgccctga atgaactgca agacgaggca gcgcggctat    2880
cgtggctggc cacgacgggc gttccttgcg cagctgtgct cgacgttgtc actgaagcgg    2940
gaagggactg gctgctattg ggcgaagtgc cggggcagga tctcctgtca tctcaccttg    3000
ctcctgccga gaaagtatcc atcatggctg atgcaatgcg gcggctgcat acgcttgatc    3060
cggctacctg cccattcgac caccaagcga aacatcgcat cgagcgagca cgtactcgga    3120
tggaagccgg tcttgtcgat caggatgatc tggacgaaga gcatcagggg ctcgcgccag    3180
ccgaactgtt cgccaggctc aaggcgagca tgcccgacgg cgaggatctc gtcgtgaccc    3240
atggcgatgc ctgcttgccg aatatcatgg tggaaaatgg ccgcttttct ggattcatcg    3300
actgtggccg gctgggtgtg gcggaccgct atcaggacat agcgttggct acccgtgata    3360
ttgctgaaga gcttggcggc gaatgggctg accgcttcct cgtgctttac ggtatcgccg    3420
ctcccgattc gcagcgcatc gccttctatc gccttcttga cgagttcttc tgaattatta    3480
acgcttacaa tttcctgatg cggtattttc tccttacgca tctgtgcggt atttcacacc    3540
gcatcaggtg gcacttttcg gggaaatgtg cgcggaaccc ctatttgttt attttctaa    3600
```

-continued

```
atacattcaa atatgtatcc gctcatgaga caataaccct gataaatgct tcaataatag    3660
cacgtgctaa aacttcattt ttaatttaaa aggatctagg tgaagatcct ttttgataat    3720
ctcatgacca aaatcccctta acgtgagttt tcgttccact gagcgtcaga ccccgtagaa   3780
aagatcaaag gatcttcttg agatccttt ttctgcgcg taatctgctg cttgcaaaca    3840 aaaaaccac cgctaccagc ggtggtttgt ttgccggatc aagagctacc aactctttt    3900 ccgaaggtaa ctggcttcag cagagcgcag ataccaaata ctgttcttct agtgtagccg   3960
tagttaggcc accacttcaa gaactctgta gcaccgccta catacctcgc tctgctaatc   4020
ctgttaccag tggctgctgc cagtggcgat aagtcgtgtc ttaccgggtt ggactcaaga   4080
cgatagttac cggataaggc gcagcggtcg ggctgaacgg ggggttcgtg cacacagccc   4140
agcttggagc gaacgaccta caccgaactg agatacctac agcgtgagct atgagaaagc   4200
gccacgcttc ccgaagggag aaaggcggac aggtatccgg taagcggcag ggtcggaaca   4260
ggagagcgca cgagggagct tccaggggga aacgcctggt atctttatag tcctgtcggg   4320
tttcgccacc tctgacttga gcgtcgattt ttgtgatgct cgtcaggggg gcggagccta   4380
tggaaaaacg ccagcaacgc ggcctttta cggttcctgg ccttttgctg gccttttgct   4440
cacatgttct t                                                         4451
```

OPTIMIZED NUCLEIC ACID ANTIBODY CONSTRUCTS ENCODING ANTI-RESPIRATORY SYNCYTIAL VIRUS (RSV) ANTIBODIES

CROSS REFERENCE TO RELATED APPLICATIONS

This application is a U.S. national phase application filed under 35 U.S.C. § 371 claiming priority to International Patent Application No. PCT/US18/32023, filed May 10, 2018, which is entitled to priority under 35 U.S.C. § 119(e) to U.S. Provisional Application No. 62/504,448, filed May 10, 2017, U.S. Provisional Application No. 62/504,460 filed May 10, 2017, U.S. Provisional Application No. 62/624,320 filed Jan. 31, 2018 and U.S. Provisional Application No. 62/624,367 filed Jan. 31, 2018, the contents of each of which are incorporated by reference herein in their entireties.

TECHNICAL FIELD

The present invention relates to methods of optimizing a nucleic acid antibody construct and to optimized structurally modified nucleic acid antibody constructs. The compositions of the invention provide improved methods for inducing immune responses, and for prophylactically and/or therapeutically immunizing individuals against an antigen.

BACKGROUND

The immunoglobulin molecule comprises two of each type of light (L) and heavy (H) chain, which are covalently linked by disulphide bonds (shown as S—S) between cysteine residues. The variable domains of the heavy chain (VH) and the light chain (VL) contribute to the binding site of the antibody molecule. The heavy-chain constant region is made up of three constant domains (CH1, CH2 and CH3) and the (flexible) hinge region. The light chain also has a constant domain (CL). The variable regions of the heavy and light chains comprise four framework regions (FRs; FR1, FR2, FR3 and FR4) and three complementarity-determining regions (CDRs; CDR1, CDR2 and CDR3). Accordingly, these are very complex genetic systems that have been difficult to assemble in vivo.

Targeted monoclonal antibodies (mAbs) represent one of the most important medical therapeutic advances of the last 25 years. This type of immune based therapy is now used routinely against a host of autoimmune diseases, treatment of cancer as well as infectious diseases. For malignancies, many of the immunoglobulin (Ig) based therapies currently used are in combination with cytotoxic chemotherapy regimens directed against tumors. This combination approach has significantly improved overall survival. Multiple mAb preparations are licensed for use against specific cancers, including Rittman (Rituximab), a chimeric mAb targeting CD20 for the treatment of Non-Hodgkins lymphoma and Ipilimumab (Yervoy), a human mAb that blocks CTLA-4 and which has been used for the treatment of melanoma and other malignancies. Additionally, Bevacizumab (Avastin) is another prominent humanized mAb that targets VEGF and tumor neovascularization and has been used for the treatment of colorectal cancer. Perhaps the most high profile mAb for treatment of a malignancy is Trastuzumab (Herceptin), a humanized preparation targeting Her2/neu that has been demonstrated to have considerable efficacy against breast cancer in a subset of patients. Furthermore, a host of mAbs are in use for the treatment of autoimmune and specific blood disorders.

In addition to cancer treatments, passive transfer of polyclonal Igs mediate protective efficacy against a number of infectious diseases including diphtheria, hepatitis A and B, rabies, tetanus, chicken-pox and respiratory syncytial virus (RSV). In fact, several polyclonal Ig preparations provide temporary protection against specific infectious agents in individuals traveling to disease endemic areas in circumstances when there is insufficient time for protective Igs to be generated through active vaccination. Furthermore, in children with immune deficiency the Palivizumab (Synagis), a mAb, which targets RSV infection, has been demonstrated to clinically protect against RSV.

Currently available therapeutic antibodies that exist in the market are human IgG1 isotypes. These antibodies include glycoproteins bearing two N-linked biantennary complex-type oligosaccharides bound to the antibody constant region (Fc), in which a majority of the oligosaccharides are core-fucosylated. It exercises effector functions of antibody-dependent cellular toxicity (ADCC) and complement-dependent cytotoxicity (CDC) through the interaction of the Fc with either leukocyte receptors (FcγRs) or complement. There is a phenomena of reduced in vivo efficacy of therapeutic antibodies (versus in vitro), thus resulting in the need for large doses of therapeutic antibodies—sometimes weekly doses of several hundred milligrams. This is mainly due to the competition between serum IgG and therapeutic antibodies for binding to FcγRIIIa on natural killer (NK) cells. Endogenous human serum IgG inhibits ADCC induced by therapeutic antibodies. Thus, there can be enhanced efficacy of non-fucosylated therapeutic antibodies in humans. Non-fucosylated therapeutic antibodies have much higher binding affinity for FcγRIIIa than fucosylated human serum IgG, which is a preferable character to conquer the interference by human plasma IgG.

Antibody based treatments are not without risks. One such risk is antibody-dependent enhancement (ADE), which occurs when non-neutralizing antiviral proteins facilitate virus entry into host cells, leading to increased infectivity in the cells. Some cells do not have the usual receptors on their surfaces that viruses use to gain entry. The antiviral proteins (i.e., the antibodies) bind to antibody Fc receptors that some of these cells have in the plasma membrane. The viruses bind to the antigen binding site at the other end of the antibody. This virus can use this mechanism to infect human macrophages, causing a normally mild viral infection to become life-threatening. The most widely known example of ADE occurs in the setting of infection with the dengue virus (DENV). It is observed when a person who has previously been infected with one serotype of DENV becomes infected many months or years later with a different serotype. In such cases, the clinical course of the disease is more severe, and these people have higher viremia compared with those in whom ADE has not occurred. This explains the observation that while primary (first) infections cause mostly minor disease (DF) in children, secondary infection (re-infection at a later date) is more likely to be associated with severe disease (DHF and/or DSS) in both children and adults. There are four antigenically different serotypes of DENV (DENV-1-DENV-4). Infection with DENV induces the production of neutralizing homotypic immunoglobulin G (IgG) antibodies which provide lifelong immunity against the infecting serotype. Infection with DENV also produces some degree of cross-protective immunity against the other three serotypes. In addition to inducing neutralizing heterotypic antibodies, infection with DENV can also induce heterotypic antibodies which neutralize the virus only partially or not at all. The production of such cross-reactive but non-neutralizing antibodies could be the reason for more severe secondary infections. Once inside the white blood cell, the virus replicates undetected, eventually generating very high virus titers which cause severe disease.

The clinical impact of mAb therapy is impressive. However, issues remain that limit the use and dissemination of this therapeutic approach. Some of these include the high cost of production of these complex biologics that can limit their use in the broader population, particularly in the developing world where they could have a great impact. For example, mAbs targeting the Ebola virus glycoprotein (GP) represent an important treatment approach against Ebola virus disease (EVD). It has been shown that individual mAbs and mAb cocktails can successfully protect small animals and non-human primates against lethal Ebola virus infection. MAb-based therapy against EVD is further supported by favorable recovery in confirmed human EVD cases that received the anti-GP mAb cocktail, ZMapp. However, the dramatic cost, slow development, and requirement for several high-dose administrations (mg/kg) represent a significant challenge for protein mAb delivery, especially during a possible outbreak.

Furthermore, the frequent requirement for repeat administrations of the mAbs to attain and maintain efficacy can be an impediment in terms of logistics and patient compliance. New antibodies that would reduce or eliminate the low in vivo efficacy of therapeutic antibodies due to competition with serum IgGs are needed. New antibodies that can eliminate antibody dependent enhancement in viruses like EVD, Dengue, HIV, RSV and others are needed. Bispecific antibodies, bifunctional antibodies, and antibody cocktails are needed to perform several functions that could prove therapeutic or prophylactic. Combination therapies are needed as well that can utilize the synthetic antibodies described herein along with immunostimulating a host system through immunization with a vaccine, including a DNA based vaccine. Additionally, the long-term stability of these antibody formulations is frequently short and less than optimal.

Thus, there remains a need in the art for an optimized synthetic antibody molecule that can be delivered to a subject in a safe and cost effective manner.

SUMMARY

In one embodiment, the invention relates to a method of generating a nucleic acid sequence encoding a structurally modified DNA encoded antibody (DMAb) comprising the steps of identifying one or more CDR region of a first DMAb, identifying one or more CDR region of a second DMAb, substituting the amino acid sequence of one or more CDR region of a second DMAb with the amino acid sequence of one or more CDR region of a first DMAb to generate an amino acid sequence of a structurally modified DMAb, and generating a nucleic acid sequence encoding a structurally modified DMAb. In one embodiment the method further comprises optimizing the nucleic acid sequence.

In one embodiment, the invention relates to a method of generating a nucleic acid sequence encoding a structurally modified DMAb comprising the steps of performing sequence alignment of an amino acid sequence or a fragment of an amino acid sequence of a first DMAb with the same from one or more additional DMAb sequences, substituting one or more amino acid residues of the amino acid sequence of the first DMAb with one or more amino acid residues of the amino acid sequence of one or more additional DMAb sequences, wherein the one or more amino acid residues are not residues in a CDR region, to generate an amino acid sequence of a structurally modified DMAb, and generating a nucleic acid sequence encoding a structurally modified DMAb. In one embodiment the method further comprises optimizing the nucleic acid sequence.

In one embodiment, the invention relates to a method of generating a nucleic acid sequence encoding a structurally modified DMAb comprising the steps of identifying amino acid residues of a DMAb that are predicted to participate in interaction at an interface of a variable heavy chain and variable light chain domain, making one or more amino acid substitutions of the identified amino acid residues, wherein the one or more substitutions is predicted to alter at least one of an isoelectic point and a surface charge at the interface, to generate an amino acid sequence of a structurally modified DMAb, and generating a nucleic acid sequence encoding a structurally modified DMAb. In one embodiment the method further comprises optimizing the nucleic acid sequence.

In one embodiment, the invention relates to a method of generating a nucleic acid sequence encoding a structurally modified DMAb comprising the steps of removing an amino acid sequence for a CH and CL domain from an amino acid sequence of a DMAb, adding an amino acid sequence of a linker between an amino acid sequence for a VH and VL domain to an amino acid sequence of a DMAb to generate an amino acid sequence of a structurally modified DMAb, performing at least one round of modeling on the generated amino acid sequence, and generating a nucleotide sequence encoding a structurally modified DMAb. In one embodiment the method further comprises optimizing the nucleic acid sequence.

In one embodiment, the method of modeling comprises at least one of linker modeling, hinge modification modeling, framework modeling, and CDR loop refinement.

In one embodiment, the linker is C-terminally linked to the VH domain and N-terminally linked to the VL domain. In one embodiment, the linker is N-terminally linked to the VH domain and C-terminally linked to the VL domain.

In one embodiment, the invention relates to a method of generating a nucleic acid sequence encoding a structurally modified DMAb comprising the steps of identifying one or more CDR region of a first DMAb, identifying one or more CDR region of a second DMAb, substituting the amino acid sequence of one or more CDR region of a second DMAb with the amino acid sequence of one or more CDR region of a first DMAb to generate an amino acid sequence of a structurally modified DMAb, removing an amino acid sequence for a CH and CL domain from an amino acid sequence of a DMAb, adding an amino acid sequence of a linker between an amino acid sequence for a VH and VL domain to an amino acid sequence of a DMAb to generate an amino acid sequence of a structurally modified DMAb, performing at least one round of modeling on the generated amino acid sequence, and generating a nucleotide sequence encoding a structurally modified DMAb. In one embodiment the method further comprises optimizing the nucleic acid sequence.

In one embodiment, the invention relates to a method of generating a nucleic acid sequence encoding a structurally modified DMAb comprising the steps of performing sequence alignment of an amino acid sequence or a fragment of an amino acid sequence of a first DMAb with the same from one or more additional DMAb sequences, substituting one or more amino acid residues of the amino acid sequence of the first DMAb with one or more amino acid residues of the amino acid sequence of one or more additional DMAb sequences, wherein the one or more amino acid residues are not residues in a CDR region, to generate an amino acid sequence of a structurally modified DMAb, removing an amino acid sequence for a CH and CL domain from an amino acid sequence of a DMAb, adding an amino acid sequence of a linker between an amino acid sequence for a VH and VL domain to an amino acid sequence of a DMAb to generate an amino acid sequence of a structurally modified DMAb, performing at least one round of modeling on the generated amino acid sequence, and generating a nucleic acid sequence encoding a structurally modified DMAb. In one embodiment the method further comprises optimizing the nucleic acid sequence.

In one embodiment, the invention relates to a method of generating a nucleic acid sequence encoding a structurally modified DMAb comprising the steps of identifying amino acid residues of a DMAb that are predicted to participate in interaction at an interface of a variable heavy chain and variable light chain domain, making one or more amino acid substitutions of the identified amino acid residues, wherein the one or more substitutions is predicted to alter at least one of an isoelectic point and a surface charge at the interface, to generate an amino acid sequence of a structurally modified DMAb, removing an amino acid sequence for a CH and CL domain from an amino acid sequence of a DMAb, adding an amino acid sequence of a linker between an amino acid sequence for a VH and VL domain to an amino acid sequence of a DMAb to generate an amino acid sequence of a structurally modified DMAb, performing at least one round of modeling on the generated amino acid sequence, and generating a nucleic acid sequence encoding a structurally modified DMAb. In one embodiment the method further comprises optimizing the nucleic acid sequence.

In one embodiment, the invention relates to a structurally modified DMAb encoded by the nucleic acid molecule generated using the methods of the invention.

In one embodiment, the invention relates to a structurally modified DMAb comprising one or more CDR region from a first DMAb and one or more constant region from a second DMAb, wherein the structurally modified DMAb exhibits at least one of higher in vivo expression and higher binding compared to a corresponding DMAb not so modified.

In one embodiment, the structurally modified DMAb exhibits at least the same or higher antigen binding specificity compared to the specificity of the structurally modified DMAb prior to having been so modified.

In one embodiment, the invention relates to a structurally modified DMAb comprising one or more amino acid substitutions, wherein the structurally modified DMAb exhibits at least one of higher in vivo expression and higher binding compared to a corresponding DMAb not so modified.

In one embodiment, the invention relates to a structurally modified DMAb comprising a CH1, CH2, hinge, VH, linker and VL domain, wherein the structurally modified DMAb exhibits at least one of higher in vivo expression and higher binding compared to a corresponding DMAb not so modified.

In one embodiment, the invention relates to a composition comprising a nucleic acid molecule comprising at least one nucleotide sequence encoding a structurally modified DMAb. In one embodiment, at least one structurally modified DMAb comprises an amino acid sequence selected from a) an amino acid sequence having at least 90% over an entire length of the encoded sequence to an amino acid sequence of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:111, SEQ ID NO:113, SEQ ID NO:115 or SEQ ID NO:119; or b) a fragment comprising at least 60% of an amino acid sequence of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108 SEQ ID NO:111, SEQ ID NO:113, SEQ ID NO:115 or SEQ ID NO:119.

In one embodiment, the nucleic acid molecule comprises at least two nucleotide sequences wherein each nucleotide sequence encodes a structurally modified DMAb. In one embodiment, each of the at least two nucleotide sequence encodes a structurally modified DMAb comprising an amino acid sequence selected from a) an amino acid sequence having at least 90% over an entire length of the encoded sequence to an amino acid sequence of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:111, SEQ ID NO:113, SEQ ID NO:115 or SEQ ID NO:119; or b) a fragment comprising at least 60% of an amino acid sequence of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108 SEQ ID NO:111, SEQ ID NO:113, SEQ ID NO:115 or SEQ ID NO:119.

In one embodiment, the nucleic acid molecule comprises a nucleotide sequence encoding a structurally modified DMAb comprising an amino acid sequence selected from SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 or SEQ ID NO:106 and a nucleotide sequence encoding a structurally modified DMAb comprising an amino acid sequence of SEQ ID NO:108.

In one embodiment, the invention relates to a method of treating a subject having a disease or disorder comprising administering a composition comprising a nucleic acid molecule comprising a nucleotide sequence encoding a structurally modified DMAb to a subject in need thereof.

BRIEF DESCRIPTION OF THE DRAWINGS

FIG. 1, comprising FIG. 1A depicts a diagram of a full graft DMAb. FIG. 1B depicts a diagram of partial grafting. Multiple modifications of amino acids in the FR1 and FR4 regions of the modified DMAb (SEQ ID NO:48) as compared to the parental DMAb (SEQ ID NO:47) are shown to the right of the modeled DMAb. FIG. 1C depicts a diagram of scaffold modification. Side chains of residues that participate in the VH VL interface are shown. Saffold modifications of the light (upper) and heavy (lower) chains (SEQ ID NO:50 and SEQ ID NO:52 respectively) are shown with the modified residues highlighted. The parental DMAb sequences are SEQ ID NO:49 and SEQ ID NO:51. FIG. 1D depicts protein ribbon images showing full and partial DMAb framework grafting. The VH-VL (yellow/blue) of a high expressing DMAb is shown in the upper left. The VH-VL (green/red) of a low expressing DMAb is shown in the upper right. The new DMAb molecule in the lower left is created by grafting the CDRs from the low expresser onto the framework of the high expresser. In the lower right is a new DMAb created by a partial graft, replacing the first 22 amino acids in the VL of the poorly expressing DMAb with those from the high expresser.

FIG. 2, comprising FIG. 2A depicts exemplary experimental results demonstrating expression of BDBV223 antibody and full and partial grafts. FIG. 2B depicts exemplary experimental results demonstrating EBOV antigen binding of BDBV223 antibody and full and partial grafts.

FIG. 3, comprising FIG. 3A depicts exemplary experimental results demonstrating expression of Z5D2 antibody and full and partial grafts. FIG. 3B depicts exemplary experimental results demonstrating EBOV antigen binding of Z5D2 antibody and full and partial grafts.

FIG. 7, comprising FIG. 7A depicts a stick and ribbon image of the predicted folding of an scFv-Fc antibody. The VL (red), VL CDRs (pink), VH (green), VH CDRs (purple), and linker (CPK) are shown. FIG. 7B and FIG. 7C depict two rotational views of a space filled model of a ScFv-Fc DMAb.

FIG. 8, comprising FIG. 8A through FIG. 8D, depicts exemplary experimental results demonstrating the effects of scFv-Fc conversion of DMAb BDBV223. FIG. 8A depicts the expression levels of the parental and ScFv-Fc modified DMAbs. FIG. 8B depicts the serum expression levels of the parental and ScFv-Fc modified DMAbs. FIG. 8C depicts the antigen binding of the parental and ScFv-Fc modified DMAbs to the glycoprotein antigen from the 1976 Ebola virus outbreak strain. FIG. 8D depicts the antigen binding of the parental and ScFv-Fc modified DMAbs to the glycoprotein antigen from the 2014 Ebola virus outbreak strain.

FIG. 9, comprising FIG. 9A depicts the expression levels of the parental and ScFv-Fc modified DMAbs over 21 days. FIG. 9B depicts the serum expression levels of the parental and ScFv-Fc modified DMAbs. FIG. 9C depicts the antigen binding of the parental and ScFv-Fc modified DMAbs to the glycoprotein antigen from the 1976 Ebola virus outbreak strain. FIG. 9D depicts the antigen binding of the parental and ScFv-Fc modified DMAbs to the glycoprotein antigen from the 2014 Ebola virus outbreak strain. FIG. 9E depicts the expression levels of the parental and ScFv-Fc modified DMAbs over 35 days. FIG. 9F depicts the normalized expression levels of the parental and ScFv-Fc modified DMAbs over 35 days.

FIG. 10, comprising FIG. 10A depicts the expression levels of the parental and ScFv-Fc modified DMAbs over 21 days. FIG. 10B depicts the antigen binding of the parental and ScFv-Fc modified DMAbs to the glycoprotein antigen from the 1976 Ebola virus outbreak strain. FIG. 10C depicts the antigen binding of the parental and ScFv-Fc modified DMAbs to the glycoprotein antigen from the 2014 Ebola virus outbreak strain. FIG. 10D depicts the expression levels of the parental and ScFv-Fc modified DMAbs over 35 days. FIG. 10E depicts the normalized expression levels of the parental and ScFv-Fc modified DMAbs over 35 days.

FIG. 15, comprising FIG. 15A depicts exemplary experimental results demonstrating the percent neutralization for Group 1 EBOMAb-10. FIG. 15B depicts exemplary experimental results demonstrating the percent neutralization for the Group 2 (EBOMAb-14) using lentivirus pseudotyped with EBOLA Zaire glycoprotein (EBOV-GP)

FIG. 16 depicts a quantification of the neutralizing activity, IC50 and IC90 of the Group 1 and Group 2 structurally modified DMAbs.

FIG. 17, comprising FIG. 17A depicts an in vivo time course expression of Group 1 DMAbs. Immunosuppressed BALB/c mice were administrated with 170 µg of DNA-plasmid encoding DMAb through intramuscular delivery followed by electroporation (IM-EP) Serum levels of DMAb were assessed over 35 days. FIG. 17B depicts an antigen binding curve for the Group 1 DMAbs. DMAbs in the serum were evaluated for reactivity to Ebola antigen. FIG. 17C depicts a Group 1 DMAb neutralization curve as evaluated using EBOV-GP pseudotyped lentivirus vector. FIG. 17D depicts an in vivo time course expression of Group 2 DMAbs. Immunosuppressed BALB/c mice were administrated with 200 µg of DNA-plasmid encoding DMAb through intramuscular delivery followed by electroporation (IM-EP) Serum levels of DMAb were assessed over 35 days. FIG. 17E depicts an antigen binding curve for the Group 2 DMAbs. DMAbs in the serum were evaluated for reactivity to Ebola antigen. FIG. 17F depicts a Group 2 DMAb neutralization curve as evaluated using EBOV-GP pseudotyped lentivirus vector.

FIG. 18, comprising FIG. 18A depicts expression data for each gene optimized DMAb. FIG. 18B depicts antigen binding for each gene optimized DMAb. These experiments were performed in vitro, in HEK293 cells.

FIG. 19, comprising FIG. 19A and FIG. 19B, depicts an in vivo analysis of expression and binding of gene optimized mouse Zika DMAb ZK190G1M3LALA. FIG. 19A depicts in vivo day 7 expression data for each gene optimized DMAb. FIG. 19B depicts antigen binding for each gene optimized DMAb.

FIG. 20, comprising FIG. 20A depicts in vivo day 7 expression data for each gene optimized DMAb. FIG. 20B depicts in vitro expression data for each gene optimized DMAb, in HEK293 cells.

FIG. 21, comprising FIG. 21A depicts in vivo day 7 binding actibity for each gene optimized DMAb. FIG. 21B depicts in vitro binding activity for each gene optimized DMAb, in HEK293 cells.

FIG. 22, comprising FIG. 22A depicts expression data for each ScFv-Fc DMAb. FIG. 22B depicts antigen binding for each ScFv-Fc DMAb. These experiments were performed in vivo.

FIG. 25 depicts a schematic diagram of an overview of DMAb in-vivo delivery and protein-engineering.

FIG. 26, comprising FIG. 26A depicts experimental results demonstrating the expression kinetics of RSV DMAbs. FIG. 26B depicts experimental results demonstrating the peak expression of RSV-DMAbs. FIG. 26C depicts experimental results demonstrating amount of DMAbs in Bronchoalveolar lavage (BAL) samples. FIG. 26D depicts experimental results demonstrating RSV-F binding.

FIG. 29, comprising FIG. 29A depicts exemplary experimental results demonstrating that average serum-level expression of 13200 ng/ml of protein human sc-Fv was achieved 7 days after treatment. FIG. 29B depicts exemplary experimental results demonstrating in-vivo expressed human sc-Fv binds to RSV-F antigen. FIG. 29C depicts exemplary experimental results demonstrating that the serum of treated mice exhibits live RSV-A virus-neutralizing activity as demonstrated by the in-vitro plaque reduction assay and results in average of 6.9 log recip. Neut. titer. FIG. 29D depicts exemplary experimental results demonstrating human sc-Fv is present in the lung of treated mice with an average concentration of 1.1 ng of human sc-Fv per µg of total protein in Bronchioalveolar-lavage (BAL).

FIG. 31, comprising FIG. 31A depicts exemplary experimental results demonstrating that CELLECTRA-3P® assisted delivery of 2.4 mg human sc-Fv in leg muscles of cotton rat results in average serum-expression of 7030 ng/ml at day 7. FIG. 31B depicts exemplary experimental results demonstrating that the serum of treated cotton rats is neutralizing in in-vitro plaque-reduction assay resulting in average of 5.4 log Recip. Neut. titer.

FIG. 32, comprising FIG. 32A depicts a schematic representations of design approaches used. Human dMAb design strategies for ScFv-Fc. The VH and VL regions were connected by a (G4S)3 linker and fused to a prototypical human IgG1 hinge and Fc. FIG. 32B depicts a diagram of the molecular organization of scFv-Fc Zika and Dengue dMAb encoding plasmids (Z-dMAb1-sc and D-dMAb1-sc) as well as the multivalent bi-directional promoter construct (Z/D-dMAb1-sc). FIG. 32C depicts a flow chart of the Experimental design, various dMAb constructs in combination or within a multivalent cassette were delivered in each tibialis anterior (TA) muscle C57BL/6 mice followed by electroporation dMAb expression and antigen binding were evaluated at Day 7 post-DNA delivery.

FIG. 34A depicts exemplary experimental results demonstrating day 2 post transfection expression of scFv-Fc dMAbs and their respective contribution in co-transfection and in the multivalent Z/D-dMAb1-sc construct was assessed. FIG. 34B depicts exemplary experimental results demonstrating the ability of the scFv-Fc dMAbs to bind Dengue (DENV1). FIG. 34C depicts exemplary experimental results demonstrating the ability of the scFv-Fc dMAbs to bind Zika antigen.

FIG. 35, comprising FIG. 35A depicts exemplary experimental results demonstrating scFv-Fc dMAb expression day 7 post electroporation (EP) mediated-dMAb transfection. Data show individual dMAb expression for Z-dMAb1-sc & D-dMAb1-sc, as well as their respective contribution when delivered in cocktail in the same animals or when individually delivered at two distinct intramuscular sites in the same animals. Data also show the contribution of Dengue and Zika scFv-Fc dMAbs when expressed in a single multivalent plasmid construct. A total of 100 µg of dMAb encoding plasmid were delivered for the Z-dMAb1-sc, D-dMAb1-sc as well as Z/D-dMAb1-sc groups, and 200 µg for the cocktail delivery and individual delivery groups, followed by EP. Sera were collected Day 7 post-treatment for quantitative ELISA assessing scFv-Fc dMAb expression in C57BL/6 mice. FIG. 35B depicts ab exemplary antigen binding assay evaluating the ability for the various constructs to recognize Zika antigen. FIG. 35C depicts an exemplary antigen binding assay evaluating the ability for the various constructs to recognize Dengue antigen.

1. DEFINITIONS

Figures 1A, 1B, 1C:
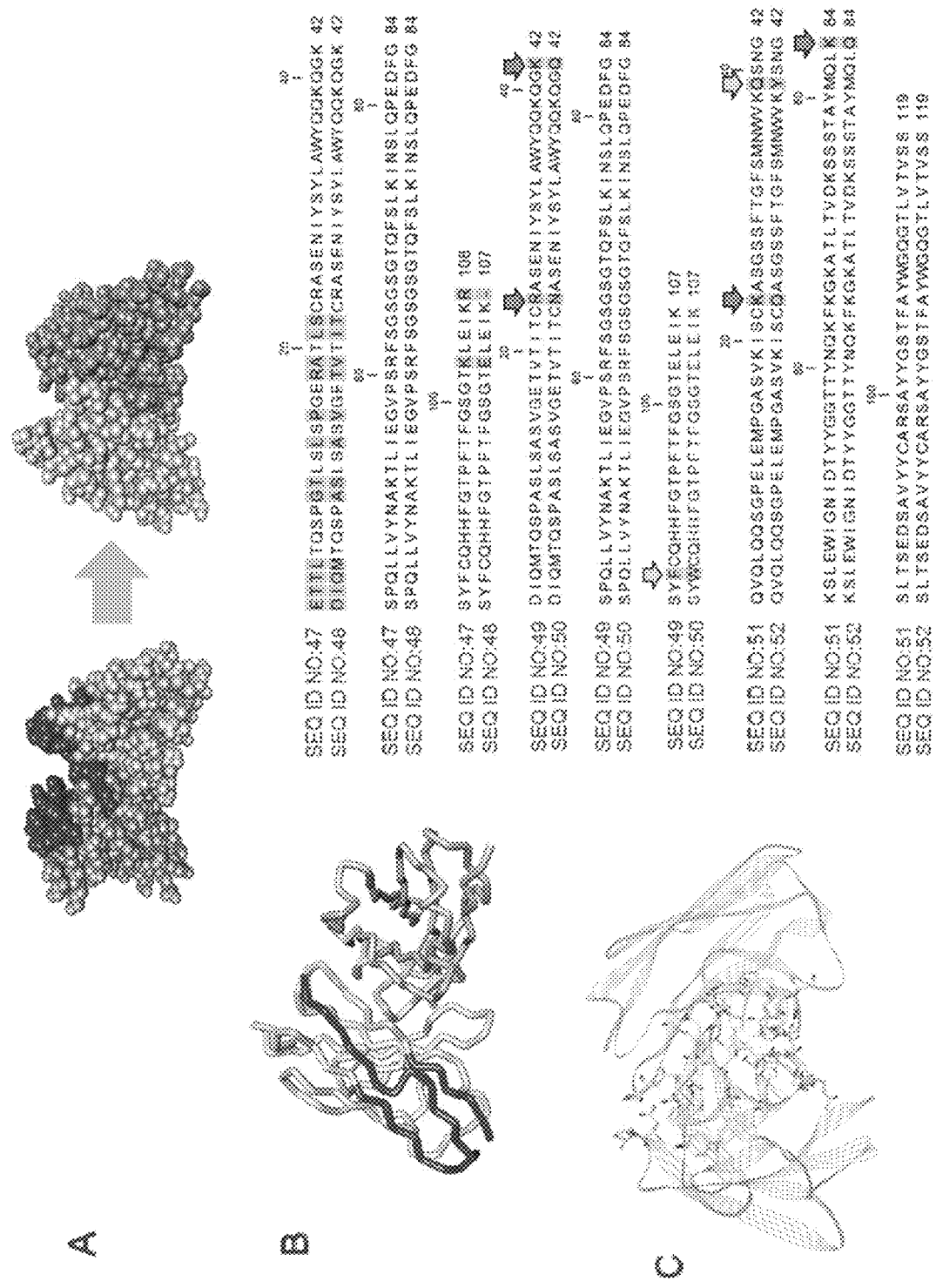
FIG. 1A through FIG. 1D, depicts exemplary models of various structurally modified DMAbs that can be generated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes an antibody as set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV promoter, EF1alpha promoter, ACTA1 promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, including a nanoplasmid or mini-circle plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. STRUCTURALLY MODIFIED DMABS

The present invention relates to compositions comprising structurally modified DNA encoded synthetic antibody (DMAb), compositions comprising a nucleic acid molecules encoding structurally modified DMAbs, methods of generating structurally modified DMAbs, and methods of use of structurally modified DMAbs.

In one embodiment, a structurally modified DMAb, comprises at least one modification to increase expression, antigen binding, stability, or a combination thereof in vivo. In one embodiment, at least one modification is made on the basis of increasing the in vivo expression of a DMAb that has been designated as a low expressing DMab. In one embodiment, at least one modification is made on the basis of increasing in vivo antigen binding of a DMAb.

In one embodiment, a candidate DMAb for being structurally modified according to the present invention is a DMAb to exhibits desirable antigen binding in vivo, but low expression. Accordingly, the structural modification to generate a desirable DMAb is to increase the expression of that DMAb in order to generate a DMAb that exhibits both desirable antigen binding and higher expression level in vivo. In one embodiment, a structurally modified DMAb comprises at least one modification that results in the increased expression over the expression level of the unmodified DMAb.

In one embodiment, a structurally modified DMAb comprises one or more modification that increases the expression of a corresponding DMAb that has not be so modified. In one embodiment, the modification includes but is not limited to full graft, partial graft, scaffold modification, ScFv-Fc conversion, and the like. However, the invention should not be limited to these types of modifications. Rather, the invention includes any type of modification that is able to increase the in vivo expression or antigen binding of a DMAb. In one embodiment, the invention relates to a nucleic acid molecule encoding a structurally modified DMAb.

Full Graft

In one embodiment, the structurally modified DMAb of the invention is a full graft DMAb. In one embodiment, full grafting relates to a method of transferring the sequence encoding at least one CDR region of a DMAb onto the backbone of a different DMAb. For example, in one embodiment, full grafting includes identifying at least one CDR region of a DMAb having low in vivo expression and modifying at least one CDR region of a DMAb having high in vivo expression levels to have the at least one CDR sequence of the low expressing DMAb.

In one embodiment, a full graft DMAb comprises a DMAb wherein at least one, at least two or all three CDRs from the variable heavy chain of one DMAb have been modified to be identical to at least one, at least two or all three CDRs from the variable heavy chain of a second DMAb. In one embodiment, a full graft DMAb comprises a DMAb wherein at least one, at least two or all three CDRs from the variable heavy chain of one DMAb have been modified to be at least 80%, 85%, 90%, 95%, 96%, 97%, 98%, or 99% identical to at least one, at least two or all three CDRs from the variable heavy chain of a second DMAb. In one embodiment, a full graft DMAb comprises a DMAb wherein at least one, at least two or all three CDRs from the variable light chain of one DMAb have been modified to be identical to at least one, at least two or all three CDRs from the variable light chain of a second DMAb.

The immunoglobulin scaffold for use in generating the full graft DMAb of the invention can be from any immunoglobulin isotype. Heavy chain immunoglobulin isotypes include, but are not limited to, IgA, including IgA1 and IgA2, IgD, IgE, IgG, including IgG1, IgG2, IgG3 and IgG4, and IgM. Light chain immunoglobulin isotypes include, but are not limited to kappa and lambda. In one embodiment, the DMAbs that serve as a basis for generation of a full graft DMAb are of the same immunoglobulin isotype. In one embodiment, the DMAbs that serve as a basis for generation of the full graft DMAb are from different immunoglobulin isotypes.

In one embodiment, the full graft DMAb of the invention has modified expression, stability, half-life, antigen binding, heavy chain-light chain pairing, tissue penetration or a combination thereof as compared to a parental DMAb.

In one embodiment, the full graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher expression than the parental DMAb.

In one embodiment, the full graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher antigen binding than the parental DMAb.

In one embodiment, the full graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold longer half-life than the parental DMAb.

In one embodiment, the full graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher stability than the parental DMAb.

In one embodiment, the full graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold greater tissue penetration than the parental DMAb.

In one embodiment, the full graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold greater heavy chain-light chain pairing than the parental DMAb.

Partial Graft

In one embodiment, the structurally modified DMAb of the invention is a partial graft DMAb. In one embodiment, partial grafting relates to a method of modifying one or more FR region, or fragment thereof, of a DMAb to contain one or more FR region, or fragment thereof, of a different DMAb. For example, in one embodiment, partial grafting includes modifying a FR region, or fragment thereof, of a DMAb having low in vivo expression to be similar to that of a second DMAb having high in vivo expression. In one embodiment, at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50 or more than 50 residues of at least one FR region are altered. In one embodiment, at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50 or more than 50 residues of multiple FR regions are altered. In one embodiment, at least 1, 2, 3, 4, 5, 6, 7, 8, 9, 10, 11, 12, 13, 14, 15, 16, 17, 18, 19, 20 or more than 20 residues are altered within close proximity to each other (e.g., at least 1, 2, 3, 4, 5, 6, 7, 8, 9, 10, 11, 12, 13, 14, 15, 16, 17, 18, 19, 20 or more than 20 residues are altered within a consecutive 30 residue region.) In one embodiment, at least 1, 2, 3, 4, 5, 6, 7, 8, 9, 10, 11, 12, 13, 14, 15, 16, 17, 18, 19, 20 or more than 20 residues are altered within a single FR (i.e., within FR1, FR2, FR3 or FR4.) In one embodiment, at least 1, 2, 3, 4, 5, 6, 7, 8, 9, 10, 11, 12, 13, 14, 15, 16, 17, 18, 19, 20 or more than 20 residues are altered within multiple FRs (e.g., within FR1 and FR4.) In an exemplary embodiment, at least 1, 2, 3, 4, 5, 6, 7, 8, 9, 10, 11, 12, 13, 14, 15, 16, 17, 18, 19 or 20 residues are altered at the N-terminus of the variable light chain.

The immunoglobulin scaffold of the DMAbs that serve as a basis for generating a partial graft DMAb of the invention can be from any immunoglobulin isotype including, but not limited to IgA, including IgA1 and IgA2, IgD, IgE, IgG, including IgG1, IgG2, IgG3 and IgG4, IgM, kappa and lambda. In one embodiment, the DMAbs that serve as a basis for generation of the partial graft DMAb are the same immunoglobulin isotype. In one embodiment, the DMAbs that serve as a basis for generation of the partial graft DMAb are different immunoglobulin isotypes.

In one embodiment, the partial graft DMAb of the invention has modified expression, stability, half-life, antigen binding, heavy chain-light chain pairing, tissue penetration or a combination thereof as compared to a parental DMAb.

In one embodiment, the partial graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher expression than the parental DMAb.

In one embodiment, the partial graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher antigen binding than the parental DMAb.

In one embodiment, the partial graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold longer half-life than the parental DMAb.

In one embodiment, the partial graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher stability than the parental DMAb.

In one embodiment, the partial graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold greater tissue penetration than the parental DMAb.

In one embodiment, the partial graft DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold greater heavy chain-light chain pairing than the parental DMAb.

Scaffold Modification

In one embodiment, the structurally modified DMAb of the invention is a scaffold modified DMAb. In one embodiment, scaffold modification relates to a method of modifying at least one amino acid residue of a DMAb to increase stabilizing interactions at the VH-VL interface or to favorably alter isoelectric point. Residues that can be modified according to the method of the invention can be identified using any method known in the art for predicting residues involved in VH-VL interactions (e.g., using bioinformatics methods for predicting residues involved in the VH-VL interface as described in Abhinandan et al., 2010, Protein Eng Des Sel, 23(9):689-697.) In various embodiments, a scaffold modified DMAb comprises one or more modifications to alter non-aromatic side chain residues to aromatic side chain residues. In one embodiment, a scaffold modified DMAb comprises one or more modifications to alter a VH-VL interface amino acid with an electrically charged side chain to an amino acid with an uncharged side chain (e.g., a lysine (K) to glutamine (Q) modification). In one embodiment, a scaffold modified DMAb comprises one or more modifications to alter a VH-VL interface amino acid with an uncharged side chain to an amino acid with a hydrophobic side chain (e.g., a Q to tyrosine (Y) modification). In one embodiment, a scaffold modified DMAb comprises one or more modifications to alter a VH-VL interface amino acid to an amino acid with an aromatic side chain (e.g., a Q to tyrosine (Y) modification). In various embodiments, a scaffold modified DMAb comprises one or more modifications within FR2 or FR3.

The immunoglobulin scaffold of the structurally modified DMAbs of the invention can be from any immunoglobulin isotype including, but not limited to IgA, including IgA1 and IgA2, IgD, IgE, IgG, including IgG1, IgG2, IgG3 and IgG4, IgM, kappa and lambda.

In one embodiment, the scaffold modified DMAb of the invention has modified expression, stability, half-life, antigen binding, heavy chain-light chain pairing, tissue penetration or a combination thereof as compared to a parental DMAb.

In one embodiment, the scaffold modified DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher expression than the parental DMAb.

In one embodiment, the scaffold modified DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher antigen binding than the parental DMAb.

In one embodiment, the scaffold modified DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold longer half-life than the parental DMAb.

In one embodiment, the scaffold modified DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher stability than the parental DMAb.

In one embodiment, the scaffold modified DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold greater tissue penetration than the parental DMAb.

In one embodiment, the scaffold modified DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold greater heavy chain-light chain pairing than the parental DMAb.

Single Chain Fv-Fc (ScFv-Fc) Conversion

In one embodiment, the structurally modified DMAb of the invention is a ScFv-Fc DMAb. In one embodiment, ScFv-Fc conversion relates to the removal of CH1 and CL regions, and the addition of a linker between VH and VL. Therefore, in one embodiment, the structurally modified DMAb of the invention comprises a DMAb encoded by nucleic acid molecule lacking an encoding sequence for the CH1 and CL domain and comprising an encoding sequence for a linker between the sequence encoding the VH domain and the sequence encoding the VL domain. In one embodiment, a ScFv-Fc DMAb is in VH-VL orientation, comprising a linker attaching the C terminus of the VH region to the N terminus of the VL region. In one embodiment, a ScFv-Fc DMAb is in VL-VH orientation, comprising a linker attaching the C terminus of the VL region to the N terminus of the VH region. In one embodiment, a linker comprises at least 10, 11, 12, 13, 14, 15, 16, 17, 18, 19, 20, or more than 20 amino acid residues. In one embodiment, a linker comprises a (G4S)3 linker, having a sequence according to GGGGSGGGGSGGGGS (SEQ ID NO:53). In another embodiment, the linker is the Whitlow linker, having an amino acid sequence GSTSGSGKPGSGEGSTKG (SEQ ID NO:109).

The immunoglobulin scaffold of the ScFv-Fc DMAb of the invention can be from any immunoglobulin isotype including, but not limited to IgA, including IgA1 and IgA2, IgD, IgE, IgG, including IgG1, IgG2, IgG3 and IgG4, IgM, kappa and lambda.

In one embodiment, the ScFv-Fc converted antibody of the invention has modified expression, stability, half-life, antigen binding, heavy chain-light chain pairing, tissue penetration or a combination thereof as compared to a parental DMAb.

In one embodiment, the ScFv-Fc DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher expression than the parental DMAb.

In one embodiment, the ScFv-Fc DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher antigen binding than the parental DMAb.

In one embodiment, the ScFv-Fc DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold longer half-life than the parental DMAb.

In one embodiment, the ScFv-Fc DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher stability than the parental DMAb.

In one embodiment, the ScFv-Fc DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold greater tissue penetration than the parental DMAb.

In one embodiment, the ScFv-Fc DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold greater heavy chain-light chain pairing than the parental DMAb.

Gene Optimization

In one embodiment, the structurally modified DMAb of the invention is a gene optimized (GO) DMAb. In one embodiment, gene optimization relates to a method in which multiple parameters affecting transcription and translation, such as codon usage, GC content, cryptic splice sites and mRNA secondary structure are weighted in multivariate regression algorithms to generate a sequence having modified expression, stability, half-life, antigen binding, or a combination thereof as compared to a parental DMAb.

In one embodiment, the gene optimized DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher expression than the parental DMAb.

In one embodiment, the gene optimized DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher antigen binding than the parental DMAb.

In one embodiment, the gene optimized DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold longer half-life than the parental DMAb.

In one embodiment, the gene optimized DMAb of the invention has at least 1.1 fold, at least 1.2 fold, fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 20 fold, at least 30 fold, at least 40 fold, at least 50 fold or greater than 50 fold higher stability than the parental DMAb.

Nucleic Acid Molecules Encoding Structurally Modified DMAbs

In one embodiment, the invention provides compositions comprising a nucleic acid molecule encoding a structurally modified DMAb. In various embodiments, the nucleic acid sequence encodes a structurally modified DMAb designed to have increased expression, stability, half-life, antigen binding, or a combination thereof over a parental DMAb. In one embodiment, the nucleic acid sequence encodes a full graft DMAb, a partial graft DMA, a scaffold modified DMAb, a gene optimized DMAb, or a ScFv-Fc conversion DMAb.

Anti-Ebola DMAb

In one embodiment, the structurally modified DMAb is an anti-Ebola DMAb. In one embodiment, a nucleic acid molecule encoding a full graft structurally modified anti-Ebola DMAb encodes a DMAb having an amino acid sequence of SEQ ID NO:6, SEQ ID NO:8, SEQ ID NO:10, SEQ ID NO:16 or SEQ ID NO:18. In one embodiment, a nucleic acid molecule encoding a full graft structurally modified anti-Ebola DMAb comprises an nucleotide sequence of SEQ ID NO:5, SEQ ID NO:7, SEQ ID NO:9, SEQ ID NO:15 or SEQ ID NO:17.

In one embodiment, a nucleic acid molecule encoding a partial graft structurally modified anti-Ebola DMAb encodes a DMAb having an amino acid sequence of SEQ ID NO:4, SEQ ID NO:14, SEQ ID NO:30 or SEQ ID NO:34. In one embodiment, a nucleic acid molecule encoding a partial graft structurally modified anti-Ebola DMAb comprises an nucleotide sequence of SEQ ID NO:3, SEQ ID NO:13, SEQ ID NO:29 or SEQ ID NO:33.

In one embodiment, a nucleic acid molecule encoding a scaffold modified structurally modified anti-Ebola DMAb encodes a DMAb having an amino acid sequence of SEQ ID NO:2 or SEQ ID NO:12. In one embodiment, a nucleic acid molecule encoding a scaffold modified structurally modified anti-Ebola DMAb comprises an nucleotide sequence of SEQ ID NO:2 or SEQ ID NO:12.

In one embodiment, a nucleic acid molecule encoding a ScFv-Fc modified anti-Ebola DMAb encodes a DMAb having an amino acid sequence of SEQ ID NO:20, SEQ ID NO:22, SEQ ID NO:24, SEQ ID NO:26, SEQ ID NO:28, SEQ ID NO:32 or SEQ ID NO:36. In one embodiment, a nucleic acid molecule encoding a ScFv-Fc modified anti-Ebola DMAb comprises an nucleotide sequence of SEQ ID NO:20, SEQ ID NO:22, SEQ ID NO:24, SEQ ID NO:26, SEQ ID NO:28, SEQ ID NO:32 or SEQ ID NO:36.

In one embodiment, a nucleic acid molecule comprises a sequence encoding a fragment of a structurally modified anti-Ebola DMAb. In one embodiment, a fragment of a nucleic acid molecule encoding a structurally modified DMAb is encodes a variable light chain region or a variable heavy chain region of a structurally modified DMAb.

In one embodiment, a nucleic acid molecule encoding one or more structurally modified anti-Ebola DMAb encodes a DMAb having an amino acid sequence having at least 90%, at least 91%, at least 92%, at least 93%, at least 94%, at least 95%, at least 96%, at least 97%, at least 98%, at least 99%, or 100% identity over an entire length of the encoded sequence to an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44 or SEQ ID NO:46.

In one embodiment, a nucleic acid molecule encoding one or more structurally modified anti-Ebola DMAb comprises a nucleotide sequence having at least 90%, at least 91%, at least 92%, at least 93%, at least 94%, at least 95%, at least 96%, at least 97%, at least 98%, at least 99%, or 100% identity over an entire length of the nucleic acid sequence to a nucleic acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43 or SEQ ID NO:45.

In one embodiment, a nucleic acid molecule comprises a sequence encoding a fragment of a structurally modified anti-Ebola DMAb. In one embodiment, a fragment of a nucleic acid molecule encoding a structurally modified anti-Ebola DMAb is encodes a variable light chain region or a variable heavy chain region of a structurally modified anti-Ebola DMAb.

In one embodiment, a nucleic acid molecule encoding one or more structurally modified anti-Ebola DMAbs comprises a nucleotide sequence encoding a fragment comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44 or SEQ ID NO:46.

In one embodiment, a nucleic acid molecule encoding one or more structurally modified anti-Ebola DMAbs comprises a fragment comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43 or SEQ ID NO:45.

In one embodiment, a nucleic acid molecule encoding one or more structurally modified anti-Ebola DMAbs comprises a nucleotide sequence encoding an amino acid sequence having at least 90%, at least 91%, at least 92%, at least 93%, at least 94%, at least 95%, at least 96%, at least 97%, at least 98%, at least 99%, or 100% identity over at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of the encoded sequence to an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44 or SEQ ID NO:46.

In one embodiment, a nucleic acid molecule encoding one or more structurally modified anti-Ebola DMAbs comprises a nucleotide sequence having at least 90%, at least 91%, at least 92%, at least 93%, at least 94%, at least 95%, at least 96%, at least 97%, at least 98%, at least 99%, or 100% identity over at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of the nucleic acid sequence to a nucleic acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43 or SEQ ID NO:45.

In one embodiment, the nucleotide sequence encoding one or more structurally modified anti-Ebola DMAbs comprises one or more RNA sequences transcribed from one or more DNA sequences encoding an amino acid sequence at least 90%, at least 91%, at least 92%, at least 93%, at least 94%, at least 95%, at least 96%, at least 97%, at least 98%, or at least 99% identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44 or SEQ ID NO:46 or a fragment of an amino acid sequence at least 90%, at least 91%, at least 92%, at least 93%, at least 94%, at least 95%, at least 96%, at least 97%, at least 98%, or at least 99% identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44 or SEQ ID NO:46.

In one embodiment, the nucleotide sequence encoding an anti-Ebola DMAb comprises one or more RNA sequences transcribed from one or more DNA sequences encoding an amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44 or SEQ ID NO:46, or a fragment of an amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44 or SEQ ID NO:46.

In one embodiment, the nucleotide sequence encoding an anti-Ebola DMAb comprises one or more RNA sequences transcribed from one or more DNA sequences at least 90%, at least 91%, at least 92%, at least 93%, at least 94%, at least 95%, at least 96%, at least 97%, at least 98%, or at least 99% identical to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43 or SEQ ID NO:45, or a fragment of a DNA sequence at least 90%, at least 91%, at least 92%, at least 93%, at least 94%, at least 95%, at least 96%, at least 97%, at least 98%, or at least 99% identical to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43 or SEQ ID NO:45.

In one embodiment, the nucleotide sequence encoding an anti-Ebola DMAb comprises one or more RNA sequence transcribed from one or more DNA sequences as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43 or SEQ ID NO:45, or a fragment of a DNA sequence as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43 or SEQ ID NO:45.

The composition of the invention can treat, prevent and/or protect against any disease, disorder, or condition associated with Ebola virus infection. In certain embodiments, the composition can treat, prevent, and or/protect against viral infection. In certain embodiments, the composition can treat, prevent, and or/protect against a condition associated with Ebola virus infection.

Anti-Zika DMAb

In one embodiment, the structurally modified DMAb is an anti-ZIKV DMAb.

In one embodiment, a nucleic acid molecule encoding a gene optimized anti-ZIKV DMAb encodes a DMAb having an amino acid sequence of SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84 or SEQ ID NO:86. In one embodiment, a nucleic acid molecule encoding a gene optimized anti-ZIKV DMAb comprises an nucleotide sequence of SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83 or SEQ ID NO:85.

In one embodiment, a nucleic acid molecule encoding a ScFv-Fc modified anti-ZIKV DMAb encodes a DMAb having an amino acid sequence of SEQ ID NO:90, SEQ ID NO:92, SEQ ID NO:94, SEQ ID NO:96, SEQ ID NO:100, SEQ ID NO:102, SEQ ID NO:104 or SEQ ID NO:106. In one embodiment, a nucleic acid molecule encoding a ScFv-Fc modified DMAb comprises an nucleotide sequence of SEQ ID NO:89, SEQ ID NO:91, SEQ ID NO:93, SEQ ID NO:95, SEQ ID NO:99, SEQ ID NO:101, SEQ ID NO:103 or SEQ ID NO:105.

In one embodiment, a nucleic acid molecule encoding one or more structurally modified anti-ZIKV DMAb encodes a DMAb having an amino acid sequence having at least 90%, at least 91%, at least 92%, at least 93%, at least 94%, at least 95%, at least 96%, at least 97%, at least 98%, at least 99%, or 100% identity over an entire length of the encoded sequence to an amino acid sequence of SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 or SEQ ID NO:106.

In one embodiment, a nucleic acid molecule encoding one or more structurally modified anti-ZIKV DMAb comprises a nucleotide sequence having at least 90%, at least 91%, at least 92%, at least 93%, at least 94%, at least 95%, at least 96%, at least 97%, at least 98%, at least 99%, or 100% identity over an entire length of the nucleic acid sequence to a nucleic acid sequence of SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103 or SEQ ID NO:105.

In one embodiment, a nucleic acid molecule comprises a sequence encoding a fragment of a structurally modified anti-ZIKV DMAb. In one embodiment, a fragment of a nucleic acid molecule encoding a structurally modified anti-ZIKV DMAb is encodes a variable light chain region or a variable heavy chain region of a structurally modified anti-ZIKV DMAb.

In one embodiment, a nucleic acid molecule encoding one or more structurally modified anti-ZIKV DMAbs comprises a nucleotide sequence encoding a fragment comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of an amino acid sequence of SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 or SEQ ID NO:106.

In one embodiment, a nucleic acid molecule encoding one or more structurally modified anti-ZIKV DMAbs comprises a fragment comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of a nucleotide sequence of SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103 or SEQ ID NO:105.

In one embodiment, a nucleic acid molecule encoding one or more structurally modified anti-ZIKV DMAbs comprises a nucleotide sequence encoding an amino acid sequence having at least 90%, at least 91%, at least 92%, at least 93%, at least 94%, at least 95%, at least 96%, at least 97%, at least 98%, at least 99%, or 100% identity over at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of the encoded sequence to an amino acid sequence of SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 or SEQ ID NO:106.

In one embodiment, a nucleic acid molecule encoding one or more structurally modified anti-ZIKV DMAbs comprises a nucleotide sequence having at least 90%, at least 91%, at least 92%, at least 93%, at least 94%, at least 95%, at least 96%, at least 97%, at least 98%, at least 99%, or 100% identity over at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of the nucleic acid sequence to a nucleic acid sequence of SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103 or SEQ ID NO:105.

In one embodiment, the nucleotide sequence encoding one or more structurally modified anti-ZIKV DMAbs comprises one or more RNA sequences transcribed from one or more DNA sequences encoding an amino acid sequence at least 90%, at least 91%, at least 92%, at least 93%, at least 94%, at least 95%, at least 96%, at least 97%, at least 98%, or at least 99% identical to SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 or SEQ ID NO:106 or a fragment of an amino acid sequence at least 90%, at least 91%, at least 92%, at least 93%, at least 94%, at least 95%, at least 96%, at least 97%, at least 98%, or at least 99% identical to SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 or SEQ ID NO:106.

In one embodiment, the nucleotide sequence encoding an anti-ZIKV DMAb comprises one or more RNA sequences transcribed from one or more DNA sequences encoding an amino acid sequence as set forth in SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 or SEQ ID NO:106, or a fragment of an amino acid sequence as set forth in SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 or SEQ ID NO:106.

In one embodiment, the nucleotide sequence encoding an anti-ZIKV DMAb comprises one or more RNA sequences transcribed from one or more DNA sequences at least 90%, at least 91%, at least 92%, at least 93%, at least 94%, at least 95%, at least 96%, at least 97%, at least 98%, or at least 99% identical to SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103 or SEQ ID NO:105 or a fragment of a DNA sequence at least 90%, at least 91%, at least 92%, at least 93%, at least 94%, at least 95%, at least 96%, at least 97%, at least 98%, or at least 99% identical to SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103 or SEQ ID NO:105.

In one embodiment, the nucleotide sequence encoding an anti-ZIKV DMAb comprises one or more RNA sequence transcribed from one or more DNA sequences as set forth in SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103 or SEQ ID NO:105, or a fragment of a DNA sequence as set forth in SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103 or SEQ ID NO:105.

The composition of the invention can treat, prevent and/or protect against any disease, disorder, or condition associated with Zika virus infection. In certain embodiments, the composition can treat, prevent, and or/protect against viral infection. In certain embodiments, the composition can treat, prevent, and or/protect against a condition associated with Zika virus infection.

Anti-DENV DMAb

In one embodiment, the structurally modified DMAb is an anti-DENV DMAb.

In one embodiment, a nucleic acid molecule encoding a ScFv-Fc structurally modified anti-DENV DMAb encodes a DMAb having an amino acid sequence of SEQ ID NO:108. In one embodiment, a nucleic acid molecule encoding a ScFv-Fc structurally modified DMAb comprises an nucleotide sequence of SEQ ID NO:107.

In one embodiment, a nucleic acid molecule encoding one or more structurally modified anti-DENV DMAb encodes a DMAb having an amino acid sequence having at least 90%, at least 91%, at least 92%, at least 93%, at least 94%, at least 95%, at least 96%, at least 97%, at least 98%, at least 99%, or 100% identity over an entire length of the encoded sequence to an amino acid sequence of SEQ ID NO:108.

In one embodiment, a nucleic acid molecule encoding one or more structurally modified anti-DENV DMAb comprises a nucleotide sequence having at least 90%, at least 91%, at least 92%, at least 93%, at least 94%, at least 95%, at least 96%, at least 97%, at least 98%, at least 99%, or 100% identity over an entire length of the nucleic acid sequence to a nucleic acid sequence of SEQ ID NO:107.

In one embodiment, a nucleic acid molecule comprises a sequence encoding a fragment of a structurally modified anti-DENV DMAb. In one embodiment, a fragment of a nucleic acid molecule encoding a structurally modified anti-DENV DMAb is encodes a variable light chain region or a variable heavy chain region of a structurally modified anti-DENV DMAb.

In one embodiment, a nucleic acid molecule encoding one or more structurally modified anti-DENV DMAbs comprises a nucleotide sequence encoding a fragment comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of an amino acid sequence of SEQ ID NO:108.

In one embodiment, a nucleic acid molecule encoding one or more structurally modified anti-DENV DMAbs comprises a fragment comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of a nucleotide sequence of SEQ ID NO:107.

In one embodiment, a nucleic acid molecule encoding one or more structurally modified anti-DENV DMAbs comprises a nucleotide sequence encoding an amino acid sequence having at least 90%, at least 91%, at least 92%, at least 93%, at least 94%, at least 95%, at least 96%, at least 97%, at least 98%, at least 99%, or 100% identity over at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of the encoded sequence to an amino acid sequence of SEQ ID NO:108.

In one embodiment, a nucleic acid molecule encoding one or more structurally modified anti-DENV DMAbs comprises a nucleotide sequence having at least 90%, at least 91%, at least 92%, at least 93%, at least 94%, at least 95%, at least 96%, at least 97%, at least 98%, at least 99%, or 100% identity over at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of the nucleic acid sequence to a nucleic acid sequence of SEQ ID NO:107.

In one embodiment, the nucleotide sequence encoding one or more structurally modified anti-DENV DMAbs comprises one or more RNA sequences transcribed from one or more DNA sequences encoding an amino acid sequence at least 90%, at least 91%, at least 92%, at least 93%, at least 94%, at least 95%, at least 96%, at least 97%, at least 98%, or at least 99% identical to SEQ ID NO:108 or a fragment of an amino acid sequence at least 90%, at least 91%, at least 92%, at least 93%, at least 94%, at least 95%, at least 96%, at least 97%, at least 98%, or at least 99% identical to SEQ ID NO:108.

In one embodiment, the nucleotide sequence encoding an anti-DENV DMAb comprises one or more RNA sequences transcribed from one or more DNA sequences encoding an amino acid sequence as set forth in SEQ ID NO:108 or a fragment of an amino acid sequence as set forth in SEQ ID NO:108.

In one embodiment, the nucleotide sequence encoding an anti-DENV DMAb comprises one or more RNA sequences transcribed from one or more DNA sequences at least 90%, at least 91%, at least 92%, at least 93%, at least 94%, at least 95%, at least 96%, at least 97%, at least 98%, or at least 99% identical to SEQ ID NO:107 or a fragment of a DNA sequence at least 90%, at least 91%, at least 92%, at least 93%, at least 94%, at least 95%, at least 96%, at least 97%, at least 98%, or at least 99% identical to SEQ ID NO:107.

In one embodiment, the nucleotide sequence encoding an anti-DENV DMAb comprises one or more RNA sequence transcribed from one or more DNA sequences as set forth in SEQ ID NO:107 or a fragment of a DNA sequence as set forth in SEQ ID NO:107.

The composition of the invention can treat, prevent and/or protect against any disease, disorder, or condition associated with DENV virus infection. In certain embodiments, the composition can treat, prevent, and or/protect against viral infection. In certain embodiments, the composition can treat, prevent, and or/protect against a condition associated with DENV virus infection.

Anti-RSV DMAb

In one embodiment, the structurally modified DMAb is an anti-RSV DMAb.

In one embodiment, a nucleic acid molecule encoding a ScFv-Fc structurally modified anti-RSV DMAb encodes a DMAb having an amino acid sequence of SEQ ID NO:113 or SEQ ID NO:117. In one embodiment, a nucleic acid molecule encoding a ScFv-Fc structurally modified DMAb comprises an nucleotide sequence of SEQ ID NO:112 or SEQ ID NO:116.

In one embodiment, a nucleic acid molecule encoding a gene optimized anti-RSV DMAb encodes a DMAb having an amino acid sequence of SEQ ID NO:111, SEQ ID NO:115 or SEQ ID NO:119. In one embodiment, a nucleic acid molecule encoding a gene optimized anti-RSV DMAb comprises an nucleotide sequence of SEQ ID NO:110, SEQ ID NO:114 or SEQ ID NO:118.

In one embodiment, a nucleic acid molecule encoding one or more structurally modified anti-RSV DMAb encodes a DMAb having an amino acid sequence having at least 90%, at least 91%, at least 92%, at least 93%, at least 94%, at least 95%, at least 96%, at least 97%, at least 98%, at least 99%, or 100% identity over an entire length of the encoded sequence to an amino acid sequence of SEQ ID NO:111, SEQ ID NO:113, SEQ ID NO:115, SEQ ID NO:117 or SEQ ID NO:119.

In one embodiment, a nucleic acid molecule encoding one or more structurally modified anti-RSV DMAb comprises a nucleotide sequence having at least 90%, at least 91%, at least 92%, at least 93%, at least 94%, at least 95%, at least 96%, at least 97%, at least 98%, at least 99%, or 100% identity over an entire length of the nucleic acid sequence to a nucleic acid sequence of SEQ ID NO:110, SEQ ID NO:112, SEQ ID NO:114, SEQ ID NO:116 or SEQ ID NO:118.

In one embodiment, a nucleic acid molecule comprises a sequence encoding a fragment of a structurally modified anti-RSV DMAb. In one embodiment, a fragment of a nucleic acid molecule encoding a structurally modified anti-RSV DMAb is encodes a variable light chain region or a variable heavy chain region of a structurally modified anti-RSV DMAb.

In one embodiment, a nucleic acid molecule encoding one or more structurally modified anti-RSV DMAbs comprises a nucleotide sequence encoding a fragment comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of an amino acid sequence of SEQ ID NO:111, SEQ ID NO:113, SEQ ID NO:115, SEQ ID NO:117 or SEQ ID NO:119.

In one embodiment, a nucleic acid molecule encoding one or more structurally modified anti-RSV DMAbs comprises a fragment comprising at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of a nucleotide sequence of SEQ ID NO:110, SEQ ID NO:112, SEQ ID NO:114, SEQ ID NO:116 or SEQ ID NO:118.

In one embodiment, a nucleic acid molecule encoding one or more structurally modified anti-RSV DMAbs comprises a nucleotide sequence encoding an amino acid sequence having at least 90%, at least 91%, at least 92%, at least 93%, at least 94%, at least 95%, at least 96%, at least 97%, at least 98%, at least 99%, or 100% identity over at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of the encoded sequence to an amino acid sequence of SEQ ID NO:111, SEQ ID NO:113, SEQ ID NO:115, SEQ ID NO:117 or SEQ ID NO:119.

In one embodiment, a nucleic acid molecule encoding one or more structurally modified anti-RSV DMAbs comprises a nucleotide sequence having at least 90%, at least 91%, at least 92%, at least 93%, at least 94%, at least 95%, at least 96%, at least 97%, at least 98%, at least 99%, or 100% identity over at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% of the nucleic acid sequence to a nucleic acid sequence of SEQ ID NO:110, SEQ ID NO:112, SEQ ID NO:114, SEQ ID NO:116 or SEQ ID NO:118.

In one embodiment, the nucleotide sequence encoding one or more structurally modified anti-RSV DMAbs comprises one or more RNA sequences transcribed from one or more DNA sequences encoding an amino acid sequence at least 90%, at least 91%, at least 92%, at least 93%, at least 94%, at least 95%, at least 96%, at least 97%, at least 98%, or at least 99% identical to SEQ ID NO:111, SEQ ID NO:113, SEQ ID NO:115, SEQ ID NO:117 or SEQ ID NO:119, or a fragment of an amino acid sequence at least 90%, at least 91%, at least 92%, at least 93%, at least 94%, at least 95%, at least 96%, at least 97%, at least 98%, or at least 99% identical to SEQ ID NO:111, SEQ ID NO:113, SEQ ID NO:115, SEQ ID NO:117 or SEQ ID NO:119.

In one embodiment, the nucleotide sequence encoding an anti-RSV DMAb comprises one or more RNA sequences transcribed from one or more DNA sequences encoding an amino acid sequence as set forth in SEQ ID NO:111, SEQ ID NO:113, SEQ ID NO:115, SEQ ID NO:117 or SEQ ID NO:119, or a fragment of an amino acid sequence as set forth in SEQ ID NO:111, SEQ ID NO:113, SEQ ID NO:115, SEQ ID NO:117 or SEQ ID NO:119.

In one embodiment, the nucleotide sequence encoding an anti-RSV DMAb comprises one or more RNA sequences transcribed from one or more DNA sequences at least 90%, at least 91%, at least 92%, at least 93%, at least 94%, at least 95%, at least 96%, at least 97%, at least 98%, or at least 99% identical to SEQ ID NO:110, SEQ ID NO:112, SEQ ID NO:114, SEQ ID NO:116 or SEQ ID NO:118 or a fragment of a DNA sequence at least 90%, at least 91%, at least 92%, at least 93%, at least 94%, at least 95%, at least 96%, at least 97%, at least 98%, or at least 99% identical to SEQ ID NO:110, SEQ ID NO:112, SEQ ID NO:114, SEQ ID NO:116 or SEQ ID NO:118.

In one embodiment, the nucleotide sequence encoding an anti-RSV DMAb comprises one or more RNA sequence transcribed from one or more DNA sequences as set forth in SEQ ID NO:110, SEQ ID NO:112, SEQ ID NO:114, SEQ ID NO:116 or SEQ ID NO:118, or a fragment of a DNA sequence as set forth in SEQ ID NO:110, SEQ ID NO:112, SEQ ID NO:114, SEQ ID NO:116 or SEQ ID NO:118.

The composition of the invention can treat, prevent and/or protect against any disease, disorder, or condition associated with RSV virus infection. In certain embodiments, the composition can treat, prevent, and or/protect against viral infection. In certain embodiments, the composition can treat, prevent, and or/protect against a condition associated with RSV virus infection.

3. DNA ENCODED ANTIBODY

As described above, the composition can comprise a recombinant nucleic acid sequence. The recombinant nucleic acid sequence can encode the structurally modified DMAb, a fragment thereof, a variant thereof, or a combination thereof. The antibody is described in more detail below.

The recombinant nucleic acid sequence can be a heterologous nucleic acid sequence. The recombinant nucleic acid sequence can include at least one heterologous nucleic acid sequence or one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; and eliminating to the extent possible cis-acting sequence motifs (i.e., internal TATA boxes).

a. Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

(3) Protease Cleavage Site

The recombinant nucleic acid sequence construct can include the heterologous nucleic acid sequence encoding the protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides. In one embodiment, the linker sequence is a (G4S)$_n$ linker, including but not limited to, the (G4S)$_3$ linker having an amino acid sequence GGGGSGGGGSGGGGS (SEQ ID NO:53). In another embodiment, the linker is the Whitlow linker, having an amino acid sequence GSTSGSGKPGSGEGSTKG (SEQ ID NO:109).

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

b. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A forth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

(3) ScFv-Fc Arrangement

In a ScFv-Fc arrangement, the recombinant nucleic acid sequence can include a sequence encoding the VH domain of the heavy chain polypeptide, and the VL domain of the light chain polypeptide, and further a linker sequence positioned between the heterologous nucleic acid sequence encoding the VH domain and VL domain.

An example of a ScFv-Fc arrangement can include the vector (and thus recombinant nucleic acid sequence construct) encoding the VH, linker, VL, hinge region, CH2, and CH3. The VH region can be N-terminally or C-terminally linked to a VL region via a linker.

c. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

d. Vector

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In some embodiments, the vector includes linear DNA, enzymatic DNA or synthetic DNA. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAXI, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be p YES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA

The one or more vectors may be an RNA molecule. In one embodiment, the RNA molecule is transcribed from a DNA sequence described herein. For example, in some embodiments, the RNA molecule encodes a structurally modified DMAb or a variant thereof or a fragment thereof. In one embodiment, an RNA molecule is a transcript generated from a DNA molecule encoding a structurally modified DMAb or a variant thereof or a fragment thereof. Accordingly, in one embodiment, the invention provides an RNA molecule encoding one or more of the DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA.

(4) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(5) Bidirectional Expression Vector

The one or more vectors may be a bidirectional expression vector. The bidirectional vector may designed to express a protein or polypeptide of interest and a reporter protein, or alternatively to express two proteins or polypeptides of interest from a single promoter. The expression may be driven by a constitutively active bidirectional human cytomegalovirus promoter ($P_{miniCMV}$). In one embodiment, a first polypeptide of interest is a DMAb and a second polypeptide of interest is an antigen. In one embodiment, a first polypeptide of interest is a first DMAb and a second polypeptide of interest is a second DMAb. In one embodiment, one or more of a first and second DMAb may be a structurally modified DMAb. A second DMAb may target the same antigen as a first DMAb, a different antigen from the same virus as a first DMAb, or an antigen of a different virus. For example, in one embodiment, the invention provides multivalent bidirectional expression vectors encoding a combination of an anti-ZIKV structurally modified DMAb and an anti-DENV structurally modified DMAb. In one embodiment, a bidirectional expression vector comprises a nucleotide sequence encoding a structurally modified DMAb comprising an amino acid sequence selected from SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104 or SEQ ID NO:106 and a nucleotide sequence encoding a structurally modified DMAb comprising an amino acid sequence of SEQ ID NO:108.

(6) Viral Vectors

Viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(7) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in WO/2008/148010, published Dec. 4, 2008. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

4. ANTIBODY

As described above, the recombinant nucleic acid sequence can encode the structurally modified DMAb, a fragment thereof, a variant thereof, or a combination thereof. The structurally modified DMAb can bind or react with the antigen, which is described in more detail below.

The structurally modified DMAb may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites. Accordingly, the antibody can be the Fab or F(ab')2. The Fab can include the heavy chain polypeptide and the light chain polypeptide. The heavy chain polypeptide of the Fab can include the VH region and the CH1 region. The light chain of the Fab can include the VL region and CL region.

The structurally modified DMAb can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The structurally modified DMAb may lack the CH1 and CL region of the heavy and light chain respectively. In such an embodiment, the structurally modified DMAb may be a single chain DMAb and comprise a flexible amino acid linker sequence which serves to tether the VL region to the VH region. The structurally modified DMAb may comprise a single chain including a VL region, a linker, a VH region, a hinge region, a CH2 region, and a CH3 region. The VH region can be N-terminally or C-terminally linked to a VL region via a linker.

The structurally modified DMAb can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarily determining regions (CDRs) from the non-human species and framework regions from a human immunoglobulin molecule.

The structurally modified DMAb can be an IgG1 antibody, an IgG2 antibody, an IgG3 antibody, an IgG4 antibody, an IgA1 antibody, an IgA2 antibody, an IgD antibody, an IgE antibody, or an IgM antibody. The structurally modified DMAb can be a chimera of any of an IgG1 antibody, an IgG2 antibody, an IgG3 antibody, an IgG4 antibody, an IgA1 antibody, an IgA2 antibody, an IgD antibody, an IgE antibody, or an IgM antibody. In some embodiments, the antibody hinge domain is modified. For example, in one embodiment, the structurally modified DMAb includes a Serine to Proline amino acid substitution in the hinge domain.

The structurally modified DMAb can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

The antibody may be modified to reduce or prevent antibody-dependent enhancement (ADE) of disease associated with the antigen as described in more detail below.

a. Bispecific Antibody

The recombinant nucleic acid sequence can encode a bispecific structurally modified DMAb, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker, including a cancer marker.

The invention provides novel bispecific antibodies comprising a first antigen-binding site that specifically binds to a first target and a second antigen-binding site that specifically binds to a second target, with particularly advantageous properties such as producibility, stability, binding affinity, biological activity, specific targeting of certain T cells, targeting efficiency and reduced toxicity. In some instances, there are bispecific antibodies, wherein the bispecific antibody binds to the first target with high affinity and to the second target with low affinity. In other instances, there are bispecific antibodies, wherein the bispecific antibody binds to the first target with low affinity and to the second target with high affinity. In other instances, there are bispecific antibodies, wherein the bispecific antibody binds to the first target with a desired affinity and to the second target with a desired affinity.

In one embodiment, the bispecific antibody is a bivalent antibody comprising a) a first light chain and a first heavy chain of an antibody specifically binding to a first antigen, and b) a second light chain and a second heavy chain of an antibody specifically binding to a second antigen.

A bispecific antibody molecule according to the invention may have two binding sites of any desired specificity. In some embodiments, one of the binding sites of an antibody molecule according to the invention is able to bind a T-cell specific receptor molecule and/or a natural killer cell (NK cell) specific receptor molecule. A T-cell specific receptor is the so called "T-cell receptor" (TCRs), which allows a T cell to bind to and, if additional signals are present, to be activated by and respond to an epitope/antigen presented by another cell called the antigen-presenting cell or APC. The T cell receptor is known to resemble a Fab fragment of a naturally occurring immunoglobulin. It is generally monovalent, encompassing .alpha.- and .beta.-chains, in some embodiments it encompasses .gamma.-chains and .delta.-chains (supra). Accordingly, in some embodiments the TCR is TCR (alpha/beta) and in some embodiments it is TCR (gamma/delta). The T cell receptor forms a complex with the CD3 T-Cell co-receptor. CD3 is a protein complex and is composed of four distinct chains. In mammals, the complex contains a CD3γ chain, a CD3δ chain, and two CD3ε chains. These chains associate with a molecule known as the T cell receptor (TCR) and the ζ-chain to generate an activation signal in T lymphocytes. Hence, in some embodiments a T-cell specific receptor is the CD3 T-Cell co-receptor. In some embodiments a T-cell specific receptor is CD28, a protein that is also expressed on T cells. CD28 can provide co-stimulatory signals, which are required for T cell activation. CD28 plays important roles in T-cell proliferation and survival, cytokine production, and T-helper type-2 development. Yet a further example of a T-cell specific receptor is CD134, also termed Ox40. CD134/OX40 is being expressed after 24 to 72 hours following activation and can be taken to define a secondary costimulatory molecule. Another example of a T-cell receptor is 4-1 BB capable of binding to 4-1 BB-Ligand on antigen presenting cells (APCs), whereby a costimulatory signal for the T cell is generated. Another example of a receptor predominantly found on T-cells is CD5, which is also found on B cells at low levels. A further example of a receptor modifying T cell functions is CD95, also known as the Fas receptor, which mediates apoptotic signaling by Fas-ligand expressed on the surface of other cells. CD95 has been reported to modulate TCR/CD3-driven signaling pathways in resting T lymphocytes.

An example of a NK cell specific receptor molecule is CD16, a low affinity Fc receptor and NKG2D. An example of a receptor molecule that is present on the surface of both T cells and natural killer (NK) cells is CD2 and further members of the CD2-superfamily. CD2 is able to act as a co-stimulatory molecule on T and NK cells.

In some embodiments the first binding site of the antibody molecule binds a target antigen and the second binding site binds a T cell specific receptor molecule and/or a natural killer (NK) cell specific receptor molecule.

In some embodiments the first binding site of the antibody molecule binds a target antigen including, but not limited to, a viral antigen (e.g., Ebolavirus GP glycan cap, Ebolavirus GP fusion loop, or Ebolavirus GP chalice base) or a self antigen (e.g., tumor antigens), and the second binding site binds a T cell specific receptor molecule and/or a natural killer (NK) cell specific receptor molecule. In some embodiments the first binding site of the antibody molecule binds a target antigen and the second binding site binds one of CD3, the T cell receptor (TCR), CD28, CD16, NKG2D, Ox40, 4-1BB, CD2, CD5 and CD95.

In some embodiments the first binding site of the antibody molecule binds a T cell specific receptor molecule and/or a natural killer (NK) cell specific receptor molecule and the second binding site binds a target antigen including, but not limited to, viral antigens (e.g., Ebolavirus GP glycan cap, Ebolavirus GP fusion loop, or Ebolavirus GP chalice base) and self antigens (e.g., tumor antigens). In some embodiments the first binding site of the antibody binds a T cell specific receptor molecule and/or a natural killer (NK) cell specific receptor molecule and the second binding site binds a target antigen. In some embodiments the first binding site of the antibody binds one of CD3, the T cell receptor (TCR), CD28, CD16, NKG2D, Ox40, 4-1BB, CD2, CD5 and CD95, and the second binding site binds a target antigen.

b. Bifunctional Antibody

The recombinant nucleic acid sequence can encode a bifunctional structurally modified DMAb, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

c. Extension of Antibody Half-Life

As described above, the structurally modified DMAb may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

d. Defucosylation

The recombinant nucleic acid sequence can encode a structurally modified DMAb that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, 0-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The structurally modified DMAb may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

e. Reduced ADE Response

The structurally modified DMAb may be modified to reduce or prevent antibody-dependent enhancement (ADE) of disease associated with the antigen, but still neutralize the antigen. For example, the antibody may be modified to reduce or prevent ADE of disease associated with DENV, which is described below in more detail, but still neutralize DENV.

In some embodiments, the antibody may be modified to include one or more amino acid substitutions that reduce or prevent binding of the antibody to FcγR1a. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA, LALA mutation, or LALA substitution. The presence of the LALA substitutions may prevent or block the antibody from binding to FcγR1a, and thus, the modified antibody does not enhance or cause ADE of disease associated with the antigen, but still neutralizes the antigen.

5. ANTIGEN

The structurally modified DMAb of the invention is directed to an antigen or fragment or variant thereof. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

In one embodiment, a synthetic antibody of the invention targets two or more antigens. In one embodiment, at least one antigen of a bispecific antibody is selected from the antigens described herein. In one embodiment, the two or more antigens are selected from the antigens described herein.

The antigen can be from any number of organisms, for example, a virus, a parasite, a bacterium, a fungus, or a mammal. The antigen can be associated with an autoimmune disease, allergy, or asthma. In other embodiments, the antigen can be associated with cancer, herpes, influenza, hepatitis B, hepatitis C, human papilloma virus (HPV), or human immunodeficiency virus (HIV).

In some embodiments, the antigen is foreign. In some embodiments, the antigen is a self-antigen.

a. Foreign Antigens

In some embodiments, the antigen is foreign. A foreign antigen is any non-self substance (i.e., originates external to the subject) that, when introduced into the body, is capable of stimulating an immune response.

(1) Viral Antigens

The foreign antigen can be a viral antigen, or fragment thereof, or variant thereof. The viral antigen can be from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Polyomaviridae, Reoviridae, Retroviridae, Rhabdoviridae, or Togaviridae. The viral antigen can be from human immunodeficiency virus (HIV), Chikungunya virus (CHIKV), dengue fever virus, papilloma viruses, for example, human papillomoa virus (HPV), polio virus, hepatitis viruses, for example, hepatitis A virus (HAV), hepatitis B virus (HBV), hepatitis C virus (HCV), hepatitis D virus (HDV), and hepatitis E virus (HEV), smallpox virus (Variola major and minor), vaccinia virus, influenza virus, rhinoviruses, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, lassa virus, arenavirus, Merkel cell polyoma virus (MCV) or cancer causing virus.

(a) Human Immunodeficiency Virus (HIV) Antigen

The viral antigen may be from Human Immunodeficiency Virus (HIV) virus. In some embodiments, the HIV antigen can be a subtype A envelope protein, subtype B envelope protein, subtype C envelope protein, subtype D envelope protein, subtype B Nef-Rev protein, Gag subtype A, B, C, or D protein, MPol protein, a nucleic acid or amino acid sequences of Env A, Env B, Env C, Env D, B Nef-Rev, Gag, or any combination thereof.

(b) Chikungunya Virus

The viral antigen may be from Chikungunya virus. Chikungunya virus belongs to the alphavirus genus of the Togaviridae family. Chikungunya virus is transmitted to humans by the bite of infected mosquitoes, such as the genus *Aedes*.

(c) Dengue Virus

The viral antigen may be from Dengue virus. The Dengue virus antigen may be one of three proteins or polypeptides (C, prM, and E) that form the virus particle. The Dengue virus antigen may be one of seven other proteins or polypeptides (NS1, NS2a, NS2b, NS3, NS4a, NS4b, NS5) which are involved in replication of the virus. The Dengue virus may be one of five strains or serotypes of the virus, including DENV-1, DENV-2, DENV-3 and DENV-4. The antigen may be any combination of a plurality of Dengue virus antigens.

Exemplary structurally modified DMAbs specific for Dengue virus include, but are not limited to, the structurally modified DMAb listed in SEQ ID NO:107, which encodes SEQ ID NO:108.

(d) Hepatitis Antigen

The viral antigen may include a hepatitis virus antigen (i.e., hepatitis antigen), or a fragment thereof, or a variant thereof. The hepatitis antigen can be an antigen or immunogen from one or more of hepatitis A virus (HAV), hepatitis B virus (HBV), hepatitis C virus (HCV), hepatitis D virus (HDV), and/or hepatitis E virus (HEV).

The hepatitis antigen can be an antigen from HAV. The hepatitis antigen can be a HAV capsid protein, a HAV non-structural protein, a fragment thereof, a variant thereof, or a combination thereof.

The hepatitis antigen can be an antigen from HCV. The hepatitis antigen can be a HCV nucleocapsid protein (i.e., core protein), a HCV envelope protein (e.g., E1 and E2), a HCV non-structural protein (e.g., NS1, NS2, NS3, NS4a, NS4b, NS5a, and NS5b), a fragment thereof, a variant thereof, or a combination thereof.

The hepatitis antigen can be an antigen from HDV. The hepatitis antigen can be a HDV delta antigen, fragment thereof, or variant thereof.

The hepatitis antigen can be an antigen from HEV. The hepatitis antigen can be a HEV capsid protein, fragment thereof, or variant thereof.

The hepatitis antigen can be an antigen from HBV. The hepatitis antigen can be a HBV core protein, a HBV surface protein, a HBV DNA polymerase, a HBV protein encoded by gene X, fragment thereof, variant thereof, or combination thereof. The hepatitis antigen can be a HBV genotype A core protein, a HBV genotype B core protein, a HBV genotype C core protein, a HBV genotype D core protein, a HBV genotype E core protein, a HBV genotype F core protein, a HBV genotype G core protein, a HBV genotype H core protein, a HBV genotype A surface protein, a HBV genotype B surface protein, a HBV genotype C surface protein, a HBV genotype D surface protein, a HBV genotype E surface protein, a HBV genotype F surface protein, a HBV genotype G surface protein, a HBV genotype H surface protein, fragment thereof, variant thereof, or combination thereof.

In some embodiments, the hepatitis antigen can be an antigen from HBV genotype A, HBV genotype B, HBV genotype C, HBV genotype D, HBV genotype E, HBV genotype F, HBV genotype G, or HBV genotype H.

(e) Human Papilloma Virus (HPV) Antigen

The viral antigen may comprise an antigen from HPV. The HPV antigen can be from HPV types 16, 18, 31, 33, 35, 45, 52, and 58 which cause cervical cancer, rectal cancer, and/or other cancers. The HPV antigen can be from HPV types 6 and 11, which cause genital warts, and are known to be causes of head and neck cancer.

The HPV antigens can be the HPV E6 or E7 domains from each HPV type. For example, for HPV type 16 (HPV16), the HPV16 antigen can include the HPV16 E6 antigen, the HPV16 E7 antigen, fragments, variants, or combinations thereof. Similarly, the HPV antigen can be HPV 6 E6 and/or E7, HPV 11 E6 and/or E7, HPV 18 E6 and/or E7, HPV 31 E6 and/or E7, HPV 33 E6 and/or E7, HPV 52 E6 and/or E7, or HPV 58 E6 and/or E7, fragments, variants, or combinations thereof.

(f) RSV Antigen

The viral antigen may comprise a RSV antigen. The RSV antigen can be a human RSV fusion protein (also referred to herein as "RSV F," "RSV F protein," and "F protein"), or fragment or variant thereof. The human RSV fusion protein can be conserved between RSV subtypes A and B. The RSV antigen can be a RSV F protein, or fragment or variant thereof, from the RSV Long strain (GenBank AAX23994.1). The RSV antigen can be a RSV F protein from the RSV A2 strain (GenBank AAB59858.1), or a fragment or variant thereof. The RSV antigen can be a monomer, a dimer, or trimer of the RSV F protein, or a fragment or variant thereof.

The RSV F protein can be in a prefusion form or a postfusion form. The postfusion form of RSV F elicits high titer neutralizing antibodies in immunized animals and protects the animals from RSV challenge.

The RSV antigen can also be human RSV attachment glycoprotein (also referred to herein as "RSV G," "RSV G protein," and "G protein"), or fragment or variant thereof. The human RSV G protein differs between RSV subtypes A and B. The antigen can be RSV G protein, or fragment or variant thereof, from the RSV Long strain (GenBank AAX23993). The RSV antigen can be RSV G protein from the RSV subtype B isolate H5601, the RSV subtype B isolate H1068, the RSV subtype B isolate H5598, the RSV subtype B isolate H1123, or a fragment or variant thereof.

In other embodiments, the RSV antigen can be human RSV non-structural protein 1 ("NS1 protein"), or fragment or variant thereof. For example, the RSV antigen can be RSV NS1 protein, or fragment or variant thereof, from the RSV Long strain (GenBank AAX23987.1). The RSV antigen human can also be RSV non-structural protein 2 ("NS2 protein"), or fragment or variant thereof. For example, the RSV antigen can be RSV NS2 protein, or fragment or variant thereof, from the RSV Long strain (GenBank AAX23988.1). The RSV antigen can further be human RSV nucleocapsid ("N") protein, or fragment or variant thereof. For example, the RSV antigen can be RSV N protein, or fragment or variant thereof, from the RSV Long strain (GenBank AAX23989.1). The RSV antigen can be human RSV Phosphoprotein ("P") protein, or fragment or variant thereof. For example, the RSV antigen can be RSV P protein, or fragment or variant thereof, from the RSV Long strain (GenBank AAX23990.1). The RSV antigen also can be human RSV Matrix protein ("M") protein, or fragment or variant thereof. For example, the RSV antigen can be RSV M protein, or fragment or variant thereof, from the RSV Long strain (GenBank AAX23991.1).

In still other embodiments, the RSV antigen can be human RSV small hydrophobic ("SH") protein, or fragment or variant thereof. For example, the RSV antigen can be RSV SH protein, or fragment or variant thereof, from the RSV Long strain (GenBank AAX23992.1). The RSV antigen can also be human RSV Matrix protein2-1 ("M2-1") protein, or fragment or variant thereof. For example, the RSV antigen can be RSV M2-1 protein, or fragment or variant thereof, from the RSV Long strain (GenBank AAX23995.1). The RSV antigen can further be human RSV Matrix protein 2-2 ("M2-2") protein, or fragment or variant thereof. For example, the RSV antigen can be RSV M2-2 protein, or fragment or variant thereof, from the RSV Long strain (GenBank AAX23997.1). The RSV antigen human can be RSV Polymerase L ("L") protein, or fragment or variant thereof. For example, the RSV antigen can be RSV L protein, or fragment or variant thereof, from the RSV Long strain (GenBank AAX23996.1).

In further embodiments, the RSV antigen can have an optimized amino acid sequence of NS1, NS2, N, P, M, SH, M2-1, M2-2, or L protein. The RSV antigen can be a human RSV protein or recombinant antigen, such as any one of the proteins encoded by the human RSV genome.

In other embodiments, the RSV antigen can be, but is not limited to, the RSV F protein from the RSV Long strain, the RSV G protein from the RSV Long strain, the optimized amino acid RSV G amino acid sequence, the human RSV genome of the RSV Long strain, the optimized amino acid RSV F amino acid sequence, the RSV NS1 protein from the RSV Long strain, the RSV NS2 protein from the RSV Long strain, the RSV N protein from the RSV Long strain, the RSV P protein from the RSV Long strain, the RSV M protein from the RSV Long strain, the RSV SH protein from the RSV Long strain, the RSV M2-1 protein from the RSV Long strain, the RSV M2-2 protein from the RSV Long strain, the RSV L protein from the RSV Long strain, the RSV G protein from the RSV subtype B isolate H5601, the RSV G protein from the RSV subtype B isolate H1068, the RSV G protein from the RSV subtype B isolate H5598, the RSV G protein from the RSV subtype B isolate H1123, or fragment thereof, or variant thereof.

Exemplary structurally modified DMAbs specific for RSV include, but are not limited to, the structurally modified DMAbs listed in SEQ ID NO:110 through SEQ ID NO:119.

(g) Influenza Antigen

The viral antigen may comprise an antigen from influenza virus. The influenza antigens are those capable of eliciting an immune response in a mammal against one or more influenza serotypes. The antigen can comprise the full length translation product HA0, subunit HA1, subunit HA2, a variant thereof, a fragment thereof or a combination thereof. The influenza hemagglutinin antigen can be derived from multiple strains of influenza A serotype H1, serotype H2, a hybrid sequence derived from different sets of multiple strains of influenza A serotype H1, or derived from multiple strains of influenza B. The influenza hemagglutinin antigen can be from influenza B.

The influenza antigen can also contain at least one antigenic epitope that can be effective against particular influenza immunogens against which an immune response can be induced. The antigen may provide an entire repertoire of immunogenic sites and epitopes present in an intact influenza virus. The antigen may be derived from hemagglutinin antigen sequences from a plurality of influenza A virus strains of one serotype such as a plurality of influenza A virus strains of serotype H1 or of serotype H2. The antigen may be a hybrid hemagglutinin antigen sequence derived from combining two different hemagglutinin antigen sequences or portions thereof. Each of two different hemagglutinin antigen sequences may be derived from a different set of a plurality of influenza A virus strains of one serotype such as a plurality of influenza A virus strains of serotype H1. The antigen may be a hemagglutinin antigen sequence derived from hemagglutinin antigen sequences from a plurality of influenza B virus strains.

In some embodiments, the influenza antigen can be H1 HA, H2 HA, H3 HA, H5 HA, or a BHA antigen.

(h) Ebola Virus

The viral antigen may be from Ebola virus. Ebola virus disease (EVD) or Ebola hemorrhagic fever (EHF) includes any of four of the five known Ebola viruses including Bundibugyo virus (BDBV), Ebola virus (EBOV), Sudan virus (SUDV), and Taï Forest virus (TAFV, also referred to as Cote d'Ivoire Ebola virus (Ivory Coast Ebolavirus, CIEBOV).

A structurally modified DMAb may be specific for an Ebola virus antigen. Exemplary structurally modified DMAbs specific for Ebola virus include, but are not limited to, the structurally modified DMAbs listed in SEQ ID NO:1 through SEQ ID NO:46.

(i) Marburg Marburgvirus

The viral antigen may be from Marburg marburgvirus. Marburg virus disease (MVD) or Marburg hemorrhagic fever (EHF) includes any of four of the five known Marburg marburgviruses including Marburg virus (MARV) and Ravn virus (RAVV).

Marburgvirus immunogens that can be used to induce broad immunity against multiple subtypes or serotypes of Marburgvirus. The antigen may be derived from a Marburg virus envelope glycoprotein.

(j) Zika Virus

The viral antigen may be from Zika virus. Zika disease is caused by infection with the Zika virus and can be transmitted to humans through the bite of infected mosquitoes or sexually transmitted between humans. The Zika antigen can include a Zika Virus Envelope protein, Zika Virus NS1 protein, or a Zika Virus Capsid protein.

A structurally modified DMAb may be specific for a Zika virus antigen. Exemplary structurally modified DMAbs specific for Zika virus include, but are not limited to, the structurally modified DMAbs listed in SEQ ID NO:63 through SEQ ID NO:106.

(2) Bacterial Antigens

The foreign antigen can be a bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-*Thermus*, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anaerobic bacterium. The bacterium can be an autotrophic bacterium or a heterotrophic bacterium. The bacterium can be a mesophile, a neutrophile, an extremophile, an acidophile, an alkaliphile, a thermophile, a psychrophile, an halophile, or an osmophile.

The bacterium can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani, Yersinia pestis, Bacillus anthraces*, methicillin-resistant *Staphylococcus aureus* (MRSA), or *Clostridium difficile*. The bacterium can be *Mycobacterium tuberculosis*.

(a) *Pseudomonas* Antigens

The bacterial antigen may be a *Pseudomonas* antigen. For example, in one embodiment, the antigen may be a *Pseudomonas aeruginosa* antigen, or fragment thereof, or variant thereof. The *Pseudomonas aeruginosa* antigen can be from a virulence factor. Virulence factors associated with *Pseudomonas aeruginosa* include, but are not limited to structural components, enzymes and toxins. A *Pseudomonas aeruginosa* virulence factor can be one of exopolysaccharide, Adhesin, lipopolysaccharide, Pyocyanin, Exotoxin A, Exotoxin S, Cytotoxin, Elastase, Alkaline protease, Phospholipase C, Rhamnolipid, and components of a bacterial secretion system.

In one embodiment, an *Pseudomonas* antigen is an extracellular polysaccharide (e.g. Alginate, Pel and Psl). In one embodiment, an antigen is one of polysaccharide synthesis locus (psl), a gene contained therein (e.g. pslA, pslB, pslC, pslD, pslE, pslF, pslG, pslH, pslI, pslJ, pslK, pslL, pslM, pslN and pslO), a protein or enzyme encoded therein (e.g. a glycosyl transferase, phosphomannose isomerase/GDP-D-mannose pyrophosphorylase, a transporter, a hydrolase, a polymerase, an acetylase, a dehydrogenase and a topoisomerase) or a product produced therefrom (e.g. Psl exopolysaccharide, referred to as "Psl").

In one embodiment, a *Pseudomonas* antigen is a component of a bacterial secretion system. Six different classes of secretion systems (types I through VI) have been described in bacteria, five of which (types I, II, II, V and VI) are found in gram negative bacteria, including *Pseudomonas aeruginosa*. In one embodiment, an antigen is one of a gene (e.g. an apr or has gene) or protein (e.g. AprD, AprE, AprF, HasD, HasE, HasF and HasR) or a secreted protein (e.g. AprA, AprX and HasAp) of a type I secretion system. In one embodiment, an antigen is one of a gene (e.g. xcpA/pilD, xphA, xqhA, xcpP to Q and xcpR to Z) or protein (e.g. GspC to M, GspAB, GspN, GspO, GspS, XcpT to XcpX, FppA) or a secreted protein (e.g. LasB, LasA, PlcH, PlcN, PlcB, CbpD, ToxA, PmpA, PrpL, LipA, LipC, PhoA, PsAP, LapA) of a type II secretion system. In one embodiment, an antigen is one of a gene (e.g. a psc, per, pop or exs gene) or protein (e.g. PscC, PscE to PscF, PscJ, PscN, PscP, PscW, PopB, PopD, PcrH and PcrV) or a secreted protein (e.g. ExoS, ExoT, ExoU and ExoY) of a type III secretion system. In one embodiment, an antigen is a regulator of a type III secretion system (e.g. ExsA and ExsC). In one embodiment, an antigen is one of a gene (e.g. estA) or protein (e.g. EstA, CupB3, CupB5 and LepB) or a secreted protein (e.g. EstA, LepA, and CupB5) of a type V secretion system. In one embodiment, an antigen is one of a gene (e.g. a HSI-I, HSI-II and HSI-III gene) or protein (e.g. Fha1, ClpV1, a VgrG protein or a Hcp protein) or a secreted protein (e.g. Hcpl) of a type VI secretion system.

(b) *Borrelia* Antigens

The bacterial antigen may be a *Borrelia* spp antigen, or fragment thereof, or variant thereof. The *Borrelia* spp antigen can be from any one of *Borrelia burgdorferi, Borrelia lusitaniae, Borrelia afzelii, Borrelia bissettii, Borreliella bavariensis, Borrelia chilensis, Borrelia garinii, Borrelia valaisiana, Borrelia spielmanii*, and *Borrelia finlandensis*.

The bacterial antigen may be a *Borrelia* spp antigen, or fragment thereof, or variant thereof. The *Borrelia* spp antigen can be from a bacterial product that allows a *Borrelia* spp to replicate or survive. Bacterial products that allow a *Borrelia* spp to replicate or survive include, but are not limited to structural components, enzymes and toxins. Such a product can be one of a lipoprotein, an outer surface protein, a product required for infectivity or persistence within vertebrate hosts, and a product involved in motility and chemotaxis.

In one embodiment, an antigen is a lipoprotein (e.g. BptA). In one embodiment, an antigen is an outer surface protein (e.g. OspA, OspB, and OspC). In one embodiment, an antigen is a product required for infectivity or persistence within vertebrate hosts (e.g. PncA, DbpA, DbpB, Bgp, P66 and VlsE).

(c) *Mycobacterium tuberculosis* Antigens

The bacterial antigen may be a *Mycobacterium tuberculosis* antigen (i.e., TB antigen or TB immunogen), or fragment thereof, or variant thereof. The TB antigen can be from the Ag85 family of TB antigens, for example, Ag85A and Ag85B. The TB antigen can be from the Esx family of TB antigens, for example, EsxA, EsxB, EsxC, EsxD, EsxE, EsxF, EsxH, EsxO, EsxQ, EsxR, EsxS, EsxT, EsxU, EsxV, and EsxW.

(3) Parasitic Antigens

The foreign antigen can be a parasite antigen or fragment or variant thereof. The parasite can be a protozoa, helminth, or ectoparasite. The helminth (i.e., worm) can be a flatworm (e.g., flukes and tapeworms), a thorny-headed worm, or a round worm (e.g., pinworms). The ectoparasite can be lice, fleas, ticks, and mites.

The parasite can be any parasite causing any one of the following diseases: Acanthamoeba keratitis, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

The parasite can be *Acanthamoeba, Anisakis, Ascaris lumbricoides*, Botfly, *Balantidium coli*, Bedbug, Cestoda (tapeworm), Chiggers, *Cochliomyia hominivorax, Entamoeba histolytica, Fasciola hepatica, Giardia lamblia*, Hookworm, *Leishmania, Linguatula serrata*, Liver fluke, *Loa loa, Paragonimus*—lung fluke, Pinworm, *Plasmodium falciparum, Schistosoma, Strongyloides stercoralis*, Mite, Tapeworm, *Toxoplasma gondii, Trypanosoma*, Whipworm, or *Wuchereria bancrofti*.

(a) Lyme Antigen

The foreign antigen may be a Lyme disease antigen. The antigen may be an outer-surface protein A antigen (OspA antigen), or fragment thereof, or variant thereof. The antigen can be from a parasite causing malaria. The Lyme disease is caused by the bacterium *Borrelia burgdorferi* and is transmitted to humans through the bite of infected *Ixodes scapularis* (Blacklegged tick or Deer tick).

(b) Malaria Antigen

The foreign antigen may be a malaria antigen (i.e., PF antigen or PF immunogen), or fragment thereof, or variant thereof. The antigen can be from a parasite causing malaria. The malaria causing parasite can be *Plasmodium falciparum*. The *Plasmodium falciparum* antigen can include the circumsporozoite (CS) antigen.

In some embodiments, the malaria antigen can be one of *P. falciparum* immunogens CS; LSA1; TRAP; CelTOS; and Ama1. The immunogens may be full length or immunogenic fragments of full length proteins.

In other embodiments, the malaria antigen can be TRAP, which is also referred to as SSP2. In still other embodiments, the malaria antigen can be CelTOS, which is also referred to as Ag2 and is a highly conserved *Plasmodium* antigen. In further embodiments, the malaria antigen can be Ama1, which is a highly conserved *Plasmodium* antigen. In some embodiments, the malaria antigen can be a CS antigen.

In other embodiments, the malaria antigen can be a fusion protein comprising a combination of two or more of the PF proteins set forth herein. For example, fusion proteins may comprise two or more of CS immunogen, ConLSA1 immunogen, ConTRAP immunogen, ConCelTOS immunogen, and ConAma1 immunogen linked directly adjacent to each other or linked with a spacer or one or more amino acids in between. In some embodiments, the fusion protein comprises two PF immunogens; in some embodiments the fusion protein comprises three PF immunogens, in some embodiments the fusion protein comprises four PF immunogens, and in some embodiments the fusion protein comprises five PF immunogens. Fusion proteins with two PF immunogens may comprise: CS and LSA1; CS and TRAP; CS and CelTOS; CS and Ama1; LSA1 and TRAP; LSA1 and CelTOS; LSA1 and Ama1; TRAP and CelTOS; TRAP and Ama1; or CelTOS and Ama1. Fusion proteins with three PF immunogens may comprise: CS, LSA1 and TRAP; CS, LSA1 and CelTOS; CS, LSA1 and Ama1; LSA1, TRAP and CelTOS; LSA1, TRAP and Ama1; or TRAP, CelTOS and Ama1. Fusion proteins with four PF immunogens may comprise: CS, LSA1, TRAP and CelTOS; CS, LSA1, TRAP and Ama1; CS, LSA1, CelTOS and Ama1; CS, TRAP, CelTOS and Ama1; or LSA1, TRAP, CelTOS and Ama1. Fusion proteins with five PF immunogens may comprise CS or CS-alt, LSA1, TRAP, CelTOS and Ama1.

(4) Fungal Antigens

The foreign antigen can be a fungal antigen or fragment or variant thereof. The fungus can be *Aspergillus* species, *Blastomyces dermatitidis, Candida* yeasts (e.g., *Candida albicans*), *Coccidioides, Cryptococcus neoformans, Cryptococcus gattii*, dermatophyte, *Fusarium* species, *Histoplasma capsulatum, Mucoromycotina, Pneumocystis jirovecii, Sporothrix schenckii, Exserohilum*, or *Cladosporium*.

b. Self Antigens

In some embodiments, the antigen is a self antigen. A self antigen may be a constituent of the subject's own body that is capable of stimulating an immune response. In some embodiments, a self antigen does not provoke an immune response unless the subject is in a disease state, e.g., an autoimmune disease.

Self antigens may include, but are not limited to, cytokines, antibodies against viruses such as those listed above including HIV and Dengue, antigens affecting cancer progression or development, and cell surface receptors or transmembrane proteins.

(1) WT-1

The self-antigen antigen can be Wilm's tumor suppressor gene 1 (WT1), a fragment thereof, a variant thereof, or a combination thereof. WT1 is a transcription factor containing at the N-terminus, a proline/glutamine-rich DNA-binding domain and at the C-terminus, four zinc finger motifs. WT1 plays a role in the normal development of the urogenital system and interacts with numerous factors, for example, p53, a known tumor suppressor and the serine protease HtrA2, which cleaves WT1 at multiple sites after treatment with a cytotoxic drug. Mutation of WT1 can lead to tumor or cancer formation, for example, Wilm's tumor or tumors expressing WT1.

(2) EGFR

The self-antigen may include an epidermal growth factor receptor (EGFR) or a fragment or variation thereof. EGFR (also referred to as ErbB-1 and HER1) is the cell-surface receptor for members of the epidermal growth factor family (EGF-family) of extracellular protein ligands. EGFR is a member of the ErbB family of receptors, which includes four closely related receptor tyrosine kinases: EGFR (ErbB-1), HER2/c-neu (ErbB-2), Her 3 (ErbB-3), and Her 4 (ErbB-4). Mutations affecting EGFR expression or activity could result in cancer.

The antigen may include an ErbB-2 antigen. Erb-2 (human epidermal growth factor receptor 2) is also known as Neu, HER2, CD340 (cluster of differentiation 340), or p185 and is encoded by the ERBB2 gene. Amplification or over-expression of this gene has been shown to play a role in the development and progression of certain aggressive types of breast cancer. In approximately 25-30% of women with breast cancer, a genetic alteration occurs in the ERBB2 gene, resulting in the production of an increased amount of HER2 on the surface of tumor cells. This overexpression of HER2 promotes rapid cell division and thus, HER2 marks tumor cells.

(3) Cocaine

The self-antigen may be a cocaine receptor antigen. Cocaine receptors include dopamine transporters.

(4) PD-1

The self-antigen may include programmed death 1 (PD-1). Programmed death 1 (PD-1) and its ligands, PD-L1 and PD-L2, deliver inhibitory signals that regulate the balance between T cell activation, tolerance, and immunopathology. PD-1 is a 288 amino acid cell surface protein molecule including an extracellular IgV domain followed by a transmembrane region and an intracellular tail.

(5) LAG-3

The self-antigen may include lymphocyte activation gene 3 (Lag-3 also known as CD223). LAG-3 is a member of the Ig superfamily that is expressed only on activated and tolerized T cells that binds MHC-II molecules and which is known to transduce inhibitory signals. LAG-3 is markedly upregulated on exhausted T cells compared to effector or memory T cells. LAG-3 negatively regulates T cell expansion by inhibiting T cell receptor induced calcium fluxes, thus controlling the size of the T cell memory pool in the context of cancer, LAG3 is unregulated on TILs and blockade of LAG-3 can enhance antitumor T cell immune responses. Blockage of LAG-3 in a viral chronic model that evokes CD8 T cells exhaustion, can invigorate the CD8 T cell responses.

(6) GITR

The self-antigen may include glucocorticoid-induced TNFR-related protein (GITR), also referred to as TNF receptor superfamily 18 (TNFRSF 18). GITR activation sends a co-activating signal to CD4+ and CD8+ T cells and prevents suppression of an immune response by regulatory T cells. Additionally, GITR-expressing effector T cells and regulatory T cells infiltrate multiple tumor types, yet there is little or no expression of GITR on non-hematopoetic cells. This distribution profile means that GITR-expressing cells can become concentrated at tumors. This combination of activities and distribution collectively makes GITR activation an attractive approach for treating a variety of cancers. The antigen binding proteins can be used to treat both solid tumors, as well as hematological cancers, including leukemia. n addition to use in treating cancer, in another embodiment, the antigen binding proteins that are provided can be used to induce or enhance an immune response against foreign antigens, such as those present on various infectious agents. Examples of antigens present on infectious agents against which an immune response can be generated include, but are not limited to proteins, glycoproteins, lipoproteins and glycolipids present on viruses, parasistes, bacteria, and other microorganisms.

(7) CD40

The self-antigen may include CD40. CD40 is a 55 kDa cell-surface antigen present on the surface of normal and neoplastic human B cells, dendritic cells, other antigen presenting cells (APCs), endothelial cells, monocytic cells, CD8+ T cells, epithelial cells, some epithelial carcinomas, and many solid tumors, including lung, breast, ovary, and colon cancers. Malignant B cells from several tumors of B-cell lineage express a high level of CD40 and appear to depend on CD40 signaling for survival and proliferation. Thus, transformed cells from patients with low- and high-grade B-cell lymphomas, B-cell acute lymphoblastic leukemia, multiple myeloma, chronic lymphocytic leukemia, and Hodgkin's disease express CD40. CD40 expression is also detected in two-thirds of acute myeloblastic leukemia cases and 50% of AIDS-related lymphomas.

(8) OX40

The self-antigen may include OX40. OX40 (also referred to as CD134) is a 50 kilodalton (KDa) glycoprotein and a member of the tumor necrosis factor receptor superfamily (TNFRSF). The ligand for OX40, OX40L (also referred to as TNFSF4, CD252), has been reported to be expressed on endothelial cells, activated antigen presenting cells including macrophages, dendritic cells, B cells and natural killer cells. Although not wishing to be bound by theory, binding between CD40 on antigen presenting cells increases OX40L expression as can lipopolysaccharide (LPS). Expression of OX40 on T cells can be induced following signaling via the T cell antigen receptor. For example, OX40 is expressed on recently activated T cells at the site of inflammation. CD4 and CD8 T cells can upregulate OX40 under inflammatory conditions.

(9) TIM-3

The self-antigen may include TIM-3. TIM-3 is a transmembrane receptor that is expressed on Th1 (T helper 1) CD4-T cells and cytotoxic CD8-T cells that secrete IFN-.gamma. TIM-3 is generally not expressed on naive T cells but rather unregulated on activated, effector T cells. TIM-3 has a role in regulating immunity and tolerance in vivo.

(10) 4-1BB

The self-antigen may include 4-1BB ligand. 4-1BB ligand is a type 2 transmembrane glycoprotein belonging to the TNF superfamily. 4-1BB ligand may be expressed on activated T Lymphocytes. 4-1BB is an activation-induced T-cell costimulatory molecule. Signaling via 4-1BB upregulates survival genes, enhances cell division, induces cytokine production, and prevents activation-induced cell death in T cells.

(11) CTLA4

The self-antigen may include CTLA-4 (Cytotoxic T-Lymphocyte Antigen 4), also known as CD152 (Cluster of differentiation 152). CTLA-4 is a protein receptor found on the surface of T cells, which lead the cellular immune attack on antigens. The antigen may be a fragment of CTLA-4, such as an extracellular V domain, a transmembrane domain, and a cytoplasmic tail, or combination thereof.

(12) IL-6

The self-antigen may include interleukin 6 (IL-6). IL-6 stimulates the inflammatory and auto-immune processes in many diseases including, but not limited to, diabetes, atherosclerosis, depression, Alzheimer's Disease, systemic lupus erythematosus, multiple myeloma, cancer, Behçet's disease, rheumatoid arthritis, sepsis, bacterial infection, viral infection, fungal infection, and the like.

(13) CD126

The self-antigen may include CD126. CD126 is the receptor for IL-6 and stimulates the inflammatory and autoimmune processes in many diseases including, but not limited to, diabetes, atherosclerosis, depression, Alzheimer's Disease, systemic lupus erythematosus, multiple myeloma, cancer, Beçhcet's disease, rheumatoid arthritis, sepsis, bacterial infection, viral infection, fungal infection, and the like.

(14) MCP-1

The self-antigen may include monocyte chemotactic protein-1 (MCP-1). MCP-1 is also referred to as chemokine (C-C motif) ligand 2 (CCL2) or small inducible cytokine A2. MCP-1 is a cytokine that belongs to the CC chemokine family. MCP-1 recruits monocytes, memory T cells, and dendritic cells to the sites of inflammation produced by either tissue injury or infection.

(15) Amyloid beta

The self-antigen may include amyloid beta (Aβ) or a fragment or a variant thereof. The Aβ antigen can comprise an Aβ(X-Y) peptide, wherein the amino acid sequence from amino acid position X to amino acid Y of the human sequence Aβ protein including both X and Y, in particular to the amino acid sequence from amino acid position X to amino acid position Y of the amino acid sequence corresponding to amino acid positions 1 to 47; the human query sequence (SEQ ID NO:62) or variants thereof. The Aβ antigen can comprise an polypeptide of Aβ(X-Y) polypeptide wherein X can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 and Y can be 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, or 15. The Aβ polypeptide can comprise a fragment that is at least 15, at least 16, at least 17, at least 18, at least 19, at least 20, at least 21, at least 22, at least 23, at least 24, at least 25, at least 30, at least 35, at least 36, at least 37, at least 38, at least 39, at least 40, at least 41, at least 42, at least 43, at least 44, at least 45, or at least 46 amino acids.

(16) IP-10

The self-antigen may include interferon (IFN)-gamma-induced protein 10 (IP-10). IP-10 is also known as small-inducible cytokine B10 or C-X-C motif chemokine 10 (CXCL10). CXCL10 is secreted by several cell types, such as monocytes, endothelial cells and fibroblasts, in response to IFN-γ.

(17) TERT

The self-antigen may include TERT (telomerase reverse transcriptase). TERT is a telomerase reverse transcriptase that synthesizes a TTAGGG tag on the end of telomeres to prevent cell death due to chromosomal shortening. Hyperproliferative cells with abnormally high expression of TERT may be targeted by immunotherapy. Recent studies demonstrate that TERT expression in dendritic cells transfected with TERT genes can induce CD8+ cytotoxic T cells and elicit a CD4+ T cells in an antigen-specific fashion.

(18) Tyrosinase

The self-antigen may include tyrosinase (Tyr). Tyr is an important target for immune mediated clearance by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as CD8+ (CTL) to attack and kill tumor cells; (3) increase T helper cell responses; (4) and increase inflammatory responses via IFN-γ and TFN-α or all of the aforementioned.

Tyrosinase is a copper-containing enzyme that can be found in plant and animal tissues. Tyrosinase catalyzes the production of melanin and other pigments by the oxidation of phenols such as tyrosine. In melanoma, tyrosinase can become unregulated, resulting in increased melanin synthesis. Tyrosinase is also a target of cytotoxic T cell recognition in subjects suffering from melanoma. Accordingly, tyrosinase can be an antigen associated with melanoma.

The antigen can comprise protein epitopes that make them particularly effective as immunogens against which anti-Tyr immune responses can be induced. The Tyr antigen can comprise the full length translation product, a variant thereof, a fragment thereof or a combination thereof.

The Tyr antigen can comprise a consensus protein. The Tyr antigen induces antigen-specific T-cell and high titer antibody responses both systemically against all cancer and tumor related cells. As such, a protective immune response is provided against tumor formation by vaccines comprising the Tyr consensus antigen. Accordingly, any user can design an immunogenic composition of the present invention to include a Tyr antigen to provide broad immunity against tumor formation, metastasis of tumors, and tumor growth. Proteins may comprise sequences homologous to the Tyr antigens, fragments of the Tyr antigens and proteins with sequences homologous to fragments of the Tyr antigens.

(19) NY-ESO-1

The self-antigen may include NY-ESO-1. NY-ESO-1 is a cancer-testis antigen expressed in various cancers where it can induce both cellular and humoral immunity. Gene expression studies have shown upregulation of the gene for NY-ESO-1, CTAG1B, in myxoid and round cell liposarcomas.

(20) MAGE

The self-antigen may include MAGE (Melanoma-associated Antigen). The MAGE antigen may include MAGE-A4 (melanoma associated antigen 4). NY-ESO-1 is a cancer-testis antigen expressed in various cancers where it can induce both cellular and humoral immunity. Gene expression studies have shown upregulation of the gene for NY-ESO-1, CTAG1B, in myxoid and round cell liposarcomas.

MAGE-A4 is expressed in male germ cells and tumor cells of various histological types such as gastrointestinal, esophageal and pulmonary carcinomas. MAGE-A4 binds the oncoprotein, Gankyrin. This MAGE-A4 specific binding is mediated by its C-terminus. Studies have shown that exogenous MAGE-A4 can partly inhibit the adhesion-independent growth of Gankyrin-overexpressing cells in vitro and suppress the formation of migrated tumors from these cells in nude mice. This inhibition is dependent upon binding between MAGE-A4 and Gankyrin, suggesting that interactions between Gankyrin and MAGE-A4 inhibit Gankyrin-mediated carcinogenesis. It is likely that MAGE expression in tumor tissue is not a cause, but a result of tumorgenesis, and MAGE genes take part in the immune process by targeting early tumor cells for destruction.

Melanoma-associated antigen 4 protein (MAGEA4) can be involved in embryonic development and tumor transformation and/or progression. MAGEA4 is normally expressed in testes and placenta. MAGEA4, however, can be expressed in many different types of tumors, for example, melanoma, head and neck squamous cell carcinoma, lung carcinoma, and breast carcinoma. Accordingly, MAGEA4 can be antigen associated with a variety of tumors.

The MAGEA4 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts.

The MAGEA4 antigen can comprise protein epitopes that make them particularly effective as immunogens against which anti-MAGEA4 immune responses can be induced. The MAGEA4 antigen can comprise the full length translation product, a variant thereof, a fragment thereof or a combination thereof.

(21) FSHR

The self-antigen may include FSHR (Follicle stimulating hormone receptor). FSHR is an antigen that is selectively expressed in women in the ovarian granulosa cells (Simoni et al., Endocr Rev. 1997, 18:739-773) and at low levels in the ovarian endothelium (Vannier et al., Biochemistry, 1996, 35:1358-1366). Most importantly, this surface antigen is expressed in 50-70% of ovarian carcinomas.

(22) Tumor Microenvironment Antigens

The self-antigen may include Tumor microenvironment antigen. Several proteins are overexpressed in the tumor microenvironment including, but not limited to, Fibroblast Activation Protein (FAP), Platelet Derived Growth Factor Receptor Beta (PDGFR-β), and Glypican-1 (GPC1). FAP is a membrane-bound enzyme with gelatinase and peptidase activity that is up-regulated in cancer-associated fibroblasts in over 90% of human carcinomas. PDGFR-β is a cell surface tyrosine kinase receptor that has roles in the regulation of many biological processes including embryonic development, angiogenesis, cell proliferation and differentiation. GPC1 is a cell surface proteoglycan that is enriched in cancer cells.

(23) PRAME

The self-antigen may include PRAME (Melanoma antigen preferentially expressed in tumors). PRAME is a protein that in humans is encoded by the PRAME gene. This gene encodes an antigen that is predominantly expressed in human melanomas and that is recognized by cytolytic T lymphocytes. It is not expressed in normal tissues, except testis. The gene is also expressed in acute leukemias. Five alternatively spliced transcript variants encoding the same protein have been observed for this gene. Proteins may comprise sequences homologous to the PRAME antigens, fragments of the PRAME antigens and proteins with sequences homologous to fragments of the PRAME antigens.

(24) Prostate Antigen

The self-antigen may include prostate antigens such as prostate-specific membrane antigen (PSMA), PSA antigen, STEAP antigen, PSCA antigen, Prostatic acid phosphatase (PAP) antigen, and other known prostate tumor antigens. PSMA is also known as glutamate carboxypeptidase II (GCPII), N-acetyl-L-aspartyl-L-glutamate peptidase I (NAALADase I), NAAG peptidase, or folate hydrolase (FOLH). PMSA is an integral membrane protein highly expressed by prostate cancer cells.

In some embodiments, the recombinant nucleic acid sequence encoding an antibody directed against PSMA (anti-PSMA antibody) may be a recombinant nucleic acid sequence including a recombinant nucleic acid sequence construct in arrangement 2.

In still other embodiments, the anti-PSMA antibody encoded by the recombinant nucleic acid sequence may be modified as described herein. One such modification is a defucosylated antibody, which as demonstrated in the Examples, exhibited increased ADCC activity as compared to commercial antibodies. The modification may be in the heavy chain, light chain, or a combination thereof. The modification may be one or more amino acid substitutions in the heavy chain, one or more amino acid substitutions in the light chain, or a combination thereof

(25) Tumor Antigen

The self-antigen may include a tumor antigen. In the context of the present invention, "tumor antigen" or "hyperproliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RUL RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/ MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

c. Other Antigens

In some embodiments, the antigen is an antigen other than a foreign antigen and/or a self-antigen. Exemplary other antigens include, but are not limited to:

(a) HIV-1 VRC01

The other antigen can be HIV-1 VRC01. HIV-1 VCR01 is a neutralizing CD4-binding site-antibody for HIV. HIV-1 VCR01 contacts portions of HIV-1 including within the gp120 loop D, the CD4 binding loop, and the V5 region of HIV-1.

(b) HIV-1 PG9

The other antigen can be HIV-1 PG9. HIV-1 PG9 is the founder member of an expanding family of glycan-dependent human antibodies that preferentially bind the HIV (HIV-1) envelope (Env) glycoprotein (gp) trimer and broadly neutralize the virus.

(c) HIV-1 4E10

The other antigen can be HIV-1 4E10. HIV-1 4E10 is a neutralizing anti-HIV antibody. HIV-1 4E10 is directed against linear epitopes mapped to the membrane-proximal external region (MPER) of HIV-1, which is located at the C terminus of the gp41 ectodomain.

(d) DV-SF1

The other antigen can be DV-SF1. DV-SF1 is a neutralizing antibody that binds the envelope protein of the four Dengue virus serotypes.

(e) DV-SF2

The other antigen can be DV-SF2. DV-SF2 is a neutralizing antibody that binds an epitope of the Dengue virus. DV-SF2 can be specific for the DENV4 serotype.

(f) DV-SF3

The other antigen can be DV-SF3. DV-SF3 is a neutralizing antibody that binds the EDIII A strand of the Dengue virus envelope protein.

6. NUCLEIC ACID VACCINE

A composition comprising a nucleic acid molecule comprising a nucleotide sequence encoding a structurally modified DMAb, a fragment thereof, a variant thereof, or a combination thereof can be administered alone or in combination to a subject in need thereof to facilitate in vivo expression and formation of an engineered DNA encoded synthetic antibody.

In one embodiment, the composition of the invention can be administered in combination with a composition that elicits an immune response in a mammal against an antigen. In one embodiment, the composition of the invention can be administered in combination with a nucleic acid encoding one or more antigens. In one embodiment, the first composition comprises a DNA vaccine.

In one embodiment, the combination of the invention comprises at least two nucleic acid molecules encoding at least two structurally modified dMAbs, wherein each dMAb targets a different antigen. For example, in one embodiment, each dMAb targets a different viral antigen of a single virus. In another embodiment, each dMAb targets a viral antigen of a different virus. In yet another embodiment, each dMAb targets a different self antigen.

In one embodiment, the combination vaccine of the invention comprises at least 2, at least 3, at least 4, at least 5, at least 6, or more than 6 nucleic acid molecules encoding at least two structurally modified dMAbs, wherein each dMAb targets a different antigen. The antigen can be a nucleic acid sequence, an amino acid sequence, a polysaccharide or a combination thereof. The nucleic acid sequence can be DNA, RNA, cDNA, a variant thereof, a fragment thereof, or a combination thereof. The amino acid sequence can be a protein, a peptide, a variant thereof, a fragment thereof, or a combination thereof. The polysaccharide can be a nucleic acid encoded polysaccharide.

In one embodiment, the immunogenic composition of the invention comprises at least two nucleic acid molecules encoding at least two structurally modified dMAbs, wherein each dMAb targets a different antigen, wherein each antigen is an antigen of a different virus. In one embodiment, the combination vaccine of the invention comprises at least 3, at least 4, at least 5, at least 6, or more than 6 nucleic acid molecules encoding at least 2, at least 3, at least 4, at least 5, at least 6 or more than 6 dMAbs, wherein the encoded dMABs target antigens from at least 2, at least 3, at least 4, at least 5, at least 6, or more than 6 different viruses.

The present invention relates to a composition comprising a recombinant nucleic acid sequence encoding a structurally modified DMAb, a fragment thereof, a variant thereof, or a combination thereof. The composition, when administered to a subject in need thereof, can result in the generation of a structurally modified DMAb in the subject. The synthetic antibody can bind a target molecule (i.e., an antigen) present in the subject. Such binding can neutralize the antigen, block recognition of the antigen by another molecule, for example, a protein or nucleic acid, and elicit or induce an immune response to the antigen.

The structurally modified DMAb can treat, prevent, and/ or protect against disease in the subject administered the composition. The structurally modified DMAb, by binding the antigen, can treat, prevent, and/or protect against disease in the subject administered the composition. The structurally modified DMAb can promote survival of the disease in the subject administered the composition. In one embodiment, the structurally modified DMAb can provide increased survival of the disease in the subject over the expected survival of a subject having the disease who has not been administered the structurally modified DMAb. In various embodiments, the structurally modified DMAb can provide at least about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, or a greater than 100% increase in survival of the disease in subjects administered the composition over the expected survival in the absence of the composition. In one embodiment, the structurally modified DMAb can provide increased protection against the disease in the subject over the expected protection of a subject who has not been administered the structurally modified DMAb. In various embodiments, the structurally modified DMAb can protect against disease in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of subjects administered the composition over the expected protection in the absence of the composition.

The composition can result in the generation of the structurally modified DMAb in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the structurally modified DMAb in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the generation of the structurally modified DMAb in the subject more quickly than the generation of an endogenous antibody in a subject who is administered an antigen to induce a humoral immune response. The composition can result in the generation of the structurally modified DMAb at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

In one embodiment, the method relates to administration of a first composition comprising a nucleic acid molecule encoding a structurally modified DMAb in combination with a second composition comprising a nucleic acid molecule encoding a second structurally modified DMAb. A first composition and a second composition may be administered concurrently or in any order. In one embodiment, a first composition and second composition are administered concurrently at different injection sites.

In one embodiment, the method relates to administration of a single composition comprising one or more nucleic acid molecules encoding two or more structurally modified DMAb. In such an embodiment, the two or more DMAbs may be encoded on a single nucleic acid molecule, or on separate nucleic acid molecules which are combined into a single composition for administration.

In one embodiment, the method relates to administration of one or more nucleic acid molecules encoding one or more structurally modified DMAb in combination with a nucleic acid vaccines that is capable of generating in a mammal an immune response against an antigen. In one embodiment, the nucleic acid vaccine comprises at least one nucleic acid molecule capable of expressing a consensus antigen in the mammal and a pharmaceutically acceptable excipient. In one embodiment, the nucleic acid molecule comprises a promoter operably linked to a coding sequence that encodes the consensus antigen.

In some embodiments, the nucleic acid molecule comprises an encoding sequence that encodes for an antigen. In some embodiments, the nucleic acid molecule includes an encoding sequence that encodes for an antigen operably linked to an IgE leader sequence on the N-terminal end of the coding sequence.

The nucleic acid molecule can further include a polyadenylation sequence attached to the C-terminal end of the coding sequence. In one embodiment, the nucleic acid molecule is codon optimized.

In some embodiments, the pharmaceutically acceptable excipient is an adjuvant. In one embodiment, the adjuvant is selected from the group consisting of: IL-12 and IL-15. In some embodiments, the pharmaceutically acceptable excipient is a transfection facilitating agent. In one embodiment, the transfection facilitating agent is a polyanion, polycation, or lipid, and more preferably poly-L-glutamate. In one embodiment, the poly-L-glutamate is at a concentration less than 6 mg/ml. In one embodiment, the nucleic acid vaccine has a concentration of total nucleic acid of 1 mg/ml or greater.

In some embodiments, the nucleic acid vaccine comprises a plurality of unique DNA plasmids, wherein each of the plurality of unique DNA plasmids encodes a polypeptide comprising a consensus antigen.

In some embodiments of the present invention, the nucleic acid vaccine can further include an adjuvant. In some embodiments, the adjuvant is selected from the group consisting of: alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. Other genes which may be useful adjuvants include those encoding: MCP-1, MIP-1-alpha, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. In some preferred embodiments, the adjuvant is selected from IL-12, IL-15, CTACK, TECK, or MEC.

In some embodiments, methods of eliciting an immune response in mammals against a consensus antigen include methods of inducing mucosal immune responses. Such methods include administering to the mammal one or more of CTACK protein, TECK protein, MEC protein and functional fragments thereof or expressible coding sequences thereof in combination with a DNA plasmid including a consensus antigen, described above. The one or more of CTACK protein, TECK protein, MEC protein and functional fragments thereof may be administered prior to, simultaneously with or after administration of the nucleic acid vaccine provided herein. In some embodiments, an isolated nucleic acid molecule that encodes one or more proteins of selected from the group consisting of: CTACK, TECK, MEC and functional fragments thereof is administered to the mammal.

The composition of the present invention can have features required of effective compositions such as being safe so that the composition does not cause illness or death; being protective against illness; and providing ease of administration, few side effects, biological stability and low cost per dose.

As described above, the composition can comprise immunogenic compositions, such as vaccines, comprising one or more antigens. The vaccine can be used to protect against any number of antigens, thereby treating, preventing, and/or protecting against antigen based pathologies. The vaccine can significantly induce an immune response of a subject administered the vaccine, thereby protecting against and treating infection by the antigen.

The vaccine can be a DNA vaccine, a peptide vaccine, or a combination DNA and peptide vaccine. The DNA vaccine can include a nucleic acid sequence encoding the antigen. The nucleic acid sequence can be DNA, RNA, cDNA, a variant thereof, a fragment thereof, or a combination thereof. The nucleic acid sequence can also include additional sequences that encode linker, leader, or tag sequences that are linked to the antigen by a peptide bond. The peptide vaccine can include a antigenic peptide, a antigenic protein, a variant thereof, a fragment thereof, or a combination thereof. The combination DNA and peptide vaccine can include the above described nucleic acid sequence encoding the antigen and the antigenic peptide or protein, in which the antigenic peptide or protein and the encoded antigen have the same amino acid sequence.

The vaccine can induce a humoral immune response in the subject administered the vaccine. The induced humoral immune response can be specific for the antigen. The induced humoral immune response can be reactive with the antigen. The humoral immune response can be induced in the subject administered the vaccine by about 1.5-fold to about 16-fold, about 2-fold to about 12-fold, or about 3-fold to about 10-fold. The humoral immune response can be induced in the subject administered the vaccine by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold.

The humoral immune response induced by the vaccine can include an increased level of neutralizing antibodies associated with the subject administered the vaccine as compared to a subject not administered the vaccine. The neutralizing antibodies can be specific for the antigen. The neutralizing antibodies can be reactive with the antigen. The neutralizing antibodies can provide protection against and/or treatment of infection and its associated pathologies in the subject administered the vaccine.

The humoral immune response induced by the vaccine can include an increased level of IgG antibodies associated with the subject administered the vaccine as compared to a subject not administered the vaccine. These IgG antibodies can be specific for the antigen. These IgG antibodies can be reactive with the antigen. Preferably, the humoral response is cross-reactive against two or more strains of the antigen. The level of IgG antibody associated with the subject administered the vaccine can be increased by about 1.5-fold to about 16-fold, about 2-fold to about 12-fold, or about 3-fold to about 10-fold as compared to the subject not administered the vaccine. The level of IgG antibody associated with the subject administered the vaccine can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to the subject not administered the vaccine.

The vaccine can induce a cellular immune response in the subject administered the vaccine. The induced cellular immune response can be specific for the antigen. The induced cellular immune response can be reactive to the antigen. Preferably, the cellular response is cross-reactive against two or more strains of the antigen. The induced cellular immune response can include eliciting a $CD8^+$ T cell response. The elicited $CD8^+$ T cell response can be reactive with the antigen. The elicited $CD8^+$ T cell response can be polyfunctional. The induced cellular immune response can include eliciting a $CD8^+$ T cell response, in which the $CD8^+$ T cells produce interferon-gamma (IFN-$\gamma$), tumor necrosis factor alpha (TNF-$\alpha$), interleukin-2 (IL-2), or a combination of IFN-$\gamma$ and TNF-$\alpha$.

The induced cellular immune response can include an increased $CD8^+$ T cell response associated with the subject administered the vaccine as compared to the subject not administered the vaccine. The $CD8^+$ T cell response associated with the subject administered the vaccine can be increased by about 2-fold to about 30-fold, about 3-fold to about 25-fold, or about 4-fold to about 20-fold as compared to the subject not administered the vaccine. The $CD8^+$ T cell response associated with the subject administered the vaccine can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to the subject not administered the vaccine.

The induced cellular immune response can include an increased frequency of CD3$^+$CD8$^+$ T cells that produce IFN-$\gamma$. The frequency of CD3$^+$CD8$^+$IFN-$\gamma^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the vaccine.

The induced cellular immune response can include an increased frequency of CD3$^+$CD8$^+$ T cells that produce TNF-$\alpha$. The frequency of CD3$^+$CD8$^+$TNF-$\alpha^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to the subject not administered the vaccine.

The induced cellular immune response can include an increased frequency of CD3$^+$CD8$^+$ T cells that produce IL-2. The frequency of CD3$^+$CD8$^+$IL-2$^+$ T cells associated with the subject administered the vaccine can be increased by at least about 0.5-fold, 1.0-fold, 1.5-fold, 2.0-fold, 2.5-fold, 3.0-fold, 3.5-fold, 4.0-fold, 4.5-fold, or 5.0-fold as compared to the subject not administered the vaccine.

The induced cellular immune response can include an increased frequency of CD3$^+$CD8$^+$ T cells that produce both IFN-$\gamma$ and TNF-$\alpha$. The frequency of CD3$^+$CD8$^+$IFN-$\gamma^+$TNF-$\alpha^+$ T cells associated with the subject administered the vaccine can be increased by at least about 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 110-fold, 120-fold, 130-fold, 140-fold, 150-fold, 160-fold, 170-fold, or 180-fold as compared to the subject not administered the vaccine.

The cellular immune response induced by the vaccine can include eliciting a CD4$^+$ T cell response. The elicited CD4$^+$ T cell response can be reactive with the desired antigen. The elicited CD4$^+$ T cell response can be polyfunctional. The induced cellular immune response can include eliciting a CD4$^+$ T cell response, in which the CD4$^+$ T cells produce IFN-$\gamma$, TNF-$\alpha$, IL-2, or a combination of IFN-$\gamma$ and TNF-$\alpha$.

The induced cellular immune response can include an increased frequency of CD3$^+$CD4$^+$ T cells that produce IFN-$\gamma$. The frequency of CD3$^+$CD4$^+$IFN-$\gamma^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the vaccine.

The induced cellular immune response can include an increased frequency of CD3$^+$CD4$^+$ T cells that produce TNF-$\alpha$. The frequency of CD3$^+$CD4$^+$TNF-$\alpha^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to the subject not administered the vaccine.

The induced cellular immune response can include an increased frequency of CD3$^+$CD4$^+$ T cells that produce IL-2. The frequency of CD3$^+$CD4$^+$IL-2$^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 45-fold, 50-fold, 55-fold, or 60-fold as compared to the subject not administered the vaccine.

The induced cellular immune response can include an increased frequency of CD3$^+$CD4$^+$ T cells that produce both IFN-$\gamma$ and TNF-$\alpha$. The frequency of CD3$^+$CD4$^+$IFN-$\gamma^+$TNF-$\alpha^+$ associated with the subject administered the vaccine can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to the subject not administered the vaccine.

The vaccine of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The vaccine can further induce an immune response when administered to different tissues such as the muscle or skin. The vaccine can further induce an immune response when administered via electroporation, or injection, or subcutaneously, or intramuscularly.

Vaccine Constructs and Plasmids

The vaccine can comprise nucleic acid constructs or plasmids that encode the one or more antigens. The nucleic acid constructs or plasmids can include or contain one or more heterologous nucleic acid sequences. Provided herein are genetic constructs that can comprise a nucleic acid sequence that encodes the antigens. The genetic construct can be present in the cell as a functioning extrachromosomal molecule. The genetic construct can be a linear minichromosome including centromere, telomeres or plasmids or cosmids. The genetic constructs can include or contain one or more heterologous nucleic acid sequences.

The genetic constructs can be in the form of plasmids expressing the antigen in any order.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer an initiation codon, a stop codon, or a polyadenylation signal.

The nucleic acid sequences can make up a genetic construct that can be a vector. The vector can be capable of expressing the antigen in the cell of a mammal in a quantity effective to elicit an immune response in the mammal. The vector can be recombinant. The vector can comprise heterologous nucleic acid encoding the antigen. The vector can be a plasmid. The vector can be useful for transfecting cells with nucleic acid encoding the antigen, which the transformed host cell is cultured and maintained under conditions wherein expression of the antigen takes place.

Coding sequences can be optimized for stability and high levels of expression. In some instances, codons are selected to reduce secondary structure formation of the RNA such as that formed due to intramolecular bonding.

The vector can comprise heterologous nucleic acid encoding the antigens and can further comprise an initiation codon, which can be upstream of the one or more cancer antigen coding sequence(s), and a stop codon, which can be downstream of the coding sequence(s) of the antigen. The initiation and termination codon can be in frame with the coding sequence(s) of the antigen. The vector can also comprise a promoter that is operably linked to the coding sequence(s) of the antigen. The promoter operably linked to the coding sequence(s) of the antigen can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the coding sequence(s) of the antigen. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, CA).

The vector can also comprise an enhancer upstream of the antigen. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, CA), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad CA). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

Based upon the sequence of pVAX1 available from Invitrogen, the following mutations were found in the sequence of pVAX1 that was used as the backbone for plasmids 1-6 set forth herein:

C>G241 in CMV promoter
C>T1942 backbone, downstream of the bovine growth hormone polyadenylation signal (bGHpolyA)
A>−2876 backbone, downstream of the Kanamycin gene
C>T3277 in pUC origin of replication (Ori) high copy number mutation (see Nucleic Acid Research 1985)
G>C 3753 in very end of pUC Ori upstream of RNASeH site Base pairs 2, 3 and 4 are changed from ACT to CTG in backbone, upstream of CMV promoter.

The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The one or more cancer antigen sequences disclosed herein can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which maybe used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

7. EXCIPIENTS AND OTHER COMPONENTS OF THE COMPOSITION

The composition may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The composition may further comprise a genetic facilitator agent.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

8. METHODS OF GENERATING A NUCLEIC ACID MOLECULE ENCODING A STRUCTURALLY MODIFIED DMAB

There are multiple engineering strategies that can be used to arrive at an engineered DMAb of the invention.

Full Grafting of DMAbs

In one embodiment, a structurally modified DMAb is generated by full grafting. In one embodiment, the method of full grafting comprises transposing the CDR regions of the variable light and variable heavy chain of the parental DMAb onto the framework of higher expressing DMAb. In one embodiment, a nucleic acid sequence encoding a structurally modified DMAb is generated from an amino acid sequence of a full graft DMAb.

In one embodiment, the nucleic acid sequence is optimized. Optimization can include one or more of the following: addition of a low GC content leader sequence to increase transcription; mRNA stability and codon optimization; addition of a kozak sequence (e.g., GCC ACC) for increased translation; addition of an IRES sequence for increased translation; addition of a WPRE sequence for increased transcription; addition of an immunoglobulin (Ig) leader sequence encoding a signal peptide; and eliminating to the extent possible cis-acting sequence motifs (i.e., internal TATA boxes).

In one embodiment, a nucleic acid molecule is generated comprising the optimized nucleic acid sequence encoding the structurally modified DMAb. Any method for generating a nucleic acid molecule can be used to generate nucleic acid molecules encoding structurally modified DMAbs of the invention. Methods of generating nucleic acid molecules comprising specific nucleotide sequences are generally known in the art.

Partial Grafting of DMAbs

In one embodiment, a structurally modified DMAb is generated by partial grafting. In one embodiment, the method of partial grafting comprises one or more of structurally alignment and comparative modeling of potential modifications. In one embodiment, the parental DMAb VL domain sequence is aligned to the VL domain of one or more validated highly expressed scaffold VL sequences. In one embodiment, comparative modeling is performed on multiple potential partial graft sequences comprising mutations that are predicted through structural super-positioning of the VL domains. In one embodiment, the method of comparative modeling includes at least one of energy minimization analysis, interface analysis, sequence property prediction, and Ramachandran analysis. A candidate partial graft DMAb is one with favorable predicted characteristics (e.g., improved stability).

In one embodiment, a nucleic acid sequence encoding a structurally modified DMAb is generated from the predicted partial graft DMAb amino acid sequence. In one embodiment, a nucleic acid sequence encoding a structurally modified DMAb is further optimized, and a nucleic acid molecule is generated comprising the optimized nucleic acid sequence encoding the structurally modified DMAb.

Scaffold Modification

In one embodiment, a structurally modified DMAb is generated by scaffold modification. In one embodiment, the method of scaffold modification comprises making one or more specific amino acid changes to the amino acid sequence of a parental DMAb to generate a structurally modified DMAb of the invention. In one embodiment, the specific amino acid changes improve at least one of stability, the heavy and light chain interface, and secretion of the structurally modified DMAb as compared to the parental DMAb. In one embodiment, the specific amino acid changes decrease aggregation of DMAbs based on variable chain interface, Pi interactions, isoelectric point, and Ramachandran analysis of the structurally modified DMAb as compared to the parental DMAb. In one embodiment, one or more specific amino acid changes are made to result in isoelectric point modification, alterations in VH-VL interface interactions or a combination thereof.

In one embodiment, a nucleic acid sequence encoding a structurally modified DMAb is generated from the modified amino acid sequence. In one embodiment, a nucleic acid sequence encoding a structurally modified DMAb is further optimized, and a nucleic acid molecule is generated comprising the optimized nucleic acid sequence encoding the structurally modified DMAb.

ScFv-Fc Structurally Modified DMAbs

In one embodiment, a parental DMAb showing low expression undergoes one or more rounds of scFv modeling. In various embodiments, ScFv modeling includes at least one of linker modeling, hinge modification modeling, framework modeling, and CDR loop refinement. In various embodiments, modeling is performed on a DMAb sequence in at least one of VH-linker-VL and VL-linker-VH formats. In one embodiment, multiple rounds of modeling are performed with various input sequences until a variant is predicted where the linker does not obscure or minimally impacts the CDRs. For example, in one embodiment, the linker of a predicted variant is predicted to obscure one or more of the CDRs, therefore another round of ScFv modeling is conducted using a new linker sequence. In one embodiment, a new linker may be longer, shorter, or have a different amino acid sequence than the previously modeled linker. In one embodiment, following one or more rounds of ScFv modeling, an analysis is conducted on the predicted structure to determine whether the predicted DMAb is a candidate for further development. For example, in one embodiment, a RMSD analysis of the region near the linker fusion sites is performed. In one embodiment, a predicted DMAb with minimal obscurity of the CDRs by the linker is selected for as a candidate DMAb. In one embodiment, a predicted DMAb with a low predicted RMSD near the linker fusion sites is selected as a candidate DMAb.

In one embodiment, a nucleic acid molecule encoding a candidate variant is optimized. In one embodiment, optimization is performed on a nucleotide sequence encoding each of the VH, linker and VL sequences individually (i.e., modular optimization of the nucleotide sequence). In one embodiment, optimization is performed on a nucleotide sequence encoding VH-linker-VL as a single nucleotide sequence. In one embodiment, optimization is performed on a nucleotide sequence encoding VL-linker-VH as a single nucleotide sequence.

In one embodiment, a nucleic acid molecule encoding a structurally modified DMAb is generated. In one embodiment, the nucleic acid molecule comprises an optimized nucleic acid sequence encoding a structurally modified DMAb.

In one embodiment, the expression level and antigen binding of the structurally modified DMAb are then compared to that of the parental DMAb. In one embodiment, a structurally modified DMAb having greater expression than the parental DMAb, and still showing antigen binding, is then further tested for in vivo expression and ability to generate an immune response in a subject.

9. METHOD OF GENERATING THE SYNTHETIC ANTIBODY

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

10. METHOD OF IDENTIFYING OR SCREENING FOR THE ANTIBODY

The present invention further relates to a method of identifying or screening for the antibody described above, which is reactive to or binds the antigen described above. The method of identifying or screening for the antibody can use the antigen in methodologies known in those skilled in art to identify or screen for the antibody. Such methodologies can include, but are not limited to, selection of the antibody from a library (e.g., phage display) and immunization of an animal followed by isolation and/or purification of the antibody.

11. METHOD OF DELIVERY OF THE COMPOSITION

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

a. Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, PA) or Elgen electroporator (Inovio Pharmaceuticals, Plymouth Meeting, PA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

12. METHOD OF TREATMENT

Also provided herein is a method of treating, protecting against, and/or preventing disease in a subject in need thereof by generating a structurally modified DMAb in the subject. The method can include administering the composition to the subject. Administration of the composition to the subject can be done using the method of delivery described above.

Upon generation of the structurally modified DMAb in the subject, the synthetic antibody can bind to or react with the antigen. Such binding can neutralize the antigen, block recognition of the antigen by another molecule, for example, a protein or nucleic acid, and elicit or induce an immune response to the antigen, thereby treating, protecting against, and/or preventing the disease associated with the antigen in the subject.

The method of delivering the vaccine or vaccination may be provided to induce a therapeutic and prophylactic immune response. The vaccination process may generate in the mammal an immune response against the antigen. The vaccine may be delivered to an individual to modulate the activity of the mammal's immune system and enhance the immune response. The delivery of the vaccine may be the transfection of the consensus antigen as a nucleic acid molecule that is expressed in the cell and delivered to the surface of the cell upon which the immune system recognized and induces a cellular, humoral, or cellular and humoral response. The delivery of the vaccine may be used to induce or elicit and immune response in mammals against the antigen by administering to the mammals the vaccine as discussed above.

The composition dose can be between 1 µg to 10 mg active component/kg body weight/time, and can be 20 µg to 10 mg component/kg body weight/time. The composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of composition doses for effective treatment can be 1, 2, 3, 4, 5, 6, 7, 8, 9, or 10.

The composition can comprise 1 or more, 2 or more, 3 or more, 4 or more, 5 or more, 6 or more, 7 or more, 8 or more, 9 or more, or 10 or more DNA vaccines encoding an antigen. The composition may comprise 1 or more, 2 or more, 3 or more, 4 or more, 5 or more, 6 or more, 7 or more, 8 or more, 9 or more, or 10 or more structurally modified DMAbs or fragments thereof.

The DNA vaccine and the nucleic acid molecule encoding a structurally modified DMAb may be administered at the same time or at different times. In one embodiment, the DNA vaccine and the nucleic acid molecule encoding a structurally modified DMAb are administered simultaneously. In one embodiment, the DNA vaccine is administered before the nucleic acid molecule encoding a structurally modified DMAb. In one embodiment, the nucleic acid molecule encoding a structurally modified DMAb is administered before the DNA vaccine.

In certain embodiments, the DNA vaccine is administered 1 or more days, 2 or more days, 3 or more days, 4 or more days, 5 or more days, 6 or more days, 7 or more days, 8 or more days, 9 or more days, 10 or more days, 11 or more days, 12 or more days, 13 or more days, or 14 or more days after the nucleic acid molecule encoding a structurally modified DMAb is administered. In certain embodiments, the DNA vaccine is administered 1 or more weeks, 2 or more weeks, 3 or more weeks, 4 or more weeks, 5 or more weeks, 6 or more weeks, 7 or more weeks, 8 or more weeks, 9 or more weeks, or 10 or more weeks after the nucleic acid molecule encoding a structurally modified DMAb is administered. In certain embodiments, the DNA vaccine is administered 1 or more months, 2 or more months, 3 or more months, 4 or more months, 5 or more months, 6 or more months, 7 or more months, 8 or more months, 9 or more months, 10 or more months, 11 or more months, or 12 or more months after the nucleic acid molecule encoding a structurally modified DMAb is administered.

In certain embodiments, the nucleic acid molecule encoding a structurally modified DMAb is administered 1 or more days, 2 or more days, 3 or more days, 4 or more days, 5 or more days, 6 or more days, 7 or more days, 8 or more days, 9 or more days, 10 or more days, 11 or more days, 12 or more days, 13 or more days, or 14 or more days after the DNA vaccine is administered. In certain embodiments, the nucleic acid molecule encoding a structurally modified DMAb is administered 1 or more weeks, 2 or more weeks, 3 or more weeks, 4 or more weeks, 5 or more weeks, 6 or more weeks, 7 or more weeks, 8 or more weeks, 9 or more weeks, or 10 or more weeks after the DNA vaccine is administered. In certain embodiments, the nucleic acid molecule encoding a structurally modified DMAb is administered 1 or more months, 2 or more months, 3 or more months, 4 or more months, 5 or more months, 6 or more months, 7 or more months, 8 or more months, 9 or more months, 10 or more months, 11 or more months, or 12 or more months after the DNA vaccine is administered.

In certain embodiments, the nucleic acid molecule encoding a structurally modified DMAb and DNA vaccine are administered once. In certain embodiments, the nucleic acid molecule encoding a structurally modified DMAb and/or the DNA vaccine are administered more than once. In certain embodiments, administration of the nucleic acid molecule encoding a structurally modified DMAb and DNA vaccine provides a persistent and systemic immune response.

13. USE IN COMBINATION WITH ANTIBIOTICS

The present invention also provides a method of treating, protecting against, and/or preventing disease in a subject in need thereof by administering a combination of the structurally modified DMAb and a therapeutic antibiotic agent.

The structurally modified DMAb and an antibiotic agent may be administered using any suitable method such that a combination of the structurally modified DMAb and antibiotic agent are both present in the subject. In one embodiment, the method may comprise administration of a first composition comprising a nucleic acid molecule encoding a structurally modified DMAb of the invention by any of the methods described in detail above and administration of a second composition comprising an antibiotic agent less than 1, less than 2, less than 3, less than 4, less than 5, less than 6, less than 7, less than 8, less than 9 or less than 10 days following administration of the synthetic antibody. In one embodiment, the method may comprise administration of a first composition comprising a nucleic acid molecule encoding a structurally modified DMAb of the invention by any of the methods described in detail above and administration of a second composition comprising an antibiotic agent more than 1, more than 2, more than 3, more than 4, more than 5, more than 6, more than 7, more than 8, more than 9 or more than 10 days following administration of the synthetic antibody. In one embodiment, the method may comprise administration of a first composition comprising an antibiotic agent and administration of a second composition comprising a nucleic acid molecule encoding a structurally modified DMAb of the invention by any of the methods described in detail above less than 1, less than 2, less than 3, less than 4, less than 5, less than 6, less than 7, less than 8, less than 9 or less than 10 days following administration of the antibiotic agent. In one embodiment, the method may comprise administration of a first composition comprising an antibiotic agent and administration of a second composition comprising a nucleic acid molecule encoding a structurally modified DMAb of the invention by any of the methods described in detail above more than 1, more than 2, more than 3, more than 4, more than 5, more than 6, more than 7, more than 8, more than 9 or more than 10 days following administration of the antibiotic agent. In one embodiment, the method may comprise administration of a first composition comprising a nucleic acid molecule encoding a structurally modified DMAb of the invention by any of the methods described in detail above and a second composition comprising an antibiotic agent concurrently. In one embodiment, the method may comprise administration of a single composition comprising a nucleic acid molecule encoding a structurally modified DMAb of the invention and an antibiotic agent.

Non-limiting examples of antibiotics that can be used in combination with the synthetic antibody of the invention include aminoglycosides (e.g., gentamicin, amikacin, tobramycin), quinolones (e.g., ciprofloxacin, levofloxacin), cephalosporins (e.g., ceftazidime, cefepime, cefoperazone, cefpirome, ceftobiprole), antipseudomonal penicillins: carboxypenicillins (e.g., carbenicillin and ticarcillin) and ureidopenicillins (e.g., mezlocillin, azlocillin, and piperacillin), carbapenems (e.g., meropenem, imipenem, doripenem), polymyxins (e.g., polymyxin B and colistin) and monobactams (e.g., aztreonam).

The present invention has multiple aspects, illustrated by the following non-limiting examples.

14. EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: Grafting and Scaffold Modification

DNA vector-encoded monoclonal antibodies (DMAbs) offer a means to generate in vivo mAbs by using electroporation (EP) to transfect skeletal muscle. In previous studies, it has been demonstrated that DMAbs can achieve high serum levels and shown protection comparable to purified mAbs in flu and pseudomonas murine challenge models. Working toward clinical application, efforts have been focused on further increasing the in vivo expression levels of DMAbs through formulation, administration, nucleotide and amino acid optimization. Multiple DMAb antibody modification strategies have been developed employing framework grafting to increase the in vivo expression levels of DMAbs without sacrificing the biology of the original mAb clone.

Figure 1D:
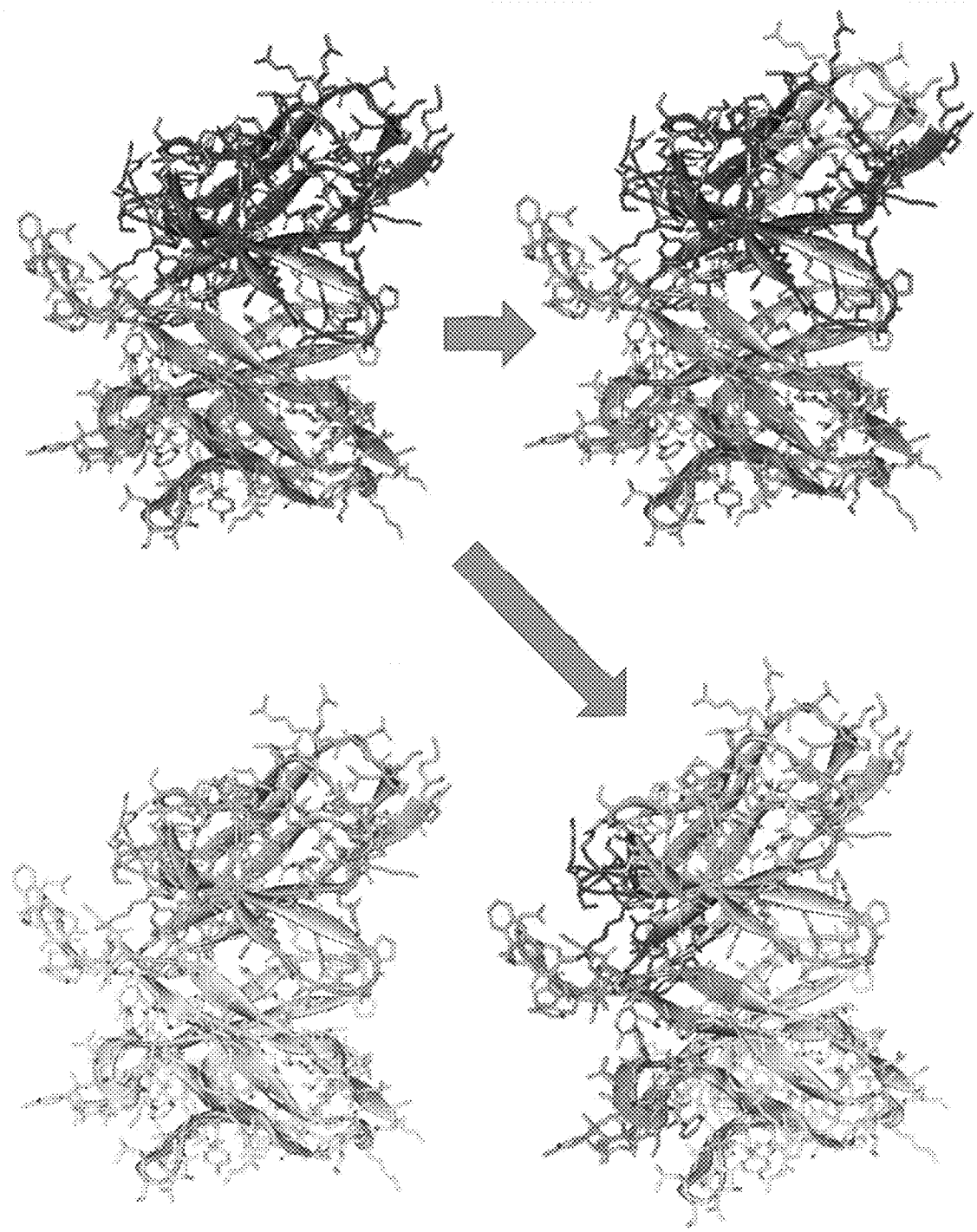

FIG. 1 provides an overview of multiple strategies used to generate optimized DMABs. Strategies include full scaffold grafting, partial scaffold grafting and scaffold modification (multiple point mutations).

Full scaffold grafting includes moving CDRs from one Fv region (VH or VL) with undesirable properties onto the framework of a second Fv which has desirable properties. The method is somewhat similar to that employed in antibody humanization. A limited selection of Fv's is available, making ideal CDR placement challenging. Expression can be impacted positively, but binding can be negatively impacted if the scaffold is not fully compatible.

Partial scaffold grafting includes altering selected regions of the scaffold, with the goal of increasing fold stability. Regions too close to the CDRs are avoided to minimize CDR perturbation. Generally, changes are made within the first 20 residues at the N terminus of the variable light chain to mimic the sequence of a DMAb having high expression.

Scaffold modification includes making a predicted series of multiple mutations to increase stabilizing interactions at the VH-VL interface or to favorably alter isoelectric point. Generally about 3 to 4 individual amino acid changes are made to increase stability The methods are now described BALB/c mice (n=8) were administrated 100 μg of DNA-plasmid encoding a DMAb in one treatment site through intramuscular delivery followed by electroporation (IM-EP). Serum levels of DMAb were quantified by ELISA at day 7. Binding of serum DMAbs was assessed by ELISA at day 7.

Partial grafts, full grafts and scaffold modification were performed on BDBV223 and Z5D2 antibodies as detailed in Table 1.

TABLE 1

| Engineered DMAbs | | |
|---|---|---|
| DMAb type | Name | Description |
| original | pGX9228 | Ebola BDBV223 |
| original | pGX9224 | Ebola Z5D2 |
| partial graft | pGX9292 | Ebola Z5D2 partial graft |
| full graft | pGX9293 | Ebola Z5D2 graft on MERSYTE_1 |
| full graft | pGX9294 | Ebola Z5D2 graft on MERSYTE_2 |
| full graft | pGX9295 | Ebola Z5D2 graft on V2L2 |
| partial graft | pGX9297 | Ebola BDBV223 partial graft |
| full graft | pGX9298 | Ebola BDBV223 graft on MERSYTE |
| full graft | pGX9299 | Ebola BDBV223 graft on V2L2 |

The results are now described

Multiple constructs were generated and screened for in vivo expression by ELISA. The partial graft method consists of replacing a portion of the variable light chain framework region from a poor expresser with that of a higher expressing DMAb. The new partial graft constructs showed increases approximately a log higher than the original DMAbs, while maintaining binding.

Figures 2A, 2B:
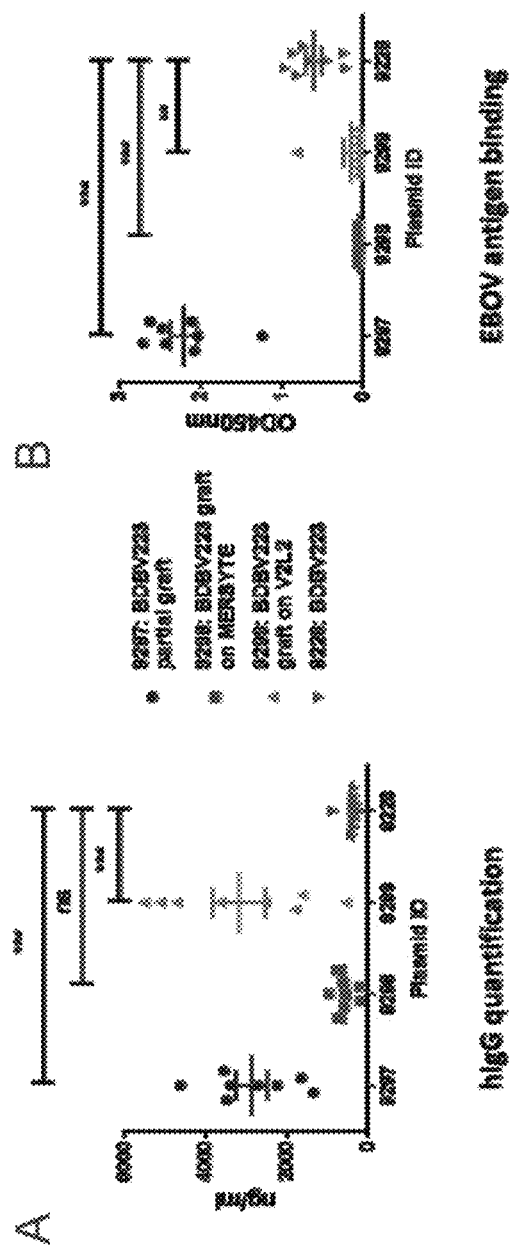
FIG. 2A through FIG. 2B, depicts exemplary experimental results demonstrating the effects of full and partial grafting of BDBV223.
Figures 3A, 3B:
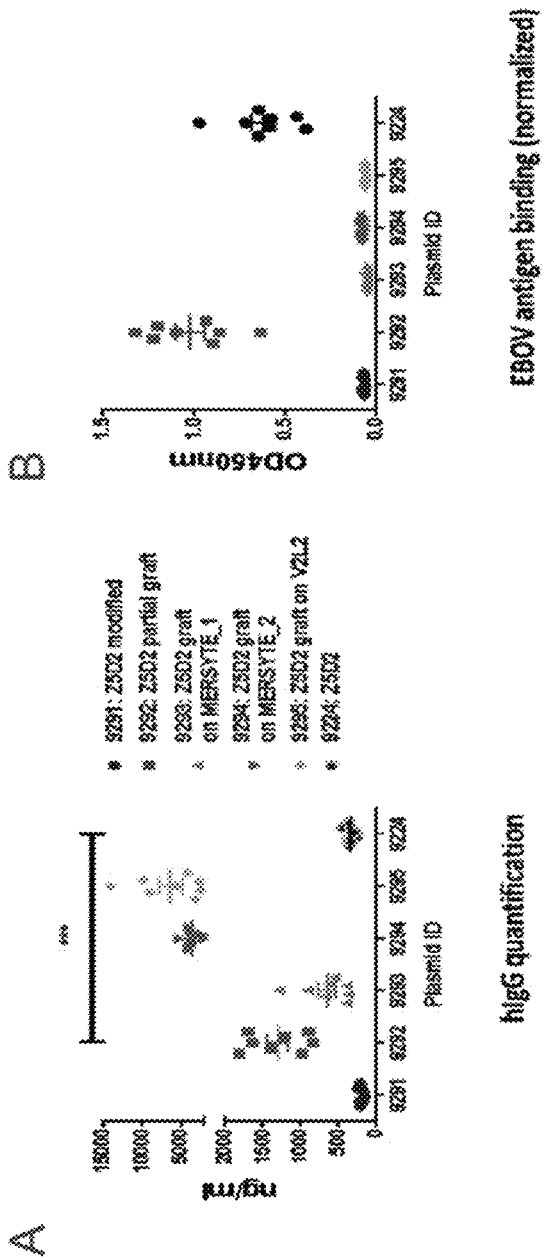
FIG. 3A through FIG. 3B, depicts exemplary experimental results demonstrating the effects of full and partial grafting and structural modification of Z5D2.
Figure 4:
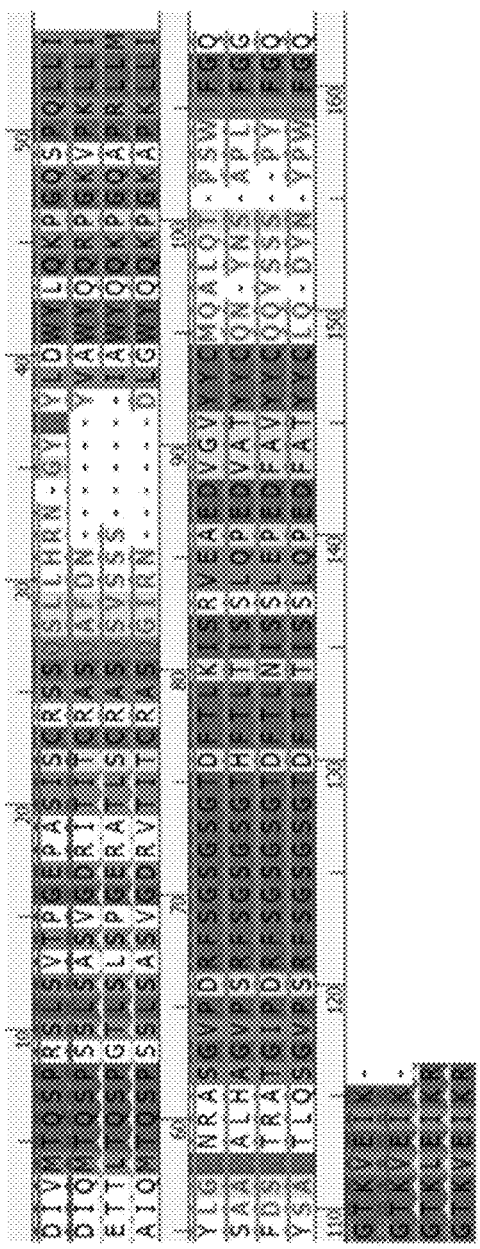
FIG. 4 depicts an alignment of multiple light chains from low expressing DMAbs (SEQ ID NO:54 through SEQ ID NO:57) with light chains from two verified highly expressing DMAbs (SEQ ID NO:58 and SEQ ID NO:59).

Partial grafting of BDBV223 resulted in an optimized antibody with enhanced expression and maintained binding (FIG. 2). In contrast, a full graft of BDBV223 onto V2L2 enhanced expression but resulted in loss of antigen binding (FIG. 2). Similar results were seen with the Z5D2 antibody. Partial grafting of Z5D2 resulted in an optimized antibody with enhanced expression and maintained binding whereas full grafting of Z5D2 resulted in loss of antigen binding (FIG. 3). FIG. 4 provides a summary of the effects of full grafting, partial grafting and scaffold modification on expression and antigen binding of Structurally modified DMAbs modified from three different parental DMAb sequences.

Example 2: Partial Graft Design

Two high-expressing DMABs (pGX9232 and pGX9214) were aligned to DMAB light chains of pGX9256 (1A2) and pGX9290 (EBV114) (FIG. 4).

Figure 5:
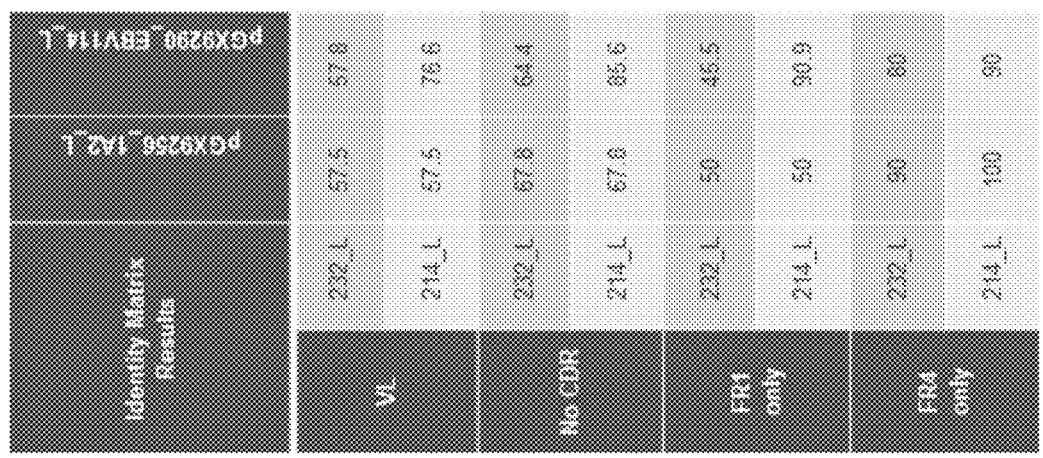
FIG. 5 depicts an identity matrix comparing the full VL, the VL excluding the CDR regions, the FR1 and the FR4 for each parental light chain of FIG. 5 with each of the verified highly expressing DMAbs.

Identity matrices with and without CDRs were calculated. Results are provided in FIG. 5. Alignment matrices were also generated using only FR1 (up to first Cys residue) and FR4. The pattern from the FR1 matrix pattern is identical to the VL and No CDR matrices. The FR4 matrix, based on only 10 residues (excluding terminal R), gives a different pattern but is highly similar overall. Without being bound by any particular theory, it is hypothesized that a higher similar score is better. Sequences for the engineered partial grafts are:

pGX9256_(232)_L (SEQ ID NO:58)
pGX9290_(232)_L (SEQ ID NO:59)
pGX9256_(214)_L (SEQ ID NO:60)
pGX9290_(214)_L (SEQ ID NO:61)

Example 3: scFv-Fc Conversion

Figure 6:
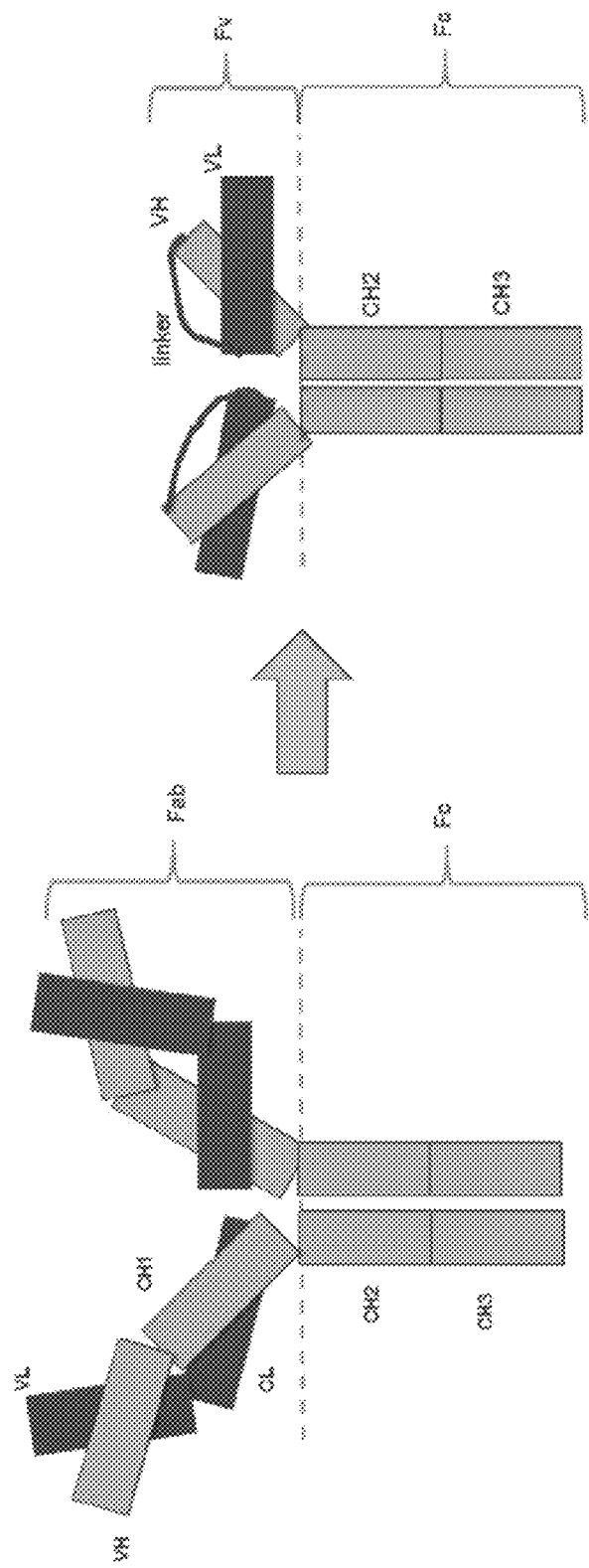
FIG. 6 depicts a diagram showing the structural differences between full length and scFv-Fc modified IgG DMAbs.
Figures 7A, 7B, 7C:
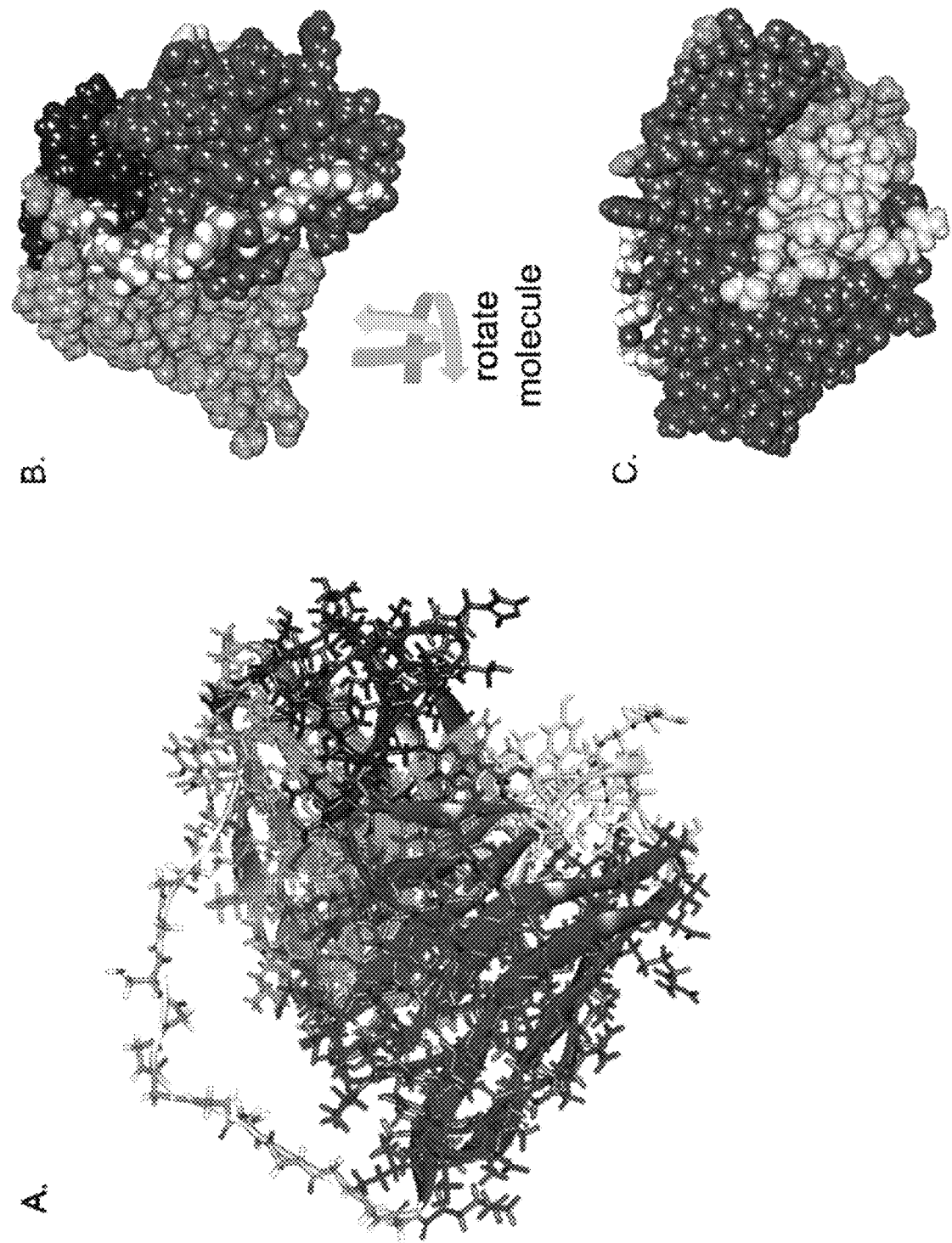
FIG. 7A through FIG. 7C, depicts protein modeling images demonstrating that the scFv-Fc linker does not interfere with CDRs.

Single chain Fv-Fc (scFv-Fc) conversion is the removal of CH1 and CL regions, and the addition of a linker between VH and VL. Conversion promotes heavy chain-light chain pairing and tissue penetration. DMAbs are converted from a full length antibody to scFv-Fc through addition of a linker (as depicted in FIGS. 6 and 7).

The methods are now described

BALB/c mice (n=5) were administrated 100 µg of DNA-plasmid encoding scFv-Fc DMAb in one treatment site through intramuscular delivery followed by electroporation (IM-EP). Serum was collected over the course of 35 days post administration.

293T cells were transfected with DNA-plasmid encoding scFv-Fc DMAb. scFv-Fc DMAbs were purified from cell supernatant using Protein A, and their normalized binding affinity was analyzed by ELISA using an identical antigen from two different Ebola virus outbreak strains, Zaire ebolavirus glycoprotein (GP) from the 1976 Mayinga strain or the 2014 Guinea strain.

TABLE 2 scFv-Fc Engineered DMAbs

| DMAb type | Name | Description |
|---|---|---|
| original | pGX9224 | Ebola Z5D2 |
| original | pGX9225 | Ebola Z1H3 |
| original | pGX9228 | Ebola BDBV223 |
| scFV-Fc | pGX9330 | Ebola Z5D2 scFv-Fc |
| scFV-Fc | pGX9331 | Ebola Z1H3 scFv-Fc |
| scFV-Fc | pGX9332 | Ebola BDBV223 scFv-Fc |

Figures 8A, 8B, 8C, 8D:
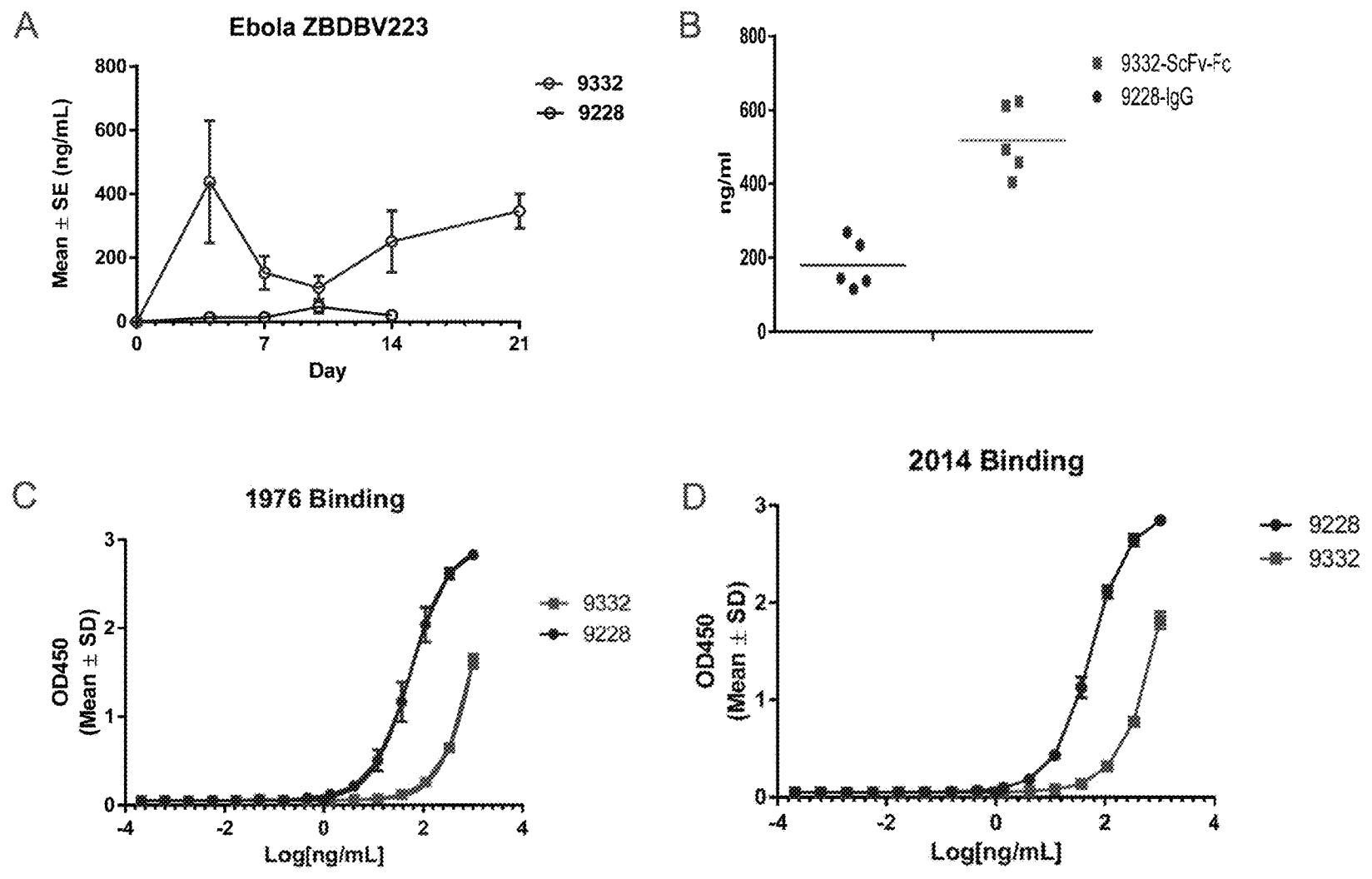
Figures 9A, 9B, 9C, 9D, 9E, 9F:
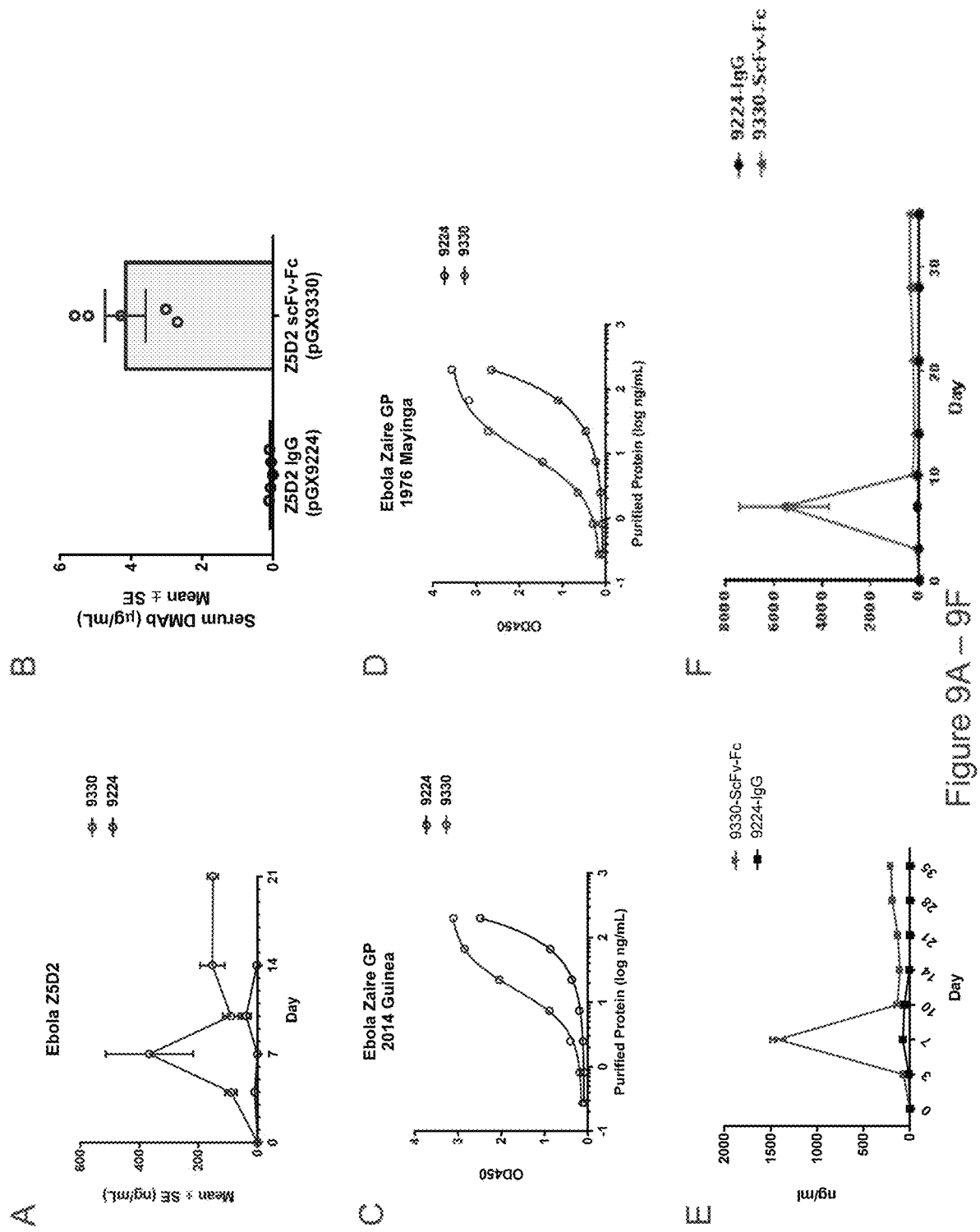
FIG. 9A through FIG. 9F, depicts exemplary experimental results demonstrating the effects of scFv-Fc conversion of DMAb Z5D2.
Figures 10A, 10B, 10C, 10D, 10E:
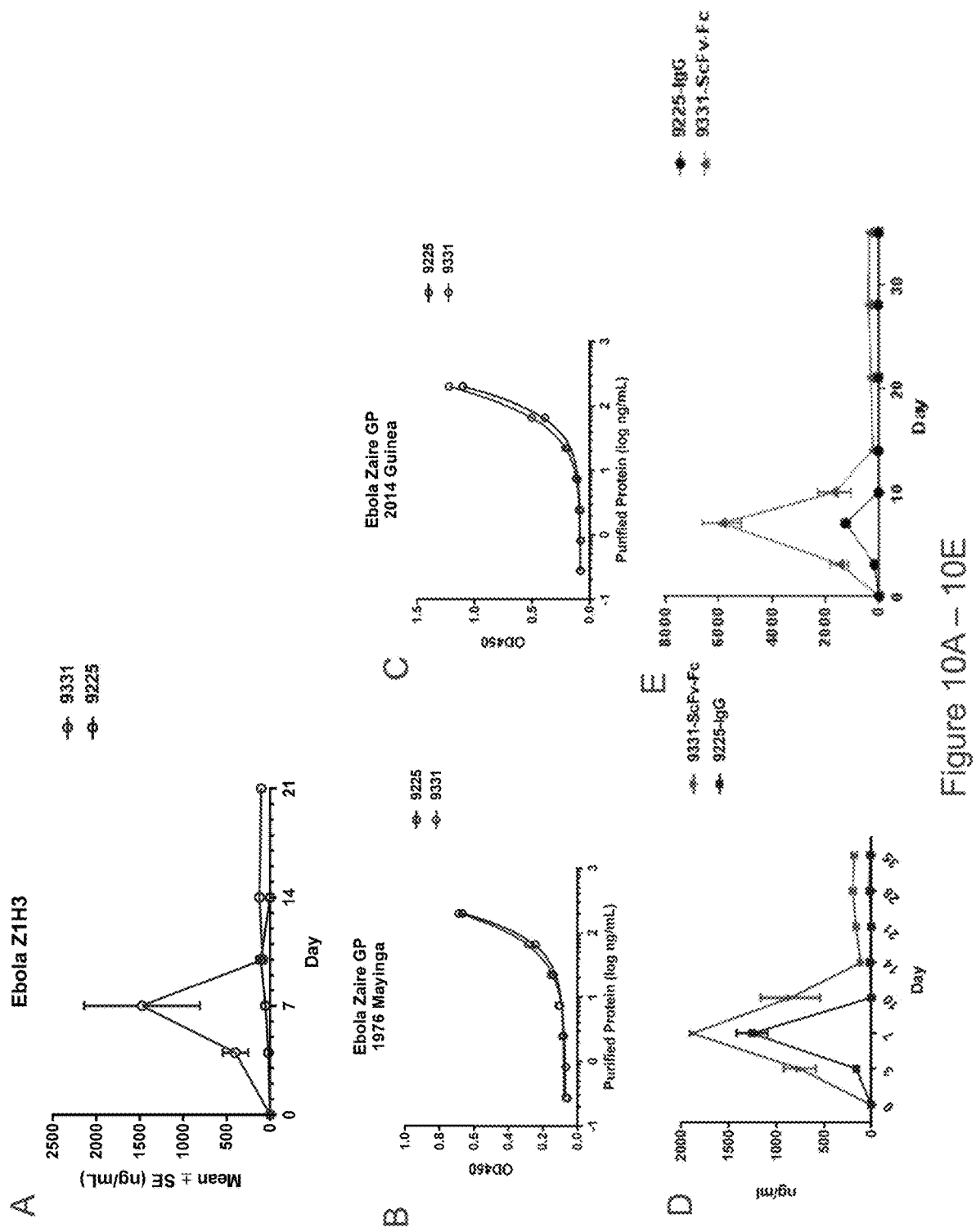
FIG. 10A through FIG. 10E, depicts exemplary experimental results demonstrating the effects of scFv-Fc conversion of DMAb Z1H3.

The results are now described scFv-Fc conversion of BDBV223 resulted in decreased antigen binding (FIG. 8). scFv-Fc conversion of Z5D2 resulted in increased expression and increased antigen binding (FIG. 9). scFv-Fc conversion of Z1H3 resulted in increased expression but had no effect on antigen binding (FIG. 10).

Example 4: scFv-Fc Design

Several possible engineering approaches exist, but many publications in the area tend to be very system-specific despite claims otherwise. Several new approaches used for design and currently being tested in dMAb space can potentially contribute ideas for scFv-Fc space.

Figure 11:
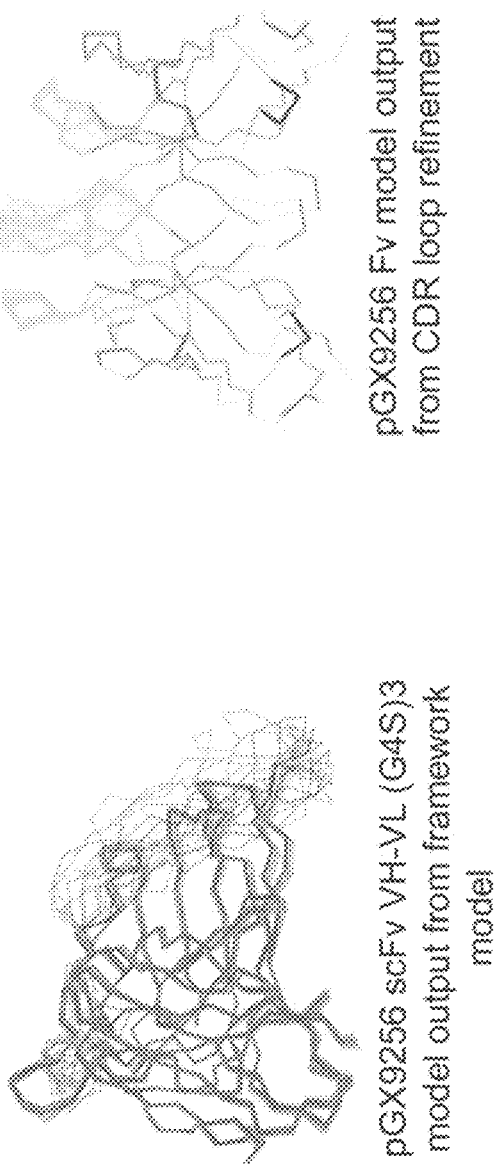
FIG. 11 depicts exemplary outputs from different steps in the ScFv-Fc modeling process.

Modeling and analysis was performed to identify structural characteristics of scFv DMAb that are associated with increased binding and/or expression. Modeling was performed on Fv and scFv in both forms (VH-VL and VL-VH) using a (G4S)3 linker. Fifteen sets of models were generated, with multiple models in each set. Scoring methods as well as structural inspection are used to assess model building at each step. FIG. 11 depicts example outputs from different steps in the modeling process which includes framework modelling and CDR loop refinement. The top 20 linker conformations were evaluated. Root-mean-square deviation (RMSD) was generated of the backbone with attention to regions near linkers.

Linker

The (G45)3 linker, having a sequence of GGGGSGGGGSGGGGS (SEQ ID NO:53) was selected for inclusion in the studies.

The results are now described

Figure 12:
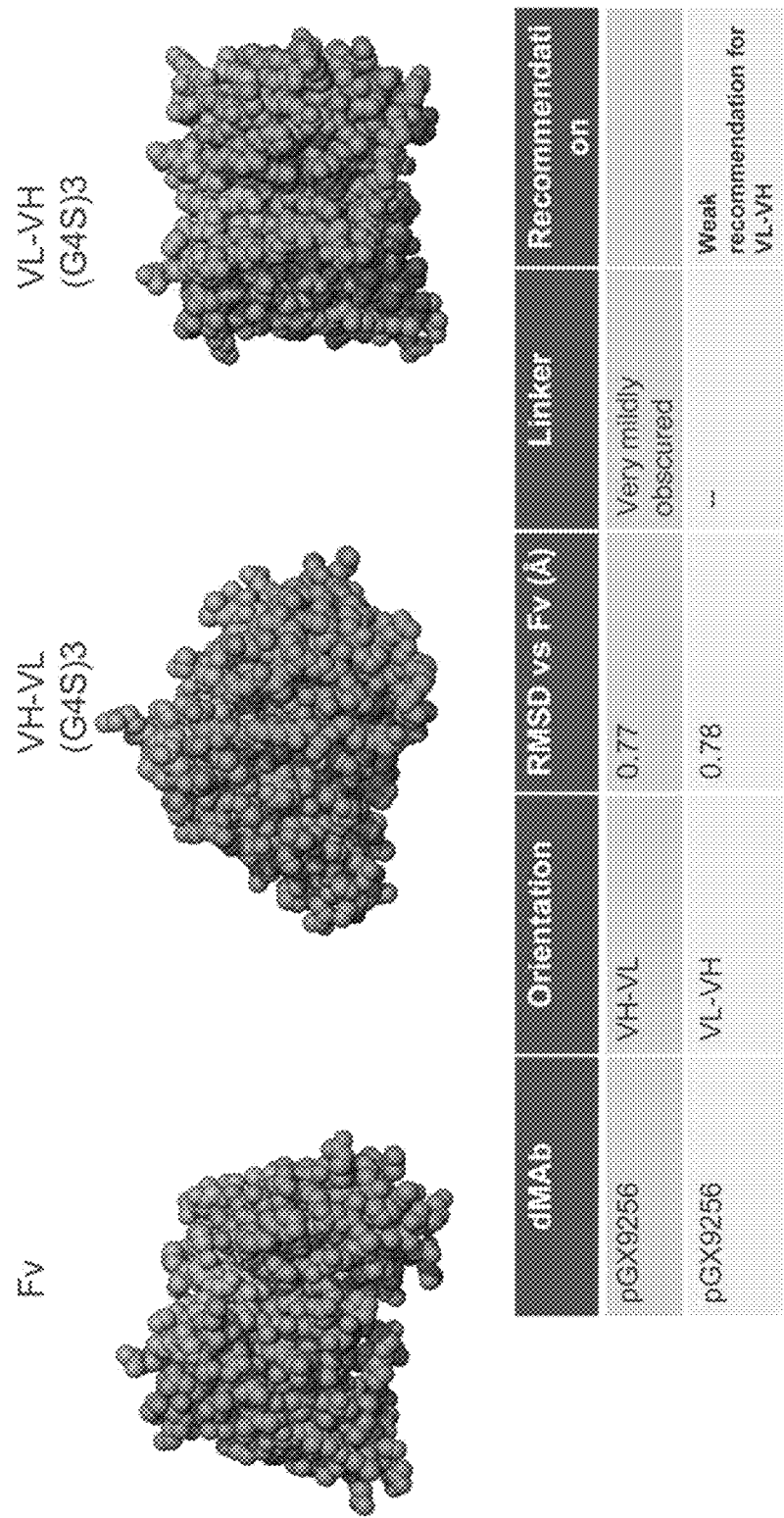
FIG. 12 depicts exemplary images of Fv, VH-VL and VL-VH modeling of pGX9256.
Figure 13:
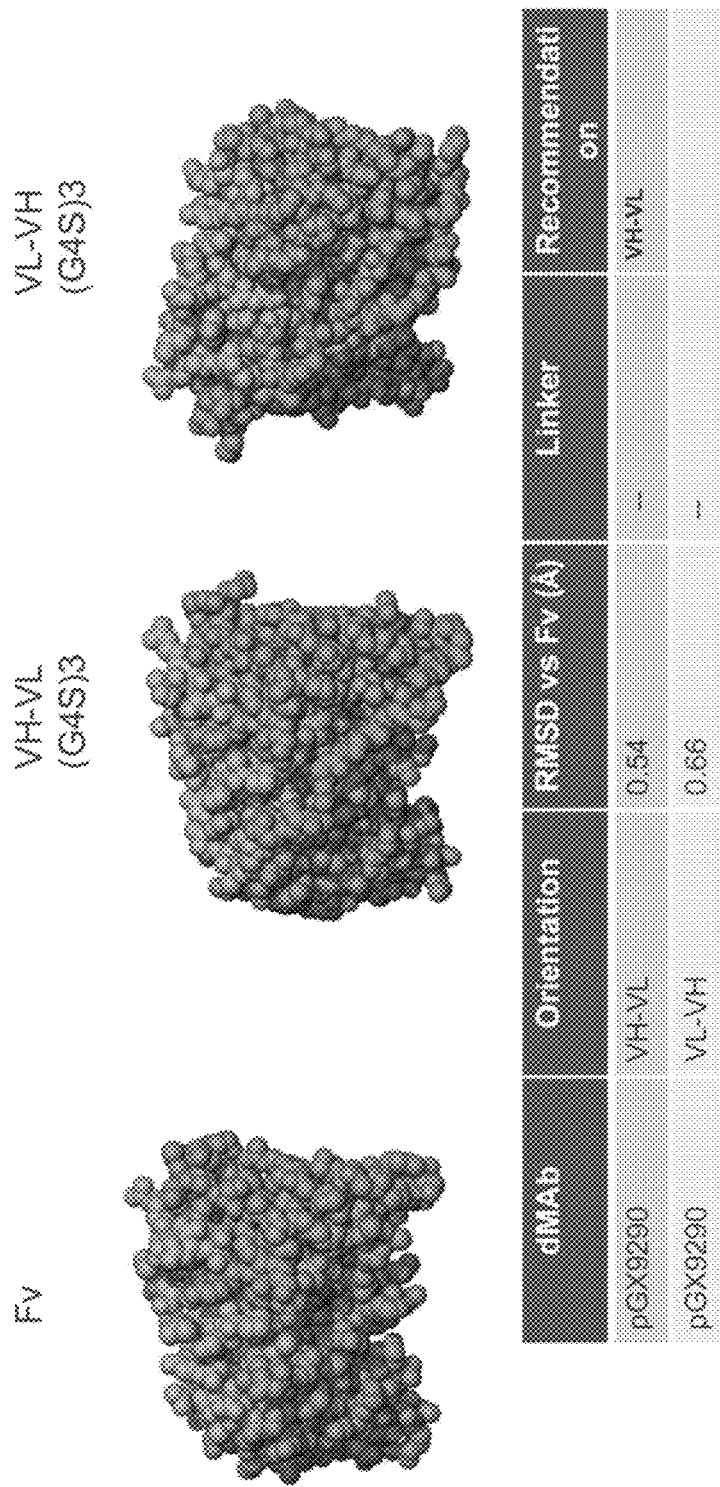
FIG. 13 depicts exemplary images of Fv, VH-VL and VL-VH modeling of pGX9290.

Predictive ScFv-Fc modeling was performed on five different parental DMAbs. Each DMAb was modeled in two orientations: VH-linker-VL and VL-linker-VH. FIG. 12 and FIG. 13 show space filled models of the ScFv-Fc DMAbs that are used to predict whether the linker is likely to obscure or interfere with the CDRs.

Table 3 provides a summary of the decision tree for identifying candidate DMAbs for further development.

| DMAb | Name | Orientation | RMSD vs Fv (Å) | Linker | Recommendation |
|---|---|---|---|---|---|
| 1A2 | pGX9256 | VH-VL | 0.77 | Very mildly obscured | |
| 1A2 | pGX9256 | VL-VH | 0.78 | — | Weak recommendation for VL-VH |
| EBV114 | pGX9290 | VH-VL | 0.54 | — | VH-VL |
| EBV114 | pGX9290 | VL-VH | 0.66 | — | |

Recommendations based on these results are in Table 3. In several cases, RMSD is within normal error for independently minimized models. In some cases, especially those where no strong signal exists between conformations, there may not be a benefit in choosing one conformation over another (VH-VL and VL-VH). In other cases, modeling indicates that one conformation may be a better candidate than another. RMSD is a simple, consistent measurement for forming a recommendation, however other criteria besides RMSD may also be informative.

Linker evaulation like that used here can detect distortion issues, but it cannot easily detect issues related to V domain association that are dependent on flexibility or intermediates in association and require greater mobility to associate (e.g., 'entropic considerations').

Example 5: Functional Assessment of Structural Reformatting and Protein Engineering Strategies for Therapeutic Gene Transfer of Synthetic DNA-Plasmid Encoding Antibodies Against Ebola Virus Disease (EVD)

Ebola virus disease (EVD) causes severe hemorrhagic fever in humans and is associated with high mortality rate. The Ebola epidemic of 2013-2015 in West Africa was by far the most fatal and the longest lasting in the recent history of emerging diseases. The challenges of such a large outbreak have underscored the need for effective EVD antiviral therapies and vaccines. While a vaccine for EVD was recently found effective in humans, vaccine protection is often not immediate and not beneficial in a therapeutic setting against acute cases of EVD. Passive immunization strategies that require the transfer of monoclonal antibodies (mAb) to confer immediate protective immunity have been used successfully in infectious disease settings including EVD. However, there are conceptual and methodological hurdles associated with antibody administration. This includes their production and optimization in vitro, their dosage in vivo, and finally the costs that are incurred during the manufacturing process. From this standpoint, the in vivo delivery of DNA-plasmid encoding antibodies offers an innovative, safe and cost effective approach to monoclonal antibody (mAb) administration.

In vivo electroporation (EP)-mediated gene delivery in mice of DNA encoding monoclonal antibodies (DMAbs) directed against various pathogens has previously been demonstrated. The current study describes two DMAbs that target Ebola virus glycoprotein (EBOV-GP), EBOMAb-10 and EBOMAb-14; it also describes the functional impact of engineered modifications consisting of reformatting Immunoglobulin (Ig) to single chain antibody (scFv-Fc) and scaffold grafting within the aforementioned DMAbs structural frames. EP-mediated gene transfer of EBOMAb-10 and EBOMAb-14 in their un-modified and modified formats leads to the secretion of functional antibodies in mice serum as assessed by EBOV-GP antigen binding by ELISA and viral neutralization in an EBOV-GP pseudotyped virus assay. These structural changes have disparate effects on EBOV-GP binding in vitro and in live cell expressing surface glycoprotein, as well as on viral neutralization. Taken together, the data described here provide the conceptual framework for the development of synthetic-DNA plasmid encoding monoclonal antibodies (DMAbs) with enhanced therapeutic potency against emerging diseases such as EVD. The study also provides the functional paradigm to assess the structural manipulations of DMAbs, and overall supports further animal testing in vivo to translate DNA-based passive immunization approaches into clinic in a safe and cost efficient manner.

The methods are now described.

Figure 14:
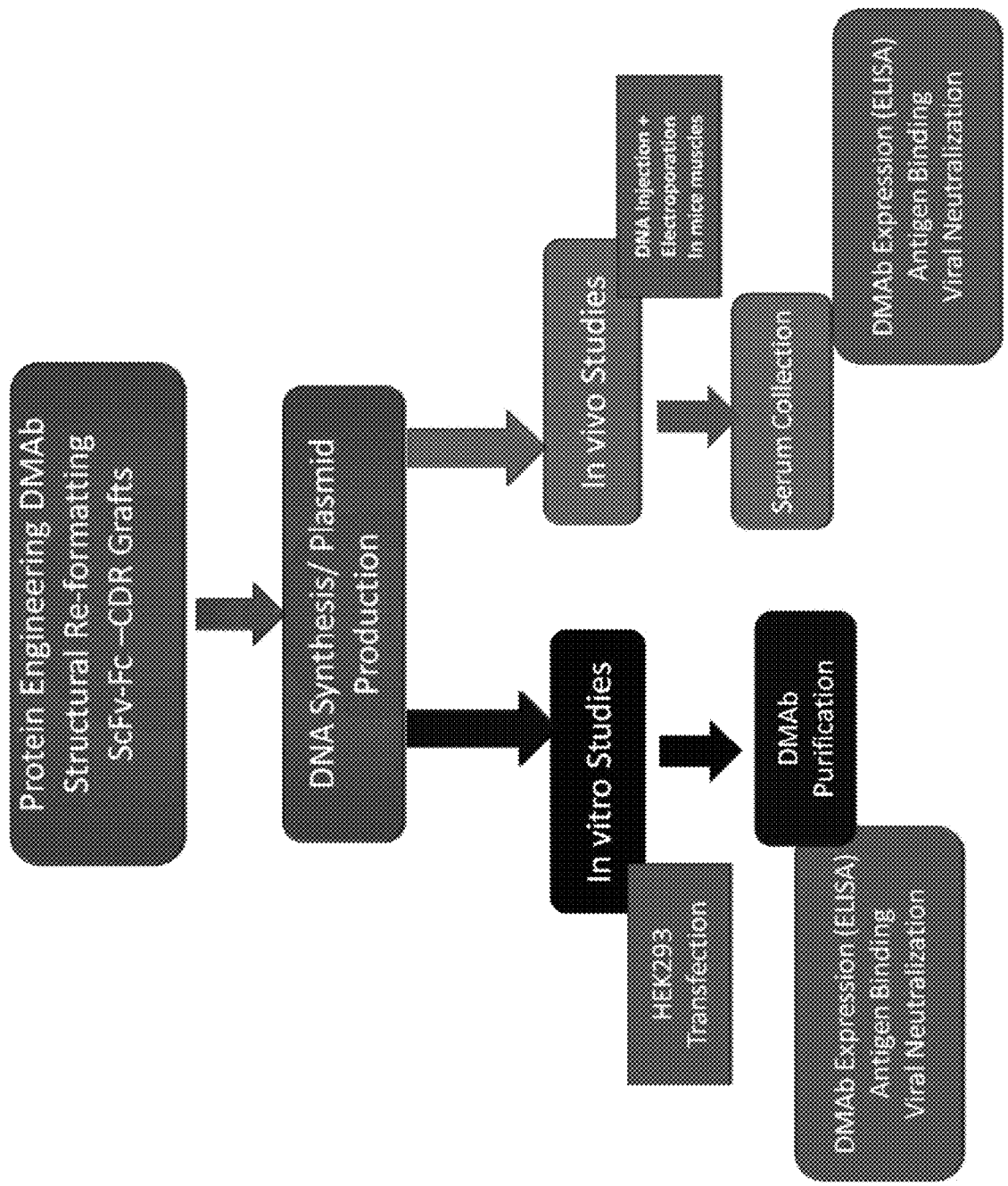
FIG. 14 depicts a flow diagram showing engineered DMAbs are synthesized as DNA plasmids and then evaluated in vitro and in vivo for antigen binding and expression.

FIG. 14 provides a flow diagram of the methods used in these studies. The DMAb design strategies used for generation of the ScFv-Fc DMAbs include 1) Linker design; 2) VH-VL Orientation; and 3) Hinge-CH2-CH3 choice. Parental DMAbs underwent partial grafting, ScFv-Fc conversion, or a combination of partial grafting and ScFv-Fc conversion.

Two groups of DMAbs were analyzed in these studies. Group 1 consists of the EBOMAb-10 DMAbs: EBOMAb-10-IgG (control), EBOMAb-10-2 (ScFv-Fc modified DMAb), EBOMAb-10-3-IgG partial graft and EBOMAb-10-4 ScFv-Fc partial graft. Group2 consists of the EBOMAb-14 DMAbs: EBOMAb-14-IgG (control), EBOMAb-14-2 (ScFv-Fc modified DMAb), EBOMAb-14-3-IgG partial graft and EBOMAb-14-4 ScFv-Fc partial graft. The sequences used in these studies are indicated in Table 4.

TABLE 4

| Name | Description | ASGCT code |
|---|---|---|
| pGX9256 | Ebola 5.6.1A2 | EBOMAb-10 |
| pGX9346 | 1A2_scFv-Fc | EBOMAb-10-2 |
| pGX9356 | 1A2_Full length_partial graft | EBOMAb-10-3 |
| pGX9357 | 1A2_scFv-Fc_partial graft | EBOMAb-10-4 |
| pGX9290 | Ebola EBV114 | EBOMAb-14 |
| pGX9345 | EBV114_scFv-Fc | EBOMAb-14-2 |
| pGX9362 | EBV114_Full length_partial graft | EBOMAb-14-3 |
| pGX9363 | EBV114_scFv-Fc_partial graft | EBOMAb-14-4 |

The results are now described.

Figures 15A, 15B:
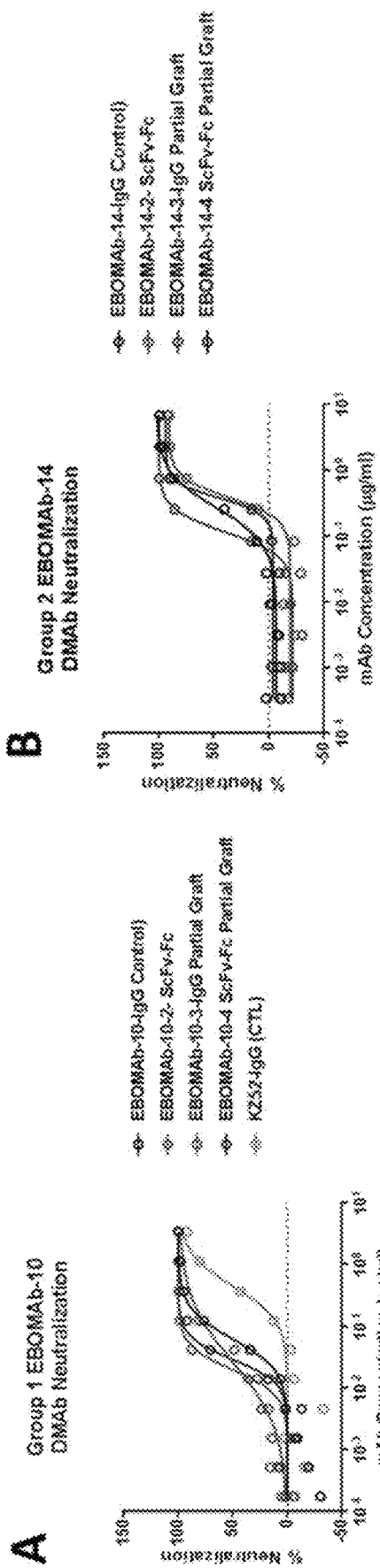
FIG. 15A through FIG. 15B, depicts exemplary experimental results demonstrating the neutralizing activity of structurally reformatted DMAbs.
Figures 17A, 17B, 17C, 17D, 17E, 17F:
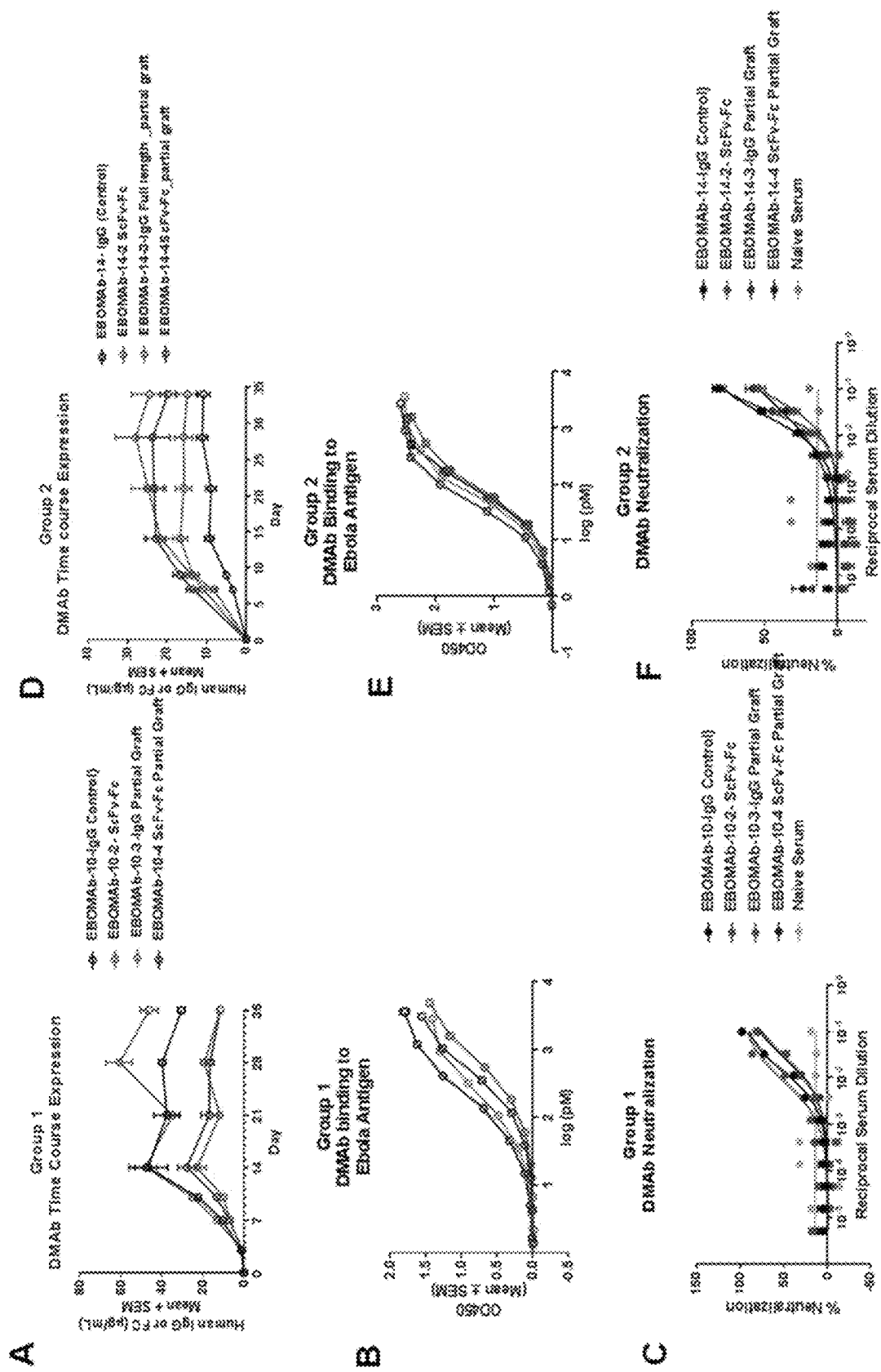
FIG. 17A through FIG. 17F, depicts exemplary experimental results demonstrating the expression and antigen binding of the Group 1 and Group 2 structurally modified DMAbs.

The neutralizing activity of structurally modified DMAbs was evaluated. All structurally reformatted DMAbs were comparable to their parental control DMAb (FIG. 15). An evaluation of the IC50 and IC90 showed that the ScFv-Fc DMAbs had a greater IC90 than that of the control DMAb whereas partial grafting modified DMAbs had a lower IC90 than that of the control (FIG. 16). Group 2 DMAbs showed increased expression as compared to the control DMAb and antigen binding was slightly increased or equivalent to control (FIG. 17).

Structurally modified DMAbs for the most part can be expressed at high level in mice, without substantial loss of function (i.e antigen binding and inhibitory potency). For EBOMAb10-3 and EBOMAb-14-3 structural modification leads to increase expression in mice, and increase inhibitory potency as calculated through IC50 & IC90

The data provide proof of concept that DMAb is a malleable tool that can be engineered for possibly higher expression and higher therapeutic efficacy Table 5 provides a listing of example Ebola DMAb plasmid constructs that utilize framework mutations, full grafts, partial grafts, and scFv-Fc conversions.

TABLE 5

| SEQ ID NO: | Sequence type | Name | Description |
|---|---|---|---|
| 1 | Nucleotide | pGX9291 | Ebola Z5D2 modified |
| 2 | Amino acid | pGX9291 | Ebola Z5D2 modified |
| 3 | Nucleotide | pGX9292 | Ebola Z5D2 partial graft |
| 4 | Amino acid | pGX9292 | Ebola Z5D2 partial graft |
| 5 | Nucleotide | pGX9293 | Ebola Z5D2 graft on MERSYTE_1 |
| 6 | Amino acid | pGX9293 | Ebola Z5D2 graft on MERSYTE_1 |
| 7 | Nucleotide | pGX9294 | Ebola Z5D2 graft on MERSYTE_2 |
| 8 | Amino acid | pGX9294 | Ebola Z5D2 graft on MERSYTE_2 |
| 9 | Nucleotide | pGX9295 | Ebola Z5D2 graft on V2L2 |
| 10 | Amino acid | pGX9295 | Ebola Z5D2 graft on V2L2 |
| 11 | Nucleotide | pGX9296 | Ebola ZBDBV223 modified |
| 12 | Amino acid | pGX9296 | Ebola ZBDBV223 modified |
| 13 | Nucleotide | pGX9297 | Ebola ZBDBV223 partial graft |
| 14 | Amino acid | pGX9297 | Ebola ZBDBV223 partial graft |
| 15 | Nucleotide | pGX9298 | Ebola ZBDBV223 graft on MERSYTE |
| 16 | Amino acid | pGX9298 | Ebola ZBDBV223 graft on MERSYTE |
| 17 | Nucleotide | pGX9299 | Ebola ZBDBV223 graft on V2L2 |
| 18 | Amino acid | pGX9299 | Ebola ZBDBV223 graft on V2L2 |
| 19 | Nucleotide | pGX9330 | Ebola Z5D2 scFv-Fc |
| 20 | Amino acid | pGX9330 | Ebola Z5D2 scFv-Fc |
| 21 | Nucleotide | pGX9331 | Ebola Z1H3 scFv-Fc |
| 22 | Amino acid | pGX9331 | Ebola Z1H3 scFv-Fc |
| 23 | Nucleotide | pGX9332 | Ebola ZBDBV223 scFv-Fc |
| 24 | Amino acid | pGX9332 | Ebola ZBDBV223 scFv-Fc |
| 25 | Nucleotide | pGX9345 | EBV114_scFv-Fc |
| 26 | Amino acid | pGX9345 | EBV114_scFv-Fc |
| 27 | Nucleotide | pGX9346 | 1A2_scFv-Fc |
| 28 | Amino acid | pGX9346 | 1A2_scFv-Fc |
| 29 | Nucleotide | pGX9356 | 1A2_Full length_partial graft |
| 30 | Amino acid | pGX9356 | 1A2_Full length_partial graft |
| 31 | Nucleotide | pGX9357 | 1A2_scFv-Fc_partial graft |
| 32 | Amino acid | pGX9357 | 1A2_scFv-Fc_partial graft |
| 33 | Nucleotide | pGX9362 | EBV114_Full length_partial graft |
| 34 | Amino acid | pGX9362 | EBV114_Full length_partial graft |
| 35 | Nucleotide | pGX9363 | EBV114_scFv-Fc_partial graft |
| 36 | Amino acid | pGX9363 | EBV114_scFv-Fc_partial graft |
| 37 | Nucleotide | pGX9224 | Ebola Z5D2 |
| 38 | Amino acid | pGX9224 | Ebola Z5D2 |
| 39 | Nucleotide | pGX9225 | Ebola Z1H3 |
| 40 | Amino acid | pGX9225 | Ebola Z1H3 |

TABLE 5-continued

| SEQ ID NO: | Sequence type | Name | Description |
|---|---|---|---|
| 41 | Nucleotide | pGX9228 | Ebola ZBDBV223 |
| 42 | Amino acid | pGX9228 | Ebola ZBDBV223 |
| 43 | Nucleotide | pGX9256 | 1A2 |
| 44 | Amino acid | pGX9256 | 1A2 |
| 45 | Nucleotide | pGX9290 | EBV114 |
| 46 | Amino acid | pGX9290 | EBV114 |

Example 6: Exploration of Gene Optimization and scFv-Fc Reformatting as Strategies to Increase In Vivo Expression Levels of DNA-Encoded Monoclonal Antibodies (DMAbs) Against Zika Virus Two antibody modification strategies were used to generate modified DMAbs targeting the Zika virus: gene optimization and scFv-Fc reformatting (FIG. 1).

Figures 18A, 18B:
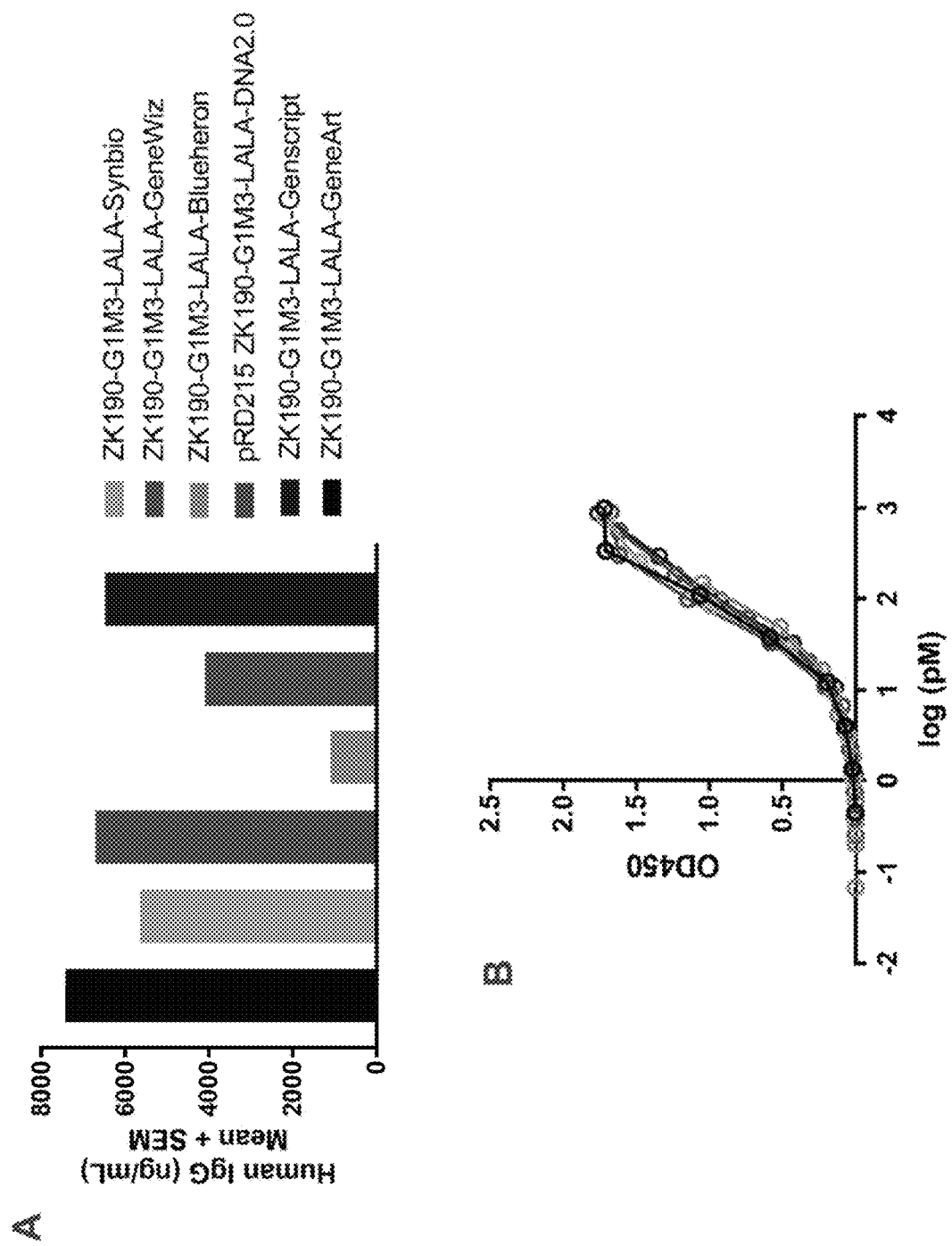
FIG. 18A and FIG. 18B, depicts an analysis of gene optimization of the codon optimized mouse Zika DMAb ZK190G1M3LALA.
Figures 19A, 19B:
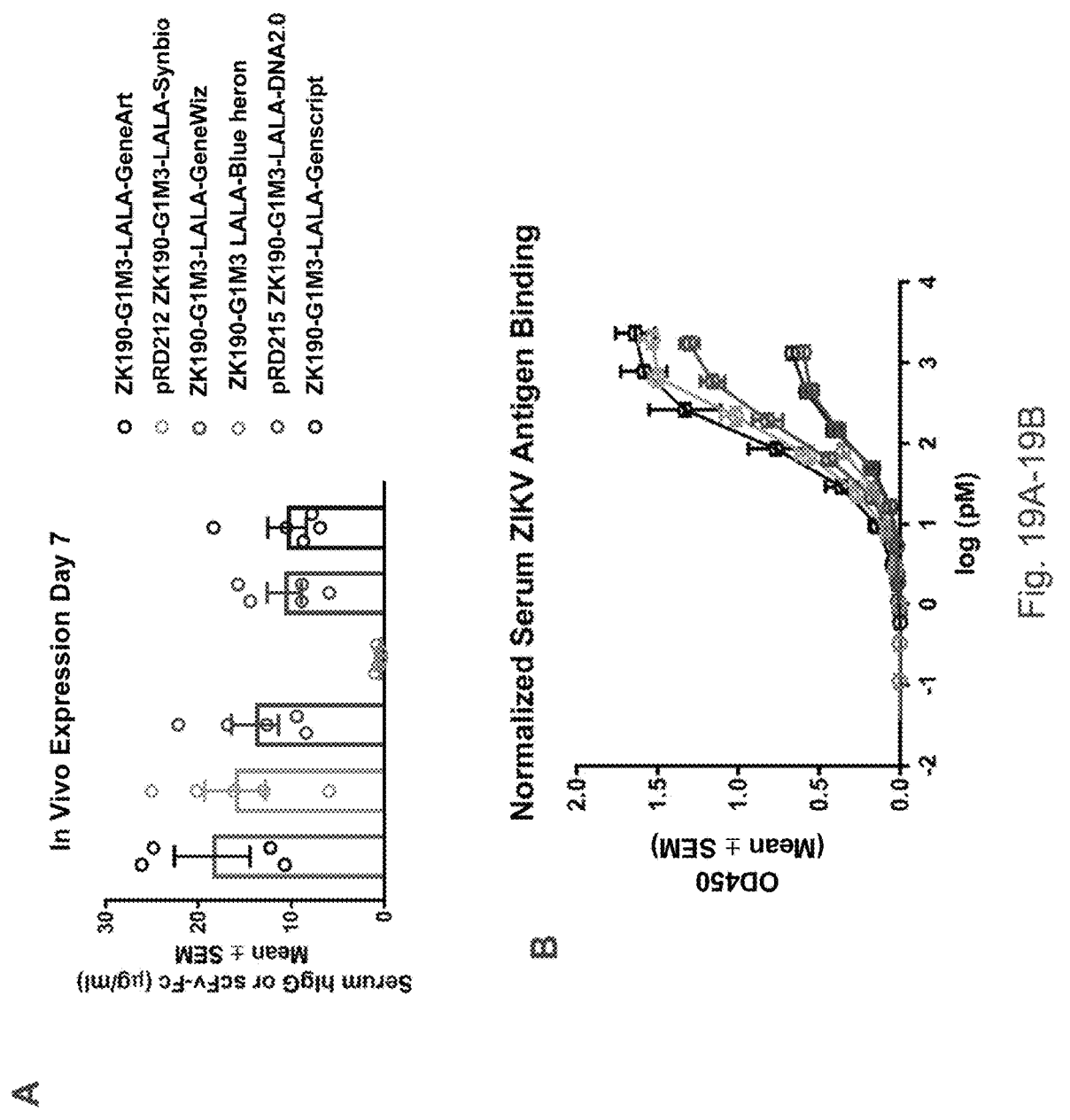
Figures 20A, 20B:
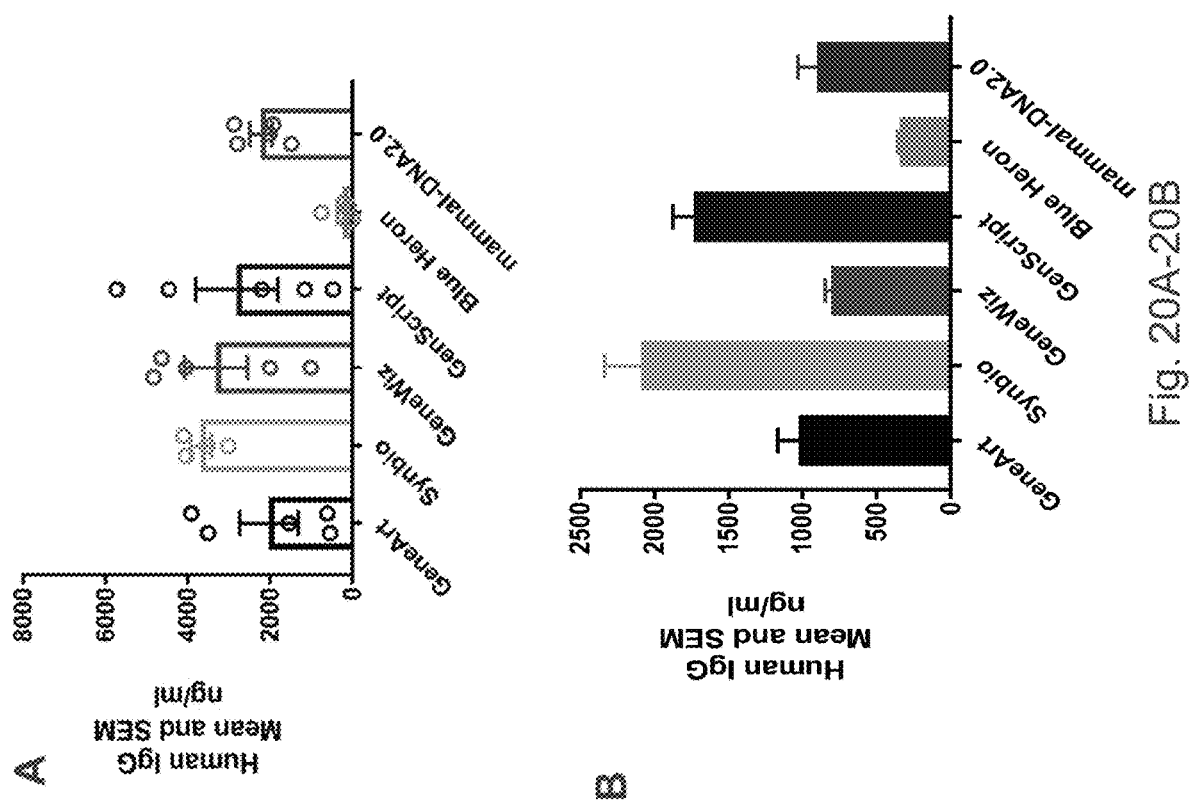
FIG. 20A and FIG. 20B, depicts an analysis of expression of gene optimized ZK185LALA FP2A codon optimized constructs.
Figures 21A, 21B:
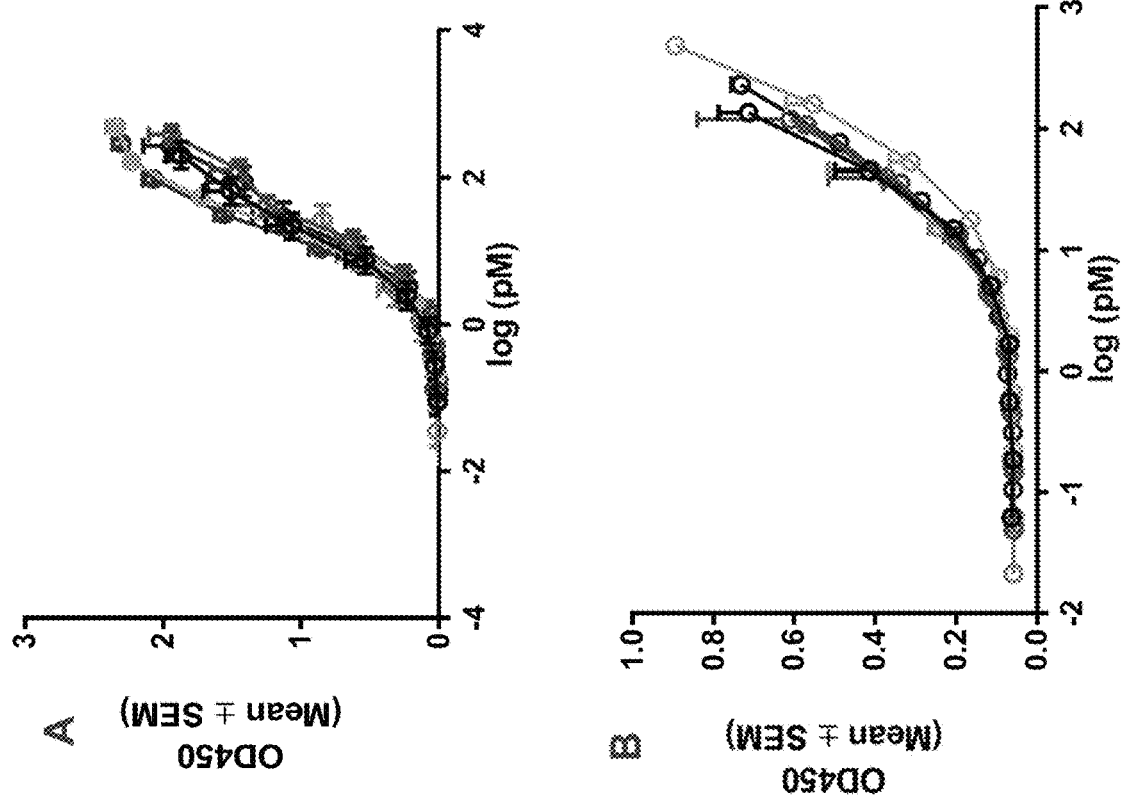
FIG. 21A and FIG. 21B, depicts an analysis of the binding capability of gene optimized ZK185LALA FP2A codon optimized constructs.

The gene optimization method consisted of selecting two full length Zika DMAb sequences and optimizing via six different algorithms. Multiple parameters affecting transcription and translation, such as codon usage, GC content, cryptic splice sites and mRNA secondary structure are weighted in proprietary multivariate regression algorithms. Much of the data referenced, however, was generated using in vitro expression systems. To find an algorithm most suited to the in vivo expression of the Zika DMAbs, BALB/c mice (n=5) were administered with 100 μg of plasmid DNA in one treatment site through intramuscular delivery followed by electroporation. Serum levels and normalized binding of DMAbs were quantified by ELISA at day 7. For ZKDMAB-1, Algorithm 1 gave the highest expression at 18 ug/ml (FIG. 18 and FIG. 19). For ZKDMAB-2, Algorithm 2 gave the highest expression of 3.5 ug/ml (FIG. 20). Consistently, both DMAbs optimized by Algorithm 6 exhibited the lowest or no expression in vivo. In most cases, binding by ELISA was retained, however several algorithms saw a decrease for ZKDMAB-1, suggesting that protein folding or conformation of the expressed DMAb could have been affected by the nucleotide sequence (FIG. 18, FIG. 19 and FIG. 21).

Additionally, single chain Fv-Fc (scFv-Fc) conversion was tested. ScFv-Fc conversion is the removal of CH1 and CL regions, and the addition of a linker between VH and VL. Conversion promotes heavy chain-light chain pairing and tissue penetration. DMAbs are converted from a full length antibody to scFv-Fc through addition of a linker (as depicted in FIG. 1).

Figure 22A:
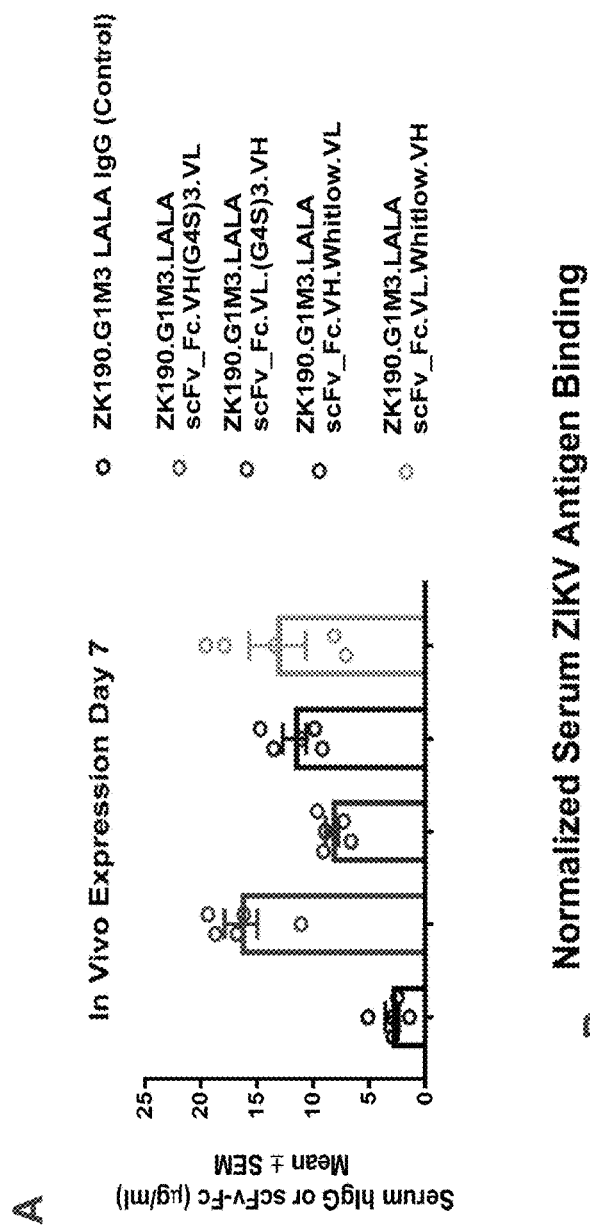
FIG. 22A and FIG. 22B, depicts an analysis of ScFv-Fc conversion of the codon optimized mouse Zika DMAb ZK190G1M3LALA.
Figure 22B:
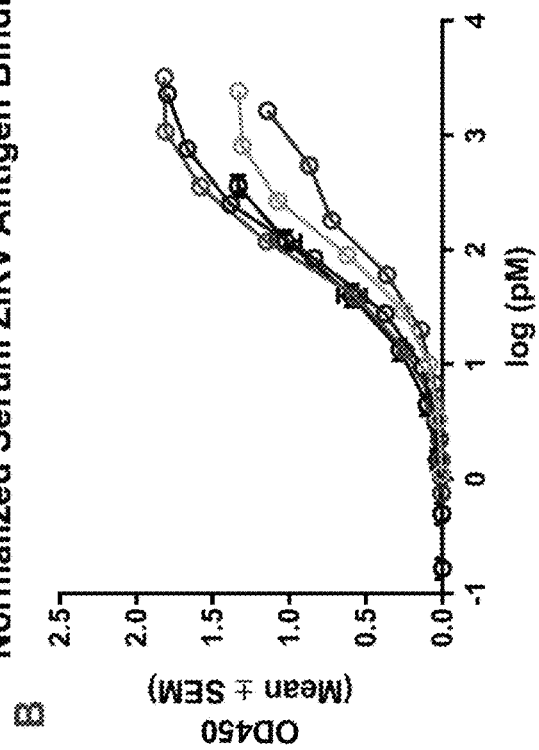
Figure 23:
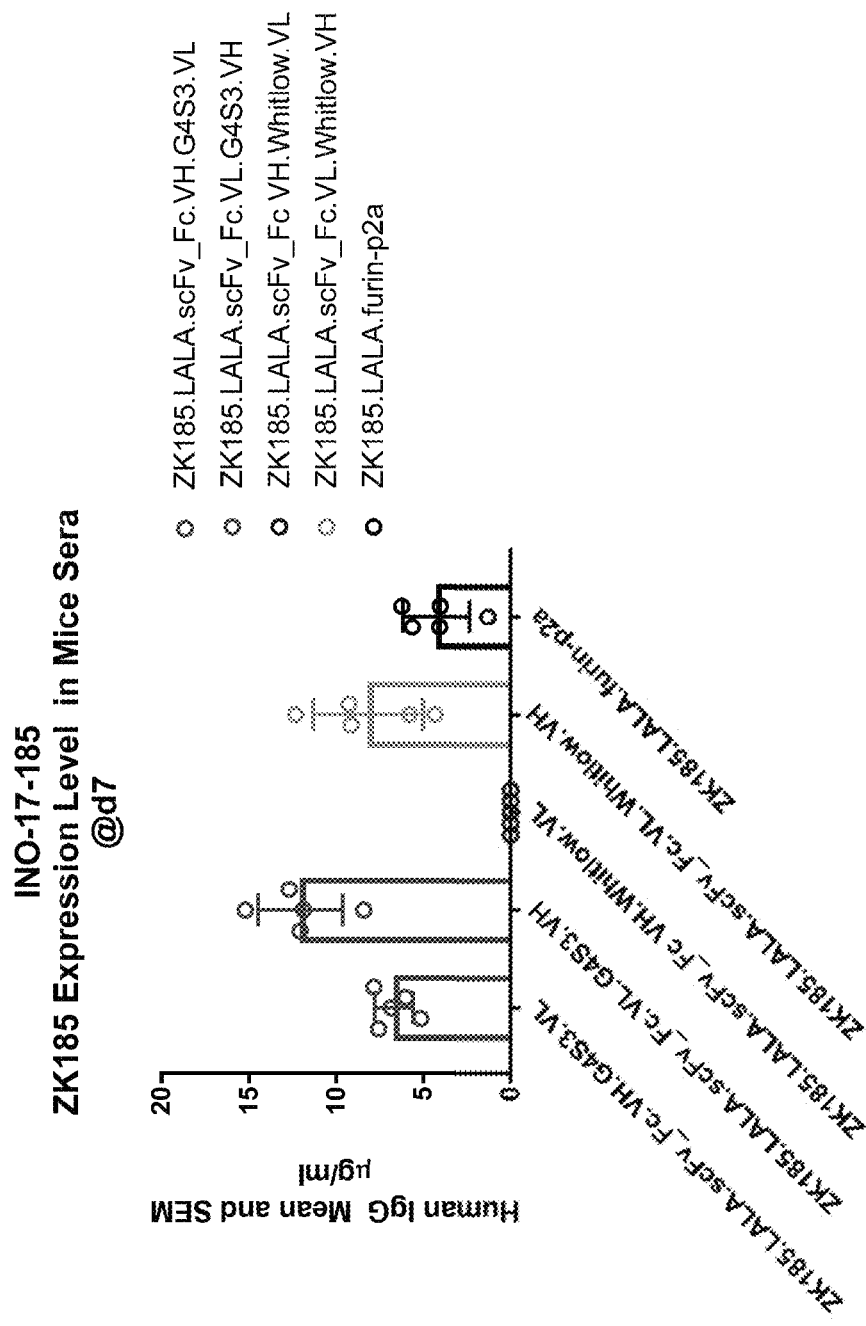
FIG. 23 depicts an analysis of the in vivo expression of ScFv-Fc conversion constructs of the ZK185LALA FP2A codon optimized DMAb.
Figure 24:
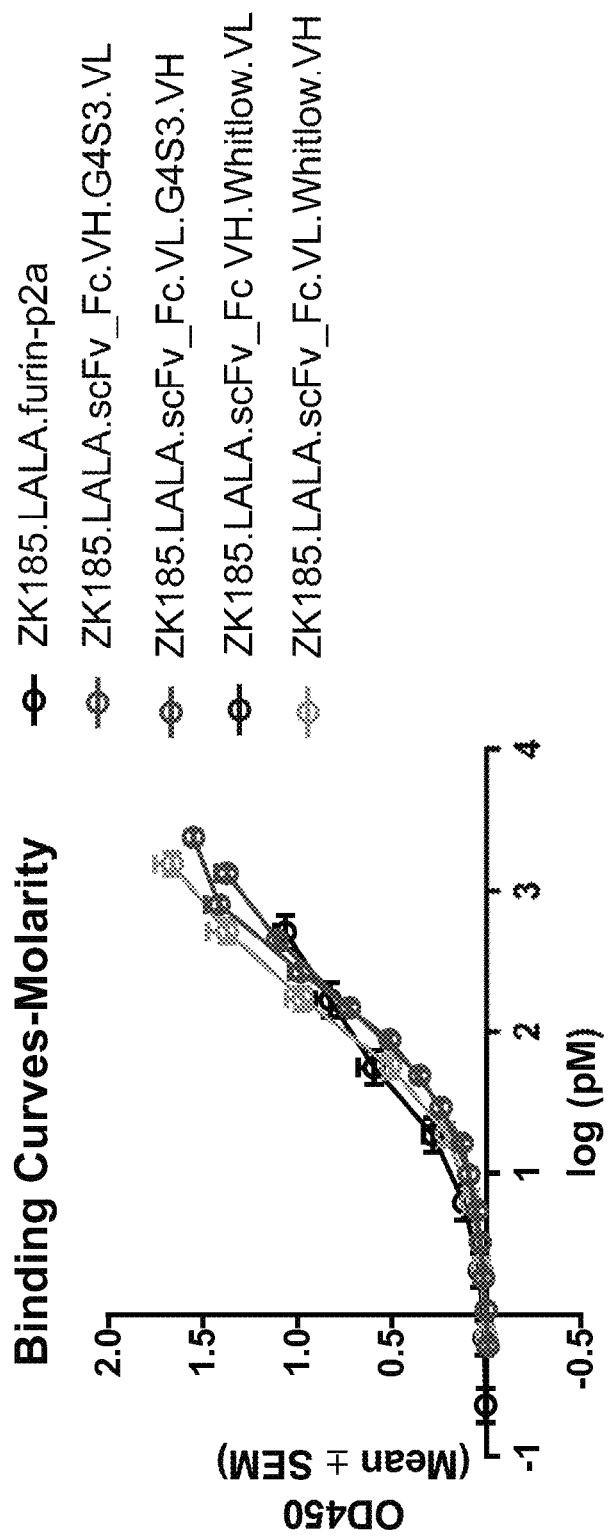
FIG. 24 depicts an analysis of the in vivo binding capability of ScFv-Fc conversion constructs of the ZK185LALA FP2A codon optimized DMAb.

Two Zika DMAbs were chosen, and from them multiple constructs were generated. They differed in their choice of linker molecule and the orientation of the VH-VL. Converting DMAbs from a full length antibody to scFv-Fc resulted in an increase in murine expression of up to 6 fold compared to the original DMAb. For ZKDMAB-1, expression of the four formats tested ranged from 16 ug/ml down to 8 ug/ml and favored the $(G_{4S})_3$ linker in the VH-VL orientation. ZKDMAB-2 saw highest expression reach 12 ug/ml using the $(G4S)_3$ linker in the VL-VH orientation. Importantly, modifications made to the majority of DMAbs retained antigen binding. Through these changes the in vivo expression levels were increased without sacrificing the biology of the original mAb clone (FIG. 22 through FIG. 24). These data demonstrate the obvious benefit of gene and protein modulation when designing DMAbs for gene therapy applications.

TABLE 6

Engineered anti-ZIKV DMAbs: GO = gene optimization; 190 = ZK190-G1M3-LALA; 185 = ZK185.LALA.furin-p2a

| SEQ ID NO: | Sequence Type | DMAb Type | Name | Description |
|---|---|---|---|---|
| 63 | Nucleotide | GO | pRD211 | 190-FP2A-mouse-GeneArt |
| 64 | Amino acid | GO | pRD211 | 190-FP2A-mouse-GeneArt |
| 65 | Nucleotide | GO | pRD212 | 190-FP2A-mouse-Synbio |
| 66 | Amino acid | GO | pRD212 | 190-FP2A-mouse-Synbio |
| 67 | Nucleotide | GO | pRD213 | 190-FP2A-mouse-Genewiz |
| 68 | Amino acid | GO | pRD213 | 190-FP2A-mouse-Genewiz |
| 69 | Nucleotide | GO | pRD214 | 190-FP2A-mouse-Blue heron |
| 70 | Amino acid | GO | pRD214 | 190-FP2A-mouse-Blue heron |
| 71 | Nucleotide | GO | pRD215 | 190-FP2A-mammal-DNA2.0 |
| 72 | Amino acid | GO | pRD215 | 190-FP2A-mammal-DNA2.0 |
| 73 | Nucleotide | GO | pRD216 | 190-FP2A-mouse-Genscript |
| 74 | Amino acid | GO | pRD216 | 190-FP2A-mouse-Genscript |
| 75 | Nucleotide | GO | pRD225 | 185-mouse-GeneArt |
| 76 | Amino acid | GO | pRD225 | 185-mouse-GeneArt |
| 77 | Nucleotide | GO | pRD227 | 185-mouse-Synbio |
| 78 | Amino acid | GO | pRD227 | 185-mouse-Synbio |
| 79 | Nucleotide | GO | pRD229 | 185-mouse-GeneWiz |
| 80 | Amino acid | GO | pRD229 | 185-mouse-GeneWiz |
| 81 | Nucleotide | GO | pRD231 | 185-mouse-GenScript |
| 82 | Amino acid | GO | pRD231 | 185-mouse-GenScript |
| 83 | Nucleotide | GO | pRD233 | 185-mouse-Blue Heron |
| 84 | Amino acid | GO | pRD233 | 185-mouse-Blue Heron |
| 85 | Nucleotide | GO | pRD234 | 185-mammal-DNA2.0 |
| 86 | Amino acid | GO | pRD234 | 185-mammal-DNA2.0 |
| 87 | Nucleotide | Parental | pGX9382 | 190 |
| 88 | Amino acid | Parental | pGX9382 | 190 |
| 89 | Nucleotide | scFv_Fc | pGX93100 | 190.scFv_Fc.VH.G4S3.VL |
| 90 | Amino acid | scFv_Fc | pGX93100 | 190.scFv_Fc.VH.G4S3.VL |
| 91 | Nucleotide | scFv_Fc | pGX93101 | 190.scFv_Fc.VL.G4S3.VH |
| 92 | Amino acid | scFv_Fc | pGX93101 | 190.scFv_Fc.VL.G4S3.VH |

TABLE 6-continued

Engineered anti-ZIKV DMAbs: GO = gene optimization; 190 = ZK190-G1M3-LALA; 185 = ZK185.LALA.furin-p2a

| SEQ ID NO: | Sequence Type | DMAb Type | Name | Description |
|---|---|---|---|---|
| 93 | Nucleotide | scFv_Fc | pGX93102 | 190.scFv_Fc VH.Whitlow.VL |
| 94 | Amino acid | scFv_Fc | pGX93102 | 190.scFv_Fc VH.Whitlow.VL |
| 95 | Nucleotide | scFv_Fc | pGX93103 | 190.scFv_Fc.VL.Whitlow.VH |
| 96 | Amino acid | scFv_Fc | pGX93103 | 190.scFv_Fc.VL.Whitlow.VH |
| 97 | Nucleotide | Parental | pGX93134 | 185 |
| 98 | Amino acid | Parental | pGX93134 | 185 |
| 99 | Nucleotide | scFv_Fc | pGX93129 | 185.scFv_Fc.VH.G4S3.VL |
| 100 | Amino acid | scFv_Fc | pGX93129 | 185.scFv_Fc.VH.G4S3.VL |
| 101 | Nucleotide | scFv_Fc | pGX93130 | 185.scFv_Fc.VL.G4S3.VH |
| 102 | Amino acid | scFv_Fc | pGX93130 | 185.scFv_Fc.VL.G4S3.VH |
| 103 | Nucleotide | scFv_Fc | pGX93131 | 185.scFv_Fc VH.Whitlow.VL |
| 104 | Amino acid | scFv_Fc | pGX93131 | 185.scFv_Fc VH.Whitlow.VL |
| 105 | Nucleotide | scFv_Fc | pGX93132 | 185.scFv_Fc.VL.Whitlow.VH |
| 106 | Amino acid | scFv_Fc | pGX93132 | 185.scFv_Fc.VL.Whitlow.VH |

Example 7: Evaluation of a Multivalent scFv-Fc DNA-Encoded Monoclonal Antibodies (DMAb) Platform Against Zika Virus (ZIKV) and Dengue Virus (DENV) Infections This study describes the engineering of two single-chain fragment variable-Fc (scFv-Fcs) DMAbs, Z-DMAb1-sc and D-DMAb1-sc that target ZIKV and DENV, respectively. It also describes the engineering of an additional DMAb that encodes both Z-DMAb1-sc and D-DMAb1-sc in a multivalent bi-directional promoter format (Z/D-DMAb1-sc). Using a murine model, the CELLECTRA®-EP technology was used to deliver intramuscularly in various cocktail combinations Z-DMAb1-sc and D-DMAb1-sc as well as individually formulated multivalent Z/D-DMAb1-sc. EP-mediated gene transfer of each of these scFv-Fc DMAbs leads to the secretion of functional scFv-Fcs in mice serum as assessed by ELISA and viral antigen binding assays. From this observation, higher scFv-Fc expression for Z-DMAb1-sc and D-DMAb1-sc was observed when expressed in the single multivalent bi-directional promoter construct (Z/D-DMAb1-sc) than when the two DNA plasmid constructs were co-formulated in a single preparation or separately delivered at two-individual muscle sites. Furthermore, the effect of these various co-formulations and multivalent combinations of the neutralization phenotype was analyzed. Taken all together these data provide evidence for adopting a multivalent scFv-Fc DMAb platform that may prove more versatile to combat infections by multiple pathogens such as ZIKV and DENV that are prevalent in overlapping endemic zones.

TABLE 7

Engineered anti-DENV DMAbs:

| SEQ ID NO: | Sequence Type | DMAb type | Name | Description |
|---|---|---|---|---|
| 107 | Nucleotide | scFv_Fc | pGX93141 | DVSF3 LALA scFv-Fc VH.G4S3.VL |
| 108 | Amino acid | scFv_Fc | pGX93141 | DVSF3 LALA scFv-Fc VH.G4S3.VL |

Example 8: Functional Characterization of In Vivo Expressed DNA-Based Monoclonal Antibodies (dMAbs) Against Respiratory Syncytial Virus (RSV)

While mAbs have been shown to be effective in providing protection against many infectious diseases their widespread use is limited. The limited in vivo half-life means multiple doses are required to maintain immunity, and the high costs and complexities involved in development, manufacture and cold chain distribution, and lack of suitable dosing methods which can be employed in the field, also hinder their global use. In response, new strategies based on the in vivo delivery of antibody genes are being developed. One such platform is dMAb, a synthetic plasmid DNA-encoded mAb. A DNA sequence encoding for a human mAb is inserted into a plasmid. As depicted in FIG. 1B, the dMAb plasmid is delivered directly to the muscle tissue and in-vivo electroporation enhances cellular uptake by myocytes. The transfected myocytes produce and secrete the mAb. The mAb enters blood circulation and can function systemically. In proof-of-concept studies dMAbs have provided protection against various infectious diseases, including influenza, pseudomonas, Zika and Ebola in pre-clinical animal models. Here will delineate the preclinical development of a dMAb targeting RSV. A RSV-dMAb could be delivered to high-risk populations to provide prophylactic protection against severe complications from RSV-infection across the season. Due to maintained expression one initial dMAb delivery would cover the whole RSV-season, re-delivery might be not necessary.

Figures 25A, 25B:
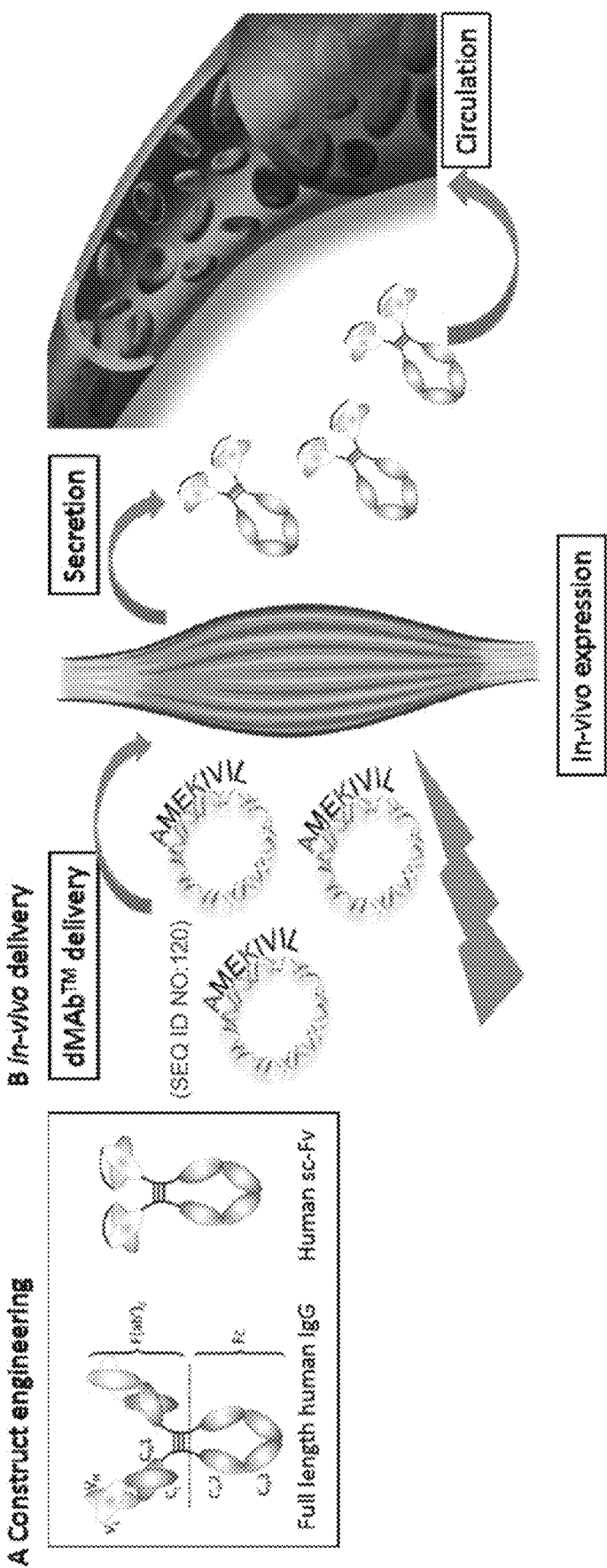
FIG. 25A depicts a schematic diagram demonstrating that DMAbs are delivered in-vivo by facilitated Electroporation using the CELLECTRA-3P® device. Transfected myocytes express and secret the protein MAb. Protein-MAb enters blood circulation.
FIG. 25B depicts a schematic diagram demonstrating that anti-RSV antibodies were engineered for scFv-Fc expression.

An anti-RSV sc-Fv encoding DNA plasmid was engineered (FIG. 25A) with an improved in-vivo expression profile compared to the full length human IgG. To further enhance systemic expression an optimized delivery protocol was employed. An optimized formulation enhances dispersion of the plasmid DNA through modifications of the extracellular matrix of the target tissue. Electroporation increases cellular uptake of the DNA molecules by target cells. The functionality of the in-vivo expressed human sc-Fv was confirmed from serum of treated mice for binding to the RSV-Fusion protein (RSV-F) antigen and neutralizing live RSV-A virus in-vitro. In addition to serum-level expression, the in-vivo expressed human sc-Fv was also detected in the lung, the location of natural RSV-infection. Dosing and delivery methods were then applied to cotton rats, the standard pre-clinical model for RSV-prophylaxis development.

Figures 26A, 26B, 26C, 26D:
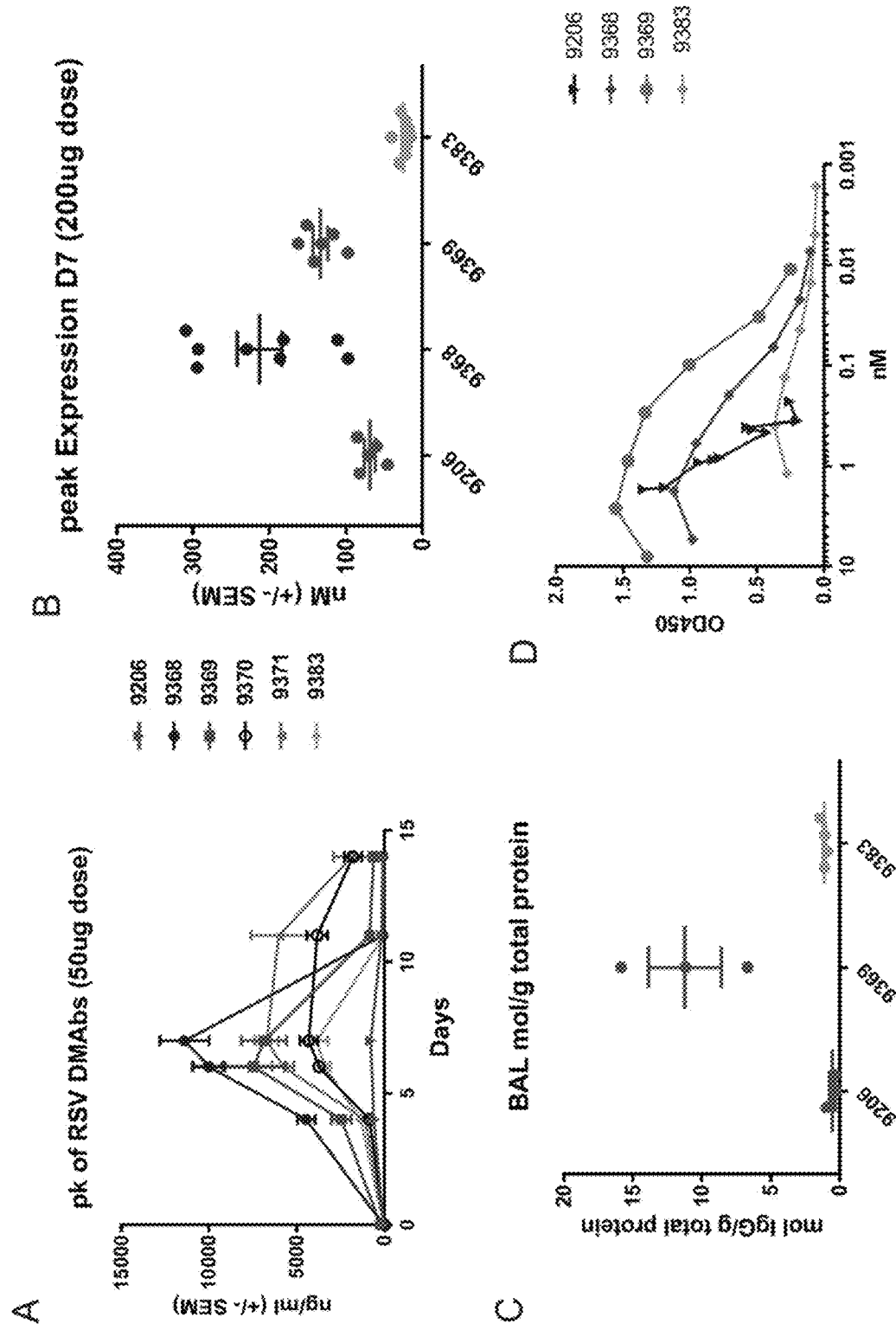
FIG. 26A through FIG. 26D, depicts expression of scFv-Fc anti-RSV DMAbs.
Figure 27:
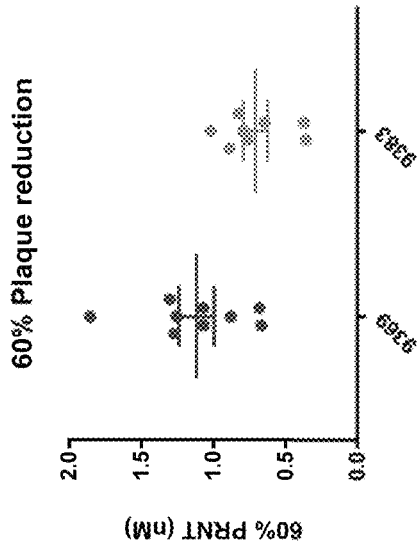
FIG. 27 depicts experimental results demonstrating neutralization of the anti-RSV DMAbs
Figure 27:
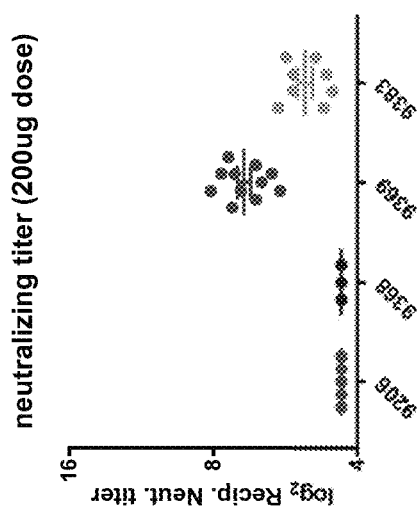
Figure 28:
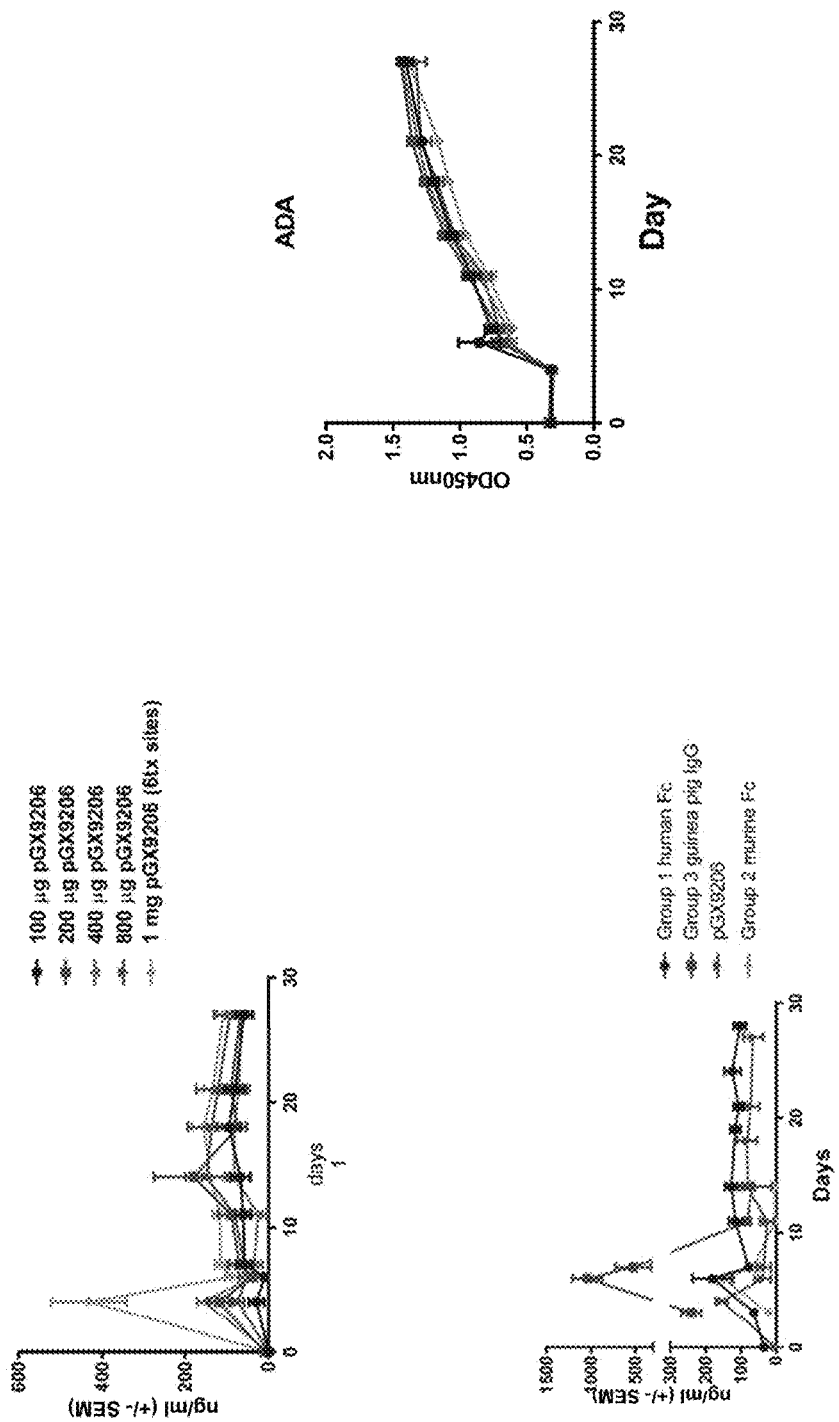
FIG. 28 depicts experimental results demonstrating anti-RSV-DMAbs in the cotton rat.
Figures 29A, 29B, 29C, 29D:
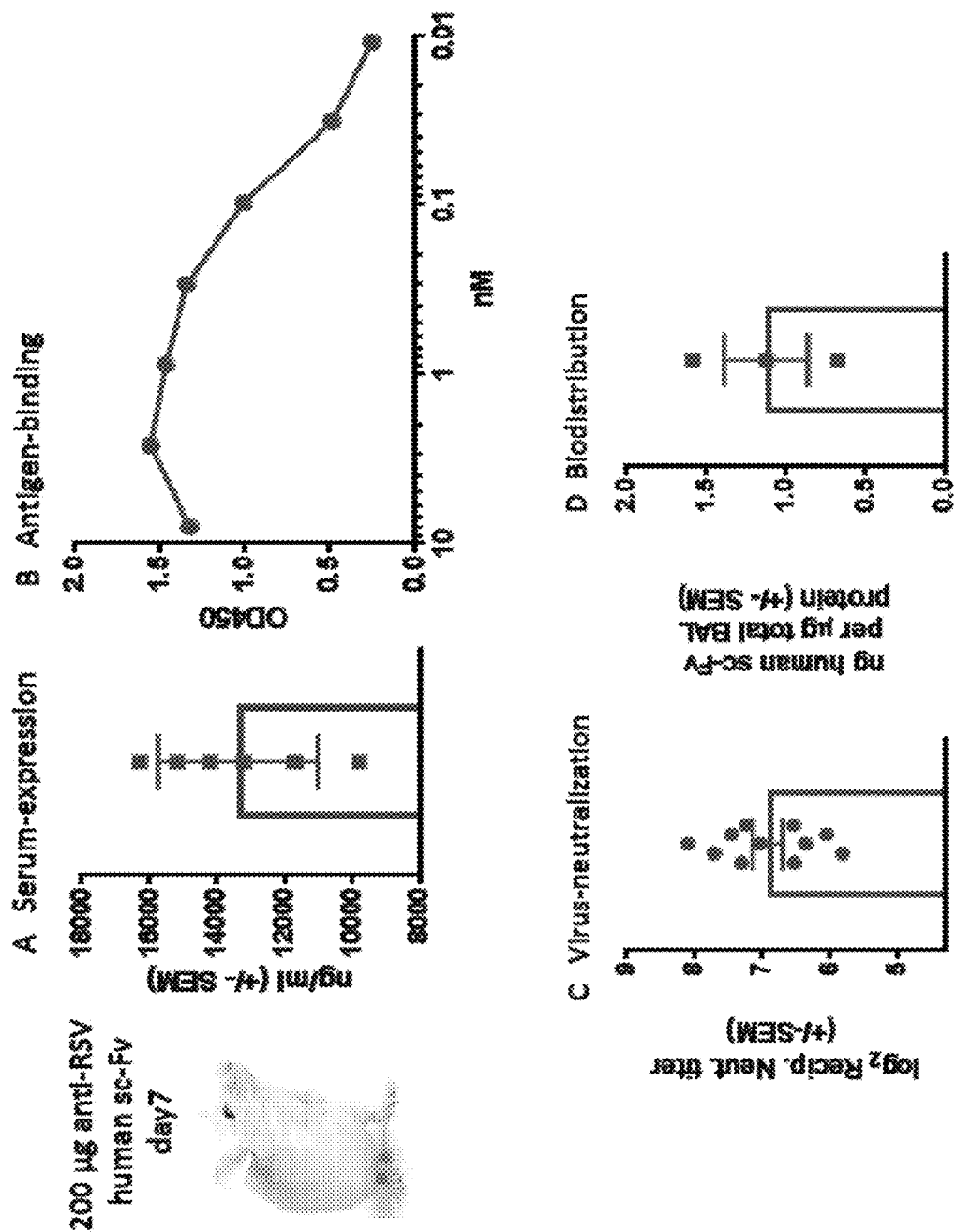
FIG. 29A through FIG. 29D, depicts exemplary experimental results demonstrating the peak expression and functionality of human sc-Fv anti RSV in immunocompetent mice. Mice were dosed with 200 µg human sc-Fv anti RSV dMAb delivered into leg muscles of balb/c mice. Delivery was assisted by CELLECTRA-3P®.
Figure 30:
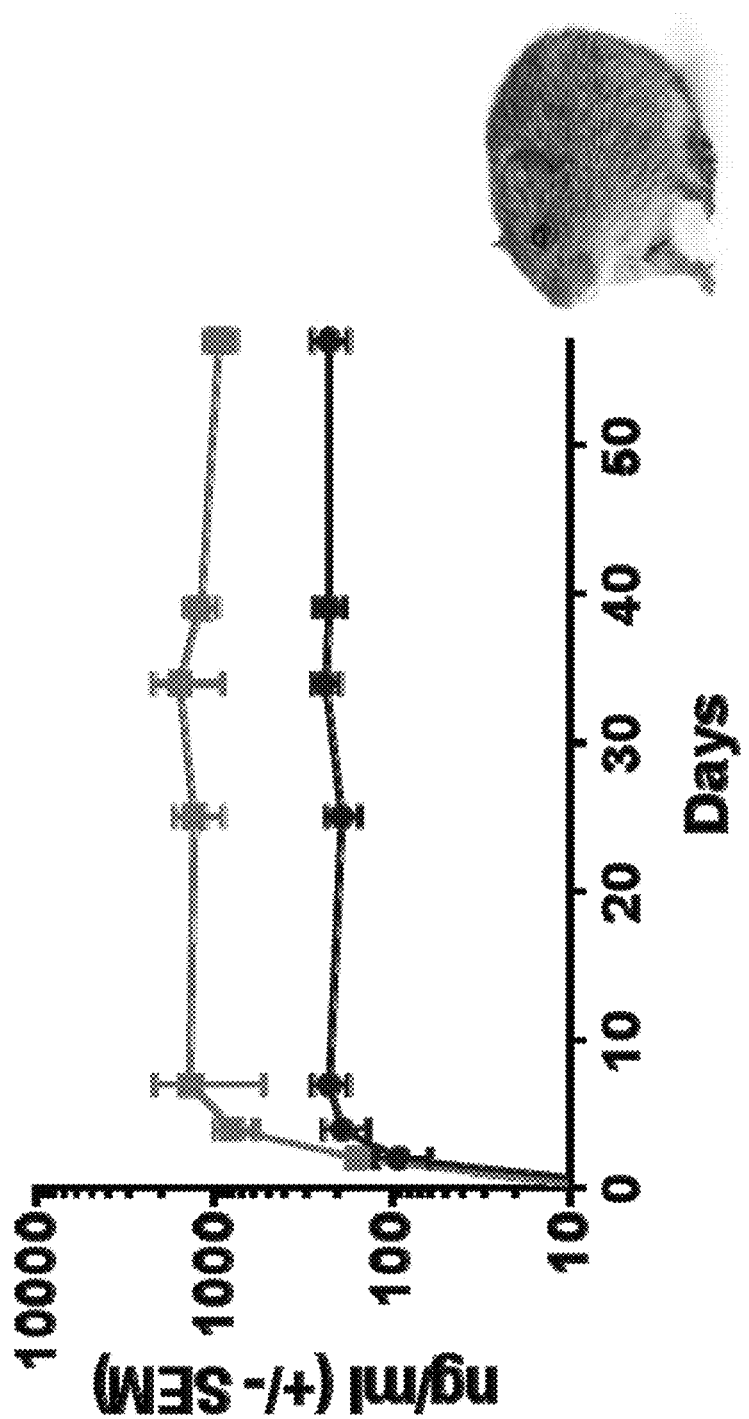
FIG. 30 depicts exemplary experimental results demonstrating the maintained expression of human sc-Fv in cotton rats. 100 µg and 800 µg of human sc-Fv was delivered into TA muscle of cotton rats. Delivery was assisted with CELLECTRA-3P®. Peak expression in serum is reached after 7 days (226 ng/ml and 1353 ng/ml respectively).
Figures 31A, 31B:
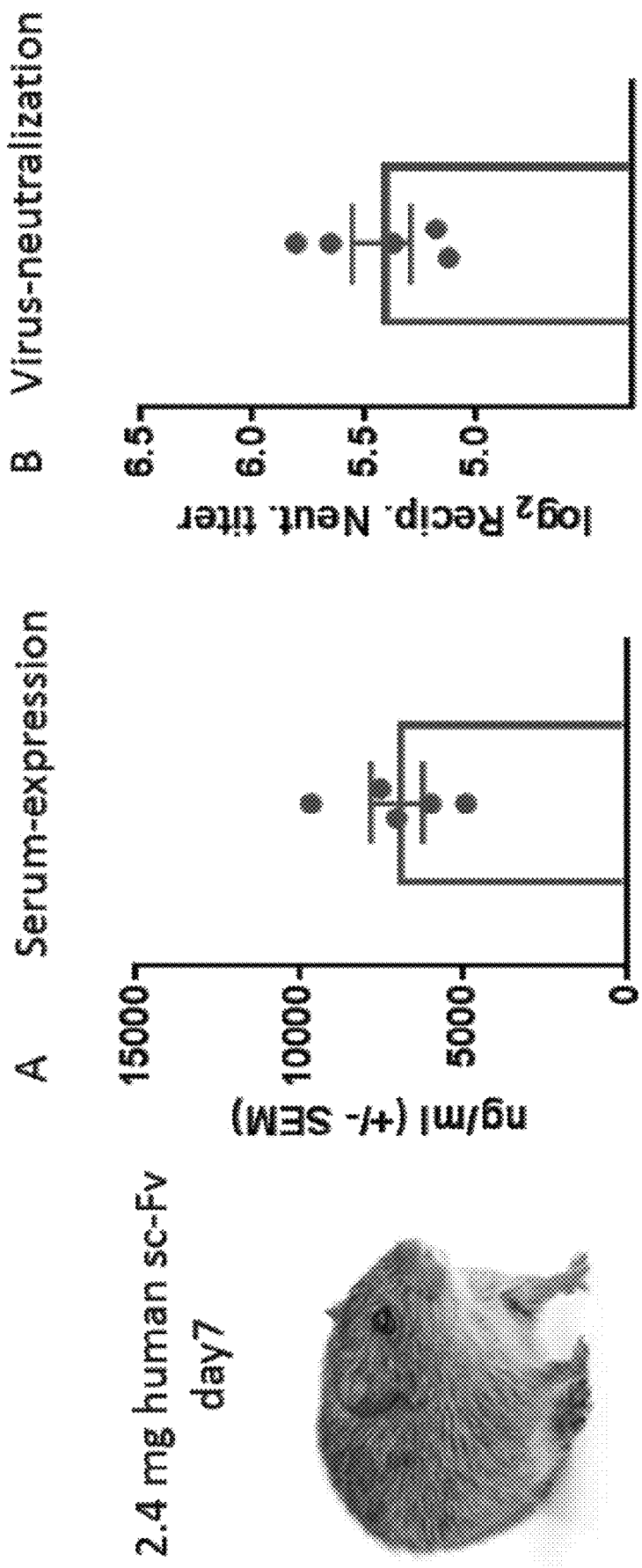
FIG. 31A and FIG. 31B, depicts exemplary experimental results demonstrating the peak expression and functionality of human sc-Fv in cotton rats.

In vivo delivery of this dMAb resulted in robust systemic levels of the antibody in the serum of mice (FIG. 26 and FIG. 29A). Matched levels of recombinant Pavilizumab provide protection from lower respiratory disease after RSV infection. In cotton rats, which is the gold-standard to model human disease following RSV infection, sustained serum-expression of the dMAb was observed up to 60 days after delivery (FIG. 30). The antibody was also detected in lung-lavage samples, demonstrating effective biodistribution (FIG. 26C and FIG. 29D). Furthermore, serum from animals harboring RSV-F dMAb was functionally active in terms of antigen binding and neutralizing live virus (FIG. 27, FIG. 29B, FIG. 29C and FIG. 31B). Experiments are designed to conduct an in-vivo live virus challenge of cotton rats. The cotton rat is considered the model of choice for preclinical development of RSV vaccines because of their high susceptibility to non-adapted human RSV and display of many features of the pathology of infection in humans.

These results suggest that the anti-RSV human sc-Fv dMAb could be an effective alternative to repetitive injections of protein-mAb throughout RSV-season. RSV-dMAb has the potential to overcome some of the hurdles associated with the passive immunization.

TABLE 8

RSV DMAb Plasmids:

| DMAb | description | Fc/ conformation | Delivery protocol |
|---|---|---|---|
| 9206 | Manni's Motavizumab | huIgG | 30 min pre-tx Sigma-HYA |
| 9368 | Palivizumab | huIgG | Co-formulation Intropharma HYA |
| 9369 | Palivizumab | huIgG sc-Fv | Co-formulation Intropharma HYA |
| 9370 | Palivizumab | muIgG | Co-formulation Intropharma HYA |
| 9371 | Palivizumab | muIgG sc-Fv | Co-formulation Intropharma HYA |
| 9283 | ADImab | huIgG | Co-formulation Hylenex |

TABLE 9

Engineered anti-RSV DMAbs:

| SEQ ID NO: | Sequence Type | DMAb type | Name |
|---|---|---|---|
| 110 | Nucleotide | GO | pGX9368 |
| 111 | Amino acid | GO | pGX9368 |
| 112 | Nucleotide | scFv-Fc | pGX9369 |
| 113 | Amino acid | scFv-Fc | pGX9369 |
| 114 | Nucleotide | GO | pGX9370 |
| 115 | Amino acid | GO | pGX9370 |
| 116 | Nucleotide | scFv-Fc | pGX9371 |
| 117 | Amino acid | scFv-Fc | pGX9371 |
| 118 | Nucleotide | GO | pGX9283 |
| 119 | Amino acid | GO | pGX9283 |

Figures 32A, 32B, 32C:
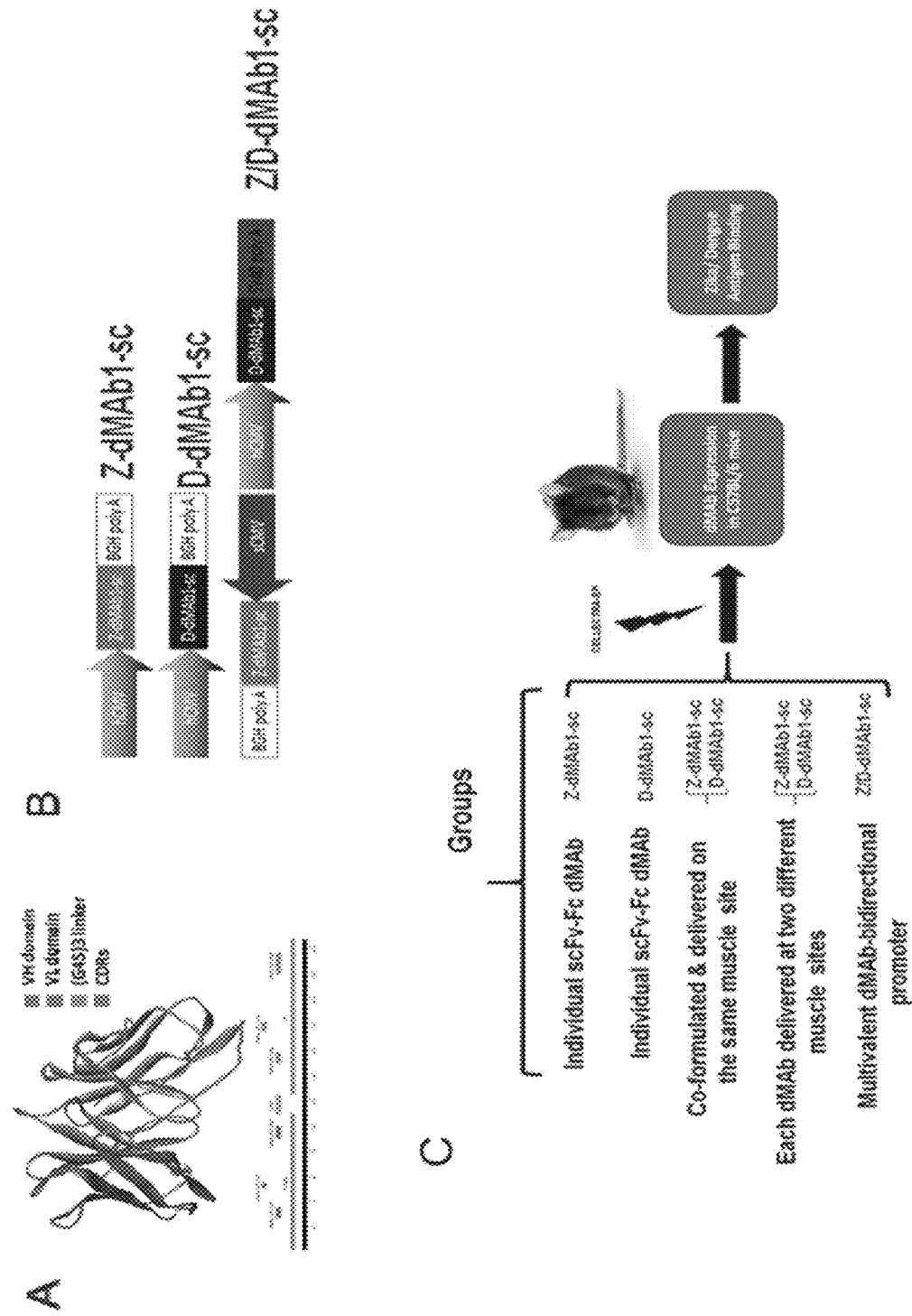
FIG. 32A through FIG. 32C, depicts schematic diagrams of the molecular and experimental design Dengue and Zika scFv-Fc were structurally-reformatted.
Figure 33:
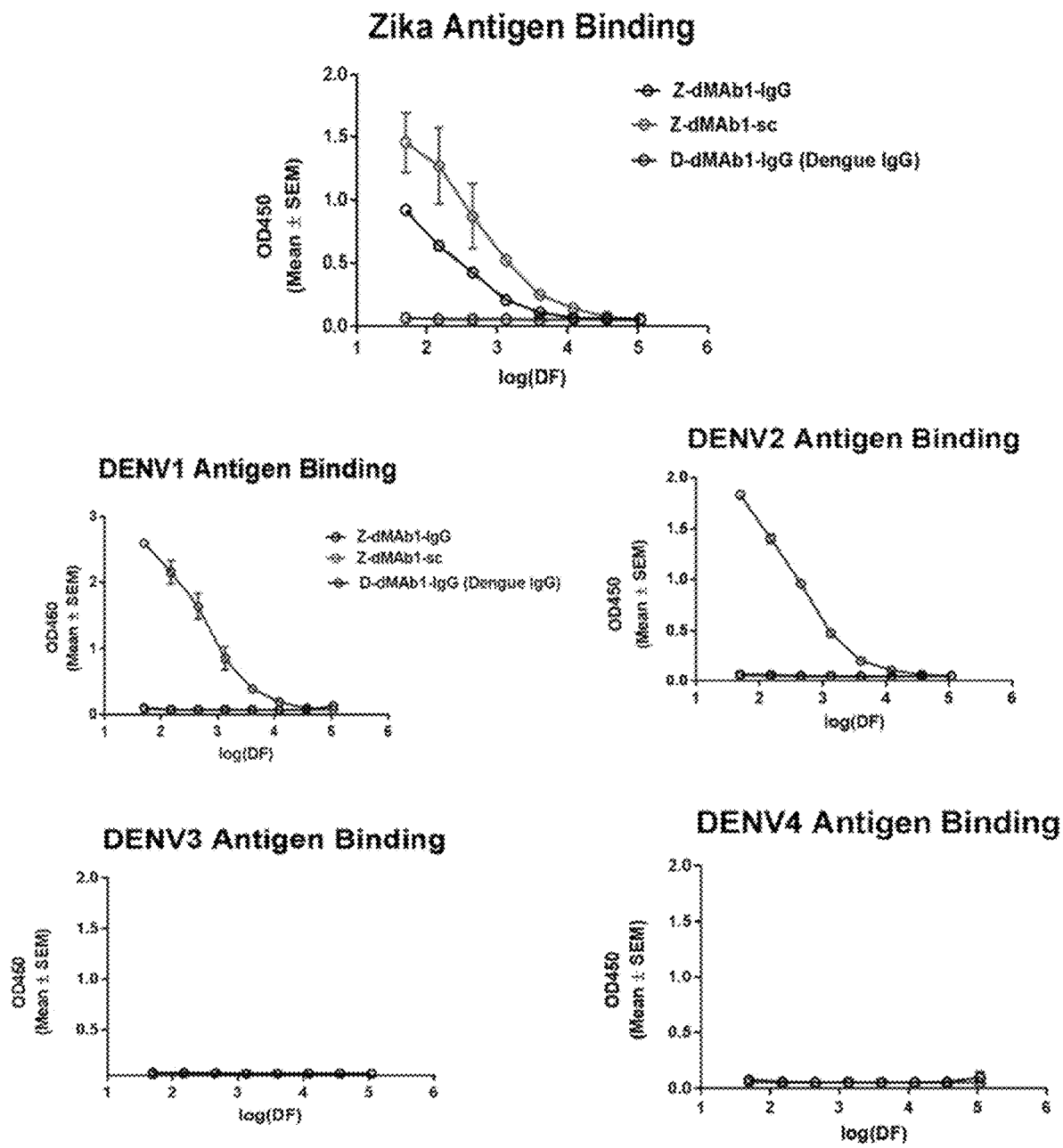
FIG. 33 depicts exemplary experimental results demonstrating an evaluation of the cross-reactivity between Zika and Dengue virus. Zika dMAb react specifically with Zika antigen. Dengue dMAb reacts specifically to DENV1 and DENV2 antigens. Plasmid encoding scFv-FC-dMAbs were transfected in 293 T cells. Day 2 post transfection supernatant containing the scFv-Fc protein were submitted to antigen binding. 96 well plates were coated with 100 µl/well 1 µg/ml of Zika or Dengue antigen (DENV1-4). Reciprocal serum dilutions one in third (⅓) serial dilutions were performed with pre-diluted serum samples on 96 well plate. Antigen binding was assessed by ELISA. Data are expressed as mean OD450±SEM FIG. 34, comprising
Figure 34A:
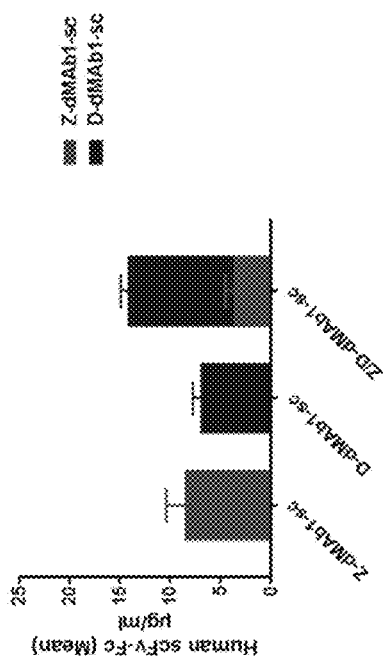
FIG. 34A through FIG. 34C, depicts exemplary experimental results demonstrating in vitro expression and antigen binding of scFV-Fc dMAbs. Plasmid encoding scFv-FC-dMAbs were transfected in 293 T cells.
Figure 34B:
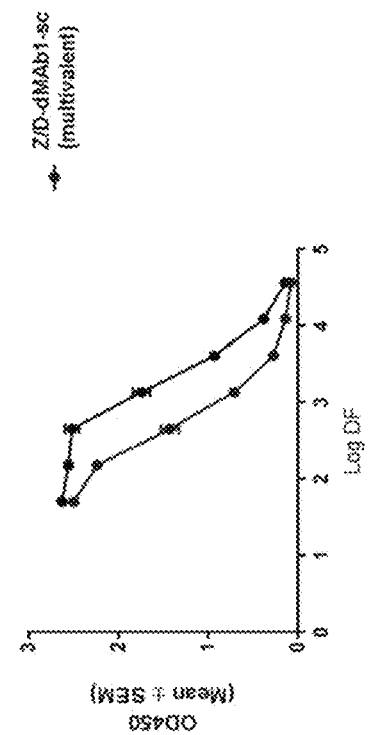
Figure 34C:
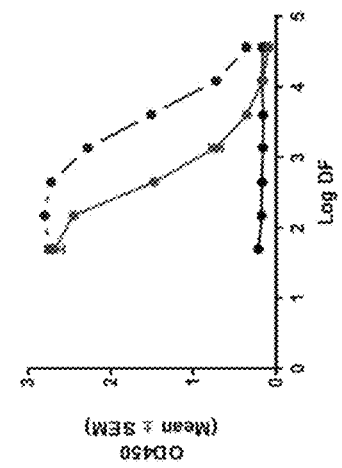
Figure 35A:
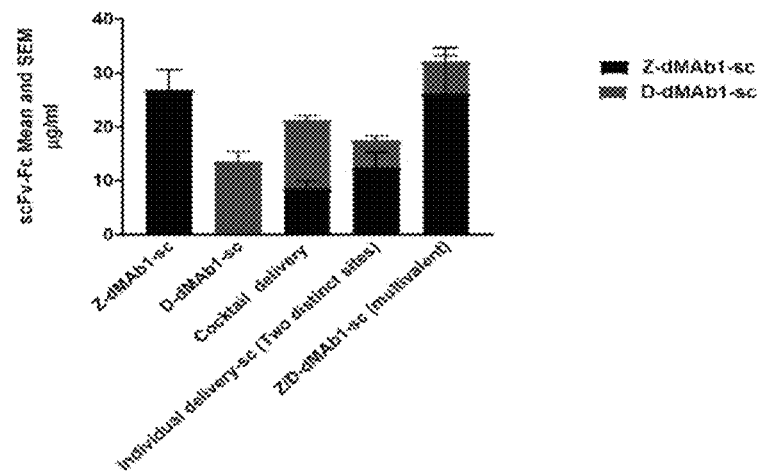
FIG. 35A through FIG. 35C, depicts exemplary experimental results demonstrating in vivo expression and antigen binding of scFv-Fc dMAbs.
Figure 35B:
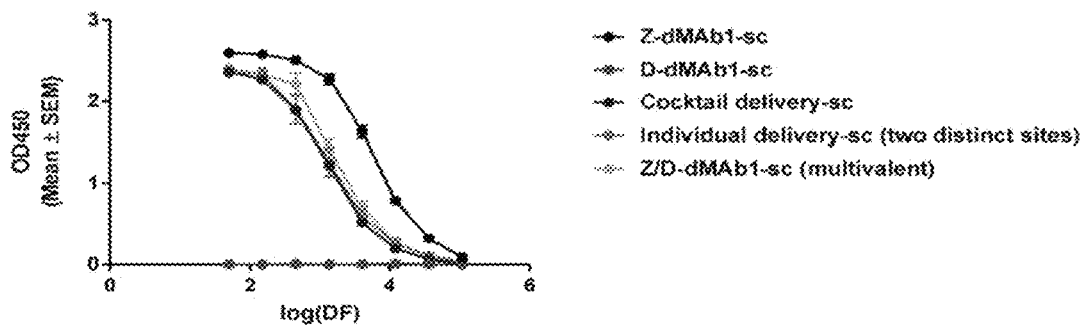
Figure 35C:
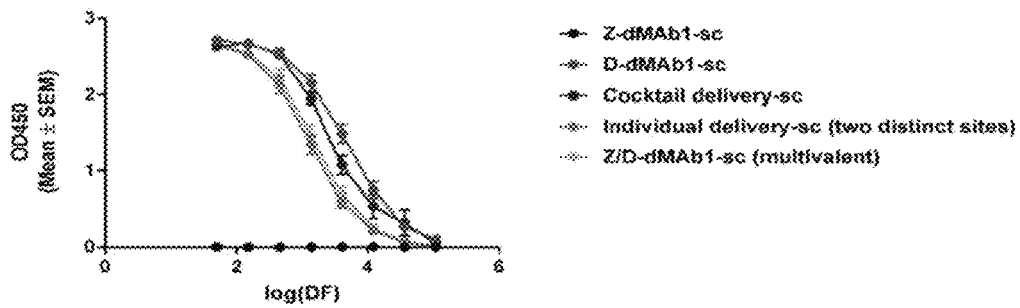

Example 9: A Multivalent scFv-Fc DNA-Encoded Monoclonal Antibodies (dMAb™) Platform Against Zika Virus (ZIKV) and Dengue Virus (DENV) Infections Zika (ZIKV) and Dengue (DENV) viruses are mosquito-borne flavivirus that cause from mild to severe pathologies varying from minor rashes to severe organ failure that could lead to death furthermore, infection by ZIKV specifically during pregnancy is associated with spontaneous abortion or severe developmental defects in newborns, including microcephaly and cognitive impairment that can be individually and societally burdensome. Previously published pre-clinical models have laid the rationale for using neutralizing monoclonal antibodies (mAbs) as basis for therapeutic intervention against ZIKV and DENV infections. While mAbs administration holds great promises as both prophylactic and curative approaches for infectious diseases there are conceptual and methodological impediments associated with the large scale administration of protein mAbs specifically for several millions people potentially at risk of contracting ZIKV or/and DENY infections. An alternative approach for treatment of these diseases is based on expression of plasmid-encoding monoclonal antibody (dMAbs) in skeletal muscles that leads to in vivo production and secretion of mAbs in the serum. In an attempt to design a more versatile dMAb platform, with increased pathogenic coverage, two single-chain fragment variable-Fc (scFv-Fcs) dMAbs were engineered, Z-dMAb1-sc and D-dMAb1-sc that target ZIKV and DENV, respectively (FIG. 32). An additional dMAb that encodes both Z-dMAb1-sc and D-dMAb1-sc in a multivalent bi-directional promoter format (Z/D-dMAb1-sc) was also engineered (FIG. 32 and Table 10). The CELLECTRA®-EP technology was used to deliver intramuscularly in a murine model various cocktail combinations of plasmid DNA encoding Z-dMAb1-sc and D-dMAb1-sc as well as individually formulated multivalent plasmid DNA encoding Z/D-dMAb1-sc dMAb. EP-mediated gene transfer of each of these scFv-Fc dMAbs leads to the secretion of functional scFv-Fcs in mice serum as assessed by ELISA and viral antigen binding assays (FIG. 33). From this observation, disparate scFv-Fc expression was noted for Z-dMAb1-sc and D-dMAb1-sc when expressed in the single multivalent bi-directional promoter construct (Z/D-dMAb1-sc) as compared to when the two DNA plasmid constructs were co-formulated in a single preparation or separately delivered at two-individual muscle sites (FIG. 34). Furthermore, how these various co-formulations and multivalent combinations affect the neutralization phenotype was analyzed (FIG. 35). The multivalent scFv-Fc dMAb platform allows the production of two functional scFv-Fc dMAbs (Z-dMAb1-sc & D-dMAb1-sc). Cocktailing/Mixing scFv-Fc Zika/Dengue dMAb appears to benefit dengue dMAb1-sc expression. Further, molecular engineering of Zika/Dengue dMAb in a bi-directional promoter platform appears to benefit significantly the expression of Dengue dMAb with no significant difference in Zika expression Taken all together these data provide support for a multivalent scFv-Fc dMAb platform that may prove more adaptable to combat infections by multiple pathogens, such as ZIKV and DENV, that are prevalent in overlapping endemic zones.

TABLE 10

Structurally Modified DMAb sequences

| SEQ ID NO: | Sequence Type | DMAb type | Name | Description |
|---|---|---|---|---|
| 89 | Nucleotide | scFv_Fc | pGX93100 | 190.scFv_Fc.VH.G4S3.VL |
| 90 | Amino acid | scFv_Fc | pGX93100 | 190.scFv_Fc.VH.G4S3.VL |
| 107 | Nucleotide | scFv_Fc | pGX93141 | DVSF3 LALA scFv-Fc VH.G4S3.VL |
| 108 | Amino acid | scFv_Fc | pGX93141 | DVSF3 LALA scFv-Fc VH.G4S3.VL |
| 126 | Nucleotide | Bidirectional scFv_Fc | pRD245 | DVSF3 LALA scFv-Fc VH.G4S3.VL and 190.scFv_Fc.VH.G4S3.VL bidirectional expression plasmid |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A composition comprising a nucleic acid molecule comprising at least one nucleotide sequence encoding a structurally modified anti-RSV DMAb, wherein the anti-RSV DMAb comprises an amino acid sequence selected from the group consisting of SEQ ID NO:111, SEQ ID NO:113, SEQ ID NO:115, SEQ ID NO:117, and SEQ ID NO:119.

2. The composition of claim 1, wherein the nucleic acid molecule comprises at least two nucleotide sequences wherein each nucleotide sequence encodes a structurally modified DMAb.

3. A method of treating RSV infection comprising administering at least one composition of claim 1 to a subject in need thereof.

4. The composition of claim 1, wherein the nucleic acid molecule comprises a nucleotide sequence selected from the group consisting of SEQ ID NO:110, SEQ ID NO:112, SEQ ID NO:114, SEQ ID NO:116 and SEQ ID NO:118.

5. The composition of claim 1, wherein the nucleic acid molecule comprises an expression vector.

* * * * *